(12) United States Patent
Eckelman et al.

(10) Patent No.: US 11,866,507 B2
(45) Date of Patent: *Jan. 9, 2024

(54) MULTISPECIFIC POLYPEPTIDE CONSTRUCTS HAVING CONSTRAINED CD3 BINDING AND METHODS OF USING THE SAME

(71) Applicant: Inhibrx, Inc., La Jolla, CA (US)

(72) Inventors: Brendan P. Eckelman, La Jolla, CA (US); Michael D. Kaplan, La Jolla, CA (US); Katelyn M. Willis, La Jolla, CA (US); Quinn Deveraux, La Jolla, CA (US); John C. Timmer, La Jolla, CA (US)

(73) Assignee: Inhibrx, Inc., La Jolla, CA (US)

( * ) Notice: Subject to any disclaimer, the term of this patent is extended or adjusted under 35 U.S.C. 154(b) by 13 days.

This patent is subject to a terminal disclaimer.

(21) Appl. No.: 15/951,137

(22) Filed: Apr. 11, 2018

(65) Prior Publication Data

US 2019/0010242 A1    Jan. 10, 2019

Related U.S. Application Data

(60) Provisional application No. 62/484,217, filed on Apr. 11, 2017.

(51) Int. Cl.
C07K 16/30 (2006.01)
C07K 16/28 (2006.01)
C07K 16/46 (2006.01)
A61P 35/00 (2006.01)

(52) U.S. Cl.
CPC .............. *C07K 16/30* (2013.01); *A61P 35/00* (2018.01); *C07K 16/28* (2013.01); *C07K 16/2809* (2013.01); *C07K 16/2827* (2013.01); *C07K 16/2863* (2013.01); *C07K 16/2887* (2013.01); *C07K 16/468* (2013.01); *C07K 2317/31* (2013.01); *C07K 2317/52* (2013.01); *C07K 2317/55* (2013.01); *C07K 2317/56* (2013.01); *C07K 2317/569* (2013.01); *C07K 2317/62* (2013.01); *C07K 2317/624* (2013.01); *C07K 2317/64* (2013.01); *C07K 2317/66* (2013.01); *C07K 2317/73* (2013.01); *C07K 2317/75* (2013.01)

(58) Field of Classification Search
CPC ........ C07K 2317/624; C07K 2317/569; C07K 2317/31; C07K 16/468; C07K 16/2809
USPC ............................................ 424/133.1, 136.1
See application file for complete search history.

(56) References Cited

U.S. PATENT DOCUMENTS

| | | | |
|---|---|---|---|
| 3,773,919 A | 11/1973 | Boswell et al. | |
| 4,522,811 A | 6/1985 | Eppstein et al. | |
| 5,151,510 A | 9/1992 | Stec et al. | |
| 5,258,498 A | 11/1993 | Huston et al. | |
| 5,500,362 A | 3/1996 | Robinson et al. | |
| 5,525,491 A | 6/1996 | Huston et al. | |
| 5,731,168 A | 3/1998 | Carter et al. | |
| 5,821,337 A | 10/1998 | Carter et al. | |
| 6,132,992 A | 10/2000 | Ledbetter et al. | |
| 7,025,962 B1 | 4/2006 | Gorman | |
| 7,183,076 B2 | 2/2007 | Arathoon et al. | |
| 8,044,178 B2 | 10/2011 | Boghaert et al. | |
| 8,669,350 B2 | 3/2014 | Chou | |
| 9,346,884 B2 | 5/2016 | Beste et al. | |
| 9,605,084 B2 | 3/2017 | Moore et al. | |
| 9,644,016 B2 | 5/2017 | Stagliano et al. | |
| 9,650,446 B2 | 5/2017 | Moore et al. | |
| 9,701,759 B2 | 7/2017 | Desjarlais et al. | |
| 10,010,626 B2 | 7/2018 | Chang et al. | |
| 10,066,015 B2 | 9/2018 | Zhukovsky et al. | |
| 10,087,250 B2 | 10/2018 | Bruenker et al. | |
| 10,093,742 B2 | 10/2018 | Timmer | |
| 10,131,710 B2 | 11/2018 | Moore et al. | |
| 10,858,417 B2 | 12/2020 | Moore et al. | |
| 2004/0220388 A1 | 11/2004 | Mertens | |
| 2005/0123546 A1 | 6/2005 | Umana et al. | |
| 2007/0004909 A1 | 1/2007 | Johnson | |
| 2007/0009523 A1 | 1/2007 | Presta | |
| 2011/0097339 A1 | 4/2011 | Holmes et al. | |
| 2011/0189203 A1 | 8/2011 | Hermans et al. | |
| 2013/0224188 A1 | 8/2013 | Eckelman et al. | |
| 2013/0273054 A1 | 10/2013 | Bossenmaier et al. | |
| 2014/0072581 A1* | 3/2014 | Dixit .................. | C07K 16/2803 424/172.1 |
| 2014/0140989 A1 | 5/2014 | Eckelman et al. | |
| 2014/0154253 A1 | 6/2014 | Ng et al. | |

(Continued)

FOREIGN PATENT DOCUMENTS

AU    2013/202755    5/2013
AU    2016/213702    8/2016

(Continued)

OTHER PUBLICATIONS

Ward et al. (Nature 341:544-546 (1989)).*
Smith-Gill et al. (J. Immunol. 139:4135-4144 (1987)).*
Kumar et al. (J. Biol. Chem. 275:35129-35136 (2000)).*
Song et al. (Biochem Biophys Res Comm 268:390-394 (2000)).*
Moore et al. (mAbs 3:6, 546-557; Nov./Dec. 2011).*
Henry etal (Frontiers in Immunology 8:1-15 (Dec. 12, 2017).*
Kim etal. (Biochimica et Biophysica Acta 1844 (2014) 1983-2001).*

(Continued)

*Primary Examiner* — Lynn A Bristol
(74) *Attorney, Agent, or Firm* — Morrison & Foerster LLP

(57) ABSTRACT

The invention relates generally to multispecific polypeptides having constrained CD3 binding. In some embodiments, the multispecific polypeptides contain cleavable linkers that, when cleaved, results in dual effector functions. Also provided are methods of making and using these multispecific polypeptides in a variety of therapeutic, diagnostic and prophylactic indications.

10 Claims, 57 Drawing Sheets

Specification includes a Sequence Listing.

(56) References Cited

U.S. PATENT DOCUMENTS

| | | | |
|---|---|---|---|
| 2014/0294823 A1 | 10/2014 | Moore et al. | |
| 2014/0363426 A1 | 12/2014 | Moore et al. | |
| 2014/0377253 A1 | 12/2014 | Harding | |
| 2015/0079088 A1 | 3/2015 | Lowman et al. | |
| 2015/0087810 A1 | 3/2015 | Moore et al. | |
| 2015/0239991 A1 | 8/2015 | Blein et al. | |
| 2015/0307628 A1 | 10/2015 | Kim et al. | |
| 2015/0322119 A1 | 11/2015 | Engelhardt | |
| 2016/0039942 A1 | 2/2016 | Cobbold et al. | |
| 2016/0122425 A1 | 5/2016 | Daugherty et al. | |
| 2016/0194399 A1 | 7/2016 | Irving et al. | |
| 2016/0207981 A1 | 7/2016 | Eckelman et al. | |
| 2016/0289324 A1 | 10/2016 | Moore et al. | |
| 2017/0015753 A1 | 1/2017 | Timmer et al. | |
| 2017/0022284 A1 | 1/2017 | Timmer et al. | |
| 2017/0037130 A1 | 2/2017 | Raum et al. | |
| 2017/0081397 A1 | 3/2017 | Stagliano et al. | |
| 2017/0114141 A1 | 4/2017 | Amann | |
| 2017/0145071 A1 | 5/2017 | Brennan et al. | |
| 2017/0198050 A1 | 7/2017 | Eckelman et al. | |
| 2017/0198051 A1 | 7/2017 | Eckelman et al. | |
| 2017/0204139 A1 | 7/2017 | Moore et al. | |
| 2017/0320958 A1 | 11/2017 | Timmer | |
| 2018/0016354 A1 | 1/2018 | Wozniak-Knopp et al. | |
| 2018/0230225 A1 | 8/2018 | Fan | |
| 2019/0100594 A1 | 4/2019 | Timmer | |
| 2019/0218515 A1* | 7/2019 | Ballesteros Nobell | A61K 39/001112 |
| 2019/0330366 A1* | 10/2019 | Eckelman | C07K 16/2809 |
| 2020/0048350 A1* | 2/2020 | Eckelman | C07K 16/28 |
| 2020/0190193 A1* | 6/2020 | Pandit | C07K 16/28 |
| 2021/0340273 A1* | 11/2021 | Timmer | C07K 14/56 |
| 2021/0380679 A1* | 12/2021 | Eckelman | C07K 16/2809 |
| 2023/0124851 A1 | 4/2023 | Eckelman et al. | |

FOREIGN PATENT DOCUMENTS

| | | |
|---|---|---|
| AU | 2015/202560 | 6/2017 |
| CN | 108084265 A | 5/2018 |
| EP | 1 378 520 | 1/2004 |
| EP | 1 736 484 | 12/2006 |
| EP | 2 914 634 | 12/2017 |
| EP | 3502140 | 6/2019 |
| JP | 2010-535032 | 11/2010 |
| JP | 2013-538204 | 10/2013 |
| WO | WO-1998/050431 | 11/1998 |
| WO | WO-2000/24884 | 5/2000 |
| WO | WO200177342 A1 | 10/2001 |
| WO | WO-2005/063816 | 7/2005 |
| WO | WO-2005/100402 | 10/2005 |
| WO | WO-2006/029879 | 3/2006 |
| WO | WO 2009/018386 | 2/2009 |
| WO | WO2009068649 A2 | 6/2009 |
| WO | WO-2009/089004 | 7/2009 |
| WO | WO2009124931 A2 | 10/2009 |
| WO | WO-2010/009391 | 1/2010 |
| WO | WO-2010/151792 | 12/2010 |
| WO | WO-2011/143545 | 11/2011 |
| WO | WO 2012/025525 | 3/2012 |
| WO | WO-2012/058768 | 5/2012 |
| WO | WO2012162067 A2 | 11/2012 |
| WO | WO2012162583 A1 | 11/2012 |
| WO | WO2013041687 A1 | 3/2013 |
| WO | WO-2013/101909 | 7/2013 |
| WO | WO 2013/128194 | 9/2013 |
| WO | WO-2014/067011 | 5/2014 |
| WO | WO-2014/099997 | 6/2014 |
| WO | WO2014089113 A1 | 6/2014 |
| WO | WO 2014/145806 | 9/2014 |
| WO | WO2014144960 A2 | 9/2014 |
| WO | WO 2015/026894 | 2/2015 |
| WO | WO 2015/197598 | 12/2015 |
| WO | WO-2015/197789 | 12/2015 |
| WO | WO-2016/020309 | 2/2016 |
| WO | WO 2016/046778 | 3/2016 |
| WO | WO2016033225 A2 | 3/2016 |
| WO | WO2016034666 A1 | 3/2016 |
| WO | WO-2016/055593 | 4/2016 |
| WO | WO-2016/086189 | 6/2016 |
| WO | WO-2016/087416 | 6/2016 |
| WO | WO-2016/105450 | 6/2016 |
| WO | WO2016097408 A1 | 6/2016 |
| WO | WO 2016/180982 | 11/2016 |
| WO | WO2016192613 A1 | 12/2016 |
| WO | WO-2017/030926 | 2/2017 |
| WO | WO2017021349 A1 | 2/2017 |
| WO | WO-2017/055398 | 4/2017 |
| WO | WO-2017/060144 | 4/2017 |
| WO | WO-2017/134440 | 8/2017 |
| WO | WO2017134140 A1 | 8/2017 |
| WO | WO2017182672 A1 | 10/2017 |
| WO | WO2018014260 A1 | 1/2018 |
| WO | WO-2018/027025 | 2/2018 |
| WO | WO-2018/127473 | 7/2018 |
| WO | WO2018167486 A1 | 9/2018 |
| WO | WO-2018/185045 | 10/2018 |
| WO | WO-2019/200022 | 10/2019 |
| WO | WO-2019/201866 | 10/2019 |
| WO | WO2020/023553 A1 | 1/2020 |
| WO | WO-2020/077257 | 4/2020 |
| WO | WO2020076970 A1 | 4/2020 |
| WO | WO2020076977 A2 | 4/2020 |
| WO | WO2020076992 A1 | 4/2020 |
| WO | WO-2021/155071 | 8/2021 |

OTHER PUBLICATIONS

Bacac et al., "CD20 Tcb (RG6026), a Novel "2:1" T Cell Bispecific Antibody for the Treatment of B Cell Malignancies," Blood (2016) 128(22):1836.

Brinkmann, U. et al., "The making of bispecific antibodies," mABS (2017) 9(2):182-212.

Bulliard et al., "Activating Fc $_\gamma$ receptors contribute to the antitumor activities of immunoregulatory receptor-targeting antibodies," J Exp Med (2013) 210(9):1685-93.

Harwood et al., "ATTACK, a novel bispecific T cell-recruiting antibody with trivalent EGFR binding and monovalent CD3 binding for cancer immunotherapy," Oncoimmunology (2018) 7(1):e1377874.

Huet et al., "Multivalent nanobodies targeting death receptor 5 elicit superior tumor killing through efficient caspase induction," mABS (2014) 6(6):1560-70.

Husain et al., "Expanding the boundaries of biotherapeutics with bispecific antibodies," BioDrugs (2018) 32(5):441-64.

Xing et al., "BiHC, a T-cell-engaging bispecific recombinant antibody, Has potent cytotoxic activity against Her2 tumor cells," Transl Oncol (2017) 10(5):780-85.

Yao et al., "Advances in targeting cell surface signalling molecules for immune modulation," Nat Rev Drug Discov (2013) 12(2):130-46.

U.S. Appl. No. 16/520,293, filed Jul. 23, 2019, by Eckelman et al. (Copy not provided). (Copy not submitted herewith pursuant to the waiver of 37 C.F.R. § 1.98(a)(2)(iii) issued by the Office dated Sep. 21, 2004).

Bacac et al., "CD20 Tcb (RG6026), a Novel "2:1" T Cell Bispecific Antibody for the Treatment of B Cell Malignancies," Blood (2016) 128:1836.

Brinkmann et al., "The making of bispecific antibodies," MABS (2017) 9(2):182-212.

Xing et al., "BiHC, a T-Cell-Engaging Bispecific Recombinant Antibody, Has Potent Cytotoxic Activity Against Her2 Tumor Cells," Transl Oncol (2017) 10(5):780-785.

Alegre et al., "Effect of a single amino acid mutation on the activating and immunosuppressive properties of a "humanized" OKT3 monoclonal antibody," J Immunol (1992) 148(11):3461-3468.

Baldrick, "Pharmaceutical Excipient Development: The Need for Preclinical Guidance," Regulatory Toxicology and Pharmacology (2000) 32(2):210-218.

(56) References Cited

OTHER PUBLICATIONS

Barre et al., "Cleavage Specificity Analysis of Six Type II Transmembrane Serine Proteases (TTSPs) Using PICS with Proteome-Derived Peptide Libraries," PLOS One (2014) 9(9):e105984.
Beliveau et al., "Probing the substrate specificities of matriptase, matriptase-2, hepsin and DESC1 with internally quenched fluorescent peptides," FEBS J (2009) 276(8):2213-2126.
Beranger et al., "Correspondence between the IMGT unique numbering for C-DOMAIN, the IMGT exon numbering, the Eu and Kabat numberings: Human IGHG," IMGT Scientific chart. Published on May 17, 2016. Retrieved on Jul. 19, 2018. Retrieved from http://www.imgt.org/IMGTScientificChart/Numbering/Hu_IGHGnber.html.
Bowie et al., "A method to identify protein sequences that fold into a known three-dimensional structure," Science (1991) 253(5016):164-170.
Bruggemann et al., "Comparison of the effector functions of human immunoglobulins using a matched set of chimeric antibodies," J Exp Med (1987) 166(5):1351-1361.
Carter et al., "Bispecific human IgG by design," J Immunol Methods (2001) 248(1-2):7-15.
Charman, "Lipids, lipophilic drugs, and oral drug delivery-some emerging concepts," J Pharm Sci (2000) 89(8):967-978.
Chen et al., "A Unique Substrate Recognition Profile for Matrix Metalloproteinase-2." J Biol Chem (2002) 277(6):4485-4491.
Chen et al., "Fusion protein linkers: property, design and functionality," Adv Drug Deliv Rev (2013) 65(10):1357-1369.
Chothia et al., "Canonical structures for the hypervariable regions of immunoglobulins," J Mol Biol (1987) 196(4):901-917.
Chothia et al., "Conformations of immunoglobulin hypervariable regions," Nature (1989) 342(6252):877-883.
Clynes et al., "Fc receptors are required in passive and active immunity to melanoma," PNAS (1998) 95(2):652-656.
Cragg et al., "Antibody specificity controls in vivo effector mechanisms of anti-CD20 reagents," Blood (2004) 103:2738-2743.
Cragg et al., "Complement-mediated lysis by anti-CD20 mAb correlates with segregation into lipid rafts," Blood (2003) 101(3):1045-1052.
Dall'Acqua et al., "Properties of Human IgG1s Engineered for Enhanced Binding to the Neonatal Fc Receptor (FcRn)*," J Biol Chem (2006) 281(33):23514-23524.
Davies et al., "Antibody-Antigen Complexes," Annu Rev Biochem (1990) 59:439-473.
Davis et al., "SEEDbodies: fusion proteins based on strand-exchange engineered domain (SEED) CH3 heterodimers in an Fc analogue platform for asymmetric binders or immunofusions and bispecific antibodies," Protein Eng Des Sel (2010) 23(4):195-202.
Deisenhofer, "Crystallographic refinement and atomic models of a human Fc fragment and its complex with fragment B of protein A from *Staphylococcus aureus* at 2.9- and 2.8 -.ANG. resolution," Biochemistry (1981) 20(9):2361-2370.
Gazzano-Santoro et al., "A non-radioactive complement-dependent cytotoxicity assay for anti-CD20 monoclonal antibody," J Immunol Methods (1997) 202(2):163-171.
Gunasekaran et al., "Enhancing antibody Fc heterodimer formation through electrostatic steering effects: applications to bispecific molecules and monovalent IgG," J Biol Chem (2010) 285(25):19637-19646.
Ha et al., "Immunoglobulin Fc Heterodimer Platform Technology: From Design to Applications in Therapeutic Antibodies and Proteins," Front Immunol (2016) 7:394.
Harris et al., "Definition and Redesign of the Extended Substrate Specificity of Granzyme B*," J Biol Chem (1998) 273(42):27364-27373.
Hellstrom et al., "Antitumor effects of L6, an IgG2a antibody that reacts with most human carcinomas," PNAS USA (1986) 83(18):7059-7063.
Hellstrom et al., "Strong antitumor activities of IgG3 antibodies to a human melanoma-associated ganglioside," PNAS USA (1985) 82(5):1499-1502.

Hernandez-Hoyos et al., "MOR209/ES414, a Novel Bispecific Antibody Targeting PSMA for the Treatment of Metastatic Castration-Resistant Prostate Cancer," Mol Cancer Ther (2016) 15(9):2155-2165.
Idusogie et al., "Engineered antibodies with increased activity to recruit complement," J Immunol (2001) 166(4):2471-2575.
Jendeberg et al., "Engineering of Fc(1) and Fc(3) from human immunoglobulin G to analyse subclass specificity for staphylococcal protein A," J Immnuol Methods (1997) 201 (1):25-34.
Kaneko et al., "Optimizing Therapeutic Antibody Function," Biodrugs (2011) 25(1):1-11.
La Rocca et al., "Zymographic detection and clinical correlations of MMP-2 and MMP-9 in breast cancer sera," British Journal of Cancer (2004) 90:1414-1421.
Laplanche et al., "Phosphorothioate-modified oligodeoxyribonucleotides. III. NMR and UV spectroscopic studies of the Rp-Rp, Sp-Sp, and Rp-Sp duplexes, [d(GGSAATTCC)]2, derived from diastereomeric O-ethyl phosphorothioates," Nucleic Acids Res (1986) 14(22):9081-9093.
Lazar et al., "Engineered antibody Fc variants with enhanced effector function," PNAS (2006) 103(11):4005-4010.
Leaver-Fay et al., "Computationally Designed Bispecific Antibodies using Negative State Repertoires," Structure (2016) 24(4):641-651.
Malmqvist, "Biospecific interaction analysis using biosensor technology," Nature (1993) 361:186-187.
Marasco et al., "Design, intracellular expression, and activity of a human anti- human immunodeficiency virus type 1 gp120 single-chain antibody," PNAS USA (1993) 90(16):7889-7893.
Merchant et al., "An efficient route to human bispecific lgG," Nat Biotechnol (1998) 16(7):677-681.
Miller, "Protein-protein recognition and the association of immunoglobulin constant domains," JMB (1990) 216(4):965-973.
Moore et al., "A novel bispecific antibody format enables simultaneous bivalent and monovalent co-engagement of distinct target antigens," MAbs (2011) 3(6):546-557.
Moore et al., "Engineered Fc variant antibodies with enhanced ability to recruit complement and mediate effector functions," MAbs (2010) 2(2):181-189.
Natsume et al., "Engineered Antibodies of IgG1/IgG3 Mixed Isotype with Enhanced Cytotoxic Activities," Cancer Res (2008) 68(10):3863-3872.
Petkova et al., "Enhanced half-life of genetically engineered human IgG1 antibodies in a humanized FcRn mouse model: potential application in humorally mediated autoimmune disease," Int Immunol (2006) 18(12):1759-1769.
Poe et al., "Human cytotoxic lymphocyte granzyme B. Its purification from granules and the characterization of substrate and inhibitor specificity," J Biol hem (1991) 266(1):98-103.
Powell et al., "Compendium of excipients for parenteral formulations," PDA J Pharm Sci Technol (1998) 52(5):238-311.
Ridgway et al., "Knobs-into-holes' engineering of antibody CH3 domains for heavy chain heterodimerization," Protein engineering (1996) 9(7):617-621.
Shields et al., "High Resolution Mapping of the Binding Site on Human IgG1 for FcγRI, FcγRII, FcγRIII, and FcRn and Design of IgG1 Variants with Improved Binding to the FcγR*," JBC (2001) 276(9):6591-6604.
Stavenhagen et al., "Enhancing the potency of therapeutic monoclonal antibodies via Fc optimization," Adv Enzyme Regul (2008) 48:152-164.
Stavenhagen et al., "Fc Optimization of Therapeutic Antibodies Enhances Their Ability to Kill Tumor Cells In vitro and Controls Tumor Expansion In vivo via Low-Affinity Activating Fcγ Receptors," Cancer Res (2007) 67(18):8882-8890.
Stec et al., Automated solid-phase synthesis, separation, and stereochemistry of phosphorothioate analogs of oligodeoxyribonucleotides, J Am Chem Soc (1984) 106(20):6077-6079.
Stein et al. "Physicochemical properties of phosphorothioate oligodeoxynucleotides," Nucleic Acids Res (1988) 16(8):3209-3221.

(56) References Cited

OTHER PUBLICATIONS

Thornberry et al., "A combinatorial approach defines specificities of members of the caspase family and granzyme B. Functional relationships established for key mediators of apoptosis," J Biol Chem (1997) 272(29):17907-17911.
Thornton et al., "Prediction of progress at last," Nature (1991) 354:105-106.
Uhlmann et al., "Antisense oligonucleotides: a new therapeutic principle," Chem Rev (1990) 90(4):543-584.
Von Kreudenstein et al., "Improving biophysical properties of a bispecific antibody scaffold to aid developability: quality by molecular design," MAbs (2013) 5(5):646-654.
Wang, "Lyophilization and development of solid protein pharmaceuticals," Int J Pharm (2000) 203(1-2):1-60.
Zalevsky et al., "Enhanced antibody half-life improves in vivo activity," Nat Biotechnol (2010) 28(2):157-159.
Zon et al., "Phosphorothioate oligonucleotides: chemistry, purification, analysis, scale-up and future directions," Anticancer Drug Res (1991) 6(6):539-568.
Taylor et al., "Nanocell targeting using engineered bispecific antibodies," Mabs (2015) 7(1):53-65.
Ohannesian et al., "Carcinoembryonic Antigen and Other Glycoconjugates Act as Ligands for Galectin-3 in Human Colon Carcinoma Cells[1]," Cancer Research (1995) 55:2191-2199.
Cheng et al., "Construction and expression of a reshaped VH domain against human CD28 molecules," Preparative Biochemistry and Biotechnology (2002) 32(3):239-251.
U.S. Appl. No. 17/283,902, filed Apr. 8, 2021, by Eckelman et al. Copy not provided). (Copy not submitted herewith pursuant to the waiver of 37 C.F. R. § 1.98(a)(2)(iii) issued by the Office dated Sep. 21, 2004).
Asano et al. "Domain order of a bispecific diabody dramatically enhances its antitumor activity beyond structural format conversion: the case of the hEx3 diabody." *Protein Engineering, Design & Selection* 26.5 (2013): 359-367.
Barthelemy et al. "Comprehensive analysis of the factors contributing to the stability and solubility of autonomous human VH domains." *Journal of Biological Chemistry* 283.6 (2008): 3639-3654.
Beiboer et al. "Guided selection of a pan carcinoma specific antibody reveals similar binding characteristics yet structural divergence between the original murine antibody and its human equivalent." *Journal of Molecular Biology* 296.3 (2000): 833-849.
Choi et al. "Predicting antibody complementarity determining region structures without classification." *Molecular BioSystems* 7.12 (2011): 3327-3334.
De Genst et al. "Antibody repertoire development in camelids." *Developmental & Comparative Immunology* 30.1-2 (2006): 187-198.
Driessens et al. "Costimulatory and coinhibitory receptors in anti-tumor immunity." *Immunological reviews* (2009) 229.1: 126-144.
Griffiths et al. "Human anti-self antibodies with high specificity from phage display libraries." *The EMBO journal* 12.2 (1993): 725-734.
Klimka et al., "Human Anti-CD30 Recombinant Antibodies by Guided Phage Antibody Selection Using Cell Panning," Br. J. Cancer (2000) 83(2):252-260.
Kuo et al., "Engineering a CD123xCD3 bispecific scFv immunofusion for the treatment of leukemia and elimination of leukemia stem cells," Protein Eng Des Sel. (2012) 25(10): 561-9.
Malia et al. "Epitope mapping and structural basis for the recognition of phosphorylated tau by the anti-tau antibody AT8." *Proteins: Structure, Function, and Bioinformatics* 84.4 (2016): 427-434.
Weidle et al. "The intriguing options of muitispecific antibody formats for treatment of cancer." *Cancer genomics & proteomics* 10.1 (2013): 1-18.
Schmiedel et al. "Expression of a bispecific dsFv-dsFv' antibody fragment in *Escherichia coli*." Protein Engineering (2000) 13:10; 725-734.
Maeda et al., "Engineering of functional chimeric protein G-Vargula luciferase," Anal Biochem. (1997) 249(2):147-52.

\* cited by examiner cx2973 cMet x EFGR
Bivalent cMet
Bivalent EGFR cx2977 cMet x EFGR
Monovalent cMet
Monovalent EGFR cx2979 cMet x EFGR
Monovalent cMet
Bivalent EGFR

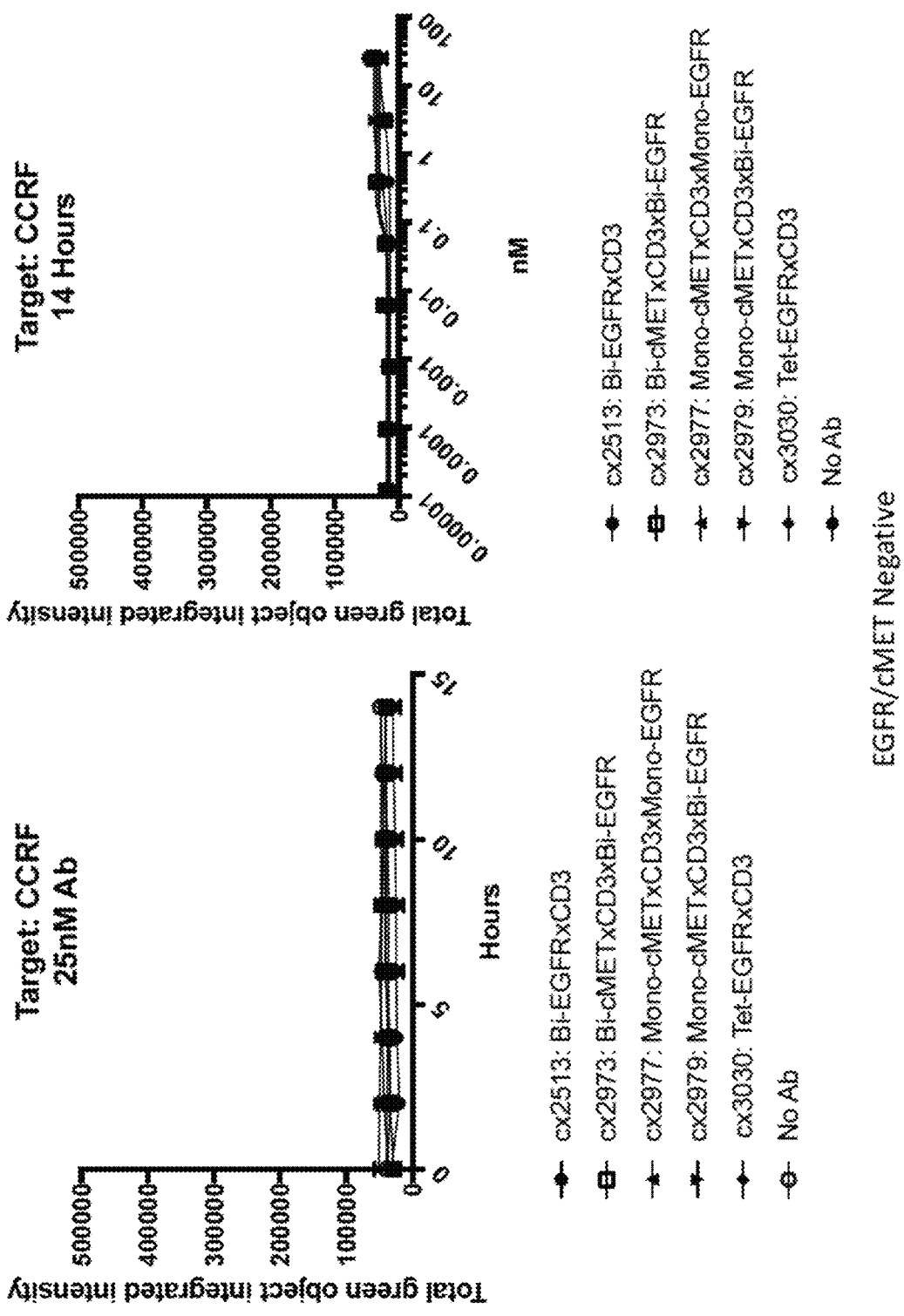

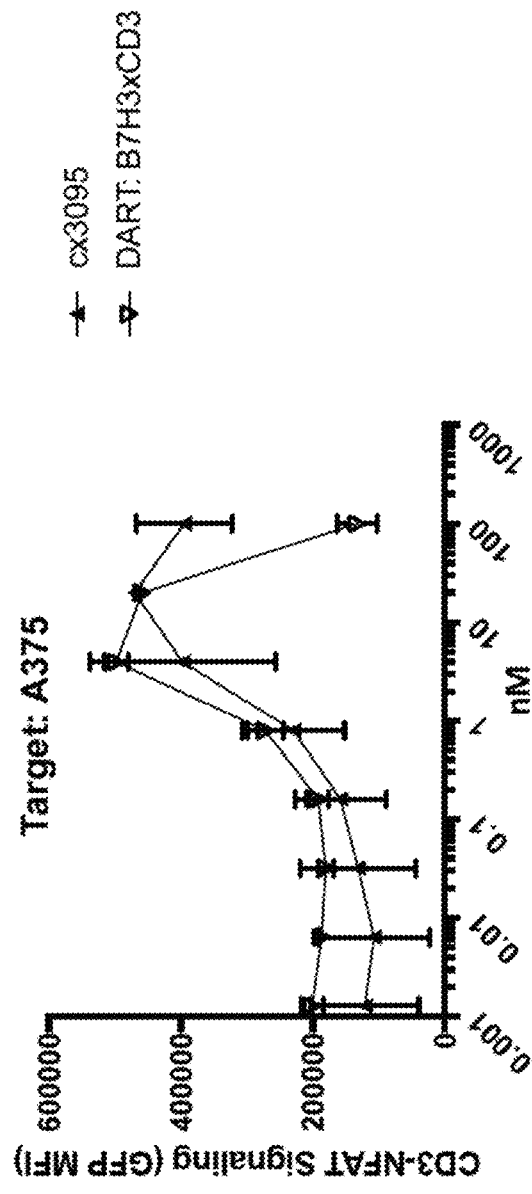
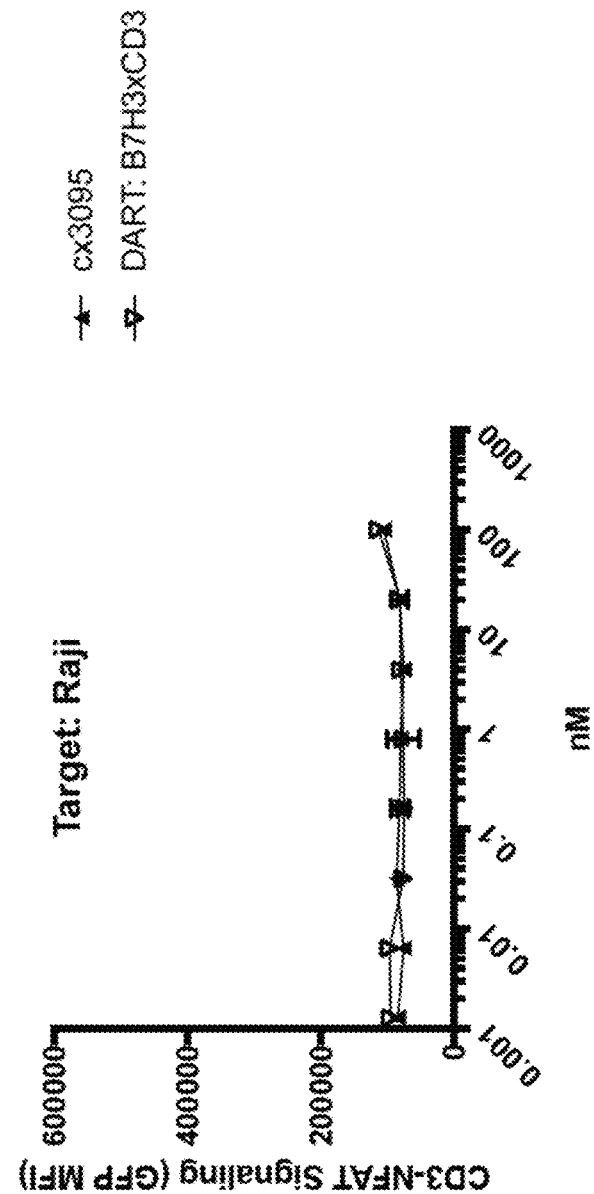
FIG. 21A
FIG. 21B

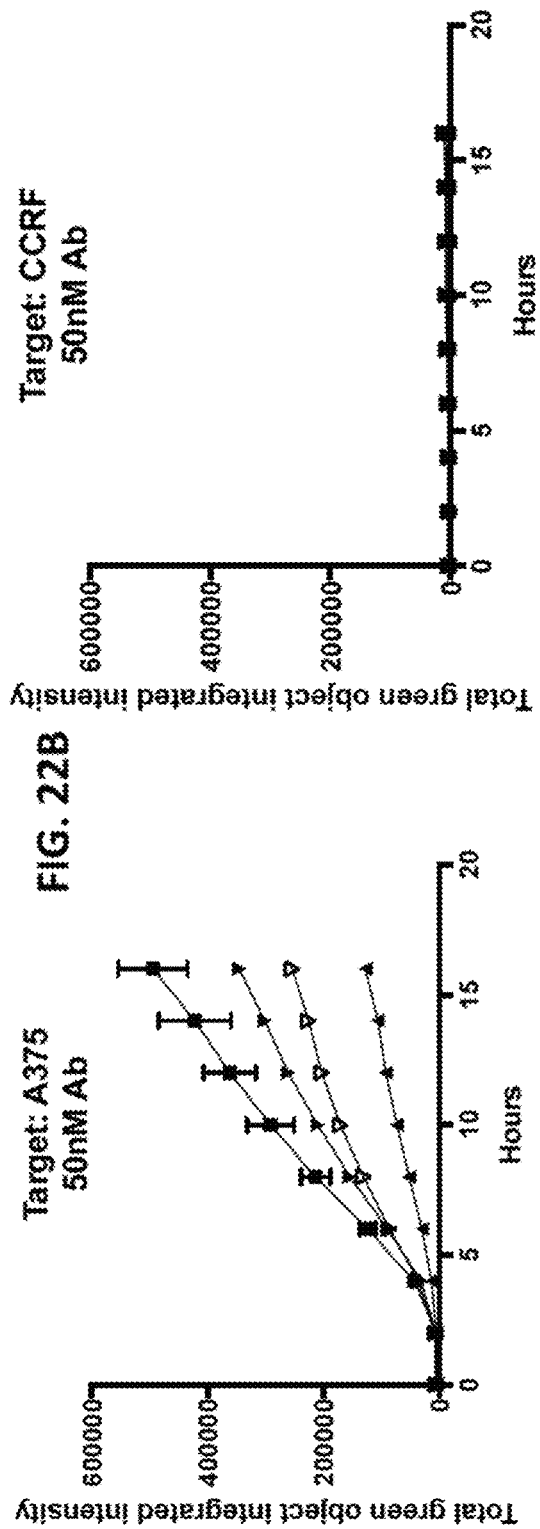
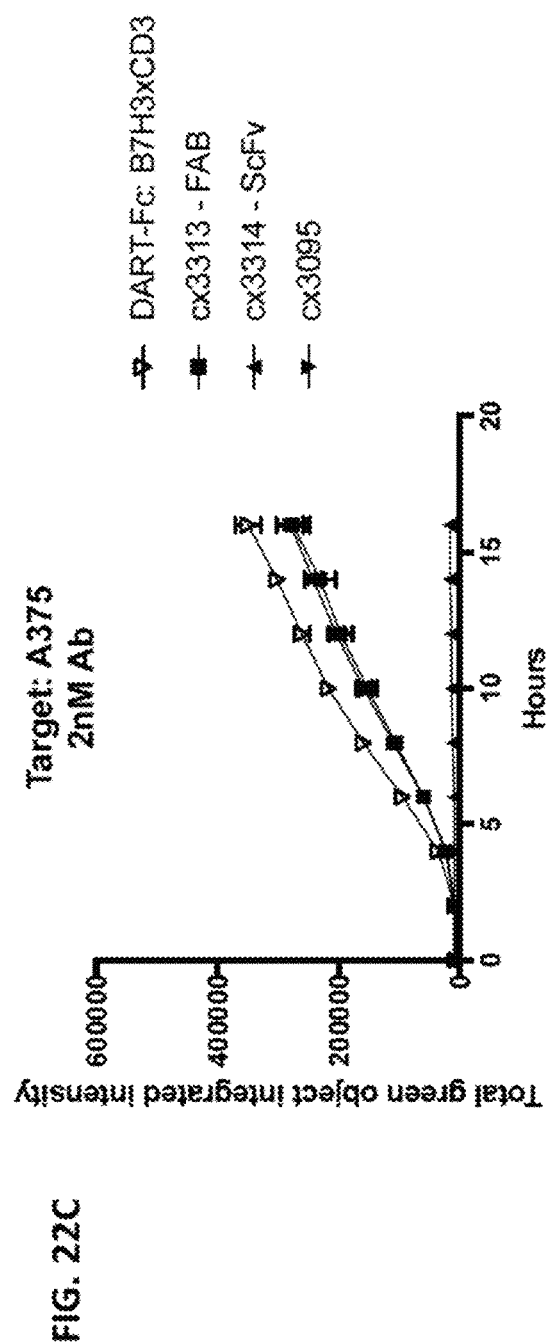
FIG. 22A
FIG. 22B
FIG. 22C

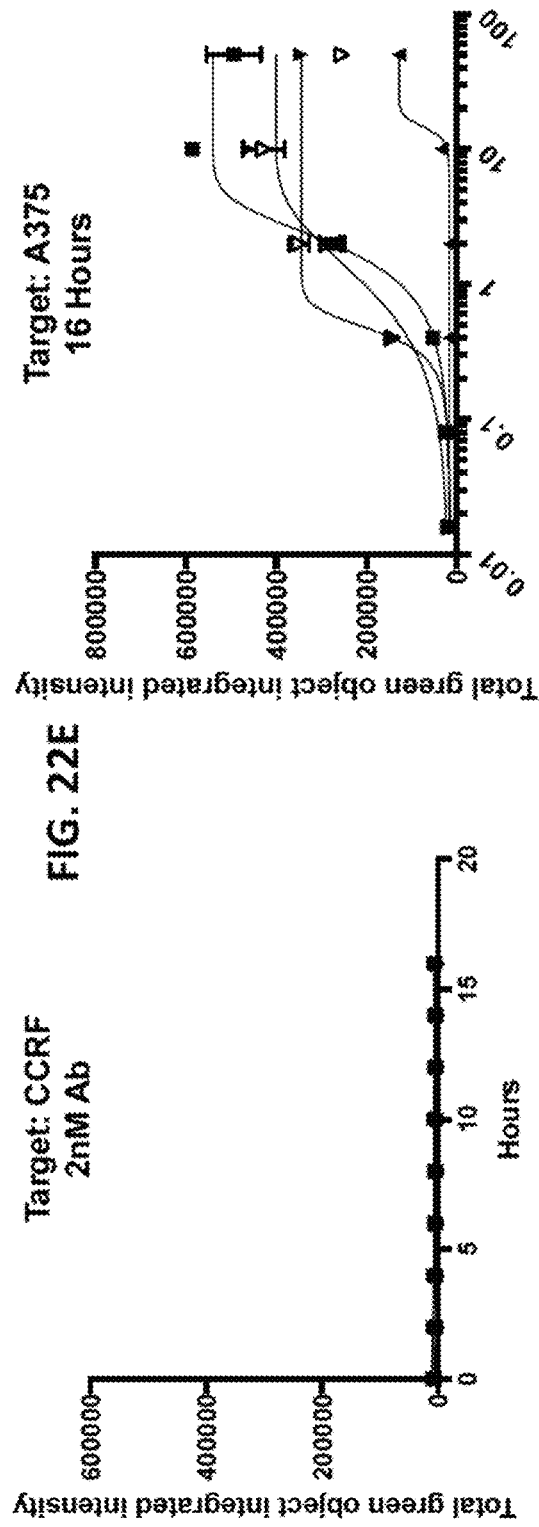
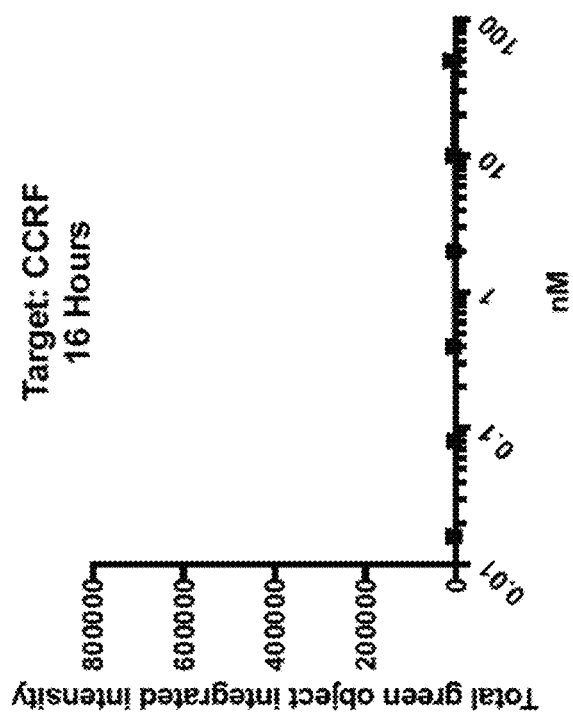
FIG. 22D
FIG. 22E
FIG. 22F

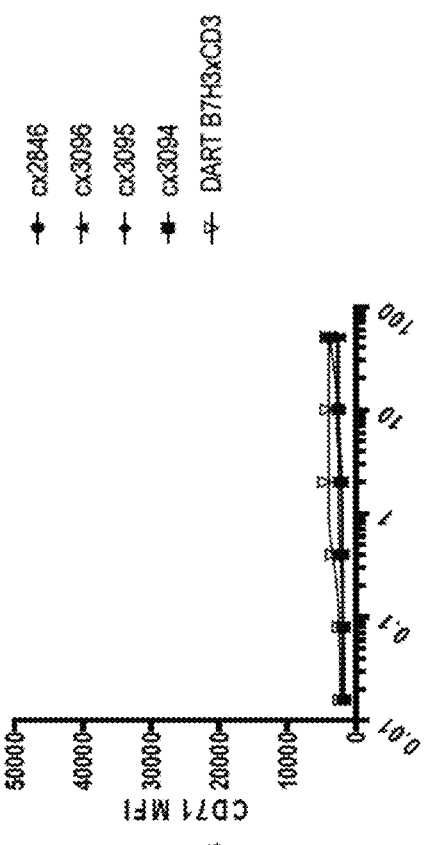
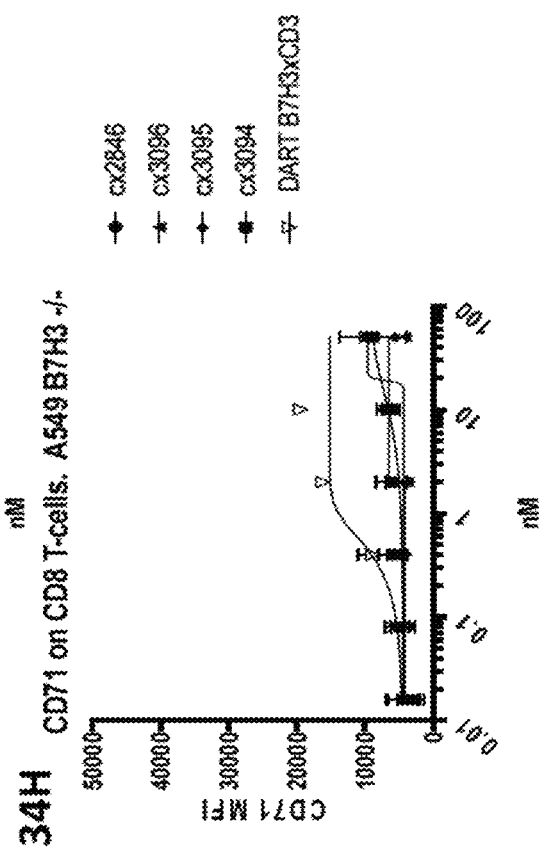
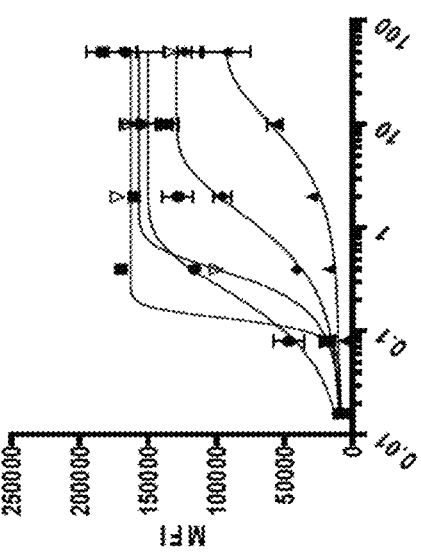
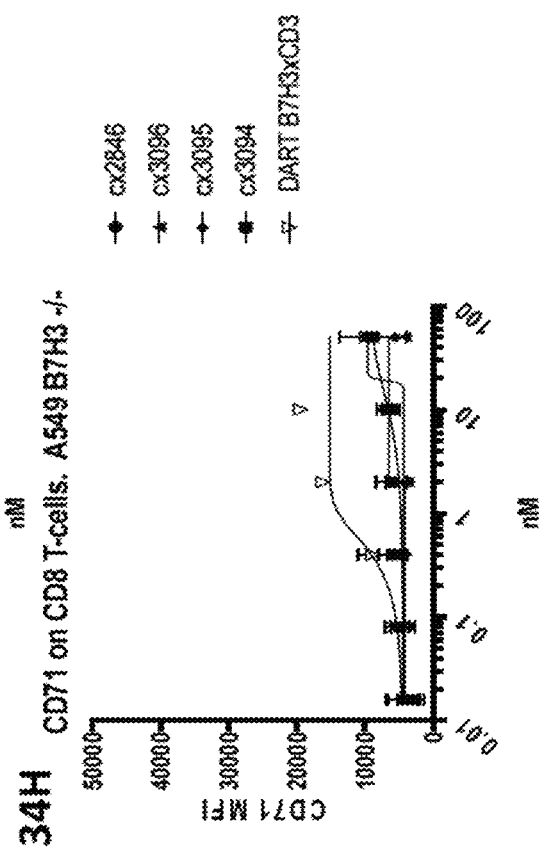

MULTISPECIFIC POLYPEPTIDE CONSTRUCTS HAVING CONSTRAINED CD3 BINDING AND METHODS OF USING THE SAME

This application claims priority from U.S. provisional application No. 62/484,217 filed Apr. 11, 2017, entitled "MULTISPECIFIC POLYPEPTIDES HAVING DUAL EFFECTOR FUNCTION AND METHODS OF USING THE SAME," the contents of which are incorporated by reference in their entirety.

INCORPORATION BY REFERENCE OF SEQUENCE LISTING

The present application is being filed along with a Sequence Listing in electronic format. The Sequence Listing is provided as a file entitled 744952000100SubSeqList.TXT, created Jun. 20, 2018 which is 174,262 bytes in size. The information in the electronic format of the Sequence Listing is incorporated by reference in its entirety.

FIELD OF THE DISCLOSURE

The invention relates generally to multispecific polypeptides having constrained CD3 binding. In some embodiments, the multispecific polypeptides contain cleavable linkers that, when cleaved, results in dual effector functions. Also provided are methods of making and using these multispecific polypeptides in a variety of therapeutic, diagnostic and prophylactic indications.

BACKGROUND OF THE DISCLOSURE

Therapeutic antibodies that cause target cell depletion generally rely on effector functions mediated via interaction with Fc-gamma-receptors (FcγRs) and complement proteins. Effector cells expressing FcγRs are predominately those of the innate immune system. T-cells are not direct effector cells involved in antibody mediated target cell depletion.

CD3 (Cluster of Differentiation 3) T-cell co-receptor is a multimeric protein composed of four distinct polypeptide chains, referred to as the ε, γ, δ, and ζ chains. The CD3 complex serves as the signaling module of the T cell receptor that associates non-covalently with the antigen-binding a/b chains of T cell receptor (TCR).

Because direct engagement of CD3 results in T-cell activation, it is a desirable target for a variety of therapeutic and/or diagnostic indications. Accordingly, there exists a need for antibodies and therapeutics that target the CD3/TCR pathway.

SUMMARY OF THE DISCLOSURE

The present disclosure provides multispecific polypeptide constructs that exhibit constrained CD3 binding. In some embodiments, the multispecific polypeptide construct is composed of a first component comprising an immunoglobulin Fc region and a second component comprising a CD3-binding region, wherein the first and second components are coupled by a linker or operably linked, wherein the Fc region is positioned N-terminal to the CD3-binding region; and one or both of the first and second components comprises an antigen binding domain that binds a tumor associated antigen (TAA). In some embodiments, the multispecific polypeptide construct, in an inactive state, is composed of a first component and a second component, wherein the first and second components are operably linked, wherein each of the first and second components comprises an antigen binding domain that binds a tumor associated antigen (TAA), wherein the first component comprises an Fc region, wherein the second component comprises a CD3-binding region, and wherein the first and second components are coupled by a cleavable linker. In some embodiments, the CD3-binding region binds CD3 (CD3ε).

In some embodiments, the antigen binding domain is positioned amino-terminally relative to the Fc region and/or carboxy-terminally relative to the CD3 binding region of the multispecific polypeptide construct. In some embodiments, the first component comprises a first antigen binding domain and the second component comprises a second antigen binding domain, wherein each of the antigen binding domains bind a tumor associated antigen (TAA). In some cases, the first antigen binding domain is positioned at the amino terminus of the multispecific construct and the second antigen binding domain is positioned at the carboxy terminus of the multispecific construct. In some embodiments, the first antigen binding domain is positioned amino-terminally relative to the Fc region and/or carboxy-terminally relative to the CD3 binding region of the multispecific polypeptide construct.

Provided herein is a multispecific polypeptide construct, wherein the multispecific construct comprises in order, from N-terminus to C-terminus: a first antigen binding domain that binds to a tumor-associated antigen (TAA); an immunoglobulin Fc region; a linker; a CD3 binding region that binds CD3 (CD3ε); and a second antigen binding domain that binds a tumor-associated antigen (TAA). Also provided is a multispecific polypeptide construct, wherein the multispecific construct comprises in order, from N-terminus to C-terminus: an immunoglobulin Fc region; a linker; a CD3 binding region that binds CD3 (CD3ε); and an antigen binding domain that binds a tumor-associated antigen (TAA). Provided is a multispecific polypeptide construct, wherein the multispecific construct comprises in order, from N-terminus to C-terminus: an antigen binding domain that binds to a tumor-associated antigen (TAA); an immunoglobulin Fc region; a linker; and a CD3 binding region that binds CD3 (CD3ε).

Among embodiments of the present disclosure are multispecific polypeptide constructs that bind at least CD3 and a second antigen, such as a tumor associated antigen (TAA). The multispecific polypeptide constructs provided herein include at least a first component that includes one or more copies of an antigen-binding domain that bind an antigen linked to an immunoglobulin Fc region, a second component that includes one or more copies of at least a binding domain that binds CD3 (referred to herein as an anti-CD3 binding domain or CD3 binding region, which are used interchangeably herein), and a linker, such as a cleavable linker, that joins the first component and the second component.

The positioning of the Fc region N-terminal to the CD3 binding region reduces or prevents the ability of the CD3 binding region to bind CD3. In some embodiments, in the uncleaved/inactive state, the first component (component #1) and the second component (component #2) of the multispecific polypeptide constructs are linked and binding to CD3 is disallowed, unless the antigen binding domain(s) are bound to their cognate antigen. This is advantageous as it prevents systemic binding of the CD3 binding region to T-cells and focuses it to site of antigen expression. This is beneficial as it eliminates a major binding sink of peripheral T-cells, allowing more favorable distribution and localization at site of antigen expression, e.g., tumor cells or the tumor microenvironment. In some cases, binding and/or engagement of CD3 is amplified or increased by inclusion of a cleavable linker joining component #1 and component #2, in which upon cleavage of the cleavable linker, such as by proteolysis, increased binding by the CD3 binding region is enabled.

In the inactive, i.e., uncleaved state, component #1 and component #2 of the multispecific polypeptide constructs are operably linked and do not bind or otherwise engage CD3 unless the antigen binding domain(s) is bound to their cognate antigen. In some embodiments, the uncleaved multispecific polypeptide constructs are capable of interacting with FcγRs and mediating innate immune effector functions, for example antibody dependent cellular cytotoxicity (ADCC) and antibody dependent cellular phagocytosis (ADCP). In some embodiments, the uncleaved multispecific polypeptide constructs are capable of interacting complement proteins, namely C1q, and mediating complement dependent cytotoxicity.

The multispecific polypeptide constructs of the disclosure generally have more than one antigen-binding domain(s). In provided aspects in which the multispecific polypeptide constructs contain a cleavable linker, once the linker joining the first and second component is cleaved, such as by protease, each component maintains at least one antigen binding domain. The first component (i.e., component #1) contains at least an Fc region and antigen binding domain. The second component (i.e., component #2) contains at least an anti-CD3 binding domain and an antigen binding domain.

Cleavage, such as by proteolysis, within the cleavable linker physically separates component #1 and component #2, each of which has therapeutic utility albeit rely on different effector cells. Component #1 contains at least one antigen binding domain and an Fc region. In some embodiments, component #1 is capable of eliciting innate immune effector functions, for example ADCC, cytokine release, degranulation and/or phagocytosis. Component #2 contains at least domain CD3 binding region and an antigen binding domain, the former of which is capable of binding CD3 (when separated from component #1). Component #2 is capable of forming an immune synapse between an antigen expression cell and a T-cell. This co-engagement mediates antigen dependent T-cell activation, cytotoxicity, cytokine release, degranulation and proliferation. In the cleaved/activated state component #2 is not operably linked to the Fc-region of component #1 and thereby component #2 does not interact with FcRn and has enhanced serum clearance if localized to a site without an antigen expressing cell. This is advantageous as it limits the systemic exposure of the activated anti-CD3 binding domain and focuses directly into antigen expressing tissues, e.g., tumor cells or the tumor microenvironment.

In some embodiments, the multispecific polypeptide is in an inactive state, i.e., uncleaved state, and binding of the CD3-binding region to CD3 is inhibited or substantially reduced when the multispecific polypeptide construct is in an uncleaved state compared to a cleaved state. In some embodiments, the multispecific polypeptide is in an activated state, and the first and second components are not operably linked. In some embodiments, the multispecific polypeptide is in an activated state, i.e., cleaved state, and the second component binds the epsilon chain of CD3 (CD3ε) and a tumor associated antigen (TAA).

In some aspects, the antigen binding domain, or independently each of the antigen binding domains, is selected from an antibody or antigen binding fragment, a natural cognate binding partner, an Anticalin (engineered lipocalin), a Darpin, a Fynomer, a Centyrin (engineered fibroneticin III domain), a cystine-knot domain, an Affilin, an Affibody, or an engineered CH3 domain. In some embodiments, the natural cognate binding partner comprises an extracellular domain or binding fragment thereof of the native cognate binding partner of the TAA, or a variant thereof that exhibits binding activity to the TAA.

In some aspects, the antigen binding domain, or independently each of the antigen binding domains, comprises an extracellular domain or binding fragment thereof of the native cognate binding partner of the TAA, or a variant thereof that exhibits binding activity to the TAA.

In some embodiments, the first component includes one or more copies of an antigen-binding domain. In some embodiments, the first component contains at least two antigen binding domains, such as two antigen binding domains. In some embodiments, the at least two antigen binding domains of the first component bind to the same TAA. In some cases, the at least two antigen binding domains of the first component binds to a different epitope of the same TAA. In some instances, the at least two antigen binding domains of the first component binds to a different epitope of the same TAA. In some embodiments, the at least two antigen binding domain of the first component bind to a different TAA.

In some embodiments, the antigen-binding domain of the first component, which, in some cases is a first antigen binding domain, includes one or more copies of an antibody or an antigen-binding fragment thereof. In some embodiments, the antigen binding domain of the first component, such as the first antigen-binding domain includes one or more copies of an antibody or an antigen-binding fragment thereof selected from the group consisting of a Fab fragment, a F(ab')$_2$ fragment, an Fv fragment, a scFv, a scAb, a dAb, a single domain heavy chain antibody, and a single domain light chain antibody. In some embodiments, the first antigen-binding domain includes one or more copies of one or more single domain antibody (sdAb) fragments, for example $V_HH$, $V_{NAR}$, engineered $V_H$ or $V_K$ domains. $V_HHs$ can be generated from camelid heavy chain only antibodies. $V_{NAR}s$ can be generated from cartilaginous fish heavy chain only antibodies. Various methods have been implemented to generate monomeric sdAbs from conventionally heterodimeric $V_H$ and $V_K$ domains, including interface engineering and selection of specific germline families.

In some embodiments, the antigen binding domain of the first component, such as the first antigen binding domain, binds an antigen, such as a tumor associated antigen (TAA). In some embodiments, the TAA is selected from the group consisting of 1-92-LFA-3, 5T4, Alpha-4 integrin, Alpha-V integrin, alpha4beta1 integrin, alpha4beta7 integrin, AGR2, Anti-Lewis-Y, Apelin J receptor, APRIL, B7-H3, B7-H4, BAFF, BTLA, C5 complement, C-242, CA9, CA19-9, (Lewis a), Carbonic anhydrase 9, CD2, CD3, CD6, CD9, CD11a, CD19, CD20, CD22, CD24, CD25, CD27, CD28, CD30, CD33, CD38, CD40, CD40L, CD41, CD44, CD44v6, CD47, CD51, CD52, CD56, CD64, CD70, CD71, CD74, CD80, CD81, CD86, CD95, CD117, CD123, CD125, CD132, (IL-2RG), CD133, CD137, CD138, CD166, CD172A, CD248, CDH6, CEACAM5 (CEA), CEACAM6 (NCA-90), CLAUDIN-3, CLAUDIN-4, cMet, Collagen, Cripto, CSFR, CSFR-1, CTLA-4, CTGF, CXCL10, CXCL13, CXCR1, CXCR2, CXCR4, CYR61, DL44, DLK1, DLL3, DLL4, DPP-4, DSG1, EDA, EDB, EGFR, EGFRviii, Endothelin B receptor (ETBR), ENPP3, EpCAM, EPHA2, EPHB2, ERBB3, F protein of RSV, FAP, FGF-2, FGF8, FGFR1, FGFR2, FGFR3, FGFR4, FLT-3, Folate receptor alpha (FRa), GAL3ST1, G-CSF, G-CSFR, GD2, GITR, GLUT1, GLUT4, GM-CSF, GM-CSFR, GP IIb/IIIa receptors, Gp130, GPIIB/IIIA, GPNMB, GRP78, HER2/neu, HER3, HER4, HGF, hGH, HVEM, Hyaluronidase, ICOS, IFNalpha, IFNbeta, IFNgamma, IgE, IgE Receptor (FceRI), IGF, IGF1R, IL1B, IL1R, IL2, IL11, IL12, IL12p40, IL-12R, IL-12Rbeta1, IL13, IL13R, IL15, IL17, IL18, IL21, IL23, IL23R, IL27/IL27R (wsx1), IL29, IL-31R, IL31/IL31R, IL2R, IL4, IL4R, IL6, IL6R, Insulin Receptor, Jagged Ligands, Jagged 1, Jagged 2, KISS1-R, LAG-3, LIF-R, Lewis X, LIGHT, LRP4, LRRC26, Ly6G6D, LyPD1, MCSP, Mesothelin, MRP4, MUC1, Mucin-16 (MUC16, CA-125), Na/K ATPase, NGF, Nicastrin, Notch Receptors, Notch 1, Notch 2, Notch 3, Notch 4, NOV, OSM-R, OX-40, PAR2, PDGF-AA, PDGF-BB, PDGFRalpha, PDGFRbeta, PD-1, PD-L1, PD-L2, Phosphatidylserine, P1GF, PSCA, PSMA, PSGR, RAAG12, RAGE, SLC44A4, Sphingosine 1 Phosphate, STEAP1, STEAP2, TAG-72, TAPA1, TEM-8, TGFbeta, TIGIT, TIM-3, TLR2, TLR4, TLR6, TLR7, TLR8, TLR9, TMEM31, TNFalpha, TNFR, TNFRS12A, TRAIL-R1, TRAIL-R2, Transferrin, Transferrin receptor, TRK-A, TRK-B, uPAR, VAP1, VCAM-1, VEGF, VEGF-A, VEGF-B, VEGF-C, VEGF-D, VEGFR1, VEGFR2, VEGFR3, VISTA, WISP-1, WISP-2, and WISP-3.

In some embodiments, the Fc region is a homodimeric Fc region. In some embodiments, the Fc region is a heterodimeric Fc region.

In some embodiments, the immunoglobulin Fc region of the first component is an IgG isotype selected from the group consisting of IgG1 isotype, IgG2 isotype, IgG3 isotype, and IgG4 subclass. In some examples, the Fc region is an Fc region of a human IgG1, a human IgG2, a human IgG3, or a human IgG4, or is an immunologically active fragment thereof. In some embodiments, the Fc region comprises a polypeptide comprises the amino acid sequence set forth in SEQ ID NO: 1 or a sequence of amino acids that has at least 90%, 91%, 92%, 93%, 94%, 95%, 96%, 97%, 98%, 99% sequence identity to SEQ ID NO:1. In some cases, the Fc region comprises a polypeptide comprises the amino acid sequence set forth in SEQ ID NO: 2 or a sequence of amino acids that has at least 90%, 91%, 92%, 93%, 94%, 95%, 96%, 97%, 98%, 99% sequence identity to SEQ ID NO:2. In some of any such embodiments, the Fc region comprises a polypeptide comprises the amino acid sequence set forth in SEQ ID NO: 4 or a sequence of amino acids that has at least 90%, 91%, 92%, 93%, 94%, 95%, 96%, 97%, 98%, 99% sequence identity to SEQ ID NO:4. In some examples, the Fc region comprises a polypeptide comprises the amino acid sequence set forth in SEQ ID NO: 5 or a sequence of amino acids that has at least 90%, 91%, 92%, 93%, 94%, 95%, 96%, 97%, 98%, 99% sequence identity to SEQ ID NO:5.

In some embodiments, the immunoglobulin Fc region is a polypeptide comprising an amino acid sequence selected from the group consisting of SEQ ID NOs: 1-6. In some embodiments, the immunoglobulin Fc region is a polypeptide comprising an amino acid sequence that is at least 50%, 60%, 65%, 70%, 75%, 80%, 85%, 90%, 91%, 92%, 93%, 94%, 95%, 96%, 97%, 98%, or 99% identical to an amino acid sequence selected from the group consisting of SEQ ID NOs: 1-6.

In some embodiments, the immunoglobulin Fc region is a polypeptide comprising an amino acid sequence that is derived from an amino acid sequence selected from the group consisting of SEQ ID NOs: 1-6. In some embodiments, the immunoglobulin Fc region is a polypeptide comprising an amino acid sequence that is derived from an amino acid sequence selected from the group consisting of SEQ ID NOs: 1-6 comprising one or modifications. In some embodiments, the immunoglobulin Fc region is a polypeptide comprising an amino acid sequence that is derived from an amino acid sequence selected from the group consisting of SEQ ID NOs: 1-6 comprising one or modifications to prevent glycosylation, to alter Fc receptor interactions, to reduce Fc receptor binding, to enhance the interaction with CD32A, to reduce the complement protein C1q binding, to extend the half-life, to enhance FcRn binding, to alter antibody-dependent cellular cytotoxicity (ADCC) and/or complement-dependent cytotoxicity (CDC), to induce heterodimerization, to prevent dimerization, to stabilize the homodimerization at the CH3:CH3 interface, and combinations thereof.

In some embodiments, the Fc is a heterodimeric Fc. In some cases, one or both Fc polypeptides of the heterodimeric Fc region comprises at least one modification to induce heterodimerization compared to a polypeptide of a homodimeric Fc region, optionally compared to the Fc polypeptide set forth in SEQ ID NO:1 or an immunologically active fragment thereof. In some embodiments, each of the Fc polypeptides of the heterodimeric Fc independently comprise at least one amino acid modification. In some cases, each of the Fc polypeptides of the heterodimeric Fc comprise a knob-into-hole modification or comprise a charge mutation to increase electrostatic complementarity of the polypeptides. In some examples, the amino acid modification is a knob-into-hole modification.

In some embodiments, the first Fc polypeptide of the heterodimeric Fc comprises the modification selected from among Thr366Ser, Leu368Ala, Tyr407Val, and combinations thereof and the second Fc polypeptide of the heterodimeric Fc comprises the modification T366W. In some cases, the first and second Fc polypeptides further comprise a modification of a non-cysteine residue to a cysteine residue, wherein the modification of the first polypeptide is at one of a position Ser354 and Y349 and the modification of the second Fc polypeptide is at the other of the position Ser354 and Y349.

In some examples, the amino acid modification is a charge mutation to increase electrostatic complementarity of the polypeptides. In some embodiments, the first and/or second Fc polypeptides comprise a modification in complementary positions, wherein the modification is replacement with an amino acid having an opposite charge to the complementary amino acid of the other polypeptide. In some embodiments, the first or second polypeptide comprise a modification in complementary positions, wherein the modification is replacement with an amino acid having an opposite charge to the complementary amino acid of the other polypeptide. In some embodiments, at least the first or second Fc polypeptides each comprise a modification in a complementary position, wherein the modification is replacement with an amino acid having an opposite charge to the complementary amino acid of the other polypeptide. In some embodiments, the first and second Fc polypeptides each comprise a modification in complementary positions, wherein the modification is replacement with an amino acid having an opposite charge to the complementary amino acid of the other polypeptide.

In some embodiments, one of the first or second Fc polypeptide of the heterodimeric Fc further comprises a modification at residue Ile253. In some instances, the modification is Ile253Arg. In some embodiments, one of the first or second Fc polypeptide of the heterodimeric Fc further comprises a modification at residue His435. In some instances, the modification is His435Arg. In some embodiments, the Fc region comprises a polypeptide that lacks Lys447.

In some embodiments, modifications within the Fc region reduce binding to Fc-receptor-gamma receptors while having minimal impact on binding to the neonatal Fc receptor (FcRn). In some embodiments, the mutated or modified Fc polypeptide includes the following mutations: Met252Tyr and Met428Leu or Met252Tyr and Met428Val (M252Y, M428L, or M252Y, M428V) using the Kabat numbering system.

In some embodiments, the Fc region comprises a polypeptide comprising at least one modification to enhance FcRn binding. In some examples, the modification is at a position selected from the group consisting of Met252, Ser254, Thr256, Met428, Asn434, and combinations thereof. In some cases, the modification is at a position selected from the group consisting of Met252Y, Ser254T, Thr256E, Met428L, Met428V, Asn434S, and combinations thereof. In some particular embodiments, the modification is at position Met252 and at position Met428. In some cases, the modification is Met252Y and Met428L. In some cases, the modification is Met252Y and Met428V.

In some embodiments, the first polypeptide of the heterodimeric Fc comprises the sequence of amino acids set forth in any of SEQ ID NOS:82, 86, 94 or 96, and the second polypeptide of the heterodimeric Fc comprises the sequence of amino acids set forth in any of SEQ ID NOS:83, 87, 90, 92, 98 or 100.

In some embodiments, the Fc region comprises a polypeptide comprising at least one amino acid modification that reduces effector function and/or reduces binding to an effector molecule selected from an Fc gamma receptor or C1q. In some examples, the one or more amino acid modification is deletion of one or more of Glu233, Leu234 or Leu235. In some aspects, the first polypeptide of the heterodimeric Fc comprises the sequence of amino acids set forth in any of SEQ ID NOS: 84, 88, 95 or 97 and the second polypeptide of the heterodimeric Fc comprises the sequence of amino acids set forth in any of SEQ ID NOS: 85, 89, 91, 93, 99 or 101.

In some embodiments, the Fc region comprises a polypeptide comprising at least one modification to enhance FcγR binding. In some cases, the modification is modification at Ser239 or Ile332. In some embodiments, the glycosylation of the Fc region is modified to enhance FcγR binding as compared to an unmodified Fc region. In some examples, the Fc region lacks or has reduced fucose content.

In some embodiments, the CD3 binding region is an anti-CD3 antibody or antigen-binding fragment. In some embodiments, the anti-CD3 antibody or antigen binding fragment comprises a variable heavy chain region (VH) and a variable light chain region (VL). In some of any such embodiments, the CD3 binding region is monovalent.

In some embodiments, the anti-CD3 antibody or antigen binding fragment is not a single chain antibody, optionally is not a single chain variable fragment (scFv). In some embodiments, the Fc is a heterodimeric Fc and the VH and VL that comprise the anti-CD3 antibody or antigen binding fragment are linked to opposite polypeptides of the heterodimeric Fc. In some embodiments, the CD3 binding region is not able to, or is not substantially able to, bind or engage CD3 unless at least one of the antigen binding domain is bound to its TAA. In some aspects, the CD3 binding region is not able to, or is not substantially able to, bind or engage CD3 unless at least two of the antigen binding domain is bound to its TAA.

In some embodiments, the multispecific polypeptide construct contains a linker that is a polypeptide linker. In some embodiments, the linker is a polypeptide of up to 25 amino acids in length. In some cases, the linker is a polypeptide of from or from about 2 to 24 amino acids, 2 to 20 amino acids, 2 to 18 amino acids, 2 to 14 amino acids, 2 to 12 amino acids, 2 to 10 amino acids, 2 to 8 amino acids, 2 to 6 amino acids, 6 to 24 amino acids, 6 to 20 amino acids, 6 to 18 amino acids, 6 to 14 amino acids, 6 to 12 amino acids, 6 to 10 amino acids, 6 to 8 amino acids, 8 to 24 amino acids, 8 to 20 amino acids, 8 to 18 amino acids, 8 to 14 amino acids, 8 to 12 amino acids, 8 to 10 amino acids, 10 to 24 amino acids, 10 to 20 amino acids, 10 to 18 amino acids, 10 to 14 amino acids, 10 to 12 amino acids, 12 to 24 amino acids, 12 to 20 amino acids, 12 to 18 amino acids, 12 to 14 amino acids, 14 to 24 amino acids, 14 to 20 amino acids, 14 to 18 amino acids, 18 to 24 amino acids, 18 to 20 amino acids or 20 to 24 amino acids. In some embodiments, the linker is a polypeptide that is 3, 4, 5, 6, 7, 8, 9, 10, 11, 12, 13, 14, 15, 16, 17, 18, 19 or 20 amino acids in length. In some cases, the linker is a cleavable linker.

In some embodiments, the first antigen binding domain and the immunoglobulin Fc polypeptide are operably linked via amino acid linkers. In some embodiments, these intra-component linkers are composed predominately of the amino acids Glycine and Serine, denoted as GS-linkers herein. The GS-linkers of the fusion proteins of the present disclosure can be of various lengths, for example 3, 4, 5, 6, 7, 8, 9, 10, 11, 12, 13, 14, 15, 16, 17, 18, 19, 20 amino acids in length.

In some embodiments, the GS-linker comprises an amino acid sequence selected from the group consisting of GGSGGS, i.e., (GGS)$_2$ (SEQ ID NO: 10); GGSGGSGGS, i.e., (GGS)$_3$ (SEQ ID NO: 11); GGSGGSGGSGGS, i.e., (GGS)$_4$ (SEQ ID NO: 12); and GGSGGSGGSGGSGGS, i.e., (GGS)$_5$ (SEQ ID NO: 13).

In some embodiments, the second component also includes one or more copies of an anti-CD3 binding domain. In some embodiments, the anti-CD3 binding domain includes one or more copies of an antibody or an antigen-binding fragment thereof. In some embodiments, the anti-CD3 binding domain includes one or more copies of an antibody or an antigen-binding fragment thereof selected from the group consisting of a Fab fragment, a F(ab')$_2$ fragment, an Fv fragment, a scFv, a scAb, a dAb, a single domain heavy chain antibody, and a single domain light chain antibody. In some embodiments, the anti-CD3 binding domain includes an Fv antibody fragment that binds CD3ε (referred to herein as an anti-CD3ε Fv fragment). In some embodiments, the anti-CD3ε Fv antibody fragment includes an amino acid sequence selected from the group of SEQ ID NO: 32-81. In some embodiments, the anti-CD3ε Fv antibody fragment includes an amino acid sequence that is at least 90%, 91%, 92%, 93%, 94%, 95%, 96%, 97%, 98%, 99% or more identical to an amino acid sequence selected from the group consisting of SEQ ID NO: 32-81. In some embodiments, the anti-CD3ε Fv antibody fragment includes a combination of an amino acid sequence selected from the group of SEQ ID NO: 32-62 and an amino acid sequence selected from the group consisting of SEQ ID NO: 63-81. In some embodiments, the anti-CD3ε Fv antibody fragment includes a combination of an amino acid sequence that is at least 90%, 91%, 92%, 93%, 94%, 95%, 96%, 97%, 98%, 99% or more identical to an amino acid sequence selected from the group consisting of SEQ ID NO: 32-62 and an amino acid sequence that is at least 90%, 91%, 92%, 93%, 94%, 95%, 96%, 97%, 98%, 99% or more identical to an amino acid sequence selected from the group consisting of SEQ ID NO: 63-81 an amino acid sequence.

In some embodiments, the anti-CD3ε Fv antibody fragment is a disulfide stabilized anti-CD3 binding Fv fragment (dsFv).

In some embodiments, the second component also includes one or more copies of an antigen-binding domain. In certain embodiments, the second component contain at least two antigen binding domains, such as two antigen binding domains. In some embodiments, the at least two antigen binding domains of the second component bind to the same TAA. In some cases, the at least two antigen binding domains of the second component binds to a different epitope of the same TAA. In some instances, the at least two antigen binding domains of the second component binds to a different epitope of the same TAA. In some embodiments, the at least two antigen binding domain of the second component bind to a different TAA.

In some embodiments, the first component contains a first antigen binding domain and the antigen binding domain of the second component is a second antigen binding domain. In some embodiments, the second antigen-binding domain of the second component binds the same antigen as the first antigen-binding domain of the first component. In some embodiments, the second antigen-binding domain of the second component binds a different epitope on the same antigen as the first antigen-binding domain of the first component. In some embodiments, the second antigen-binding domain of the second component binds the epitope on the same antigen as the first antigen-binding domain of the first component.

In some embodiments, the antigen binding domain of the second component, such as the second antigen-binding domain, includes one or more copies of an antibody or an antigen-binding fragment thereof. In some embodiments, the second antigen-binding domain includes one or more copies of an antibody or an antigen-binding fragment thereof selected from the group consisting of a Fab fragment, a F(ab')$_2$ fragment, an Fv fragment, a scFv, a scAb, a dAb, a single domain heavy chain antibody, and a single domain light chain antibody. In some embodiments, the second antigen-binding domain includes one or more copies of one or more single domain antibody (sdAb) fragments, for example $V_H H$, $V_{NAR}$, engineered $V_H$ or $V_K$ domains. $V_H$Hs can be generated from camelid heavy chain only antibodies. $V_{NAR}$s can be generated from cartilaginous fish heavy chain only antibodies. Various methods have been implemented to generate monomeric sdAbs from conventionally heterodimeric $V_H$ and $V_K$ domains, including interface engineering and selection of specific germline families.

In some embodiments, the antigen binding domain of the second component, such as the second antigen-binding domain, binds an antigen, such as a tumor associated antigen (TAA). In some embodiments, the TAA is selected from the group consisting of 1-92-LFA-3, 5T4, Alpha-4 integrin, Alpha-V integrin, alpha4beta1 integrin, alpha4beta7 integrin, AGR2, Anti-Lewis-Y, Apelin J receptor, APRIL, B7-H3, B7-H4, BAFF, BTLA, C5 complement, C-242, CA9, CA19-9, (Lewis a), Carbonic anhydrase 9, CD2, CD3, CD6, CD9, CD11a, CD19, CD20, CD22, CD24, CD25, CD27, CD28, CD30, CD33, CD38, CD40, CD40L, CD41, CD44, CD44v6, CD47, CD51, CD52, CD56, CD64, CD70, CD71, CD74, CD80, CD81, CD86, CD95, CD117, CD123, CD125, CD132, (IL-2RG), CD133, CD137, CD138, CD166, CD172A, CD248, CDH6, CEACAM5 (CEA), CEACAM6 (NCA-90), CLAUDIN-3, CLAUDIN-4, cMet, Collagen, Cripto, CSFR, CSFR-1, CTLA-4, CTGF, CXCL10, CXCL13, CXCR1, CXCR2, CXCR4, CYR61, DL44, DLK1, DLL3, DLL4, DPP-4, DSG1, EDA, EDB, EGFR, EGFRviii, Endothelin B receptor (ETBR), ENPP3, EpCAM, EPHA2, EPHB2, ERBB3, F protein of RSV, FAP, FGF-2, FGF8, FGFR1, FGFR2, FGFR3, FGFR4, FLT-3, Folate receptor alpha (FRa), GAL3ST1, G-CSF, G-CSFR, GD2, GITR, GLUT1, GLUT4, GM-CSF, GM-CSFR, GP IIb/IIIa receptors, Gp130, GPIIB/IIIA, GPNMB, GRP78, HER2/neu, HER3, HER4, HGF, hGH, HVEM, Hyaluronidase, ICOS, IFNalpha, IFNbeta, IFNgamma, IgE, IgE Receptor (FceRI), IGF, IGF1R, IL1B, IL1R, IL2, IL11, IL12, IL12p40, IL-12R, IL-12Rbeta1, IL13, IL13R, IL15, IL17, IL18, IL21, IL23, IL23R, IL27/IL27R (wsx1), IL29, IL-31R, IL31/IL31R, IL2R, IL4, IL4R, IL6, IL6R, Insulin Receptor, Jagged Ligands, Jagged 1, Jagged 2, KISS1-R, LAG-3, LIF-R, Lewis X, LIGHT, LRP4, LRRC26, Ly6G6D, LyPD1, MCSP, Mesothelin, MRP4, MUC1, Mucin-16 (MUC16, CA-125), Na/K ATPase, NGF, Nicastrin, Notch Receptors, Notch 1, Notch 2, Notch 3, Notch 4, NOV, OSM-R, OX-40, PAR2, PDGF-AA, PDGF-BB, PDG-FRalpha, PDGFRbeta, PD-1, PD-L1, PD-L2, Phosphatidylserine, P1GF, PSCA, PSMA, PSGR, RAAG12, RAGE, SLC44A4, Sphingosine 1 Phosphate, STEAP1, STEAP2, TAG-72, TAPA1, TEM-8, TGFbeta, TIGIT, TIM-3, TLR2, TLR4, TLR6, TLR7, TLR8, TLR9, TMEM31, TNFalpha, TNFR, TNFRS12A, TRAIL-R1, TRAIL-R2, Transferrin, Transferrin receptor, TRK-A, TRK-B, uPAR, VAP1, VCAM-1, VEGF, VEGF-A, VEGF-B, VEGF-C, VEGF-D, VEGFR1, VEGFR2, VEGFR3, VISTA, WISP-1, WISP-2, and WISP-3.

In some embodiments, the antigen binding domain of the second component, such as the second antigen binding domain, and the anti-CD3-binding domain are operably linked via amino acid linkers. In some embodiments, these intra-component linkers are composed predominately of the amino acids Glycine and Serine, denoted as GS-linkers herein. The GS-linkers of the fusion proteins of the present disclosure can be of various lengths, for example 5, 6, 7, 8, 9, 10, 11, 12, 13, 14, 15, 16, 17, 18, 19, 20 amino acids in length.

In some embodiments, the GS-linker comprises an amino acid sequence selected from the group consisting of GGSGGS, i.e., (GGS)$_2$ (SEQ ID NO: 10); GGSGGSGGS, i.e., (GGS)$_3$ (SEQ ID NO: 11); GGSGGSGGSGGS, i.e., (GGS)$_4$ (SEQ ID NO: 12); and GGSGGSGGSGGSGGS, i.e., (GGS)$_5$ (SEQ ID NO: 13).

Provided herein is a multispecific polypeptide construct, the multispecific polypeptide construct comprising a first component comprising a heterodimeric Fc region and a second component comprising an anti-CD3 antibody or antigen-binding fragment comprising a variable heavy chain region (VH) and a variable light chain region (VL), wherein: the VH and VL that comprise the anti-CD3 antibody or antigen binding fragment are linked to opposite polypeptides of the heterodimeric Fc; the first and second components are coupled by a cleavable linker, wherein the heterodimeric Fc region is positioned N-terminal to the anti-CD3 antibody; and one or both of the first and second components comprises an antigen binding domain that binds a tumor associated antigen (TAA).

In some embodiments, binding of the CD3-binding region to CD3 is substantially reduced when the multispecific polypeptide construct is in an uncleaved state compared to a cleaved state. In some embodiments, in a cleaved state, the first and second components are not linked.

In some embodiments, the cleavable linker is a polypeptide. In some embodiments, the cleavable linker is a polypeptide that is a substrate for a protease. In some embodiments, the protease is produced by an immune effector cell, by a tumor, or by cells present in the tumor microenvironment. In some embodiments, the protease is produced by a tumor that is in proximity to cells that express CD3ε and/or is produced by a tumor that is co-localized with cells that express CD3ε in a tissue, and wherein the protease cleaves the cleavable linker in the multispecific polypeptide construct when the multispecific polypeptide construct is exposed to the protease. In some embodiments, the protease is produced by a tumor that is in proximity to cells that express one or more tumor associated antigens (TAA) and/or is produced by a tumor that is co-localized with cells that express the target TAA(s) in a tissue, and wherein the protease cleaves the cleavable linker in the multispecific polypeptide construct when the multispecific polypeptide construct is exposed to the protease. In some embodiments, the protease is produced by an immune effector cell. In some embodiments, the protease is produced by an immune effector cell that is in proximity to cells that express the TAA. In some examples, the protease is produced by an immune effector cell and the immune effector cell is an activated T cell, a natural killer (NK) cell, or an NK T cell. In some embodiments, the protease cleaves the cleavable linker in the multispecific polypeptide construct when the multispecific polypeptide construct is exposed to the protease. In some embodiments, the protease is produced an immune effector cell that is in proximity to cells that express the TAA and wherein the protease cleaves the cleavable linker in the multispecific polypeptide construct when the multispecific polypeptide construct is exposed to the protease.

In some embodiments, the cleavable linker is a polypeptide of up to 50 amino acids in length. In some embodiments, the cleavable linker is a polypeptide of up to 25 amino acids in length. In some embodiments, the cleavable linker is a polypeptide of up to 15 amino acids in length.

In some embodiments, the cleavable linker is a substrate for a protease selected from the proteases described herein. In some embodiments, the cleavable linker is a substrate for a protease selected from the group consisting of uPA, legumain, matriptase (also referred to herein as MT-SP1 or MTSP1), ADAM17, BMP-1, TMPRSS3, TMPRSS4, MMP-9, MMP-12, MMP-13, MMP-14, and any combination thereof. In some embodiments, the cleavable linker is a substrate for a protease selected from the group consisting of uPA, legumain, and matriptase. In some embodiments, the protease is selected from among matriptase, a matrix metalloprotease (MMP), granzyme B, and combinations thereof.

In some embodiments, the protease is granzyme B. In some examples, the cleavable linker comprises an amino acid sequence of the general formula P4 P3 P2 P1 ↓ P1' (SEQ ID NO: 150), wherein P4 is amino acid I, L, Y, M, F, V, or A; P3 is amino acid A, G, S, V, E, D, Q, N, or Y; P2 is amino acid H, P, A, V, G, S, or T; P1 is amino acid D or E; and P1' is amino acid I, L, Y, M, F, V, T, S, G or A. In some embodiments, the cleavable linker comprises an amino acid sequence of the general formula P4 P3 P2 P1 ↓ P1' (SEQ ID NO: 151), wherein P4 is amino acid I or L; P3 is amino acid E; P2 is amino acid P or A; P1 is amino acid D; and P1' is amino acid I, V, T, S, or G. In some examples, the cleavable linker comprises the amino acid sequence IEPDI (SEQ ID NO:136), LEPDG (SEQ ID NO:152, LEADT (SEQ ID NO:137), IEPDG (SEQ ID NO:138), IEPDV (SEQ ID NO:139), IEPDS (SEQ ID NO:140), IEPDT (SEQ ID NO:141) or LEADG (SEQ ID NO:153). In some cases, the cleavable linker comprises an amino acid sequence selected from the group consisting of SEQ ID NOs:22, 105-112, 136-141, 148, 150-153.

In some embodiments, the protease is matriptase. In some cases, the cleavable linker comprises the sequence P1QAR↓(A/V) (SEQ ID NO: 154), wherein P1 is any amino acid; or the cleavable linker comprises the sequence RQAR(A/V) (SEQ ID NO: 155). In some examples, the cleavable linker comprises the sequence RQARV (SEQ ID NO: 156). In some cases, the cleavable linker comprises an amino acid sequence selected from the group consisting of SEQ ID NOs: 23, 154-156.

In some embodiments, the protease is an MMP. In some examples, the MMP is MMP-2. In some embodiments, the cleavable linker comprises the general formula P3 P2 P1 ↓ P1' (SEQ ID NO: 157), wherein P3 is P, V or A; P2 is Q or D; P1 is A or N; and P1' is L, I or M. In some cases, the cleavable linker comprises the general formula P3 P2 P1 ↓ P1' (SEQ ID NO: 158), wherein is P; P2 is Q or D; P1 is A or N; and P1' is L or I. IN some embodiments, the cleavable linker comprises the sequence PAGL (SEQ ID NO:24). In some embodiments, the cleavable linker is a substrate for a matrix metalloprotease (MMP).

In some embodiments, the multispecific polypeptide construct comprises at least (i) a first polypeptide comprising the first Fc polypeptide of the heterodimeric Fc region, the linker and the VH domain of the anti-CD3 antibody or antigen binding fragment; and (ii) a second polypeptide comprising the second Fc polypeptide of the heterodimeric Fc region, the linker and the VL domain of the anti-CD3 antibody or antigen binding fragment, wherein one or both of the first and second polypeptide comprise at least one antigen-binding domain that binds to a tumor associated antigen (TAA). In some instances, only one of the first or second polypeptide comprises the at least one antigen-binding domain that binds a TAA.

In some of any of the provided embodiments, the antigen binding domain(s) results in monovalent, bivalent, trivalent, or tetravalent binding to the TAA. In some embodiments, the one or more antigen binding domains that bind TAA independently are selected from an sdAb, an scFv or a Fab. In some embodiments, the one or more antigen binding domains that binds a TAA is a TAA is a single chain molecule, such as a single chain antibody fragment containing a VH and a VL, for example an sdAb or an scFv. In some embodiments, at least one of the antigen binding domains is a Fab containing a first chain comprising a VH-CH1 (Fd) and a second chain comprising a VL-CL.

In some embodiments, the at least one antigen binding domain is positioned amino-terminally relative to the Fc region and/or is positioned carboxy-terminally relative to the CD3 binding region of one of the first or second polypeptide of the multispecific polypeptide construct. In some cases, the at least one antigen binding domain is positioned amino-terminally relative to the Fc region of the multispecific construct and the second antigen binding domain is positioned carboxy-terminally relative to the CD3 binding region of the multispecific construct.

In some embodiments, the at least one of the antigen binding domain(s) is a Fab. In some embodiments, the multispecific polypeptide construct comprises: (i) a first polypeptide comprising the first Fc polypeptide of the heterodimeric Fc region, the linker and the VH domain of the anti-CD3 antibody or antigen binding fragment; (ii) a second polypeptide comprising the second Fc polypeptide of the heterodimeric Fc region, the linker and the VL domain of the anti-CD3 antibody or antigen binding fragment, and (iii) a third polypeptide comprising a VH-CH1 (Fd) or VL-CL of a Fab antibody fragment that binds to a tumor-associated antigen, wherein the first and/or second polypeptide further comprises the other of the VH-CH1 (Fd) or VL-CL of the Fab antibody fragment. In some cases, only one of the first or second polypeptide comprises the other of the VH-CH1 (Fd) or VL-CL of the Fab antibody fragment. In some embodiments, both the first or second polypeptide comprises the other of the VH-CH1 (Fd) or VL-CL of the Fab antibody fragment. In some cases, the other of the VH-CH1 (Fd) or VL-CL of the Fab antibody fragment is positioned amino-terminally relative to the Fc region and/or at the carboxy-terminally relative to the CD3 binding region of one of the first or second polypeptide of the multispecific polypeptide construct. In some embodiments, the other of the VH-CH1 (Fd) or VL-CL of the Fab antibody fragment is positioned amino-terminally relative to the Fc region of the first polypeptide or second polypeptide and at the carboxy-terminally relative to the CD3 binding region of the other of the first or second polypeptide.

In some examples, the antigen binding domain, or independently each of the antigen binding domains, binds to a tumor antigen selected from among 1-92-LFA-3, 5T4, Alpha-4 integrin, Alpha-V integrin, alpha4beta1 integrin, alpha4beta7 integrin, AGR2, Anti-Lewis-Y, Apelin J receptor, APRIL, B7-H3, B7-H4, BAFF, BTLA, C5 complement, C-242, CA9, CA19-9, (Lewis a), Carbonic anhydrase 9, CD2, CD3, CD6, CD9, CD11a, CD19, CD20, CD22, CD24, CD25, CD27, CD28, CD30, CD33, CD38, CD40, CD40L, CD41, CD44, CD44v6, CD47, CD51, CD52, CD56, CD64, CD70, CD71, CD74, CD80, CD81, CD86, CD95, CD117, CD123, CD125, CD132, (IL-2RG), CD133, CD137, CD138, CD166, CD172A, CD248, CDH6, CEACAM5 (CEA), CEACAM6 (NCA-90), CLAUDIN-3, CLAUDIN-4, cMet, Collagen, Cripto, CSFR, CSFR-1, CTLA-4, CTGF, CXCL10, CXCL13, CXCR1, CXCR2, CXCR4, CYR61, DL44, DLK1, DLL3, DLL4, DPP-4, DSG1, EDA, EDB, EGFR, EGFRviii, Endothelin B receptor (ETBR), ENPP3, EpCAM, EPHA2, EPHB2, ERBB3, F protein of RSV, FAP, FGF-2, FGF8, FGFR1, FGFR2, FGFR3, FGFR4, FLT-3, Folate receptor alpha (FRa), GAL3ST1, G-CSF, G-CSFR, GD2, GITR, GLUT1, GLUT4, GM-CSF, GM-CSFR, GP IIb/IIIa receptors, Gp130, GPIIB/IIIA, GPNMB, GRP78, HER2/neu, HER3, HER4, HGF, hGH, HVEM, Hyaluronidase, ICOS, IFNalpha, IFNbeta, IFNgamma, IgE, IgE Receptor (FceRI), IGF, IGF1R, IL1B, IL1R, IL2, IL11, IL12, IL12p40, IL-12R, IL-12Rbeta1, IL13, IL13R, IL15, IL17, IL18, IL21, IL23, IL23R, IL27/IL27R (wsx1), IL29, IL-31R, IL31/IL31R, IL2R, IL4, IL4R, IL6, IL6R, Insulin Receptor, Jagged Ligands, Jagged 1, Jagged 2, KISS1-R, LAG-3, LIF-R, Lewis X, LIGHT, LRP4, LRRC26, Ly6G6D, LyPD1, MCSP, Mesothelin, MRP4, MUC1, Mucin-16 (MUC16, CA-125), Na/K ATPase, NGF, Nicastrin, Notch Receptors, Notch 1, Notch 2, Notch 3, Notch 4, NOV, OSM-R, OX-40, PAR2, PDGF-AA, PDGF-BB, PDG-FRalpha, PDGFRbeta, PD-1, PD-L1, PD-L2, Phosphatidylserine, P1GF, PSCA, PSMA, PSGR, RAAG12, RAGE, SLC44A4, Sphingosine 1 Phosphate, STEAP1, STEAP2, TAG-72, TAPA1, TEM-8, TGFbeta, TIGIT, TIM-3, TLR2, TLR4, TLR6, TLR7, TLR8, TLR9, TMEM31, TNFalpha, TNFR, TNFRS12A, TRAIL-R1, TRAIL-R2, Transferrin, Transferrin receptor, TRK-A, TRK-B, uPAR, VAP1, VCAM-1, VEGF, VEGF-A, VEGF-B, VEGF-C, VEGF-D, VEGFR1, VEGFR2, VEGFR3, VISTA, WISP-1, WISP-2, and WISP-3.

In some embodiments, the multispecific antigen binding domain comprises at least a first antigen binding domain and a second antigen binding domain, wherein the first antigen binding domain and second antigen binding domain bind to the same TAA. In some cases, the first antigen binding domain and the second antigen binding domain binds a different epitope of the same TAA. In some instances, the first antigen binding domain and the second antigen binding domain binds the same epitope of the same TAA. In some embodiments, the multispecific antigen binding domain comprises at least a first antigen binding domain and a second antigen binding domain wherein the first antigen binding domain and the second antigen binding domain bind a different TAA.

In some embodiments, the multispecific polypeptide construct comprises a first linking peptide (LP1) between the first antigen binding domain and the immunoglobulin Fc polypeptide region (Fc region). In some embodiments, the multispecific polypeptide construct comprises a second linking peptide (LP2) between the anti-CD3 binding domain (CD3 binding region) and the second antigen binding domain. In some embodiments, the multispecific polypeptide construct comprises a first linking peptide (LP1) between the first antigen binding domain and the immunoglobulin Fc polypeptide region (Fc region) and a second linking peptide (LP2) between the anti-CD3 binding domain (CD3 binding region) and the second antigen binding domain.

In some embodiments, the multispecific polypeptide construct in the uncleaved state has the structural arrangement from N-terminus to C-terminus as follows: first antigen binding domain-LP1-immunoglobulin Fc polypeptide linker region (Fc region)-linker (such as a cleavable linker)-anti-CD3 binding domain-LP2-second antigen binding domain. In some embodiments, the multispecific polypeptide construct in the uncleaved state has the structural arrangement from N-terminus to C-terminus as follows: second antigen binding domain-LP2-anti-CD3 binding domain (CD3 binding region)-linker (such as a cleavable linker)-immunoglobulin Fc polypeptide linker region-LP1-first antigen binding domain. In some examples, the linker is a cleavable linker. In some embodiments, the two linking peptides are not identical to each other. In some cases, LP1 or LP2 is independently a peptide of about 1 to 20 amino acids in length. In some examples, LP1 or LP2 independently comprise a peptide that is or comprises any Gly-Ser linker as set forth in SEQ ID NOs: 10-13, 119, 135, 147, 149.

In some embodiments, the multispecific construct is a construct having any of the structural arrangements shown in FIG. 1. In some embodiments, the multispecific construct is a bispecific construct having the structural arrangement shown in FIG. 2. In some embodiments, the bispecific construct has a structural arrangement from N-terminus to C-terminus as follows. The N-terminal end of the bispecific construct includes a first antigen binding domain that binds a tumor associated antigen (TAA). The first binding domain binds a first epitope on the TAA target. Coupled to the first antigen binding domain is a central immunoglobulin Fc polypeptide region that regulates FcγR interactions and/or FcRn interaction. In some embodiments, the central immunoglobulin Fc polypeptide region is heterodimeric. The immunoglobulin Fc polypeptide region is coupled to a cleavable linker that contains one or more proteolytic cleavage sites located at a position C-terminal to the end of the immunoglobulin Fc polypeptide region. In some embodiments, the one or more proteolytic cleavage sites is a substrate for matriptase, a matrix metalloprotease (MMP), or granzyme B. The cleavable linker is attached to an anti-CD3 binding sequence located C-terminal from the Fc region and in some cases, at the distal end of the second component.

In some embodiments, the anti-CD3 antibody or antigen binding fragment is an Fv antibody fragment. In some embodiments, the Fv antibody fragment comprises a disulfide stabilized anti-CD3 binding Fv fragment (dsFv). In some embodiments, the anti-CD3 binding sequence is an Fv antibody fragment that has an engineered to include a disulfide linkage between the variable heavy chain (VH) and variable light chain (VL) regions, thereby producing a disulfide stabilized anti-CD3 binding Fv fragment (dsFv). In some embodiments, the VH and VL domains that comprise the anti-CD3 Fv are operably linked to opposite members of a heterodimeric Fc region. In these embodiments, the anti-CD3 Fv binds CD3 in a monovalent fashion. The anti-CD3 dsFv does not engage CD3 when the cleavable linkers are intact, i.e., in an uncleaved or inactive state. The C-terminus of the bispecific construct includes a second antigen binding domain that binds a TAA. In some embodiments, the second antigen binding domain binds the same TAA as the first antigen binding domain located in within the first component. In some embodiments, the second antigen binding domain binds a second epitope on the TAA, wherein the second epitope is non-competitive with the first epitope on the TAA. In some embodiment, the second antigen binding domain binds a distinct TAA from that of the first antigen binding domain.

In some embodiments, each of the first antigen binding domain and the second antigen binding domain of the bispecific construct includes one or more copies of an antibody or an antigen-binding fragment thereof. In some embodiments, each of the first antigen binding domain and the second antigen binding domain of the bispecific construct includes one or more copies of an antibody or an antigen-binding fragment thereof selected from the group consisting of a Fab fragment, a F(ab')$_2$ fragment, an Fv fragment, a scFv, a scAb, a dAb, a single domain heavy chain antibody, and a single domain light chain antibody. In some embodiments, the antigen binding domain, or independently each of the antigen binding domains, is an antibody or antigen-binding fragment thereof selected from the group consisting of a Fab fragment, a F(ab')$_2$ fragment, an Fv fragment, a scFv, a scAb, a dAb, a single domain heavy chain antibody, and a single domain light chain antibody. In some embodiments, the each of the first antigen binding domain and the second antigen binding domain of the bispecific construct includes one or more copies of one or more single domain antibody (sdAb) fragments, for example $V_H H$, $V_{NAR}$, engineered $V_H$ or $V_K$ domains. $V_H Hs$ can be generated from natural camelid heavy chain only antibodies, genetically modified rodents that produce heavy chain only antibodies, or naïve/synthetic camelid or humanized camelid single domain antibody libraries. $V_{NAR}s$ can be generated from cartilaginous fish heavy chain only antibodies. Various methods have been implemented to generate monomeric sdAbs from conventionally heterodimeric $V_H$ and $V_K$ domains, including interface engineering and selection of specific germline families.

In some embodiments, the antibody or antigen-binding fragment is an sdAb. In some cases, the sdAb is a human or humanized sdAb. In some aspects, the sdAb is VHH, VNAR, an engineered VH domain or an engineered VK domain. In some examples, the antibody or antigen-binding fragment thereof is an scFv. In some cases, the antibody or antigen-binding fragment thereof is a Fab.

In some of any of the provided embodiments, the anti-CD3 antibody or antigen-binding fragment comprises a VH CDR1 comprising the amino acid sequence TYAMN (SEQ ID NO: 16); a VH CD2 comprising the amino acid sequence RIRSKYNNYATYYADSVKD (SEQ ID NO: 17); a VH CDR3 comprising the amino acid sequence HGNFGN-SYVSWFAY (SEQ ID NO: 18), a VL CDR1 comprising the amino acid sequence RSSTGAVTTSNYAN (SEQ ID NO: 19); a VL CDR2 comprising the amino acid sequence GTNKRAP (SEQ ID NO: 20); and a VL CDR3 comprising the amino acid sequence ALWYSNLWV (SEQ ID NO: 21).

In some embodiments, the anti-CD3 dsFv comprises: a VH having the amino acid sequence of any of SEQ ID NOS: 14, 44, and 32-62 or a sequence that exhibits at least 90%, 91%, 92%, 93%, 94%, 95%, 96%, 97%, 98% or 99% sequence identity to any of SEQ ID NOS: 14, 44, and 32-62; and a VL having the amino acid sequence of any of SEQ ID NOS: 15, 72, and 63-81 or a sequence that exhibits at least 90%, 91%, 92%, 93%, 94%, 95%, 96%, 97%, 98% or 99% sequence identity to any of SEQ ID NOS: 14, 44, and 32-62. In some cases, the anti-CD3 dsFv comprises the amino acid sequence of SEQ ID NO: 14 and the amino acid sequence of SEQ ID NO: 15. In some cases, the anti-CD3 dsFv comprises the amino acid sequence of SEQ ID NO: 44 and the amino acid sequence of SEQ ID NO: 72.

In some embodiments, the immunoglobulin Fc region of the first component is an IgG isotype selected from the group consisting of IgG1 isotype, IgG2 isotype, IgG3 isotype, and IgG4 subclass. In some embodiments, the immunoglobulin Fc region is a polypeptide comprising an amino acid sequence selected from the group consisting of SEQ ID NOs: 1-6. In some embodiments, the immunoglobulin Fc region is a polypeptide comprising an amino acid sequence that is at least 50%, 60%, 65%, 70%, 75%, 80%, 85%, 90%, 91%, 92%, 93%, 94%, 95%, 96%, 97%, 98%, or 99% identical to an amino acid sequence selected from the group consisting of SEQ ID NOs: 1-6.

In some embodiments, the immunoglobulin Fc region is a polypeptide comprising an amino acid sequence that is derived from an amino acid sequence selected from the group consisting of SEQ ID NOs: 1-6. In some embodiments, the immunoglobulin Fc region is a polypeptide comprising an amino acid sequence that is derived from an amino acid sequence selected from the group consisting of SEQ ID NOs: 1-6 comprising one or modifications. In some embodiments, the immunoglobulin Fc region is a polypeptide comprising an amino acid sequence that is derived from an amino acid sequence selected from the group consisting of SEQ ID NOs: 1-6 comprising one or modifications to prevent glycosylation, to alter Fc receptor interactions, to reduce Fc receptor binding, to enhance the interaction with CD32A, to reduce the complement protein C1q binding, to extend the half-life, to enhance FcRn binding, to alter antibody-dependent cellular cytotoxicity (ADCC) and/or complement-dependent cytotoxicity (CDC), to induce heterodimerization, to prevent dimerization, to stabilize the homodimerization at the CH3:CH3 interface, and combinations thereof. In some embodiments, modifications within the Fc region reduce binding to Fc-receptor-gamma receptors while have minimal impact on binding to the neonatal Fc receptor (FcRn). In some embodiments, the mutated or modified Fc polypeptide includes the following mutations: Met252Tyr and Met428Leu or Met252Tyr and Met428Val (M252Y, M428L, or M252Y, M428V) using the Kabat numbering system.

In some embodiments, the first antigen binding domain and the immunoglobulin Fc polypeptide are operably linked via amino acid linkers. In some embodiments, these intra-component linkers are composed predominately of the amino acids Glycine and Serine, denoted as GS-linkers herein. The GS-linkers of the fusion proteins of the present disclosure can be of various lengths, for example 5, 6, 7, 8, 9, 10, 11, 12, 13, 14, 15, 16, 17, 18, 19, 20 amino acids in length.

In some embodiments, the GS-linker comprises an amino acid sequence selected from the group consisting of GGSGGS, i.e., (GGS)$_2$ (SEQ ID NO: 10); GGSGGSGGS, i.e., (GGS)$_3$ (SEQ ID NO: 11); GGSGGSGGSGGS, i.e., (GGS)$_4$ (SEQ ID NO: 12); and GGSGGSGGSGGSGGS, i.e., (GGS)$_5$ (SEQ ID NO: 13).

In some embodiments, the anti-CD3ε dsFv antibody fragment includes an amino acid sequence selected from the group consisting of SEQ ID NO: 32-81. In some embodiments, the anti-CD3ε dsFv antibody fragment includes an amino acid sequence that is at least 90%, 91%, 92%, 93%, 94%, 95%, 96%, 97%, 98%, 99% or more identical to an amino acid sequence selected from the group consisting of SEQ ID NO: 32-81. In some embodiments, the anti-CD3ε Fv antibody fragment includes a combination of an amino acid sequence selected from the group of SEQ ID NO: 32-62 and an amino acid sequence selected from the group consisting of SEQ ID NO: 63-81. In some embodiments, the anti-CD3ε Fv antibody fragment includes a combination of an amino acid sequence that is at least 90%, 91%, 92%, 93%, 94%, 95%, 96%, 97%, 98%, 99% or more identical to an amino acid sequence selected from the group consisting of SEQ ID NO: 32-62 and an amino acid sequence that is at least 90%, 91%, 92%, 93%, 94%, 95%, 96%, 97%, 98%, 99% or more identical to an amino acid sequence selected from the group consisting of SEQ ID NO: 63-81 an amino acid sequence.

In some embodiments, the second antigen binding domain and the anti-CD3-binding domain are operably linked via amino acid linkers. In some embodiments, these intra-component linkers are composed predominately of the amino acids Glycine and Serine, denoted as GS-linkers herein. The GS-linkers of the fusion proteins of the present disclosure can be of various lengths, for example 5, 6, 7, 8, 9, 10, 11, 12, 13, 14, 15, 16, 17, 18, 19, 20 amino acids in length.

In some embodiments, the GS-linker comprises an amino acid sequence selected from the group consisting of GGSGGS, i.e., (GGS)$_2$ (SEQ ID NO: 10); GGSGGSGGS, i.e., (GGS)$_3$ (SEQ ID NO: 11); GGSGGSGGSGGS, i.e., (GGS)$_4$ (SEQ ID NO: 12); and GGSGGSGGSGGSGGS, i.e., (GGS)$_5$ (SEQ ID NO: 13).

In some embodiments, the cleavable linker is a polypeptide. In some embodiments, the cleavable linker is a polypeptide that is a substrate for a protease. In some embodiments, the protease is produced by a tumor that is in proximity to cells that express CD3ε and/or is produced by a tumor that is co-localized with cells that express CD3ε in a tissue, and wherein the protease cleaves the cleavable linker in the multispecific polypeptide construct when the multispecific polypeptide construct is exposed to the protease. In some embodiments, the protease is produced by a tumor that is in proximity to cells that express one or more tumor associated antigens (TAA) and/or is produced by a tumor that is co-localized with cells that express the target TAA(s) in a tissue, and wherein the protease cleaves the cleavable linker in the multispecific polypeptide construct when the multispecific polypeptide construct is exposed to the protease.

In some embodiments, the cleavable linker is a polypeptide of up to 50 amino acids in length. In some embodiments, the cleavable linker is a polypeptide of up to 25 amino acids in length. In some embodiments, the cleavable linker is a polypeptide of up to 15 amino acids in length. In some embodiments, the cleavable linker is a substrate for a protease selected from the proteases described herein. In some embodiments, the cleavable linker is a substrate for a protease selected from the group consisting of uPA, legumain, matriptase (also referred to herein as MT-SP1 or MTSP1), ADAM17, BMP-1, TMPRSS3, TMPRSS4, MMP-9, MMP-12, MMP-13, MMP-14, and any combination thereof. In some embodiments, the cleavable linker is a substrate for a protease selected from the group consisting of uPA, legumain, and matriptase. In some embodiments, the cleavable linker is a substrate for a matrix metalloprotease (MMP).

In some embodiments, the multispecific construct also includes an agent conjugated to the multispecific construct. In some embodiments, the agent is a therapeutic agent. In some embodiments, the agent is a detectable moiety. In some embodiments, the detectable moiety is a diagnostic agent. In some embodiments, the agent is conjugated to the multispecific construct via a linker. In some embodiments, the linker is a cleavable linker. In some embodiments, the linker is a non-cleavable linker.

In some embodiments, the anti multispecific construct described herein is used in conjunction with one or more additional agents or a combination of additional agents. Suitable additional agents include current pharmaceutical and/or surgical therapies for an intended application, such as, for example, cancer. For example, the multispecific construct can be used in conjunction with an additional chemotherapeutic or anti-neoplastic agent.

In some embodiments, the multispecific construct and additional agent are formulated into a single therapeutic composition, and the multispecific construct and additional agent are administered simultaneously. In some embodiments, the multispecific construct and additional agent are separate from each other, e.g., each is formulated into a separate therapeutic composition, and the multispecific construct and the additional agent are administered simultaneously, or the multispecific construct and the additional agent are administered at different times during a treatment regimen. For example, the multispecific construct is administered prior to the administration of the additional agent, the multispecific construct is administered subsequent to the administration of the additional agent, or the multispecific construct and the additional agent are administered in an alternating fashion. As described herein, the multispecific construct and additional agent are administered in single doses or in multiple doses.

In some embodiments, the multispecific construct naturally contains one or more disulfide bonds. In some embodiments, the multispecific construct can be engineered to include one or more disulfide bonds.

The disclosure also provides an isolated nucleic acid molecule or polynucleotide encoding at least a portion of a multispecific construct described herein and/or one or more nucleic acid molecules encoding a multispecific construct described herein, such as for example, at least a first nucleic acid encoding at least a portion of the first component of the multispecific construct and a second nucleic acid encoding at least a portion of the second component of the multispecific construct, as well as vectors that include these isolated nucleic acid sequences.

Among the provided embodiments is a polynucleotide(s) encoding any of the provided multispecific polypeptide constructs. Also provided is a polynucleotide encoding a polypeptide chain of any of the provided multispecific polypeptide constructs. Further provided is a polynucleotide, comprising a first nucleic acid sequence encoding a first polypeptide of any of the provided multispecific constructs and a second nucleic acid sequence encoding a second polypeptide of the multispecific construct, wherein the first and second nucleic acid sequence are separated by an internal ribosome entry site (IRES), or a nucleic acid encoding a self-cleaving peptide or a peptide that causes ribosome skipping. In some cases, the first nucleic acid sequence and second nucleic acid sequence are operably linked to the same promoter. In some embodiments, the multispecific polypeptide construct comprises a third polypeptide chain, and the polynucleotide further comprises a third nucleic acid encoding the third polypeptide of the multispecific construct. In some embodiments, the third nucleic acid is separated from the first and/or second polypeptide by an internal ribosome entry site (IRES), or a nucleic acid encoding a self-cleaving peptide or a peptide that causes ribosome skipping and/or the third nucleic acid sequence is operably linked to the same promoter as the first and/or second nucleic acid sequence. In some examples, the nucleic acid encoding a self-cleaving peptide or a peptide that causes ribosome skipping is selected from a T2A, a P2A, a E2A or a F2A (SEQ ID NOS: 159-164, or encoded by the sequence set forth in SEQ ID NO: 165).

Provided herein is a vector comprising any of the provided polynucleotides. In some embodiments, the vector is an expression vector. In some examples, the vector is a viral vector or a eukaryotic vector, optionally wherein the eukaryotic vector is a mammalian vector.

Provided is a cell, comprising any of the provided polynucleotides or vectors. In some cases, the cell is recombinant or isolated. In some examples, the cell is a mammalian cell. In some examples, the cell is a HEK293 or CHO cell.

The disclosure provides methods of producing a multispecific construct by culturing a cell under conditions that lead to expression of the multispecific construct, wherein the cell comprises such a nucleic acid molecule(s). In some embodiments, the cell comprises such a vector.

Provided herein is a method of producing a multispecific polypeptide construct, the method comprising introducing into a cell any of the provided polynucleotides or vectors and culturing the cell under conditions to that lead to expression of the multispecific construct to produce the multispecific polypeptide construct. Also provided is a method of producing a multispecific polypeptide construct, the method comprising culturing any of the provided cells under conditions in which the multispecific polypeptide is expressed or produced by the cell. In some cases, the cell is a mammalian cell. In some examples, the cell is a HEK293 or CHO cell. In some embodiments, the method further includes isolating or purifying the multispecific polypeptide construct from the cell. In some cases, the multispecific polypeptide construct is a heterodimer.

Provided herein is a multispecific polypeptide construct produced by any of the provided methods.

Provided herein is a method of stimulating or inducing an immune response, the method comprising contacting a target cell and a T cell with the any of the provided multispecific polypeptide constructs or pharmaceutical compositions, said target cell expressing a tumor associated antigen recognized by the multispecific polypeptide construct. In some embodiments, the target cell is a tumor cell expressing the tumor associated antigen (TAA).

In some embodiments, the multispecific polypeptide construct comprises a cleavable linker that functions as a substrate for a protease and the inducing or stimulating the immune response is increased in the presence of the protease. In some cases, the protease is produced by an immune effector cell, by a tumor, or by cells present in the tumor microenvironment.

In some embodiments, the protease is produced by an immune effector cell and the immune effector cell is an activated T cell, a natural killer (NK) cell, or an NK T cell. In some instances, the immune effector cell is in proximity to cells that express the antigen. In some embodiments, the protease is produced by a tumor that is in proximity to cells that express the TAA in a tissue and/or produced by a tumor that is co-localized with TAA in a tissue, and wherein the protease cleaves the cleavable linker in the multispecific polypeptide construct when the multispecific polypeptide construct is exposed to the protease. In some examples, the protease is selected from among matriptase, a matrix metalloprotease (MMP), granzyme B, and combinations thereof. In some instances, the protease is granzyme B.

In some embodiments, the contacting is carried out ex vivo or in vitro. In some embodiments, the contacting is carried out in vivo in a subject.

Provided is a method of stimulating or inducing an immune response in a subject, the method comprising administering, to a subject in need thereof, a therapeutically effective amount of any of the provided multispecific conjugates or pharmaceutical compositions. In some cases, the method increases cell-mediated immunity. In some embodiments, the method increases T-cell activity. In some embodiments, the method increases cytolytic T-cell (CTL) activity. In some examples, the immune response is increased against a tumor or cancer. In some embodiments, the method treats a disease or condition in the subject.

The present disclosure also provides methods of treating, preventing, delaying the progression of or otherwise ameliorating a symptom of one or more pathologies or alleviating a symptom associated with such pathologies, by administering a multispecific polypeptide construct of the disclosure to a subject in which such treatment or prevention is desired. Provided herein is a method of treating a disease or condition in a subject, the method comprising administering, to a subject in need thereof, a therapeutically effective amount of any of the provided multispecific conjugates or pharmaceutical compositions. In some embodiments, the disease or condition is a tumor or a cancer.

In some embodiments of any of the provided method, the subject, such as the subject to be treated is, e.g., human or other mammal. In some embodiments of any of the provided method, the subject is a human. In some embodiments, the subject is a non-human mammal, such as a non-human primate, companion animal (e.g., cat, dog, horse), farm animal, work animal, or zoo animal. In some embodiments, the subject is a rodent.

A multispecific polypeptide construct of the disclosure used in any of the embodiments of these methods and uses can be administered at any stage of the disease. For example, such a multispecific polypeptide construct can be administered to a patient suffering cancer of any stage, from early to metastatic. The terms subject and patient are used interchangeably herein.

A multispecific polypeptide construct of the disclosure used in any of the embodiments of these methods and uses can be used in a treatment regimen comprising neoadjuvant therapy.

A multispecific polypeptide construct of the disclosure used in any of the embodiments of these methods and uses can be administered either alone or in combination with one or more additional agents, including small molecule inhibitors, other antibody-based therapies, polypeptide or peptide-based therapies, nucleic acid-based therapies and/or other biologics. In some embodiments, a multispecific polypeptide construct is administered in combination with one or more additional agents such as, by way of non-limiting example, a chemotherapeutic agent, such as an alkylating agent, an anti-metabolite, an anti-microtubule agent, a topoisomerase inhibitor, a cytotoxic antibiotic, and any other nucleic acid damaging agent. In some embodiments, the additional agent is a taxane, such as paclitaxel (e.g., Abraxane®). In some embodiments, the additional agent is an anti-metabolite, such as gemcitabine. In some embodiments, the additional agent is an alkylating agent, such as platinum-based chemotherapy, such as carboplatin or cisplatin. In some embodiments, the additional agent is a targeted agent, such as a kinase inhibitor, e.g., sorafenib or erlotinib. In some embodiments, the additional agent is a targeted agent, such as another antibody, e.g., a monoclonal antibody (e.g., bevacizumab), a bispecific antibody, or a multispecific antibody. In some embodiments, the additional agent is a proteasome inhibitor, such as bortezomib or carfilzomib. In some embodiments, the additional agent is an immune modulating agent, such as lenolidomnde or IL-2. In some embodiments, the additional agent is radiation. In some embodiments, the additional agent is an agent considered standard of care by those skilled in the art. In some embodiments, the additional agent is a chemotherapeutic agent well known to those skilled in the art. In some embodiments, the multispecific polypeptide construct and the additional agent(s) are formulated in a single composition. In some embodiments, the multispecific polypeptide construct and the additional agent(s) are administered as two or more separate compositions. In some embodiments, the multispecific polypeptide construct and the additional agent(s) are administered simultaneously. In some embodiments, the multispecific polypeptide construct and the additional agent(s) are administered sequentially.

In some embodiments, the additional agent(s) is a chemotherapeutic agent, such as a chemotherapeutic agent selected from the group consisting of docetaxel, paclitaxel, abraxane (i.e., albumin-conjugated paclitaxel), doxorubicin, oxaliplatin, carboplatin, cisplatin, irinotecan, and gemcitabine.

In some embodiments, the additional agent(s) is a checkpoint inhibitor, a kinase inhibitor, an agent targeting inhibitors in the tumor microenvironment, and/or a T cell or NK agonist. In some embodiments, the additional agent(s) is radiation therapy, alone or in combination with another additional agent(s) such as a chemotherapeutic or anti-neoplastic agent. In some embodiments, the additional agent(s) is a vaccine, an oncovirus, and/or a DC-activating agent such as, by way of non-limiting example, a toll-like receptor (TLR) agonist and/or α-CD40. In some embodiments, the additional agent(s) is a tumor-targeted antibody designed to kill the tumor via ADCC or via direct conjugation to a toxin (e.g., an antibody drug conjugate (ADC)).

In some embodiments, the checkpoint inhibitor is an inhibitor of a target selected from the group consisting of CTLA-4, LAG-3, PD-1, PDL1, TIGIT, TIM-3, B7H3, B7H4, and Vista. In some embodiments, the kinase inhibitor is selected from the group consisting of B-RAFi, MEKi, and Btk inhibitors, such as ibrutinib. In some embodiments, the kinase inhibitor is crizotinib. In some embodiments, the tumor microenvironment inhibitor is selected from the group consisting of an IDO inhibitor, an α-CSF1R inhibitor, an α-CCR4 inhibitor, a TGF-beta, a myeloid-derived suppressor cell, or a T-regulatory cell. In some embodiments, the agonist is selected from the group consisting of OX40, GITR, CD137, CD28, ICOS, CD27, and HVEM. In some embodiments, the checkpoint inhibitor is an antibody that binds a target selected from CTLA-4, PD-1, and/or PD-L1. In some embodiments, the checkpoint inhibitor is an anti-CTLA4 antibody, an anti-PD-1 antibody, and an anti-PD-L1 antibody, and/or combinations thereof. In some embodiments, the checkpoint inhibitor is an anti-CTLA4 antibody such as, e.g., Yervoy™. In some embodiments, the checkpoint inhibitor is an anti-PD-1 antibody such as, e.g., Opdivo™ and/or Keytruda™.

In some embodiments, the inhibitor is a CTLA-4 inhibitor. In some embodiments, the inhibitor is a LAG-3 inhibitor. In some embodiments, the inhibitor is a PD-1 inhibitor. In some embodiments, the inhibitor is a PDL1 inhibitor. In some embodiments, the inhibitor is a TIGIT inhibitor. In some embodiments, the inhibitor is a TIM-3 inhibitor. In some embodiments, the inhibitor is a B7H3 inhibitor. In some embodiments, the inhibitor is a B7H4 inhibitor. In some embodiments, the inhibitor is a Vista inhibitor. In some embodiments, the inhibitor is a B-RAFi inhibitor. In some embodiments, the inhibitor is a MEKi inhibitor. In some embodiments, the inhibitor is a Btk inhibitor. In some embodiments, the inhibitor is ibrutinib. In some embodiments, the inhibitor is crizotinib. In some embodiments, the inhibitor is an IDO inhibitor. In some embodiments, the inhibitor is an α-CSF1R inhibitor. In some embodiments, the inhibitor is an α-CCR4 inhibitor. In some embodiments, the inhibitor is a TGF-beta. In some embodiments, the inhibitor is a myeloid-derived suppressor cell. In some embodiments, the inhibitor is a T-regulatory cell.

In some embodiments, the agonist is OX40. In some embodiments, the agonist is GITR. In some embodiments, the agonist is CD137. In some embodiments, the agonist is CD28. In some embodiments, the agonist is ICOS. In some embodiments, the agonist is CD27. In some embodiments, the agonist is HVEM.

In some embodiments, the multispecific polypeptide construct is administered during and/or after treatment in combination with one or more additional agents such as, for example, a chemotherapeutic agent, an anti-inflammatory agent, and/or an immunosuppressive agent. In some embodiments, the multispecific polypeptide construct and the additional agent are formulated into a single therapeutic composition, and the multispecific polypeptide construct and additional agent are administered simultaneously. Alternatively, the multispecific polypeptide construct and additional agent are separate from each other, e.g., each is formulated into a separate therapeutic composition, and the multispecific polypeptide construct and the additional agent are administered simultaneously, or the multispecific polypeptide construct and the additional agent are administered at different times during a treatment regimen. For example, the multispecific polypeptide construct is administered prior to the administration of the additional agent, the multispecific polypeptide construct is administered subsequent to the administration of the additional agent, or the multispecific polypeptide construct and the additional agent are administered in an alternating fashion. As described herein, the multispecific polypeptide construct and additional agent are administered in single doses or in multiple doses.

In some embodiments, the multispecific polypeptide construct and the additional agent(s) are administered simultaneously. For example, the multispecific polypeptide construct and the additional agent(s) can be formulated in a single composition or administered as two or more separate compositions. In some embodiments, the multispecific polypeptide construct and the additional agent(s) are administered sequentially, or the multispecific polypeptide construct and the additional agent are administered at different times during a treatment regimen.

In addition to the elements described above, the multispecific polypeptide construct can contain additional elements such as, for example, amino acid sequence N- or C-terminal of the multispecific polypeptide construct. For example, a multispecific polypeptide construct can include a targeting moiety to facilitate delivery to a cell or tissue of interest. Multispecific polypeptide construct can be conjugated to an agent, such as a therapeutic agent, a detectable moiety or a diagnostic agent. Examples of agents are disclosed herein.

The multispecific polypeptide construct can also include any of the conjugated agents, linkers and other components described herein in conjunction with a multispecific polypeptide construct of the disclosure.

The disclosure also pertains to immunoconjugates comprising a multispecific polypeptide construct conjugated to a cytotoxic agent such as a toxin (e.g., an enzymatically active toxin of bacterial, fungal, plant, or animal origin, or fragments thereof), or a radioactive isotope (i.e., a radioconjugate). Suitable cytotoxic agents for use in targeting diseased T cells such as in a T cell-derived lymphoma include, for example, dolastatins and derivatives thereof (e.g. auristatin E, AFP, MMAD, MMAF, MMAE). In some embodiments, the agent is a dolastatin. In some embodiments, the agent is an auristatin or derivative thereof. In some embodiments, the agent is a maytansinoid or maytansinoid derivative. In some embodiments, the agent is DM1 or DM4. In some embodiments, the agent is a duocarmycin or derivative thereof. In some embodiments, the agent is a calicheamicin or derivative thereof. In some embodiments, the agent is a pyrrolobenzodiazepine.

In some embodiments, the linker between the multispecific polypeptide construct and the cytotoxic agent is cleavable. In some embodiments, the linker is non-cleavable. In some embodiments, two or more linkers are present. The two or more linkers are all the same, e.g., cleavable or non-cleavable, or the two or more linkers are different, e.g., at least one cleavable and at least one non-cleavable.

The multispecific polypeptide constructs and conjugates thereof are useful in methods for treating a variety of disorders and/or diseases. Non-liming examples of disease include: all types of cancers (breast, lung, colorectal, prostate, melanomas, head and neck, pancreatic, etc.), rheumatoid arthritis, Crohn's disuse, SLE, cardiovascular damage, ischemia, etc. For example, indications would include leukemias, including T-cell acute lymphoblastic leukemia (T-ALL), lymphoblastic diseases including multiple myeloma, and solid tumors, including lung, colorectal, prostate, pancreatic, and breast, including triple negative breast cancer. For example, indications include bone disease or metastasis in cancer, regardless of primary tumor origin; breast cancer, including by way of non-limiting example, ER/PR+ breast cancer, Her2+ breast cancer, triple-negative breast cancer; colorectal cancer; endometrial cancer; gastric cancer; glioblastoma; head and neck cancer, such as esophageal cancer; lung cancer, such as by way of non-limiting example, non-small cell lung cancer; multiple myeloma ovarian cancer; pancreatic cancer; prostate cancer; sarcoma, such as osteosarcoma; renal cancer, such as by way of nonlimiting example, renal cell carcinoma; and/or skin cancer, such as by way of nonlimiting example, squamous cell cancer, basal cell carcinoma, or melanoma. In some embodiments, the cancer is a squamous cell cancer. In some embodiments, the cancer is a skin squamous cell carcinoma. In some embodiments, the cancer is an esophageal squamous cell carcinoma. In some embodiments, the cancer is a head and neck squamous cell carcinoma. In some embodiments, the cancer is a lung squamous cell carcinoma.

Also provided is a pharmaceutical composition comprising any of the multispecific polypeptide constructs provided herein and a pharmaceutically acceptable carrier. In some cases, the pharmaceutical composition is sterile. Pharmaceutical compositions according to the disclosure can include a multispecific polypeptide construct of the disclosure and a carrier. These pharmaceutical compositions can be included in kits, such as, for example, diagnostic kits.

One skilled in the art will appreciate that the antibodies of the disclosure have a variety of uses. For example, the proteins of the disclosure are used as therapeutic agents for a variety of disorders. The antibodies of the disclosure are also used as reagents in diagnostic kits or as diagnostic tools, or these antibodies can be used in competition assays to generate therapeutic reagents.

BRIEF DESCRIPTION OF DRAWINGS

FIG. 4A depicts an example of a multispecific polypeptide construct containing the same cleavable linker in each polypeptide chain to couple each Fc polypeptide of the heterodimeric Fc to a domain of the CD3 binding region (exemplary construct cx1762 is shown). In the format shown in FIG. 4A, the construct is depicted in its uncleaved state. An alternative version of a construct is shown in FIG. 4B in which only a single cleavable linker is employed to link the Fc region to the CD3 binding domain, designated half cleaved (exemplary construct cx3238 is shown). FIG. 4C depicts a structure that represents the C-terminal portion of the format of the constructs in FIGS. 4A and 4B when fully cleaved (exemplary construct cx2190 is shown). Constructs representing the proteolytic cleavage product can be produced recombinantly by co-expressing the various chains depicted. FRa-targeting sdAb are positioned at the C-terminal position in each construct.

In FIG. 5A, cx2513 has an EGFR-targeting sdAb positioned at the C-termini of each chain of the heterodimer and thereby displays bivalent binding to EGFR. In FIG. 5B, cx3030 has EGFR-targeting sdAbs positioned at both the N and C-termini of each chain of the heterodimer and thereby displays tetravalent binding to EGFR. FIG. 5C, cx2973 has a cMET-targeting sdAb positioned at the N-termini and an EGFR-targeting sdAb positioned at the C-termini of each chain of the heterodimer and thereby displays bivalent binding to each cMET and EGFR. In FIG. 5D, cx2979 has a cMET-targeting sdAb positioned at the N-termini of one chain of the heterodimer and an EGFR-targeting sdAb positioned at the C-termini of each chain of the heterodimer and thereby displays monovalent binding cMET and bivalent binding to EGFR. In FIG. 5E, cx2977 has a cMET-targeting sdAb positioned at the N-termini and an EGFR-targeting sdAb positioned at the C-termini of one or the other chain of the heterodimer and thereby displays monovalent binding to each cMET and EGFR.

FIG. 10C is a zoomed in view around the main peak shown in FIG. 10B.

FIG. 12A and FIG. 12C shows binding to Ovcar5 cells (a FRa positive ovarian cancer cell line). FIG. 12B and FIG. 12D depicts the lack binding to T-cells. FIG. 12A and FIG. 12B display histograms of the normalized cell counts vs fluorescence at the 100 nM of each construct. The full titration of each construct on the various cell types are shown in FIG. 12C and FIG. 12D. The secondary anti-human APC antibody only control is shown in the filled black trace, while the positive control anti-CD3 binding is shown in the open trance, and cx1356, cx681 and cx1547 are shown in the gray shaded traces in FIG. 12A and FIG. 12B.

FIG. 13A shows binding to an EGFR positive cell line, Colo-205 at 100 nM. FIG. 13B demonstrates the lack of binding to T-cells at 100 nM. Binding is displayed as histograms of the normalized cell counts vs fluorescence. The secondary anti-human APC antibody only control is shown in the filled black trace, while the positive control anti-CD3 binding is shown in the open trance, and cx3030 is shown in the gray shaded trace.

FIGS. 14A and 14C show the comparative histograms of the 100 nM concentration for each construct. The secondary anti-human APC antibody only control is shown in the filled black trace and various B7H3-targeted CD3 engaging constructs are shown in the white non-shared traces. FIGS. 14B and 14D show titrations of binding by various constructs to BH73 and CD3, respectively.

FIG. 15A shows binding to a 5T4 positive cell line, Ovcar-5 at 400 nM. FIG. 15B demonstrates the lack binding to T-cells at 400 nM. Binding is displayed as histograms of the normalized cell counts vs fluorescence. The secondary anti-human APC antibody only control is shown in the filled black trace, the while the positive control anti-CD3 binding is shown in the open trance, and cx3262 and cx3315 are shown in the gray shaded traces.

FIG. 16A and FIG. 16C shows binding to Ramos cells (a CD20 positive cell line). FIG. 16B and FIG. 16D demonstrates the lack binding to T-cells. FIG. 16A-16B display histograms of the normalized cell counts vs fluorescence at 100 nM of each construct. The full titration of each construct on the various cell types are shown in FIG. 16C-16D. The secondary anti-human APC antibody only control is shown in the filled black trace, while the positive control anti-CD3 binding is shown in the open trance, and cx3309 is shown in the gray shaded traces.

FIG. 20A-20D is a series of graphs demonstrating the antigen-dependent T-cell activating capacity of various EGFR and EGFR/cMET-targeted constrained CD3 engagers. Notably, the T-cell activating capacity is enhanced with increased valencey or an additional target antigen binding specificity. T-cell activation kinetics mediated by the various constructs on antigen positive A431 cells is depicted in FIG. 20A or antigen negative CCRF-CEM cells FIG. 20C. The potency of T-cell activation by the various constructs on antigen positive A431 cells is depicted in FIG. 20B or antigen negative CCRF-CEM cells in FIG. 20D. Herein the Jurkat CD3 NFAT-GFP reporter cell line was used.

FIG. 21A-21B depicts the capacity to mediate target antigen specific T-cell activation by a representative B7H3-targeted constrained CD3 engaging construct, cx3095 and an alternative DART-Fc format targeting B7H3 and CD3. Jurkat CD3 NFAT-GFP reporter cells were used to assess T-cell activation in the presence of a B7H3 positive cell line, A375 (FIG. 21A) and B7H3 negative cell line, Raji (FIG. 21B).

FIG. 22A-22F depicts the capacity to mediate target antigen specific T-cell activation by representative B7H3-targeted constrained CD3 engaging constructs, and an alternative DART-Fc format targeting B7H3 and CD3. Notably the constrained CD3 engaging constructs utilize either a B7H3-targeted sdAb, scFv, or FAB. Jurkat CD3 NFAT-GFP reporter cells were used to assess T-cell activation in the presence of a B7H3 positive cell line, A375 (FIG. 22A, 22C, 22E) and B7H3 negative cell line, CCRF (FIG. 22B, 22D, 22F). The kinetics of T-cell activation mediated by 50 nM (FIGS. 22A and 22B) or 2 nM (FIG. 22C or 22D) of each construct is shown. Also shown is the potency of T-cell activation mediated by each construct on the antigen positive (FIG. 22E) and negative (FIG. 22F) cell lines.

FIG. 27A-27B show the kinetics of T-cell activation by 2 nM of various constructs on antigen positive and negative cells, respectively. FIG. 27C-27D show the magnitude of T-cell activating capacity by 2 nM of various constructs on antigen positive and negative cells, respectively. FIG. 27E-27F show the potency of T-cell activating capacity various constructs with differing linker lengths on antigen positive and negative cells, respectively. A Jurkat CD3 NFAT-GFP reporter cell line was used to assess T-cell activation. Constrained CD3 proteins only effectively engage and cluster CD3 on T cells when bound to a second antigen on target cells.

FIG. 28A demonstrates that cx1547 does not induce T-cell mediated cytotoxicity of an antigen-negative cell line (NCI-H460). FIG. 28B demonstrates that cx1547 induces T-cell mediated cytotoxicity of an antigen-positive cell line (Ovcar5). FIG. 28C shows the kinetics of T-cell mediated cytotoxicity towards OVCAR5 cells induced by cx1547 at 3 nM. cx1547 induced T-cell mediated cytotoxicity only in antigen positive cell lines. Cytotoxicity was monitored using a caspase-3/7 fluorogenic substrate of differentially labeled target cells on an Incucyte ZOOM imager. Effector to target cell ratio (E:T) was assessed at 20:1 and 10:1 in this assay.

FIG. 29F depicts the measurement at 50 nM of each construct on A549 cell in which B7H3 expression has been knocked down. Notably all constructs display B7H3-dependent T-cell mediated cytotoxicity.

FIG. 31D and FIG. 31E show the potency of the two formats of FRα CD3 engager at 24 and 40 hours, respectively. Graph F. demonstrates that no substantial cytotoxicity is mediated by any construct in the absence of FRα expression on the target cell.

FIG. 34A-34H depicts the capacity to active CD4 (FIGS. 34A and 34E) and CD8 (FIGS. 34C and 34G) T-cells in a target-dependent manner by representative B7H3-targeted constrained CD3 engaging constructs and an alternative DART-Fc format targeting B7H3 and CD3. T-cells were incubated with the B7H3 positive cell line A375 (FIG. 34A, 34C, 34E, 34G) or the B7H3 knock-down A549 cell line (FIG. 34B, 34D, 34F, 34H) and activation markers CD25 and CD71 were assessed by flow cytometry. These data demonstrate B7H3-dependent T-cell activation capacities of the constructs used.

FIG. 38A depicts the flow plot of the relative prevalence of the tumor cells (EpCAM+) and infiltrating lymphocytes (CD45+) in the dissociated ovarian tumor sample. FIG. 38B shows the viability (CellTiterGlo) of the adherent tumor cells following treatment with a conventional FRα antibody or cx1547 after a 6 day incubation. FIG. 38C shows the INFγ production following treatment with an FRα antibody or cx1547 after a 6 day incubation. FIG. 38D shows representative images of the remaining adherent tumor cells following the 6 day treatment with no antibody (left), a conventional FRα antibody (middle) or cx1547 (right).

DETAILED DESCRIPTION

The present disclosure provides constrained T-cell engaging fusion proteins in the form of multispecific polypeptide constructs that bind at least CD3 and a second antigen. The multispecific polypeptide constructs provided herein include at least a first component that includes one or more copies of an antigen-binding domain that bind an antigen operably linked to an immunoglobulin Fc region, a second component that includes one or more copies of at least a binding domain that binds CD3 (referred to herein as an anti-CD3 binding domain or a CD3 binding region, which are terms that are used interchangeably herein), and a linker, such as a polypeptide linker, that joins the first component and the second component. In some embodiments, the antigen is a tumor associated antigen (TAA). In some embodiments, the linker is a cleavable linker.

Figure 1:
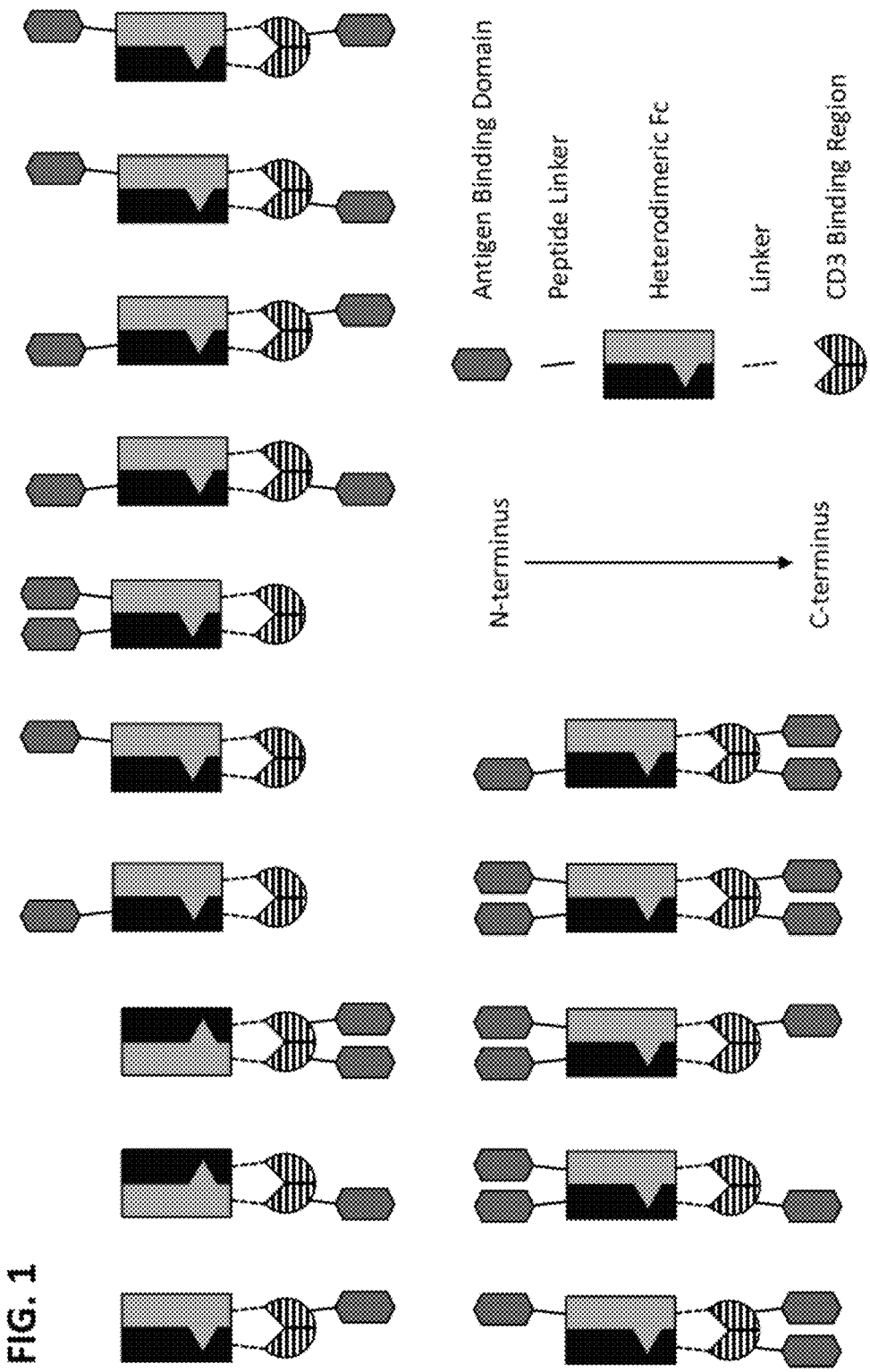
FIG. 1 is a schematic of the basic components of the multispecific polypeptide constructs of the present disclosure having constrained CD3 binding. The antigen binding domain(s) are positioned at the amino and/or carboxy termini. The Fc region, such as a heterodimeric Fc region, is positioned N-terminal to the CD3 binding region. This positioning of the Fc in close proximity to the CD3 binding region obstructs CD3 binding.

The provided multispecific polypeptide constructs include a configuration in which the first component containing the Fc region is N-terminal to the second component containing the CD3 binding region. In such an embodiment, the first and second components are joined via a linker that is C-terminal to the end of the Fc region. In some embodiments the antigen binding domain(s) are positioned on the amino-terminal (N-term) region of the multispecific polypeptide construct. In some embodiments, the antigen binding domain(s) are positioned on the carboxy-terminal (C-term) region of the multispecific polypeptide construct. In some embodiments, the antigen binding domain(s) are positioned on both the N- and C-terminal regions of the multispecific polypeptide construct. Various configurations of a multispecific polypeptide construct as provided herein are shown in FIG. 1.

The provided multispecific polypeptide constructs exhibit constrained T-cell engaging activity because such constructs only substantially bind to CD3 once an antigen is bound via the antigen-bind domain. This is exemplified in the Examples and Figures provided herein, which demonstrate the ability of constrained CD3 engaging proteins to efficiently bind TAA positive cells, while having little to no binding of T cells. This unique property allows constrained CD3 engaging proteins to distribute to sites where TAA is present without binding to peripheral T cells. This format is distinct from other CD3 engaging multispecific constructs, in that constitutive CD3 binding is disallowed or eliminated, providing a significant benefit by avoiding peripheral T-cell binding and permitting superior distribution to the site(s) where antigen is present as recognized by the antigen binding domain. For example, as shown in the Examples, the constrained CD3 engaging format enables similar potency to the DART-Fc format (e.g. published PCT Appl. No. WO2017/030926), however, binding to peripheral T-cell is significantly attenuated. Furthermore, other CD3 engaging constructs mediate antigen-dependent T-cell activation, however, the multispecific polypeptide constructs provided herein mediate both antigen dependent T-cell binding and activation.

The constrained T-cell engaging activity of the provided multispecific polypeptide constructs is due, in some aspects, to the positioning of the Fc region N-terminal to the CD3-binding region. In some embodiments, such positioning reduces, attenuates, dampens and/or prevents CD3 binding by the CD3 binding region. In the absence of antigen binding by the antigen binding domain, the multispecific polypeptide constructs provided herein demonstrate reduced or eliminated CD3 binding and T-cell activating capacity. In some embodiments, in the presence of an antigen binding event mediated by the antigen binding domain(s) of the multispecific polypeptide constructions, the capacity to bind CD3 by the CD3 binding region is greatly enhanced. In some embodiments, in the presence of an antigen binding event mediated by the antigen binding domains(s) of the multispecific polypeptide constructs the capacity to activate T-cells is greatly enhanced. Engagement of its cognate antigen by the antigen binding domain(s) within the multispecific polypeptide construct leads to subsequent T-cell engagement and mediates antigen-dependent T-cell activation, such as cytotoxicity, cytokine release, degranulation and proliferation. In some embodiments, the provided multispecific polypeptide constructs can be used to increase an immune response, such as to enhance T-cell activity, including cytolytic (or cytotoxic) T-cell activity. The modulation of the immune response can, in some aspects, treat a disease or condition in a subject.

In some embodiments, the one or more antigen binding domains bind an antigen on a tumor cell or a cell of the tumor microenvironment. In some aspects, the provided multispecific polypeptide constructs can be used to increase immune responses, such as T-cell activity, e.g. cytotoxicity activity, against a tumor or cancer. In some embodiments, the provided multispecific polypeptide constructs can be used to treat a tumor or cancer in the subject.

The multispecific polypeptide constructs of the disclosure ensure that there will be no binding of T-cells via CD3 in peripheral blood, as the CD3 binding region of these constructs is constrained or otherwise blocked and/or inhibited by the presence of the Fc region. Thus, the multispecific polypeptide constructs of the disclosure provide a number of advantages. In some aspects, these constructs limit the sink effect caused by binding all T-cells. In some aspects, these constructs reduce systemic toxicity.

In some embodiments, the provided multispecific polypeptide constructs of the disclosure allow for controlled biodistribution to a desired site in a subject, such as, for example, a site of tumor-associated antigen (TAA) expression. Sites of TAA expression include, for example, tumor and the surrounding tumor microenvironment.

Figure 2:
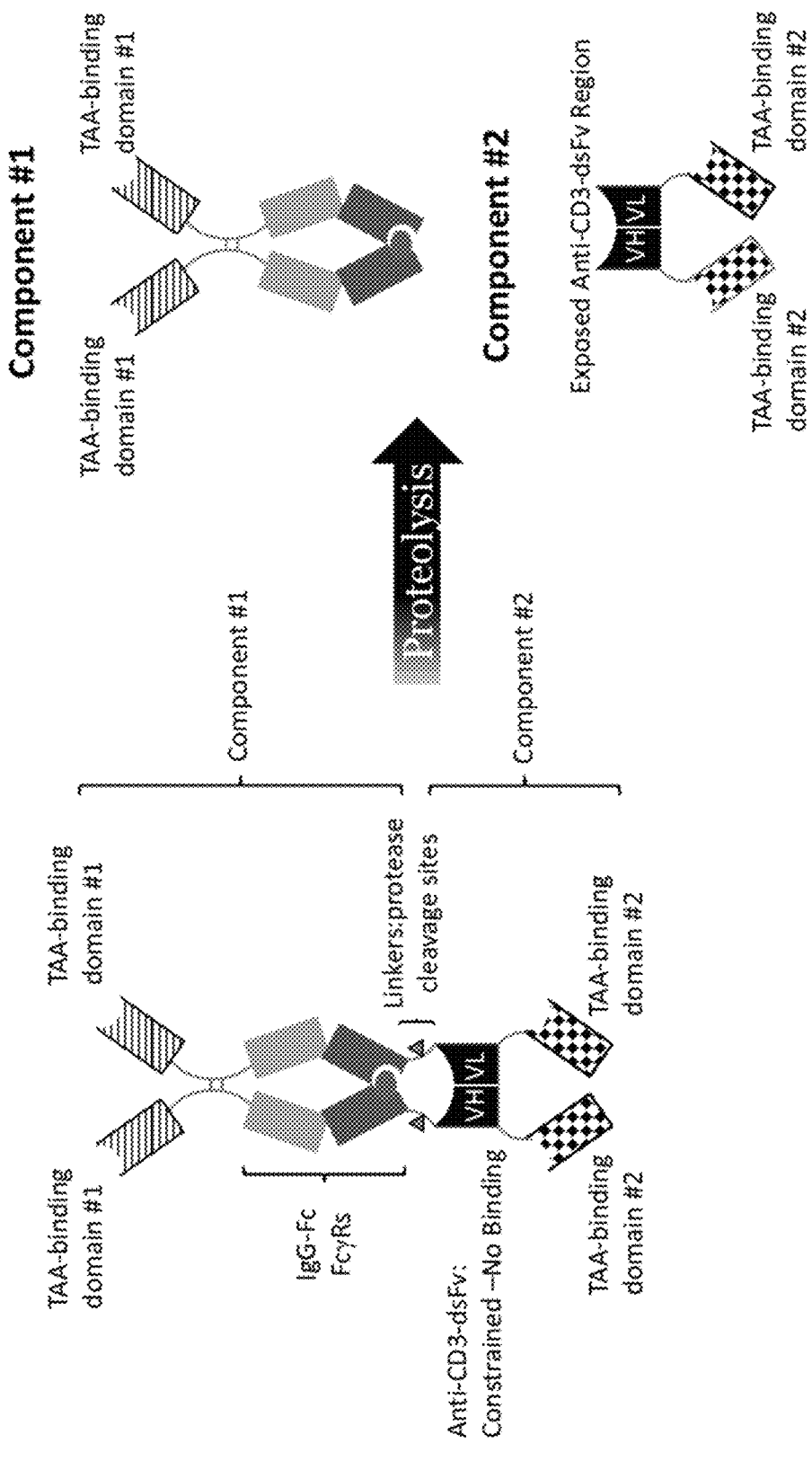
FIG. 2 is an illustration depicting an exemplary structure of a multispecific molecule of the disclosure containing a cleavable linker and having dual effector functions, wherein proteolytic cleavage of the cleavable linker results in activation of the multispecific polypeptide construct to produce two components that each have biological activity.

In some embodiments, the multispecific polypeptide constructs of the disclosure exhibit specificity for CD3 and one or more other antigen. In some embodiments, the multispecific polypeptide constructs can contain more than one antigen binding domain able to bind one or more TAA, such as 2, 3 or 4 antigen binding domains, see e.g. FIG. 1. In some embodiments, the one or more antigen binding domains bind the same antigen. In some embodiments, the multispecific polypeptide constructs include more than one antigen binding domains that bind distinct epitopes on the same antigen. In some embodiments, the multispecific polypeptide constructs include more than one antigen binding domain that bind one or more distinct antigens. In some embodiments, the multispecific polypeptide constructs include more than one antigen binding domains that bind distinct epitopes on the same antigens as well as include additional antigen binding domains that bind to one or more distinct antigens. In some aspects, the provided multispecific polypeptide constructs are bispecific polypeptide constructs, such that they are able to bind to CD3 and to another antigen, such as a TAA, via binding of the antigen-binding domain of the multispecific polypeptide construct. In some examples, the provided multispecific polypeptide constructs are bispecific polypeptide constructs that provide tetravalent engagement of one or more TAA through the use of a first antigen-binding domain and a second antigen-binding domain. For example, in some embodiments, the bispecific polypeptide constructions include a first antigen-binding single domain antibody (sdAb) and a second antigen-binding sdAb as shown in FIGS. 1 and 2.

In some embodiments, the multispecific polypeptide constructs provided herein exist in two states in terms of capacity to bind CD3 and subsequently activate T-cells: (1) the "inactive" state, i.e. uncleaved state, occurs when there is no binding of any or all of the antigen binding domain(s), such that the CD3 binding is constrained and T-cell interaction is obviated, and (2) the "active" state occurs upon antigen binding by any or all of the antigen binding domain(s), such that the CD3 binding region is able to bind CD3 and the T-cell interaction is allowed.

In some embodiments, the Fc region is linked to the CD3 binding domain via a linker or linkers. In some embodiments, the Fc region is linked to the CD3 binding region via a non-cleavable inker or linkers. In some embodiments, the Fc region is linked to the CD3 binding region via a cleavable linker or an otherwise labile linker or linkers.

In some embodiments, the Fc region and the CD3 binding region are linked by a cleavable linker. In some aspects, enhanced CD3 binding occurs following cleavage of the cleavable linker. In some such aspects, the "active" state can be further amplified via several mechanisms, including via cleavage of the linker joining the CD3 binding region and the Fc region. In some embodiments, the cleavable linker is a linker that contains a substrate recognition site for a protease. In some embodiments, wherein the Fc region and the CD3 binding region are linked by a cleavable linker, enhanced CD3 binding may occur following cleavage within the linker(s).

In some aspects, the multispecific polypeptide constructs of the disclosure allow for therapeutic efficacy in the absence of proteolysis.

In some embodiments, the Fc region is a homodimeric Fc region. In some embodiments, the Fc region is a heterodimeric Fc region. In some embodiments, the Fc region is a monomeric Fc region. In some embodiments, the Fc region of the multispecific polypeptide constructs are capable of interacting with FcγRs and mediating innate immune effector functions, for example, antibody dependent cellular toxicity (ADCC) and antibody dependent cellular phagocytosis (ADCP). In some embodiments, the Fc region of the multispecific polypeptide constructs are capable of interacting with complement proteins, namely C1q, and mediating complement dependent cytotoxicity. Thus, in some aspects, the multispecific polypeptide constructs of the disclosure allow for multiple immune effector mechanisms, including innate immune effectors and T-cells.

In some embodiments, wherein the Fc region and the CD3 binding region are operably linked by a cleavable linker, cleavage of the linker(s) between the Fc region and the CD3 binding region may separate the multispecific polypeptide constructs into a first and second component. Depending on the composition of the multispecific polypeptide construct, the first and second component may have distinct functionalities. In some embodiments, the Fc region is a region that exhibits one or more effector functions, such as ADCC, CDC or ADCP functions. In such examples, the multispecific polypeptide constructs of the disclosure can be used to produce a self-amplifying system. For example, the multispecific constructs can be used as follows: ADCC mediated by NK cell following TAA targeting and CD16 binding of Fc region results in the release granzyme B that is capable of extracellular proteolysis and cleavage of linkers between the first and second components of the multispecific polypeptide constructs.

In some embodiments, the linker is a cleavable linker. The multispecific polypeptide constructs provide a two-in-one therapeutic moiety having dual effector functions, wherein proteolytic activation of the multispecific polypeptide constructs produces two components that each have biological activity. The multispecific polypeptide constructs of the disclosure are capable of providing Fc-mediated effector functions, such as for example, ADCC (e.g., release of Granzyme B by NK cells), ADCP, and/or CDC.

It is contemplated that the constrained CD3 engaging constructs are amenable for use with any TAA-binding domain, allowing better therapeutic exposure within the tumor or tumor-microenvironment by avoiding interactions with peripheral T-cells and mediating potent TAA-dependent T-cell cytotoxicity The incorporation of a protease cleavable linker between the Fc and the components of the CD3 binding domain enables for amplification of the T-cell activating capacity by allowing full exposure of the CD3 binding domain. Depending on the specific linker included, the amplification step can be mediated by tumor associated proteases or by granzymes released following antigen dependent-T-cell activation. If a tumor protease cleavable linker is included the amplification is mediated by the tumor or tumor-microenvironment. Whereas, if a granzyme B cleavable linker is included the amplification may be self-mediated by T-cells following antigen-dependent activation. Furthermore, in cases wherein an effector enabled Fc is included in the construct, amplification may be mediated by granzymes released from NK cell that occurs through an ADCC mechanism.

In some embodiments, the protease is a protease that is produced in the tumor microenvironment and/or upon T cell activation induced by initial binding of the CD3 binding region to CD3 in the tumor microenvironment via binding of the antigen binding domain(s) to a TAA. In some embodiments, the protease is granzyme B. In some aspects, the multispecific polypeptide constructs of the disclosure leverage the ability of a protease within the tumor microenvironment and/or granzyme B to cleave the linker within the multispecific polypeptide construct at a position below the Fc immunoglobulin polypeptide, thereby generating two therapeutically active proteins with, in some cases, distinct effector cell engagement. In some aspects, upon cleavage of the cleavable linker, the cleaved first portion or component retains Fc-effector functions and bivalent targeting of a first antigen, such as, e.g., a TAA, via a first antigen-binding domain, and the second portion or component retains the ability for T-cell engagement, as separation of the CD3 binding region from the Fc region allows for CD3 binding. The cleaved second portion or component also, in some cases, retains the ability for binding to a TAA, which can be a bivalent binding via a second antigen-binding domain.

In some embodiments, the second portion or component contains a CD3 binding region that is monovalent to CD3, such that there will be no activation of T-cell unless there is TAA present. In some aspects, where the multivalent polypeptide construct contains a cleavable linker, the cleaved second portion or component allows for TAA-dependent, T-cell-mediated cytotoxicity. In some cases, the cleaved second portion or component ensures there will be no FcRn interaction. Furthermore, the cleaved second portion or component will be sufficiently small in size, for example, only ~50 kDa, which will ensure rapid clearance if, for any reason, the cleaved second portion or component distributes outside tumor site after cleavage and/or if it is aberrantly cleaved outside of the tumor site.

In some embodiments, the multispecific polypeptide constructs of the disclosure allow for T-cell and NK cell mediated cytotoxicity to occur simultaneously. In some cases, such activity can occur in a multispecific polypeptide construct in which is contained a first antigen binding domain, e.g., a first anti-TAA antigen binding domain, and a second antigen binding domain, e.g., a second anti-TAA antigen binding domain, that can target distinct and/or non-competing epitopes on a given TAA.

In some aspects, the multispecific polypeptide constructs of the disclosure provide a number of advantages over current bispecific therapeutics. The multispecific polypeptide constructs of the disclosure are smaller than a conventional therapeutic antibody, e.g., 150 kDa vs. 125 kDa, which will allow for better target, e.g. tumor, penetration. First, the size of the entire multispecific polypeptide construct provides long half-life for the uncleaved construct, and upon cleavage of the construct, the cleaved second portion or component will be sufficiently small to ensure a short half-life. In some aspects, the multispecific polypeptide constructs of the disclosure exhibit reduced systemic toxicity or toxicity of any area outside the tumor and/or tumor microenvironment, since CD3 binding by the CD3 binding region depends on TAA engagement before CD3 engagement will occur. In some cases, the inclusion of a cleavable linker specific to a protease of the tumor environments reduces CD3 binding by the multispecific constructs until proteolytic activation and TAA engagement, thereby amplifying or enhancing the CD3 engagement.

The multispecific polypeptide constructs of the disclosure are designed to ensure that the protease that cleaves the cleavable linker does not need to be tumor-biased (e.g., does not need to be differently expressed only at a tumor site and/or in the tumor environment). Rather, these multispecific polypeptide constructs only require that the protease is present in the same location as the TAA. The valency of these constructs will drive biodistribution and retention within the tumor and/or tumor microenvironment.

All publications and patent documents cited herein are incorporated herein by reference as if each such publication or document was specifically and individually indicated to be incorporated herein by reference. Citation of publications and patent documents is not intended as an admission that any is pertinent prior art, nor does it constitute any admission as to the contents or date of the same. The invention having now been described by way of written description, those of skill in the art will recognize that the invention can be practiced in a variety of embodiments and that the foregoing description and examples below are for purposes of illustration and not limitation of the claims that follow.

I. Definitions

Unless otherwise defined, scientific and technical terms used in connection with the present disclosure shall have the meanings that are commonly understood by those of ordinary skill in the art. The term "a" entity or "an" entity refers to one or more of that entity. For example, a compound refers to one or more compounds. As such, the terms "a", "an", "one or more" and "at least one" can be used interchangeably. Further, unless otherwise required by context, singular terms shall include pluralities and plural terms shall include the singular. Generally, nomenclatures utilized in connection with, and techniques of, cell and tissue culture, molecular biology, and protein and oligo- or polynucleotide chemistry and hybridization described herein are those well-known and commonly used in the art. Standard techniques are used for recombinant DNA, oligonucleotide synthesis, and tissue culture and transformation (e.g., electroporation, lipofection). Enzymatic reactions and purification techniques are performed according to manufacturer's specifications or as commonly accomplished in the art or as described herein. The foregoing techniques and procedures are generally performed according to conventional methods well known in the art and as described in various general and more specific references that are cited and discussed throughout the present specification. See e.g., Sambrook et al. Molecular Cloning: A Laboratory Manual (2d ed., Cold Spring Harbor Laboratory Press, Cold Spring Harbor, N.Y. (1989)). The nomenclatures utilized in connection with, and the laboratory procedures and techniques of, analytical chemistry, synthetic organic chemistry, and medicinal and pharmaceutical chemistry described herein are those well-known and commonly used in the art. Standard techniques are used for chemical syntheses, chemical analyses, pharmaceutical preparation, formulation, and delivery, and treatment of patients.

As utilized in accordance with the present disclosure, the following terms, unless otherwise indicated, shall be understood to have the following meanings:

As used herein, the term "antibody" refers to immunoglobulin molecules and antigen-binding portions of immunoglobulin (Ig) molecules, i.e., molecules that contain an antigen binding site that specifically binds (immunoreacts with) an antigen. By "specifically bind" or "immunoreacts with" or "immunospecifically bind" is meant that the antibody reacts with one or more antigenic determinants of the desired antigen and does not react with other polypeptides or binds at much lower affinity ($K_d > 10^{-6}$). Antibodies include, but are not limited to, polyclonal, monoclonal, chimeric, fully human, domain antibody, single chain, Fab, and F(ab')$_2$ fragments, Fvs, scFvs, and a Fab expression library.

The basic antibody structural unit is known to comprise a tetramer. Each tetramer is composed of two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function. In general, antibody molecules obtained from humans relate to any of the classes IgG, IgM, IgA, IgE and IgD, which differ from one another by the nature of the heavy chain present in the molecule. Certain classes have subclasses as well, such as IgG$_1$, IgG$_2$, IgG$_3$, IgG$_4$, and others. Furthermore, in humans, the light chain may be a kappa chain or a lambda chain.

The term "monoclonal antibody" (mAb) or "monoclonal antibody composition", as used herein, refers to a population of antibody molecules that contain only one molecular species of antibody molecule consisting of a unique light chain gene product and a unique heavy chain gene product. In particular, the complementarity determining regions (CDRs) of the monoclonal antibody are identical in all the molecules of the population. MAbs contain an antigen binding site capable of immunoreacting with a particular epitope of the antigen characterized by a unique binding affinity for it.

The term "antigen-binding site" or "binding portion" refers to the part of the immunoglobulin molecule that participates in antigen binding. The antigen binding site is formed by amino acid residues of the N-terminal variable ("V") regions of the heavy ("H") and light ("L") chains. Three highly divergent stretches within the V regions of the heavy and light chains, referred to as "hypervariable regions," are interposed between more conserved flanking stretches known as "framework regions," or "FRs". Thus, the term "FR" refers to amino acid sequences that are naturally found between, and adjacent to, hypervariable regions in immunoglobulins. In an antibody molecule, the three hypervariable regions of a light chain and the three hypervariable regions of a heavy chain are disposed relative to each other in three dimensional space to form an antigen-binding surface. The antigen-binding surface is complementary to the three-dimensional surface of a bound antigen, and the three hypervariable regions of each of the heavy and light chains are referred to as "complementarity-determining regions," or "CDRs." The assignment of amino acids to each domain is in accordance with the definitions of Kabat Sequences of Proteins of Immunological Interest (National Institutes of Health, Bethesda, Md. (1987 and 1991)), or Chothia & Lesk J. Mol. Biol. 196:901-917 (1987), Chothia et al. Nature 342:878-883 (1989).

As used herein, the term "epitope" includes any specific portion of an antigen targeted by an antibody, antibody fragment or other binding domain. The term "epitope" includes any protein region to which specific binding is directed. The term "epitope" includes any protein determinant capable of specific binding to an immunoglobulin or T-cell receptor. Epitopic determinants usually consist of chemically active surface groupings of molecules such as amino acids or sugar side chains and usually have specific three dimensional structural characteristics, as well as specific charge characteristics. For example, antibodies may be raised against N-terminal, central, or C-terminal peptides of a polypeptide. In addition, antibodies may be raised against linear or discontinuous epitopes of a polypeptide. An antibody is said to specifically bind an antigen when the dissociation constant is ≤1 µM; for example, in some embodiments ≤100 nM and in some embodiments, ≤10 nM and does not display binding to other proteins either closely related or distinct.

As used herein, the terms "specific binding," "immunological binding," and "immunological binding properties" refer to the non-covalent interactions of the type that occur between an immunoglobulin molecule and an antigen for which the immunoglobulin is specific. The strength, or affinity of immunological binding interactions can be expressed in terms of the dissociation constant ($K_d$) of the interaction, wherein a smaller $K_d$ represents a greater affinity. Immunological binding properties of selected polypeptides can be quantified using methods well known in the art. One such method entails measuring the rates of antigen-binding site/antigen complex formation and dissociation, wherein those rates depend on the concentrations of the complex partners, the affinity of the interaction, and geometric parameters that equally influence the rate in both directions. Thus, both the "on rate constant" ($K_{on}$) and the "off rate constant" ($K_{off}$) can be determined by calculation of the concentrations and the actual rates of association and dissociation. (See Nature 361:186-87 (1993)). The ratio of $K_{off}/K_{on}$ enables the cancellation of all parameters not related to affinity and is equal to the dissociation constant $K_d$. (See, generally, Davies et al. (1990) Annual Rev Biochem 59:439-473). An antibody of the present disclosure is said to specifically bind to EGFR, when the binding constant ($K_d$) is ≤1 µM, for example, in some embodiments ≤100 nM, in some embodiments ≤10 nM, and in some embodiments ≤100 pM to about 1 pM, as measured by assays such as radioligand binding assays or similar assays known to those skilled in the art.

The term "isolated polynucleotide" as used herein shall mean a polynucleotide of genomic, cDNA, or synthetic origin or some combination thereof, which by virtue of its origin the "isolated polynucleotide" (1) is not associated with all or a portion of a polynucleotide in which the "isolated polynucleotide" is found in nature, (2) is operably linked to a polynucleotide that it is not linked to in nature, or (3) does not occur in nature as part of a larger sequence. Polynucleotides in accordance with the disclosure include the nucleic acid molecules encoding the heavy chain immunoglobulin molecules shown herein, and nucleic acid molecules encoding the light chain immunoglobulin molecules shown herein.

The term "isolated protein" referred to herein means a protein of cDNA, recombinant RNA, or synthetic origin or some combination thereof, which by virtue of its origin, or source of derivation, the "isolated protein" (1) is not associated with proteins found in nature, (2) is free of other proteins from the same source, e.g., free of murine proteins, (3) is expressed by a cell from a different species, or (4) does not occur in nature.

The term "polypeptide" is used herein as a generic term to refer to native protein, fragments, or analogs of a polypeptide sequence. Hence, native protein fragments, and analogs are species of the polypeptide genus. Polypeptides in accordance with the disclosure comprise the heavy chain immunoglobulin molecules shown herein, and the light chain immunoglobulin molecules shown herein, as well as antibody molecules formed by combinations comprising the heavy chain immunoglobulin molecules with light chain immunoglobulin molecules, such as kappa light chain immunoglobulin molecules, and vice versa, as well as fragments and analogs thereof.

The term "naturally-occurring" as used herein as applied to an object refers to the fact that an object can be found in nature. For example, a polypeptide or polynucleotide sequence that is present in an organism (including viruses) that can be isolated from a source in nature and that has not been intentionally modified by man in the laboratory or otherwise is naturally-occurring.

The term "operably linked" as used herein refers to positions of components so described are in a relationship permitting them to function in their intended manner. A control sequence "operably linked" to a coding sequence is ligated in such a way that expression of the coding sequence is achieved under conditions compatible with the control sequences.

The term "control sequence" as used herein refers to polynucleotide sequences that are necessary to effect the expression and processing of coding sequences to which they are ligated. The nature of such control sequences differs depending upon the host organism in prokaryotes, such control sequences generally include promoter, ribosomal binding site, and transcription termination sequence in eukaryotes, generally, such control sequences include promoters and transcription termination sequence. The term "control sequences" is intended to include, at a minimum, all components whose presence is essential for expression and processing, and can also include additional components whose presence is advantageous, for example, leader sequences and fusion partner sequences. The term "polynucleotide" as referred to herein means nucleotides of at least 10 bases in length, either ribonucleotides or deoxynucleotides or a modified form of either type of nucleotide. The term includes single and double stranded forms of DNA.

The term oligonucleotide referred to herein includes naturally occurring, and modified nucleotides linked together by naturally occurring, and non-naturally occurring oligonucleotide linkages. Oligonucleotides are a polynucleotide subset generally comprising a length of 200 bases or fewer. In some embodiments, oligonucleotides are 10 to 60 bases in length, for example, in some embodiments, 12, 13, 14, 15, 16, 17, 18, 19, or 20 to 40 bases in length. Oligonucleotides are usually single stranded, e.g., for probes, although oligonucleotides may be double stranded, e.g., for use in the construction of a gene mutant. Oligonucleotides of the disclosure are either sense or antisense oligonucleotides.

The term "naturally occurring nucleotides" referred to herein includes deoxyribonucleotides and ribonucleotides. The term "modified nucleotides" referred to herein includes nucleotides with modified or substituted sugar groups and the like. The term "oligonucleotide linkages" referred to herein includes oligonucleotide linkages such as phosphorothioate, phosphorodithioate, phosphoroselerloate, phosphorodiselenoate, phosphoroanilothioate, phoshoraniladate, phosphoronmidate, and the like. See e.g., LaPlanche et al. Nucl. Acids Res. 14:9081 (1986); Stec et al. J. Am. Chem. Soc. 106:6077 (1984), Stein et al. Nucl. Acids Res. 16:3209 (1988), Zon et al. Anti Cancer Drug Design 6:539 (1991); Zon et al. Oligonucleotides and Analogues: A Practical Approach, pp. 87-108 (F. Eckstein, Ed., Oxford University Press, Oxford England (1991)); Stec et al. U.S. Pat. No. 5,151,510; Uhlmann and Peyman Chemical Reviews 90:543 (1990). An oligonucleotide can include a label for detection, if desired.

As used herein, the twenty conventional amino acids and their abbreviations follow conventional usage. See Immunology—A Synthesis (2nd Edition, E. S. Golub and D. R. Gren, Eds., Sinauer Associates, Sunderland7 Mass. (1991)). Stereoisomers (e.g., D-amino acids) of the twenty conventional amino acids, unnatural amino acids such as α-,α-disubstituted amino acids, N-alkyl amino acids, lactic acid, and other unconventional amino acids may also be suitable components for polypeptides of the present disclosure. Examples of unconventional amino acids include: 4 hydroxyproline, γ-carboxyglutamate, ε-N,N,N-trimethyllysine, ε-N-acetyllysine, O-phosphoserine, N-acetylserine, N-formylmethionine, 3-methylhistidine, 5-hydroxylysine, σ-N-methylarginine, and other similar amino acids and imino acids (e.g., 4-hydroxyproline). In the polypeptide notation used herein, the left-hand direction is the amino terminal direction and the right-hand direction is the carboxy-terminal direction, in accordance with standard usage and convention.

Similarly, unless specified otherwise, the left-hand end of single-stranded polynucleotide sequences is the 5' end the left-hand direction of double-stranded polynucleotide sequences is referred to as the 5' direction. The direction of 5' to 3' addition of nascent RNA transcripts is referred to as the transcription direction sequence regions on the DNA strand having the same sequence as the RNA and that are 5' to the 5' end of the RNA transcript are referred to as "upstream sequences", sequence regions on the DNA strand having the same sequence as the RNA and that are 3' to the 3' end of the RNA transcript are referred to as "downstream sequences".

As applied to polypeptides, the term "substantial identity" means that two peptide sequences, when optimally aligned, such as by the programs GAP or BESTFIT using default gap weights, share at least 80 percent sequence identity, for example, in some embodiments, at least 90 percent sequence identity, in some embodiments, at least 95 percent sequence identity, and in some embodiments, at least 99 percent sequence identity.

In some embodiments, residue positions that are not identical differ by conservative amino acid substitutions.

As discussed herein, minor variations in the amino acid sequences of antibodies or immunoglobulin molecules are contemplated as being encompassed by the present disclosure, providing that the variations in the amino acid sequence maintain at least 75%, for example, in some embodiments, at least 80%, 90%, 95%, and in some embodiments 99%. In particular, conservative amino acid replacements are contemplated. Conservative replacements are those that take place within a family of amino acids that are related in their side chains. Genetically encoded amino acids are generally divided into families: (1) acidic amino acids are aspartate, glutamate; (2) basic amino acids are lysine, arginine, histidine; (3) non-polar amino acids are alanine, valine, leucine, isoleucine, proline, phenylalanine, methionine, tryptophan, and (4) uncharged polar amino acids are glycine, asparagine, glutamine, cysteine, serine, threonine, tyrosine. The hydrophilic amino acids include arginine, asparagine, aspartate, glutamine, glutamate, histidine, lysine, serine, and threonine. The hydrophobic amino acids include alanine, cysteine, isoleucine, leucine, methionine, phenylalanine, proline, tryptophan, tyrosine and valine. Other families of amino acids include (i) serine and threonine, which are the aliphatic-hydroxy family; (ii) asparagine and glutamine, which are the amide containing family; (iii) alanine, valine, leucine and isoleucine, which are the aliphatic family; and (iv) phenylalanine, tryptophan, and tyrosine, which are the aromatic family. For example, it is reasonable to expect that an isolated replacement of a leucine with an isoleucine or valine, an aspartate with a glutamate, a threonine with a serine, or a similar replacement of an amino acid with a structurally related amino acid will not have a major effect on the binding or properties of the resulting molecule, especially if the replacement does not involve an amino acid within a framework site. Whether an amino acid change results in a functional peptide can readily be determined by assaying the specific activity of the polypeptide derivative. Assays are described in detail herein.

Fragments or analogs of antibodies or immunoglobulin molecules can be readily prepared by those of ordinary skill in the art. In some embodiments, amino- and carboxy-termini of fragments or analogs occur near boundaries of functional domains. Structural and functional domains can be identified by comparison of the nucleotide and/or amino acid sequence data to public or proprietary sequence databases. Computerized comparison methods are used to identify sequence motifs or predicted protein conformation domains that occur in other proteins of known structure and/or function. Methods to identify protein sequences that fold into a known three-dimensional structure are known. Bowie et al. Science 253:164 (1991). Thus, the foregoing examples demonstrate that those of skill in the art can recognize sequence motifs and structural conformations that may be used to define structural and functional domains in accordance with the disclosure.

In some embodiments, amino acid substitutions are those that: (1) reduce susceptibility to proteolysis, (2) reduce susceptibility to oxidation, (3) alter binding affinity for forming protein complexes, (4) alter binding affinities, and (4) confer or modify other physicochemical or functional properties of such analogs. Analogs can include various muteins of a sequence other than the naturally-occurring peptide sequence. For example, single or multiple amino acid substitutions (for example, conservative amino acid substitutions) may be made in the naturally-occurring sequence (for example, in the portion of the polypeptide outside the domain(s) forming intermolecular contacts. A conservative amino acid substitution should not substantially change the structural characteristics of the parent sequence (e.g., a replacement amino acid should not tend to break a helix that occurs in the parent sequence, or disrupt other types of secondary structure that characterizes the parent sequence). Examples of art-recognized polypeptide secondary and tertiary structures are described in Proteins, Structures and Molecular Principles (Creighton, Ed., W. H. Freeman and Company, New York (1984)); Introduction to Protein Structure (C. Branden and J. Tooze, eds., Garland Publishing, New York, N.Y. (1991)); and Thornton et at. Nature 354:105 (1991).

The term "polypeptide fragment" as used herein refers to a polypeptide that has an amino terminal and/or carboxy-terminal deletion and/or one or more internal deletion(s), but where the remaining amino acid sequence is identical to the corresponding positions in the naturally-occurring sequence deduced, for example, from a full length cDNA sequence. Fragments typically are at least 5, 6, 8 or 10 amino acids long, for example, in some embodiments, at least 14 amino acids long, in some embodiments, at least 20 amino acids long, usually at least 50 amino acids long, and in some embodiments, at least 70 amino acids long. The term "analog" as used herein refers to polypeptides that are comprised of a segment of at least 25 amino acids that has substantial identity to a portion of a deduced amino acid sequence and that has specific binding to EGFR, under suitable binding conditions. Typically, polypeptide analogs comprise a conservative amino acid substitution (or addition or deletion) with respect to the naturally-occurring sequence. Analogs typically are at least 20 amino acids long, for example, in some embodiments, at least 50 amino acids long or longer, and can often be as long as a full-length naturally-occurring polypeptide.

The term "agent" is used herein to denote a chemical compound, a mixture of chemical compounds, a biological macromolecule, or an extract made from biological materials.

As used herein, the terms "label" or "labeled" refers to incorporation of a detectable marker, e.g., by incorporation of a radiolabeled amino acid or attachment to a polypeptide of biotinyl moieties that can be detected by marked avidin (e.g., streptavidin containing a fluorescent marker or enzymatic activity that can be detected by optical or calorimetric methods). In certain situations, the label or marker can also be therapeutic. Various methods of labeling polypeptides and glycoproteins are known in the art and may be used. Examples of labels for polypeptides include, but are not limited to, the following: radioisotopes or radionuclides (e.g., $^3$H, $^{14}$C, $^{15}$N, $^{35}$S, $^{90}$Y, $^{99}$Tc, $^{111}$In, $^{125}$I, $^{131}$I), fluorescent labels (e.g., a fluorophore, rhodamine, lanthanide phosphors), enzymatic labels (e.g., horseradish peroxidase, p-galactosidase, luciferase, alkaline phosphatase), chemiluminescent, biotinyl groups, predetermined polypeptide epitopes recognized by a secondary reporter (e.g., leucine zipper pair sequences, binding sites for secondary antibodies, metal binding domains, epitope tags). In some embodiments, labels are attached by spacer arms of various lengths to reduce potential steric hindrance. The term "pharmaceutical agent or drug" as used herein refers to a chemical compound or composition capable of inducing a desired therapeutic effect when properly administered to a patient.

As used herein, "substantially pure" means an object species is the predominant species present (i.e., on a molar basis it is more abundant than any other individual species in the composition), and a substantially purified fraction is a composition wherein the object species comprises at least about 50 percent (on a molar basis) of all macromolecular species present.

Generally, a substantially pure composition will comprise more than about 80 percent of all macromolecular species present in the composition, for example, in some embodiments, more than about 85%, 90%, 95%, and 99%. In some embodiments, the object species is purified to essential homogeneity (contaminant species cannot be detected in the composition by conventional detection methods) wherein the composition consists essentially of a single macromolecular species.

The term patient includes human and veterinary subjects.

Other chemistry terms herein are used according to conventional usage in the art, as exemplified by The McGraw-Hill Dictionary of Chemical Terms (Parker, S., Ed., McGraw-Hill, San Francisco (1985)).

II. Multispecific Polypeptide Constructs

Provided herein is a multispecific polypeptide construct containing a first component containing an immunoglobulin Fc region and a second component comprising a CD3-binding region, wherein the first and second components are coupled by a linker, wherein the Fc region is positioned N-terminal to the CD3-binding region; and one or both of the first and second components comprises an antigen binding domain that binds a tumor associated antigen (TAA).

In some embodiments, the multispecific polypeptide construct contains in order, from N-terminus to C-terminus: an immunoglobulin Fc region; a linker; a CD3 binding region that binds CD3 (CD3ε); and an antigen binding domain that binds a tumor-associated antigen (TAA). In some embodiments, the multispecific polypeptide construct contains in order, from N-terminus to C-terminus: an antigen binding domain that binds to a tumor-associated antigen (TAA); an immunoglobulin Fc region; a linker; and a CD3 binding region that binds CD3 (CD3ε). In some embodiments, the multispecific polypeptide construct contains at least a first antigen binding domain that binds a TAA and a second antigen binding domain that binds a TAA. In some embodiments, the multispecific polypeptide construct contains, in order, from N-terminus to C-terminus: a first antigen binding domain that binds to a tumor-associated antigen (TAA); an immunoglobulin Fc region; a linker; a CD3 binding region that binds CD3 (CD3ε); and a second antigen binding domain that binds a tumor-associated antigen (TAA).

Each of the components of the multispecific polypeptide constructs of the disclosure is described in more detail below.

1. Anti-CD3 Binding Domains:

The multispecific polypeptide constructs of the disclosure include one or more copies of an anti-CD3 binding domain. The anti-CD3 binding domains of the disclosure activate T cells via engagement of CD3ε on the T cells. The anti-CD3 binding domains of the disclosure agonize, stimulate, activate, and/or otherwise augment CD3-mediated T cell activation. Biological activities of CD3 include, for example, T cell activation and other signaling through interaction between CD3 and the antigen-binding subunits of the T-Cell Receptor (TCR). For example, the anti-CD3 binding domains of the disclosure completely or partially activate T cells via engagement of CD3ε on T cells by partially or completely modulating, e.g., agonizing, stimulating, activating or otherwise augmenting CD3-mediated T cell activation.

In preferred embodiments, the anti-CD3 binding domains of the disclosure specifically bind the epsilon chain of CD3, also known as CD3ε. The anti-CD3ε binding domains of the disclosure activate T cells via engagement of CD3ε on the T cells. The anti-CD3ε binding domains of the disclosure include monoclonal antibodies, such as, for example, mammalian monoclonal antibodies, primate monoclonal antibodies, fully human monoclonal antibodies, as well as humanized monoclonal antibodies and chimeric antibodies, as well as antigen-binding fragments thereof. In some embodiments, the anti-CD3ε binding domain includes one or more copies of an antibody or an antigen-binding fragment thereof.

In some embodiments, the anti-CD3ε binding domain includes one or more copies of an antibody or an antigen-binding fragment thereof selected from the group consisting of a Fab fragment, a F(ab')$_2$ fragment, an Fv fragment, a scFv, a scAb, a dAb, a single domain heavy chain antibody, and a single domain light chain antibody. In some embodiments, the anti-CD3 binding domain includes an Fv antibody fragment that binds CD3ε (referred to herein as an anti-CD3ε Fv fragment). In some embodiments, the anti-CD3ε Fv antibody fragment is a disulfide stabilized anti-CD3 binding Fv fragment (dsFv). In some embodiments, the anti-CD3 binding domain is monovalent for binding CD3.

In some embodiments, the anti-CD3ε binding domain thereof includes a variable heavy chain (Hv) comprising the amino acid sequence of SEQ ID NO: 14. In some embodiments, the anti-CD3ε binding domain includes a variable light chain (Lv) comprising the amino acid sequence of SEQ ID NO: 15. In some embodiments, the anti-CD3ε binding domain thereof includes a variable heavy chain (Hv) comprising the amino acid sequence of SEQ ID NO: 14 and a variable light chain (Lv) comprising the amino acid sequence of SEQ ID NO: 15. In some embodiments, the anti-CD3ε binding domain thereof includes a variable heavy chain (Hv) comprising the amino acid sequence of SEQ ID NO: 44. In some embodiments, the anti-CD3ε binding domain includes a variable light chain (Lv) comprising the amino acid sequence of SEQ ID NO: 72. In some embodiments, the anti-CD3ε binding domain thereof includes a variable heavy chain (Hv) comprising the amino acid sequence of SEQ ID NO: 44 and a variable light chain (Lv) comprising the amino acid sequence of SEQ ID NO: 72. In some embodiments, the anti-CD3ε binding domain thereof includes a combination of a heavy chain variable region amino acid sequence and a light chain variable region amino acid sequence comprising an amino acid sequence selected from the group of SEQ ID NO: 32-81. In some embodiments, the anti-CD3ε binding domain thereof includes a combination of a heavy chain variable region amino acid sequence selected from the group of SEQ ID NO: 32-62 and a light chain variable region amino acid sequence comprising an amino acid sequence selected from the group of SEQ ID NO: 63-81.

In some embodiments, the anti-CD3ε binding domain thereof includes a variable heavy chain (Hv) comprising an amino acid sequence that is at least 90%, 91%, 92%, 93%, 94%, 95%, 96%, 97%, 98%, 99% or more identical to the amino acid sequence of SEQ ID NO: 14. In some embodiments, the anti-CD3ε binding domain includes a variable light chain (Lv) comprising an amino acid sequence that is at least 90%, 91%, 92%, 93%, 94%, 95%, 96%, 97%, 98%, 99% or more identical to the amino acid sequence of SEQ ID NO: 15. In some embodiments, the anti-CD3ε binding domain thereof includes a variable heavy chain (Hv) comprising an amino acid sequence that is at least 90%, 91%, 92%, 93%, 94%, 95%, 96%, 97%, 98%, 99% or more identical to the amino acid sequence of SEQ ID NO: 14 and a variable light chain (Lv) comprising an amino acid sequence that is at least 90%, 91%, 92%, 93%, 94%, 95%, 96%, 97%, 98%, 99% or more identical to the amino acid sequence of SEQ ID NO: 15.

In some embodiments, the anti-CD3ε binding domain thereof includes a variable heavy chain (Hv) comprising an amino acid sequence that is at least 90%, 91%, 92%, 93%, 94%, 95%, 96%, 97%, 98%, 99% or more identical to the amino acid sequence of SEQ ID NO: 44. In some embodiments, the anti-CD3ε binding domain includes a variable light chain (Lv) comprising an amino acid sequence that is at least 90%, 91%, 92%, 93%, 94%, 95%, 96%, 97%, 98%, 99% or more identical to the amino acid sequence of SEQ ID NO: 72. In some embodiments, the anti-CD3ε binding domain thereof includes a variable heavy chain (Hv) comprising an amino acid sequence that is at least 90%, 91%, 92%, 93%, 94%, 95%, 96%, 97%, 98%, 99% or more identical to the amino acid sequence of SEQ ID NO: 44 and a variable light chain (Lv) comprising an amino acid sequence that is at least 90%, 91%, 92%, 93%, 94%, 95%, 96%, 97%, 98%, 99% or more identical to the amino acid sequence of SEQ ID NO: 72.

In some embodiments, the anti-CD3ε Fv antibody fragment includes an amino acid sequence selected from the group of SEQ ID NO: 32-81. In some embodiments, the anti-CD3ε Fv antibody fragment includes an amino acid sequence that is at least 90%, 91%, 92%, 93%, 94%, 95%, 96%, 97%, 98%, 99% or more identical to an amino acid sequence selected from the group consisting of SEQ ID NO: 32-81. In some embodiments, the anti-CD3ε Fv antibody fragment includes a combination of an amino acid sequence selected from the group of SEQ ID NO: 32-62 and an amino acid sequence selected from the group consisting of SEQ ID NO: 63-81. In some embodiments, the anti-CD3ε Fv antibody fragment includes a combination of an amino acid sequence that is at least 90%, 91%, 92%, 93%, 94%, 95%, 96%, 97%, 98%, 99% or more identical to an amino acid sequence selected from the group consisting of SEQ ID NO: 32-62 and an amino acid sequence that is at least 90%, 91%, 92%, 93%, 94%, 95%, 96%, 97%, 98%, 99% or more identical to an amino acid sequence selected from the group consisting of SEQ ID NO: 63-81 an amino acid sequence.

In some embodiments, the anti-CD3ε binding domain includes a combination of a VH CDR1 sequence, a VH CDR2 sequence, and a VH CDR3 sequence, wherein at least one of the VH CDR1 sequence, the VH CDR2 sequence, and the VH CDR3 sequence is selected from a VH CDR1 sequence that includes at least the amino acid sequence TYAMN (SEQ ID NO: 16); a VH CD2 sequence that includes at least the amino acid sequence RIRSKYNNYATYYADSVKD (SEQ ID NO: 17); and a VH CDR3 sequence that includes at least the amino acid sequence HGNFGNSYVSWFAY (SEQ ID NO: 18).

In some embodiments, the anti-CD3ε binding domain includes a combination of a VL CDR1 sequence, a VL CDR2 sequence, and a VL CDR3 sequence, wherein at least one of the VL CDR1 sequence, the VL CDR2 sequence, and the VL CDR3 sequence is selected from a VL CDR1 sequence that includes at least the amino acid sequence RSSTGAVTTSNYAN (SEQ ID NO: 19); a VL CDR2 sequence that includes at least the amino acid sequence GTNKRAP (SEQ ID NO: 20); and a VL CDR3 sequence that includes at least the amino acid sequence ALWYSNLWV (SEQ ID NO: 21).

In some embodiments, the anti-CD3ε binding domain includes a VH CDR1 sequence that includes at least the amino acid sequence TYAMN (SEQ ID NO: 16); a VH CD2 sequence that includes at least the amino acid sequence RIRSKYNNYATYYADSVKD (SEQ ID NO: 17); a VH CDR3 sequence that includes at least the amino acid sequence HGNFGNSYVSWFAY (SEQ ID NO: 18), a VL CDR1 sequence that includes at least the amino acid sequence RSSTGAVTTSNYAN (SEQ ID NO: 19); a VL CDR2 sequence that includes at least the amino acid sequence GTNKRAP (SEQ ID NO: 20); and a VL CDR3 sequence that includes at least the amino acid sequence ALWYSNLWV (SEQ ID NO: 21).

In some embodiments, the anti-CD3ε binding domain includes a combination of a VH CDR1 sequence, a VH CDR2 sequence, and a VH CDR3 sequence, wherein at least one of the VH CDR1 sequence, the VH CDR2 sequence, and the VH CDR3 sequence is selected from a VH CDR1 sequence that includes a sequence that is at least 90%, 91%, 92%, 93%, 94%, 95%, 96%, 97%, 98%, 99% or more identical to the amino acid sequence TYAMN (SEQ ID NO: 16); a VH CD2 sequence that includes a sequence that is at least 90%, 91%, 92%, 93%, 94%, 95%, 96%, 97%, 98%, 99% or more identical to the amino acid sequence RIRSKYNNYATYYADSVKD (SEQ ID NO: 17); and a VH CDR3 sequence that includes a sequence that is at least 90%, 91%, 92%, 93%, 94%, 95%, 96%, 97%, 98%, 99% or more identical to the amino acid sequence HGNFGNSYVSWFAY (SEQ ID NO: 18).

In some embodiments, the anti-CD3ε binding domain includes a combination of a VL CDR1 sequence, a VL CDR2 sequence, and a VL CDR3 sequence, wherein at least one of the VL CDR1 sequence, the VL CDR2 sequence, and the VL CDR3 sequence is selected from a VL CDR1 sequence that includes a sequence that is at least 90%, 91%, 92%, 93%, 94%, 95%, 96%, 97%, 98%, 99% or more identical to the amino acid sequence RSSTGAVTTSNYAN (SEQ ID NO: 19); a VL CDR2 sequence that includes a sequence that is at least 90%, 91%, 92%, 93%, 94%, 95%, 96%, 97%, 98%, 99% or more identical to the amino acid sequence GTNKRAP (SEQ ID NO: 20); and a VL CDR3 sequence that includes a sequence that is at least 90%, 91%, 92%, 93%, 94%, 95%, 96%, 97%, 98%, 99% or more identical to the amino acid sequence ALWYSNLWV (SEQ ID NO: 21).

In some embodiments, the anti-CD3ε binding domain includes a VH CDR1 sequence that is at least 90%, 91%, 92%, 93%, 94%, 95%, 96%, 97%, 98%, 99% or more identical to the amino acid sequence TYAMN (SEQ ID NO: 16); a VH CD2 sequence that is at least 90%, 91%, 92%, 93%, 94%, 95%, 96%, 97%, 98%, 99% or more identical to the amino acid sequence RIRSKYNNYATYYADSVKD (SEQ ID NO: 17); a VH CDR3 sequence that is at least 90%, 91%, 92%, 93%, 94%, 95%, 96%, 97%, 98%, 99% or more identical to the amino acid sequence HGNFGNSYVSWFAY (SEQ ID NO: 18), a VL CDR1 sequence that is at least 90%, 91%, 92%, 93%, 94%, 95%, 96%, 97%, 98%, 99% or more identical to the amino acid sequence RSSTGAVTTSNYAN (SEQ ID NO: 19); a VL CDR2 sequence that is at least 90%, 91%, 92%, 93%, 94%, 95%, 96%, 97%, 98%, 99% or more identical to the amino acid sequence GTNKRAP (SEQ ID NO: 20); and a VL CDR3 sequence that is at least 90%, 91%, 92%, 93%, 94%, 95%, 96%, 97%, 98%, 99% or more identical to the amino acid sequence ALWYSNLWV (SEQ ID NO: 21).

In some embodiments, the anti-CD3ε binding domain thereof is an Fv fragment that includes a combination of heavy chain variable amino acid sequence and a light chain variable amino acid sequence. In some embodiments, the anti-CD3ε binding domain thereof is an Fv fragment that includes a combination of heavy chain variable amino acid sequence and a light chain variable amino acid sequence comprising an amino acid sequence that is at least 90%, 91%, 92%, 93%, 94%, 95%, 96%, 97%, 98%, 99% or more identical to an amino acid sequence selected from the group consisting of SEQ ID NOs: 32-81. In some embodiments, the anti-CD3ε binding domain thereof is an Fv fragment that includes a combination of heavy chain variable amino acid sequence and a light chain variable amino acid sequence comprising an amino acid sequence selected from the group consisting of SEQ ID NOs: 32-81. In some embodiments, the anti-CD3ε binding domain thereof is an Fv fragment that includes a combination of heavy chain variable amino acid sequence selected from the group of SEQ ID NO: 32-62 and an amino acid sequence selected from the group consisting of SEQ ID NO: 63-81. In some embodiments, the anti-CD3ε binding domain thereof is an Fv fragment that includes a combination of heavy chain variable amino acid sequence that is at least 90%, 91%, 92%, 93%, 94%, 95%, 96%, 97%, 98%, 99% or more identical to an amino acid sequence selected from the group consisting of SEQ ID NO: 32-62 and an amino acid sequence that is at least 90%, 91%, 92%, 93%, 94%, 95%, 96%, 97%, 98%, 99% or more identical to an amino acid sequence selected from the group consisting of SEQ ID NO: 63-81 an amino acid sequence.

2. Immunoglobulin Fc Polypeptides:

The first component of the multispecific polypeptide constructs of the disclosure includes an immunoglobulin Fc region. In some embodiments, the immunoglobulin Fc region is an IgG isotype selected from the group consisting of IgG1 isotype, IgG2 isotype, IgG3 isotype, and IgG4 subclass. In some embodiments, the Fc region is a human Fc. In some embodiments, the immunoglobulin Fc region is a polypeptide comprising an amino acid sequence selected from the group consisting of SEQ ID NOs: 1-6. In some embodiments, the immunoglobulin Fc region contains an Fc chain that is an immunologically active fragment of any of SEQ ID Nos: 1-6. In some embodiments, the immunoglobulin Fc region contains an Fc polypeptide chain that is at least 50%, 60%, 65%, 70%, 75%, 80%, 85%, 90%, 91%, 92%, 93%, 94%, 95%, 96%, 97%, 98%, or 99% identical to the amino acid sequence of any of SEQ ID NOs: 1-6 or an immunologically active fragment thereof.

In some embodiments, the multispecific polypeptide construct is a dimer formed by polypeptides, each containing an Fc. In some specific embodiments, identical or substantially identical polypeptides will be dimerized to create a homodimer. In some embodiments, the dimer is a homodimer in which the two polypeptides of the multispecific polypeptide construct are the same. In other cases, the Fc region is formed by Fc domains that are mutated or modified to promote heterodimerization in which different polypeptides can be dimerized to yield a heterodimer. Thus, in some embodiments, the dimer is a heterodimer in which two polypeptide chains of the multispecific polypeptide construct are different. Exemplary modifications to promote heterodimerization are known, including any as described below.

In general, the Fc region is responsible for effector functions, such as complement-dependent cytotoxicity (CDC) and antibody-dependent cell cytotoxicity (ADCC), in addition to the antigen-binding capacity, which is the main function of immunoglobulins. Additionally, the FcRn sequence present in the Fc region plays the role of regulating the IgG level in serum by increasing the in vivo half-life by conjugation to an in vivo FcRn receptor. In some embodiments, such functions can be altered, such as reduced or enhanced, in an Fc for use with the provided multispecific polypeptide constructs.

In some embodiments, the Fc region of the provided multispecific polypeptide constructs exhibit one or more effector functions. In some cases, the Fc region is capable of providing Fc-mediated effector functions, such as for example, ADCC (e.g., release of granzyme B by NK cells), ADCP, and/or CDC. Thus, in some embodiments in which the multispecific polypeptide constructs contain a cleavable linker, cleavage of the linker can produce two components that each have biological activity: the CD3-binding region that is able to bind and engage CD3 on a T cell and the Fc region linked to the TAA-antigen binding domain that can exhibit target-specific effector function.

In some embodiments, the Fc region includes an Fc polypeptide that is mutated or modified to alter one or more effector functions. Various examples of mutations to Fc polypeptides to alter, such as reduce, effector function are known, including any as described below. In some embodiments, reference to amino acid substitutions in an Fc region is by EU numbering by Kabat (also called Kabat numbering) unless described with reference to a specific SEQ ID NO. EU numbering is known and is according to the most recently updated IMGT Scientific Chart (IMGT®, the international ImMunoGeneTics information system®, imgt.org/IMGTScientificChart/Numbering/Hu_IGHGnber.html (created: 17 May 2001, last updated: 10 Jan. 2013) and the EU index as reported in Kabat, E. A. et al. Sequences of Proteins of Immunological interest. 5th ed. US Department of Health and Human Services, NIH publication No. 91-3242 (1991).

In some embodiments, provided multispecific polypeptide constructs that contain an Fc region that exhibits reduced effector functions, may be a desirable candidate for applications in which constrained CD3 binding is desired yet certain effector functions (such as CDC and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the multispecific polypeptide constructs and/or cleaved components thereof lack FcγR binding (hence likely lacking ADCC activity), but retains FcRn binding ability. The primary cells for mediating ADCC, NK cells, express FcγRIII only, whereas monocytes express FcγRI, FcγRII and FcγRIII. Non-limiting examples of in vitro assays to assess ADCC activity of a molecule of interest is described in U.S. Pat. No. 5,500,362 (see, e.g., Hellstrom, I. et al. *Proc. Nat'l Acad. Sci. USA* 83:7059-7063 (1986)) and Hellstrom, I et al., *Proc. Nat'l Acad. Sci. USA* 82:1499-1502 (1985); U.S. Pat. No. 5,821,337 (see Bruggemann, M. et al., *J. Exp. Med.* 166:1351-1361 (1987)). Alternatively, non-radioactive assay methods may be employed (see, for example, ACTI™ non-radioactive cytotoxicity assay for flow cytometry (CellTechnology, Inc. Mountain View, Calif; and CytoTox 96™ non-radioactive cytotoxicity assay (Promega, Madison, Wis.). Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes et al. *Proc. Nat'l Acad. Sci. USA* 95:652-656 (1998). C1q binding assays may also be carried out to confirm that the multispecific polypeptide construct or cleaved components thereof is unable to bind C1q and hence lacks CDC activity. See, e.g., C1q and C3c binding ELISA in WO 2006/029879 and WO 2005/100402. To assess complement activation, a CDC assay may be performed (see, for example, Gazzano-Santoro et al., *J. Immunol. Methods* 202:163 (1996); Cragg, M. S. et al., *Blood* 101:1045-1052 (2003); and Cragg, M. S. and M. J. Glennie, *Blood* 103:2738-2743 (2004)). FcRn binding and in vivo clearance/half-life determinations can also be performed using methods known in the art (see, e.g., Petkova, S. B. et al., *Int'l. Immunol.* 18(12):1759-1769 (2006)).

In some embodiments, the immunoglobulin Fc region or immunologically active fragment thereof is an IgG isotype. For example, the immunoglobulin Fc region of the fusion protein is of human IgG1 isotype, having an amino acid sequence:

```
                                               (SEQ ID NO: 1)
PAPELLGGPS  VFLFPPKPKD  TLMISRTPEV  TCVVVDVSHE

DPEVKFNWYV  DGVHVHNAKT  KPREEQYNST  YRVVSVLTVL

HQDWLNGKEY  KCKVSNKALP  APIEKTISKA  KGQPREPQVY

TLPPSRDELT  KNQVSLTCLV  KGFYPSDIAV  EWESNGQPEN

NYKTTPPVLD  SDGSFFLYSK  LTVDKSRWQQ  GNVFSCSVMH

EALHNHYTQK  SLSLSPGK
```

In some embodiments, the immunoglobulin Fc region or immunologically active fragment thereof comprises a human IgG1 polypeptide sequence that is at least 50%, 60%, 65%, 70%, 75%, 80%, 85%, 90%, 91%, 92%, 93%, 94%, 95%, 96%, 97%, 98%, or 99% identical to the amino acid sequence of SEQ ID NO: 1.

In some embodiments, the human IgG1 Fc region is modified to alter antibody-dependent cellular cytotoxicity (ADCC) and/or complement-dependent cytotoxicity (CDC), e.g., the amino acid modifications described in Natsume et al., 2008 Cancer Res, 68(10): 3863-72; Idusogie et al., 2001 J Immunol, 166(4): 2571-5; Moore et al., 2010 mAbs, 2(2): 181-189; Lazar et al., 2006 PNAS, 103(11): 4005-4010, Shields et al., 2001 JBC, 276(9): 6591-6604; Stavenhagen et al., 2007 Cancer Res, 67(18): 8882-8890; Stavenhagen et al., 2008 Advan. Enzyme Regul., 48: 152-164; Alegre et al, 1992 J Immunol, 148: 3461-3468; Reviewed in Kaneko and Niwa, 2011 Biodrugs, 25(1):1-11, the contents of each of which are hereby incorporated by reference in their entireties.

In some embodiments, the Fc region, such as the human IgG1 Fc region is modified to enhance ADCC activity or CDC activity. Examples of mutations that enhance ADCC include modification at Ser239 and Ile332, for example Ser239Asp and Ile332Glu (S239D, I332E). Examples of mutations that enhance CDC include modifications at Lys326 and Glu333. In some embodiments, the Fc region is modified at one or both of these positions, for example Lys326Ala and/or Glu333Ala (K326A and E333A) using the Kabat numbering system.

In some embodiments, the human IgG1 Fc region fusion proteins of the present disclosure lack or have reduced Fucose attached to the N-linked glycan-chain at N297. There are numerous ways to prevent fucosylation, including but not limited to production in a FUT8 deficient cell line; addition inhibitors to the mammalian cell culture media, for example Castanospermine; and metabolic engineering of the production cell line. In some embodiments, the human IgG1 Fc region is modified at amino acid Asn297 (Boxed, Kabat Numbering) to prevent glycosylation of the fusion protein, e.g., Asn297Ala (N297A) or Asn297Asp (N297D).

In some embodiments, the Fc region of the fusion protein is altered at one or more of the following positions to reduce Fc receptor binding: Leu 234 (L234), Leu235 (L235), Asp265 (D265), Asp270 (D270), Ser298 (S298), Asn297 (N297), Asn325 (N325) or Ala327 (A327). For example, Leu 234Ala (L234A), Leu235Ala (L235A), Asp265Asn (D265N), Asp270Asn (D270N), Ser298Asn (S298N), Asn297Ala (N297A), Asn325Glu (N325E) or Ala327Ser (A327S). In some embodiments, the Fc region of the fusion protein is modified at amino acid Leu235 (Boxed in SEQ ID NO:1 above, Kabat Numbering) to alter Fc receptor interactions, e.g., Leu235Glu (L235E) or Leu235Ala (L235A). In some embodiments, the Fc region of the fusion protein is modified at amino acid Leu234 (Boxed in SEQ ID NO:1 above, Kabat Numbering) to alter Fc receptor interactions, e.g., Leu234Ala (L234A). In some embodiments, the Fc region of the fusion protein is altered at both amino acid 234 and 235, e.g., Leu234Ala and Leu235Ala (L234A/L235A) or Leu234Val and Leu235Ala (L234V/L235A). In preferred embodiments, modifications within the Fc region reduce binding to Fc-receptor-gamma receptors while have minimal impact on binding to the neonatal Fc receptor (FcRn).

In some embodiments, the human IgG Fc region is modified to enhance FcRn binding. Examples of Fc mutations that enhance binding to FcRn are Met252Tyr, Ser254Thr, Thr256Glu (M252Y, S254T, T256E, respectively) (Kabat numbering, Dall'Acqua et al 2006, *J. Biol Chem Vol.* 281(33) 23514-23524), Met428Leu and Asn434Ser (M428L, N434S) (Zalevsky et al 2010 *Nature Biotech, Vol.* 28(2) 157-159) (EU index of Kabat et al 1991 *Sequences of Proteins of Immunological Interest*). In some embodiments, the mutated or modified Fc polypeptide includes the following mutations: Met252Tyr and Met428Leu or Met252Tyr and Met428Val (M252Y, M428L, or M252Y, M428V) using the Kabat numbering system.

In some embodiments, the Fc region of the fusion protein is lacking an amino acid at one or more of the following positions to reduce Fc receptor binding: Glu233 (E233), Leu234 (L234), or Leu235 (L235). In these embodiments, Fc deletion of these three amino acids reduces the complement protein C1q binding.

```
                                          (SEQ ID NO: 2)
PAPGGPSVFL FPPKPKDTLM ISRTPEVTCV VVDVSHEDPE

VKFNWYVDGV EVHNAKTKPR EEQYNSTYRV VSVLTVLHQD

WLNGKEYKCK VSNKALPAPI EKTISKAKGQ PREPQVYTLP

PSRDELTKNQ VSLTCLVKGF YPSDIAVEWE SNGQPENNYK

TTPPVLDSDG SFFLYSKLTV DKSRWQQGNV FSCSVMHEAL

HNHYTQKSLS LSPGK
```

In some embodiments, the Fc region of the fusion protein is altered at Gly236 (boxed in SEQ ID NO:1 above) to reduce Fc receptor binding. For example, wherein Gly236 is deleted from the fusion protein. In some embodiments, the human IgG1 Fc region is modified at amino acid Gly236 to enhance the interaction with CD32A, e.g., Gly236Ala (G236A).

In some embodiments, the human IgG1 Fc region lacks Lys447 (EU index of Kabat et al 1991 *Sequences of Proteins of Immunological Interest*).

In some embodiments, the fusion or immunologically active fragment thereof comprises a human IgG2 polypeptide sequence that is at least 50%, 60%, 65%, 70%, 75%, 80%, 85%, 90%, 91%, 92%, 93%, 94%, 95%, 96%, 97%, 98%, or 99% identical to the amino acid sequence of SEQ ID NO: 2.

In some embodiments, the immunoglobulin Fc region or immunologically active fragment of the fusion protein is of human IgG2 isotype, having an amino acid sequence:

```
                                          (SEQ ID NO: 3)
PAPPVAGPSV FLFPPKPKDT LMISRTPEVT CVVVDVSHED

PEVQFNWYVD GVEVHNAKTK PREEQFNSTF RVVSVLTVVH

QDWLNGKEYK CKVSNKGLPA PIEKTISKTK GQPREPQVYT

LPPSREEMTK NQVSLTCLVK GFYPSDISVE WESNGQPENN

YKTTPPMLDS DGSFFLYSKL TVDKSRWQQG NVFSCSVMHE

ALHNHYTQKS LSLSPGK
```

In some embodiments, the fusion or immunologically active fragment thereof comprises a human IgG2 polypeptide sequence that is at least 50%, 60%, 65%, 70%, 75%, 80%, 85%, 90%, 91%, 92%, 93%, 94%, 95%, 96%, 97%, 98%, or 99% identical to the amino acid sequence of SEQ ID NO: 3.

In some embodiments, the human IgG2 Fc region is modified at amino acid Asn297 (Boxed, to prevent to glycosylation of the antibody, e.g., Asn297Ala (N297A) or Asn297Asp (N297D). In some embodiments, the human IgG2 Fc region lacks Lys447 (EU index of Kabat et al 1991 *Sequences of Proteins of Immunological Interest*).

In some embodiments, the immunoglobulin Fc region or immunologically active fragment of the fusion protein is of human IgG3 isotype, having an amino acid sequence:

```
                                          (SEQ ID NO: 4)
PAPELLGGPS VFLFPPKPDK TLMISRTPEV TCVVVDVSHE

DPEVQFKWYV DGVEVHNAKT KPREEQYNST FRVVSVLTVL

HQDWLNGKEY KCKVSNKALP APIEKTISKT KGQPREPQVY

TLPPSREEMT KNQVSLTCLV KGFYPSDIAV EWESSGQPEN

NYNTTPPMLD SDGSFFLYSK LTVDKSRWQQ GNIFSCSVMH

EALHNRFTQK SLSLSPGK
```

In some embodiments, the antibody or immunologically active fragment thereof comprises a human IgG3 polypeptide sequence that is at least 50%, 60%, 65%, 70%, 75%, 80%, 85%, 90%, 91%, 92%, 93%, 94%, 95%, 96%, 97%, 98%, or 99% identical to the amino acid sequence of SEQ ID NO: 4.

In some embodiments, the human IgG3 Fc region is modified at amino acid Asn297 (Boxed, Kabat Numbering) to prevent to glycosylation of the antibody, e.g., Asn297Ala (N297A) or Asn297Asp (N297D). In some embodiments, the human IgG3 Fc region is modified at amino acid 435 to extend the half-life, e.g., Arg435His (R435H). In some embodiments, the human IgG3 Fc region lacks Lys447 (EU index of Kabat et al 1991 *Sequences of Proteins of Immunological Interest*).

In some embodiments, the immunoglobulin Fc region or immunologically active fragment of the fusion protein is of human IgG4 isotype, having an amino acid sequence:

```
                                          (SEQ ID NO: 5)
PAPEFLGGPS VFLFPPKPDK TLMISRTPEV TCVVVDVSQE

DPEVQFNWYV DGVEVHNAKT KPREEQFNST YRVVSVLTVL

HQDWLNGKEY KCKVSNKGLP SSIEKTISKA KGQPREPQVY

TLPPSQEEMT KNQVSLTCLV KGFYPSDIAV EWESNGQPEN

NYKTTPPVLD SDGSFFLYSR LTVDKSRWQE GNVFSCSVMH

EALHNHTQK SLSLSLGK
```

In some embodiments, the antibody or immunologically active fragment thereof comprises a human IgG4 polypeptide sequence that is at least 50%, 60%, 65%, 70%, 75%, 80%, 85%, 90%, 91%, 92%, 93%, 94%, 95%, 96%, 97%, 98%, or 99% identical to the amino acid sequence of SEQ ID NO: 5.

In some embodiments, the immunoglobulin Fc region or immunologically active fragment of the fusion protein is of human IgG4 isotype, having an amino acid sequence:

```
                                          (SEQ ID NO: 6)
PAPELLGGPS VFLFPPKPKD TLMISRTPEV TCVVVDVSQE

DPEVQFNWYV DGVEVHNAKT KPREEQFNST YRVVSVLTVL

HQDWLNGKEY KCKVSNKGLP SSIEKTISKA KGQPREPQVY
```

-continued

```
TLPPSQEEMT KNQVSLTCLV KGFYPSDIAV EWESNGQPEN

NYKTTPPVLD SDGSFFLYSR LTVDKSRWQE GNVFSCSVMH

EALHNHYTQK SLSLSLGK
```

In some embodiments, the antibody or immunologically active fragment thereof comprises a human IgG4 polypeptide sequence that is at least 50%, 60%, 65%, 70%, 75%, 80%, 85%, 90%, 91%, 92%, 93%, 94%, 95%, 96%, 97%, 98%, or 99% identical to the amino acid sequence of SEQ ID NO: 6.

In other embodiments, the human IgG4 Fc region is modified at amino acid 235 to alter Fc receptor interactions, e.g., Leu235Glu (L235E). In some embodiments, the human IgG4 Fc region is modified at amino acid Asn297 (Boxed, Kabat Numbering) to prevent to glycosylation of the antibody, e.g., Asn297Ala (N297A) or Asn297Asp (N297D). In some embodiments, the human IgG4 Fc region lacks Lys447 (EU index of Kabat et al 1991 *Sequences of Proteins of Immunological Interest*).

In some embodiments, the human IgG Fc region is modified to stabilize the homodimerization at the CH3:CH3 interface by introducing two disulfide bonds by changing Ser354 to Cys (S354C) and Tyr349 to Cys (Y349C) (S354C/Y349C).

In some embodiments, the human IgG Fc region is modified to induce heterodimerization. Various methods are known for promoting heterodimerization of complementary Fc polypeptides, see e.g. Ridgway et al, Protein Eng. 9:617-621 (1996); Merchant et al, Nat. Biotechnol. 16(7): 677-81 (1998); Moore et al. (2011) MAbs, 3:546-57; Von Kreudenstein et al. MAbs, (2013) 5:646-54; Gunasekaran et al. (2010) J. Biol. Chem., 285:19637-46; Leaver-Fay et al. (2016) Structure, 24:641-51; Ha et al. (2016) Frontiers in Immunology, 7:1; Davis et al. (2010) Protein Eng Des Sel, 23:195-202; published international PCT Appl. No. WO 1998/050431, WO 2009/089004, WO2011143545 WO 2014/067011, WO 2012/058768, WO2018027025; published U.S. patent Appl. No. US20140363426, US20150307628, US20180016354, US20150239991; and U.S. Pat. Nos. 5,731,168, 7,183,076, 9,701,759, 9,605,084, and 9,650,446. Methods to promote heterodimerization of Fc chains include mutagenesis of the Fc region, such as by including a set of "knob-into-hole" mutations or including mutations to effect electrostatic steering of the Fc to favor attractive interactions among different polypeptide chains. For example, in some embodiments, the Fc polypeptides of a heterodimer includes a mutation to alter charge polarity across the Fc dimer interface such that coexpression of electrostatically matched Fc chains support favorable attractive interactions thereby promoting desired Fc heterodimer formation, whereas unfavorable repulsive charge interactions suppress unwanted Fc homodimer formation (Guneskaran et al. (2010) JBC, 285: 19637-19646). When co-expressed in a cell, association between the chains is possible but the chains do not substantially self-associate due to charge repulsion. Other strategies for generating a heterodimeric Fc include mixing human IgG and IgA CH3 domain segments to create a complementary CH3 heterodimer, which is referred to as a SEED Fc.

In some embodiments, to promote heterodimerization both polypeptides of the Fc heterodimer contain paired or complementary amino acid modifications. Exemplary paired amino acid modification of polypeptides of an Fc fusion are set forth in Table 1.

TABLE 1

Paired amino acids of Heterodimeric Fc

| First Fc polypeptide | Second Fc Polypeptide |
|---|---|
| T366W | T366S/L368W/Y407V |
| T366W/S354C | T366S/L368A/Y407V/Y349C |
| S364H/F405A | Y349T/Y349F |
| T350V/L351Y/F405A/Y407V | T350V/T366L/K392L/T394W |
| K360D/D399M/Y407A | E345R/Q347R/T366V/K409V |
| K409D/K392D | D399K/E356K |
| K360E/K409W | Q347R/D399V/F405T |
| L360E/K409W/Y349C | Q347R/399V/F405T/S354C |
| K370E/K409W | E357N/D399V/F405T |

In some embodiments, modifications include introduction of a protuberance (knob) into a first Fc polypeptide and a cavity (hole) into a second Fc polypeptide such that the protuberance is positionable in the cavity to promote complexing of the first and second Fc-containing polypeptides. Amino acids targeted for replacement and/or modification to create protuberances or cavities in a polypeptide are typically interface amino acids that interact or contact with one or more amino acids in the interface of a second polypeptide.

In some embodiments, a first Fc polypeptide that is modified to contain protuberance (hole) amino acids include replacement of a native or original amino acid with an amino acid that has at least one side chain which projects from the interface of the first Fc polypeptide and is therefore positionable in a compensatory cavity (hole) in an adjacent interface of a second polypeptide. Most often, the replacement amino acid is one which has a larger side chain volume than the original amino acid residue. One of skill in the art knows how to determine and/or assess the properties of amino acid residues to identify those that are ideal replacement amino acids to create a protuberance. In some embodiments, the replacement residues for the formation of a protuberance are naturally occurring amino acid residues and include, for example, arginine (R), phenylalanine (F), tyrosine (Y), or tryptophan (W). In some examples, the original residue identified for replacement is an amino acid residue that has a small side chain such as, for example, alanine, asparagine, aspartic acid, glycine, serine, threonine, or valine.

In some embodiments, a second Fc polypeptide that is modified to contain a cavity (hole) is one that includes replacement of a native or original amino acid with an amino acid that has at least one side chain that is recessed from the interface of the second polypeptide and thus is able to accommodate a corresponding protuberance from the interface of a first polypeptide. Most often, the replacement amino acid is one which has a smaller side chain volume than the original amino acid residue. One of skill in the art knows how to determine and/or assess the properties of amino acid residues to identify those that are ideal replacement residues for the formation of a cavity. Generally, the replacement residues for the formation of a cavity are naturally occurring amino acids and include, for example, alanine (A), serine (S), threonine (T) and valine (V). In some examples, the original amino acid identified for replacement is an amino acid that has a large side chain such as, for example, tyrosine, arginine, phenylalanine, or tryptophan.

The CH3 interface of human IgG1, for example, involves sixteen residues on each domain located on four anti-parallel β-strands which buries 1090 A2 from each surface (see e.g., Deisenhofer et al. (1981) Biochemistry, 20:2361-2370; Miller et al., (1990) J Mol. Biol., 216, 965-973; Ridgway et al., (1996) Prot. Engin., 9: 617-621; U.S. Pat. No. 5,731, 168). Modifications of a CH3 domain to create protuberances or cavities are described, for example, in U.S. Pat. No. 5,731,168; International Patent Applications WO98/50431 and WO 2005/063816; and Ridgway et al., (1996) Prot. Engin., 9: 617-621. In some examples, modifications of a CH3 domain to create protuberances or cavities are typically targeted to residues located on the two central anti-parallel β-strands. The aim is to minimize the risk that the protuberances which are created can be accommodated by protruding into the surrounding solvent rather than being accommodated by a compensatory cavity in the partner CH3 domain.

For example, in some embodiments the heterodimeric Fc includes a polypeptide having an amino acid modification within the CH3 domain at Thr366, which when replaced with a more bulky amino acid, e.g., Try (T366W), is able to preferentially pair with a second CH3 domain having amino acid modifications to less bulky amino acids at positions Thr366, Leu368, and Tyr407, e.g., Ser, Ala and Val, respectively (T366S/L368A/Y407V). Heterodimerization via CH3 modifications can be further stabilized by the introduction of a disulfide bond, for example by changing Ser354 to Cys (S354C) and Tyr349 to Cys (Y349C) on opposite CH3 domains (Reviewed in Carter, 2001 Journal of Immunological Methods, 248: 7-15).

The resulting multispecific polypeptide constructs can be purified by any suitable method such as, for example, by affinity chromatography over Protein A or Protein G columns. Where two nucleic acid molecules encoding different polypeptides are transformed into cells, formation of homo- and heterodimers will occur. Conditions for expression can be adjusted so that heterodimer formation is favored over homodimer formation.

Techniques for recovery of heterodimers from homodimers based on a differential affinity of the heterodimers for an affinity reagent are known. In some aspects, such techniques include designing a heterodimer so that one of the Fc polypeptide chains does not bind to the affinity reagent protein A. In some cases, one of the polypeptide chain can contain one or more amino acid substitution to abrogate or reduce affinity for the protein A reagent in one of the polypeptides of the Fc heterodimer, see e.g. WO2017134440, WO2010151792, Jendeberg et al. (Jendeberg et al., (1997) J. Immunol. Methods, 201(1): 25-34. In some of these embodiments, the Fc region may be modified at the protein-A binding site on one member of the heterodimer so as to prevent protein-A binding and thereby enable more efficient purification of the heterodimeric fusion protein. An exemplary modification within this binding site is Ile253, for example Ile253Arg (I253R). In some embodiments, the modification may be H435R or H435R/Y436F. In some embodiments, an Fc polypeptide of an Fc heterodimer can contain a modification so that it is capable of binding protein A but not protein G (pA+/pG−). Exemplary pA+/pG− amino acid modifications include an Fc containing serine at position 428, serine at position 434 and optionally histidine at position 436, with reference to human IgG1 or comprising these residues at the corresponding positions in human IgG 2, 3, or 4. In some aspects, such amino acid modifications in one IgG Fc polypeptide at positions 428, 434 and optionally 436 reduces or prevents the binding of protein G, enhancing the purification of the protein.

In some embodiments, any of such modifications to confer differential affinity to an affinity reagent can be combined with any one or more other amino acid modifications described above. For example, the I253R modification may be combined with either the T366S/L368A/Y407V modifications or with the T366W modifications. The T366S/L368A/Y407V modified Fc is capable of forming homodimers as there is no steric occlusion of the dimerization interface as there is in the case of the T336W modified Fc. Therefore, in some embodiments, the I253R modification is combined with the T366S/L368A/Y407V modified Fc to disallow purification any homodimeric Fc that may have formed. Similar modifications can be employed by combining T366S/L368A/Y407V and H453R.

In some embodiments, the Fc regions of the heterodimeric molecule additionally can contain one or more other Fc mutation, such as any described above. In some embodiments, the heterodimer molecule contains an Fc region with a mutation that reduces effector function.

In some embodiments, one Fc polypeptide of a heterodimeric Fc comprises the sequence of amino acids set forth in any of SEQ ID NOS:82, 86, 94 or 96, and the other Fc polypeptide of the heterodimeric Fc contains the sequence of amino acids set forth in any of SEQ ID NOS:83, 87, 90, 92, 98 or 100. In some embodiments, one Fc polypeptide of a heterodimeric Fc comprises the sequence of amino acids set forth in any of SEQ ID NOS: 84, 88, 95 or 97 and the other Fc polypeptide of the heterodimeric Fc comprises the sequence of amino acids set forth in any of SEQ ID NOS: 85, 89, 91, 93, 99 or 101.

In some embodiments, the human IgG Fc region is modified to prevent dimerization. In these embodiments, the fusion proteins of the present disclosure are monomeric. For example modification at residue Thr366 to a charged residue, e.g. Thr366Lys, Thr366Arg, Thr366Asp, or Thr366Glu (T366K, T366R, T366D, or T366E, respectively), prevents CH3-CH3 dimerization.

In some embodiments, the Fc region of the fusion protein is altered at one or more of the following positions to reduce Fc receptor binding: Leu 234 (L234), Leu235 (L235), Asp265 (D265), Asp270 (D270), Ser298 (S298), Asn297 (N297), Asn325 (N325) or Ala327 (A327). For example, Leu 234Ala (L234A), Leu235Ala (L235A), Asp265Asn (D265N), Asp270Asn (D270N), Ser298Asn (S298N), Asn297Ala (N297A), Asn325Glu (N325E) or Ala327Ser (A327S). In preferred embodiments, modifications within the Fc region reduce binding to Fc-receptor-gamma receptors while have minimal impact on binding to the neonatal Fc receptor (FcRn).

In some embodiments, the fusion protein contains a polypeptide derived from an immunoglobulin hinge region. The hinge region can be selected from any of the human IgG subclasses. For example, the fusion protein may contain a modified IgG1 hinge having the sequence of EPKSSDKTH-TCPPC (SEQ ID NO: 7), where in the Cys220 that forms a disulfide with the C-terminal cysteine of the light chain is mutated to serine, e.g., Cys220Ser (C220S). In other embodiments, the fusion protein contains a truncated hinge having a sequence DKTHTCPPC (SEQ ID NO: 8).

In some embodiments, the fusion protein has a modified hinge from IgG4, which is modified to prevent or reduce strand exchange, e.g., Ser228Pro (S228P), having the sequence ESKYGPPCPPC (SEQ ID NO: 9). In some embodiments, the fusion protein contains linker polypeptides. In other embodiments, the fusion protein contains linker and hinge polypeptides.

3. Linkers

The provided multispecific polypeptide constructs contain a linker that joins or couples the first component containing the immunoglobulin Fc region and the second component containing the CD3 binding region. In some embodiments, the linker is positioned at the end of the C-terminal region of the Fc region, such that the Fc region is N-terminal to the CD3 binding region. Because the provided multispecific polypeptide constructs are multimers, such as dimers, the provided constructs include a linker joining the first Fc polypeptide and a first domain (e.g. VH) of the CD3 binding region of the first polypeptide and the second Fc polypeptide and second domain (e.g. VL) of the CD3 binding region of the second polypeptide. Typically, the linkers present in the first and second polypeptides of the multispecific polypeptide construct are the same. Thus, in some embodiments, each domain of the CD3 binding domain is linked via a linker, such as the same linker, to opposite polypeptides of the Fc, such as heterodimeric Fc.

Various polypeptide linkers for use in fusion proteins are known (see e.g. Chen et al. (2013) Adv. Drug. Deliv. 65:1357-1369; and International PCT publication No. WO 2014/099997, WO2000/24884; U.S. Pat. Nos. 5,258,498; 5,525,491; 5,525,491, 6,132,992).

In some embodiments, the linker is chosen so that, when the CD3 binding region is joined to the Fc region of the multispecific polypeptide conjugate, the CD3 binding region is constrained and not able to, or not substantially able to, bind or engage CD3 on the surface of a cell, e.g. T cell, upon contact of the multispecific polypeptide construct with the cell. Various assays can be employed to assess binding or engagement of CD3 by the multispecific polypeptide construct, including assays to assess T cell binding, NFAT activation using a reporter system, cytolytic T cell activity, cytokine production and/or expression of T cell activation markers. Exemplary assays are shown in the provided Examples. Typically, the linker also is one that ensures correct folding of the polypeptide construct, does not exhibit a charge that would be inconsistent with the activity or function of the linked polypeptides or form bonds or other interactions with amino acid residues in one or more of the domains that would impede or alter activity of the linked polypeptides. In some embodiment, the linker is a polypeptide linker. The polypeptide linker can be a flexible linker or a rigid linker or a combination of both. In some aspects, the linker is a short, medium or long linker. In some embodiments, the linker is up to 40 amino acids in length. In some embodiments, the linker is up to 25 amino acids in length. In some embodiments, the linker is at least or is at least about 2 amino acids in length. In some aspects, a suitable length is, e.g., a length of at least one and typically fewer than about 40 amino acid residues, such as 2-25 amino acid residues, 5-20 amino acid residues, 5-15 amino acid residues, 8-12 amino acid. In some embodiments, the linker is from or from about 2 to 24 amino acids, 2 to 20 amino acids, 2 to 18 amino acids, 2 to 14 amino acids, 2 to 12 amino acids, 2 to 10 amino acids, 2 to 8 amino acids, 2 to 6 amino acids, 6 to 24 amino acids, 6 to 20 amino acids, 6 to 18 amino acids, 6 to 14 amino acids, 6 to 12 amino acids, 6 to 10 amino acids, 6 to 8 amino acids, 8 to 24 amino acids, 8 to 20 amino acids, 8 to 18 amino acids, 8 to 14 amino acids, 8 to 12 amino acids, 8 to 10 amino acids, 10 to 24 amino acids, 10 to 20 amino acids, 10 to 18 amino acids, 10 to 14 amino acids, 10 to 12 amino acids, 12 to 24 amino acids, 12 to 20 amino acids, 12 to 18 amino acids, 12 to 14 amino acids, 14 to 24 amino acids, 14 to 20 amino acids, 14 to 18 amino acids, 18 to 24 amino acids, 18 to 20 amino acids or 20 to 24 amino acids. In some embodiments, the linker is 2, 3, 4, 5, 6, 7, 8, 9, 10, 11, 12, 13, 14, 15, 16, 17, 18, 19 or 20 amino acids in length.

In certain aspects, the longer the linker length, the greater the CD3 binding when the multispecific polypeptide conjugate is bounds to its antigen, e.g. TAA. Thus, in some aspects, the linker is greater than 12 amino acids in length, such as greater than 13, 14, 15, 16, 17 or 18 amino acids in length. In some embodiments, the linker is 12 to 40 amino acids in length, 12 to 30 amino acids, 12 to 24 amino acids, 12 to 18 acids, 12 to 15 amino acids, 15 to 40 amino acids, 15 to 30 amino acids, 15 to 24 amino acids, 15 to 18 amino acids, 18 to 40 amino acids, 18 to 30 amino acids, 18 to 24 amino acids, 24 to 40 amino acids, 24 to 30 amino acids or 30 to 40 amino acids.

The linkers can be naturally-occurring, synthetic or a combination of both. Particularly suitable linker polypeptides predominantly include amino acid residues selected from Glycine (Gly), Serine (Ser), Alanine (Ala), and Threonine (Thr). For example, the linker may contain at least 75% (calculated on the basis of the total number of residues present in the peptide linker), such as at least 80%, at least 85%, or at least 90% of amino acid residues selected from Gly, Ser, Ala, and Thr. The linker may also consist of Gly, Ser, Ala and/or Thr residues only. In some embodiments, the linker contains 1-25 glycine residues, 5-20 glycine residues, 5-15 glycine residues, or 8-12 glycine residues. In some aspects, suitable peptide linkers typically contain at least 50% glycine residues, such as at least 75% glycine residues. In some embodiments, a peptide linker comprises glycine residues only. In some embodiments, a peptide linker comprises glycine and serine residues only.

In some embodiments, these linkers are composed predominately of the amino acids Glycine and Serine, denoted as GS-linkers herein. In some embodiments, the linker contains (GGS)n, wherein n is 1 to 10, such as 1 to 5, for example 1 to 3, such as GGS(GGS)n (SEQ ID NO:171), wherein n is 0 to 10. In particular embodiments, the linker contains the sequence (GGGGS)n (SEQ ID NO: 173), wherein n is 1 to 10 or n is 1 to 5, such as 1 to 3. In further embodiments, the linker contains (GGGGGS)n (SEQ ID NO:172), wherein n is 1 to 4, such as 1 to 3. The linker can include combinations of any of the above, such as repeats of 2, 3, 4, or 5 GS, GGS, GGGGS, and/or GGGGGS linkers may be combined. In some embodiments, such a linker is 2, 3, 4, 5, 6, 7, 8, 9, 10, 11, 12, 13, 14, 15, 16, 17, 18 or 19 amino acids in length.

In some embodiments, the linker is (in one-letter amino acid code): GGS, GGGGS (SEQ ID NO: 149), or GGGGGS (SEQ ID NO: 135). In some embodiments, the GS-linker comprises an amino acid sequence of GGSGGS, i.e., (GGS)$_2$ (SEQ ID NO: 10); GGSGGSGGS, i.e., (GGS)$_3$ (SEQ ID NO: 11); GGSGGSGGSGGS, i.e., (GGS)$_4$ (SEQ ID NO: 12); GGSGGSGGSGGSGGS, i.e., (GGS)$_5$ (SEQ ID NO: 13); GGGGSGGGGSGGGGS, i.e., (G5S)$_3$ (SEQ ID NO: 119), GGSGGGGSGGGGSGGGGS (SEQ ID NO: 147) and GGGGSGGGGSGGGGS (SEQ ID NO:170). In some embodiments, the linker is GGGG (SEQ ID NO:103). In some of any of the above examples, serine can be replaced with alanine (e.g., (Gly4Ala) or (Gly3Ala)).

In some embodiments, the linker includes a peptide linker having the amino acid sequence Gly$_x$Xaa-Gly$_y$-Xaa-Gly$_n$ (SEQ ID NO:174), wherein each Xaa is independently selected from Alanine (Ala), Valine (Val), Leucine (Leu), Isoleucine (Ile), Methionine (Met), Phenylalanine (Phe), Tryptophan (Trp), Proline (Pro), Glycine (Gly), Serine (Ser), Threonine (Thr), Cysteine (Cys), Tyrosine (Tyr), Asparagine (Asn), Glutamine (Gln), Lysine (Lys), Arginine (Arg), Histidine (His), Aspartate (Asp), and Glutamate (Glu), and wherein x, y, and z are each integers in the range from 1-5. In some embodiments, each Xaa is independently selected from the group consisting of Ser, Ala, and Thr. In a specific variation, each of x, y, and z is equal to 3 (thereby yielding a peptide linker having the amino acid sequence Gly-Gly-Gly-Xaa-Gly-Gly-Gly-Xaa-Gly-Gly-Gly (SEQ ID NO:175), wherein each Xaa is selected as above.

In some embodiments, the linker is serine-rich linkers based on the repetition of a (SSSSG)y (SEQ ID NO:185) motif where y is at least 1, though y can be 2, 3, 4, 5, 6, 7, 8 and 9.

In some cases, it may be desirable to provide some rigidity into the peptide linker. This may be accomplished by including proline residues in the amino acid sequence of the peptide linker. Thus, in some embodiments, a linker comprises at least one proline residue in the amino acid sequence of the peptide linker. For example, a peptide linker can have an amino acid sequence wherein at least 25% (e.g., at least 50% or at least 75%) of the amino acid residues are proline residues. In one particular embodiment, the peptide linker comprises proline residues only.

In some aspects, a peptide linker comprises at least one cysteine residue, such as one cysteine residue. For example, in some embodiments, a linker comprises at least one cysteine residue and amino acid residues selected from the group consisting of Gly, Ser, Ala, and Thr. In some such embodiments, a linker comprises glycine residues and cysteine residues, such as glycine residues and cysteine residues only. Typically, only one cysteine residue will be included per peptide linker. One example of a specific linker comprising a cysteine residue includes a peptide linker having the amino acid sequence $Gly_m$-Cys-$Gly_n$, wherein n and m are each integers from 1-12, e.g., from 3-9, from 4-8, or from 4-7. In a specific variation, such a peptide linker has the amino acid sequence GGGGG-C-GGGGG (SEQ ID NO:177).

In some embodiments, the linker of the fusion protein is a structured or constrained linker. In particular embodiments, the structured linker contains the sequence (AP)n or (EAAAK)n (SEQ ID NO:178), wherein n is 2 to 20, preferably 4 to 10, including but not limited to, AS-(AP)n-GT (SEQ ID NO:179) or AS-(EAAAK)n-GT (SEQ ID NO:180), wherein n is 2 to 20, such as 2, 3, 4, 5, 6, 7, 8, 9, 10, 11, 12, 13, 14 or 15. In other embodiments, the linker comprises the sequences (GGGGA)n (SEQ ID NO:181), (PGGGS)n (SEQ ID NO:182), (AGGGS)n (SEQ ID NO:183) or GGS-(EGKSSGSGSESKST)n-GGS (SEQ ID NO:184), wherein n is 2 to 20. In some embodiments, the linker is SSSASASSA (SEQ ID NO:186), GSPGSPG (SEQ ID NO:187), or ATTTGSSPGPT (SEQ ID NO:176). In some embodiments, such linkers, by virtue of their structure, may be more resistant to proteolytic degradation, thereby offering an advantage when injected in vivo.

In some embodiments, the linker is not a cleavable linker, also called non-cleavable linker. In some embodiments, the linker is not a cleavable by a protease. In some embodiments, a linker that is not a cleavable linker or that is not cleavable by a protease is one that is generally stable for in vivo delivery or recombinant production. In some aspects, a linker that is not cleavable by a protease includes those that do not contain at least one peptide bond which preferably lies within a cleavable peptide sequence or recognition site of a protease. In particular embodiments, a non-cleavable linker is not a target substrate for a protease, such that it is not preferentially or specifically cleaved by a protease compared to a linker that contains a substrate recognition site for the same protease.

In some embodiments, the linker is a cleavable linker. In some aspects, a cleavable linker is a linker that includes a sequence that is a substrate for a protease due to the presence of at least one bond that can be broken under physiological conditions. In some cases, a cleavable linker is susceptible to or sensitive to cleavage under specific conditions that exist in vivo, such as following exposure to an extracellular protease, including those present in cellular environments in vivo. In some cases, the protease may be present in a particular physiological microenvironment, such as the tumor microenvironment, thereby restricting the sites at which cleavage may occur.

A protease typically exhibits specificity or preference for cleavage of a particular target substrate compared to another non-target substrate. Such a degree of specificity can be determined based on the rate constant of cleavage of a sequence, e.g. linker, which is a measure of preference of a protease for its substrate and the efficiency of the enzyme. Any method to determine the rate of increase of cleavage over time in the presence of various concentrations of substrate can be used to calculate the specificity constant. For example, a substrate is linked to a fluorogenic moiety, which is released upon cleavage by a protease. By determining the rate of cleavage at different protease concentrations the specificity constant for cleavage ($k_{on}/K_m$) can be determined for a particular protease towards a particular linker. In some embodiments, a cleavable linker is a linker that is capable of being specifically cleaved by a protease at a rate of about at least $1\times10^4$ $M^{-1}S^{-1}$, or at least $5\times10^4$ $M^{-1}S$, at least $10\times10^4$ $M^{-1}S$. at least $10\times10^5$ $M^{-1}S$ or more.

Cleavable Linker

In some embodiments, the multispecific polypeptide constructs of the disclosure include a cleavable linker that joins the first and second components. In some embodiments, the cleavable linker includes an amino acid sequence that can serve as a substrate for a protease, usually an extracellular protease. For example, the cleavable linker may include a cleavage sequence containing at least one peptide bond which preferably lies within a cleavable peptide sequence of a protease. Suitable proteases include, for example, matrix metalloproteases (MMP), cysteine proteases, serine proteases and plasmin activators, which are formed or activated in intensified manner in diseases such as rheumatoid arthritis or cancer, leading to excessive tissue degradation, inflammations and metastasis. In particular embodiments, the protease is a protease that is produced by a tumor, an activated immune effector cell (e.g. a T cell or a NK cell), or a cell in a tumor microenvironment. In some embodiments, the protease is a granzyme B, a matriptase or an MMP, such as MMP-2.

The cleavable linker may be selected based on a protease that is produced by a tumor that is in proximity to cells that express the target and/or produced by a tumor that is co-localized in tissue with the desired target of the multispecific polypeptide constructs. There are reports in the literature of increased levels of proteases having known substrates in a number of cancers, e.g., solid tumors. See, e.g., La Rocca et al, (2004) British J. of Cancer 90(7): 1414-1421.

In some embodiments, the cleavable linker that joins the first and second component multispecific polypeptide construct is cleaved by a protease produced by an immune effector cell that is activated by one of the components. For example, multispecific polypeptide constructs that encompass an effector enabled or enhanced IgG Fc region are capable of eliciting ADCC when engaged with the target antigen. Central to ADCC is the release of granzyme B and perforin from the effector cells, namely NK cells and cytotoxic T-cells. Upon release granzyme B enters the target cell in a perforin dependent manner wherein it mediates apoptosis. Importantly, granzyme B is active within the extracellular synapse between the effector cell and the target cell. In some embodiments, the cleavable linker that joins the first and second component multispecific polypeptide construct is cleaved by granzyme B. Granzyme B is released during effector cell activation mediated by one of the components of the multispecific polypeptide construct. In some embodiments, granzyme B and other proteases can be produced by immune effector cells, including activated T cells or NK cells. In some embodiments, activation of T cells by CD3 engagement upon binding of a TAA by a multispecific polypeptide construct may release such proteases, which then can cleave a specific cleavable linker thereby potentiating or increasing activity of the CD3 binding molecule to engage CD3. In some embodiments, the cleavage can amplify or increase the activity achieved by the multispecific construct when bound to TAA in an uncleaved state.

Exemplary substrates include but are not limited to substrates cleavable by one or more of the following enzymes or proteases: ADAMS, ADAMTS, e.g. ADAM8; ADAM9; ADAM10; ADAM12; ADAM15; ADAM17/TACE; ADAMDEC1; ADAMTS1; ADAMTS4; ADAMTS5; aspartate proteases, e.g., BACE or Renin; aspartic cathepsins, e.g., Cathepsin D or Cathepsin E; Caspases, e.g., Caspase 1, Caspase 2, Caspase 3, Caspase 4, Caspase 5, Caspase 6, Caspase 7, Caspase 8, Caspase 9, Caspase 10, or Caspase 14; cysteine cathepsins, e.g., Cathepsin B, Cathepsin C, Cathepsin K, Cathepsin L, Cathepsin S, Cathepsin V/L2, Cathepsin X/Z/P; Cysteine proteinases, e.g., Cruzipain; Legumain; Otubain-2; KLKs, e.g., KLK4, KLK5, KLK6, KLK7, KLK8, KLK10, KLK11, KLK13, or KLK14; Metallo proteinases, e.g., Meprin; Neprilysin; PSMA; BMP-1; MMPs, e.g., MMP1, MMP2, MMP3, MMP7, MMP8, MMP9, MMP10, MMP11, MMP12, MMP13, MMP14, MMP15, MMP16, MMP17, MMP19, MMP20, MMP23, MMP24, MMP26, or MMP27, serine proteases, e.g., activated protein C, Cathepsin A, Cathepsin G, Chymase, coagulation factor proteases (e.g., FVIIa, FIXa, FXa, FXIa, FXIIa), Elastase, granzyme B, Guanidinobenzoatase, HtrA1, Human Neutrophil Elastase, Lactoferrin, Marapsin, NS3/4A, PACE4, Plasmin, PSA, tPA, Thrombin, Tryptase, uPA; Type II Transmembrane Serine Proteases (TTSPs), e.g., DESC1, DPP-4, FAP, Hepsin, Matriptase-2, Matriptase, TMPRSS2, TMPRSS3, or TMPRSS4; and any combination thereof.

In some embodiments, the cleavable linker is cleaved by multiple proteases, e.g., 2 or more proteases, 3 or more proteases, 4 or more proteases, and so on.

In some embodiments, the cleavable linker is selected for use with a specific protease, for example a protease that is known to be produced by a tumor that is in proximity to cells that express the target and/or produced by a tumor that is co-localized with the target of the multispecific polypeptide construct.

In some embodiments, the cleavable linker contains a substrate recognition site or cleavage site for a particular protease, which is the sequence recognized by the active site of a protease that is cleaved by a protease. Typically, for example, for a serine protease, a cleavage sequence is made up of the P1-P4 and P1'-P4' amino acids in a substrate, where cleavage occurs after the P1 position. Typically, a cleavage sequence for a serine protease is six residues in length to match the extended substrate specificity of many proteases, but can be longer or shorter depending upon the protease. Typically, the cleavable linker includes a P1-P1' scissile bond sequence that is recognized by a protease. In some aspects, the cleavable linker is engineered to introduce a peptide bond able to be cleaved by a specific protease, for example by introducing a substrate recognition site sequence or cleavage sequence of the protease.

In some embodiments, the cleavable linker includes a combination of two or more substrate sequences. In some embodiments, each substrate sequence is cleaved by the same protease. In some embodiments, at least two of the substrate sequences are cleaved by different proteases. In some embodiments, the cleavable linker comprises an amino acid that is a substrate for granzyme B. In some embodiments, a granzyme B cleavable linker contains an amino acid sequence having the general formula P4 P3 P2 P1 ↓ P1' (SEQ ID NO: 150), wherein P4 is amino acid I, L, Y, M, F, V, or A; P3 is amino acid A, G, S, V, E, D, Q, N, or Y; P2 is amino acid H, P, A, V, G, S, or T; P1 is amino acid D or E; and P1' is amino acid I, L, Y, M, F, V, T, S, G or A. In some embodiments, a granzyme B cleavable linker contains an amino acid sequence having the general formula P4 P3 P2 P1 ↓ P1' (SEQ ID NO: 151), wherein P4 is amino acid I or L; P3 is amino acid E; P2 is amino acid P or A; P1 is amino acid D; and P1' is amino acid I, V, T, S, or G.

In some embodiments, the substrate for granzyme B comprises the amino acid sequence LEAD (SEQ ID NO: 22), LEPG (SEQ ID NO: 142), or LEAE (SEQ ID NO:143). In some embodiments, the cleavable linker contains the amino acid sequence the cleavable linker comprises the amino acid sequence IEPDI (SEQ ID NO:136), LEPDG (SEQ ID NO:152, LEADT (SEQ ID NO:137), IEPDG (SEQ ID NO:138), IEPDV (SEQ ID NO:139), IEPDS (SEQ ID NO:140), IEPDT (SEQ ID NO:141), IEPDP (SEQ ID NO:144), LEPDG (SEQ ID NO:152) or LEADG (SEQ ID NO:153).

In some embodiments, the cleavable linker comprises an amino acid that is a substrate for matriptase. In some embodiments, the cleavable linker comprises the sequence P4QAR↓(A/V) (SEQ ID NO: 154), wherein P4 is any amino acid. In some embodiments, the cleavable linker comprises the sequence RQAR(A/V) (SEQ ID NO: 155). In some embodiments, the substrate for matriptase comprises the amino acid sequence RQAR (SEQ ID NO: 23). In some embodiments, the cleavable linker comprises the amino acid sequence RQARV (SEQ ID NO: 156).

In some embodiments, the cleavable linker comprises an amino acid that is a substrate for one or more matrix metalloproteases (MMPs). In some embodiments, the MMP is MMP-2. In some embodiments, the cleavable linker contains. the general formula P3 P2 P1 ↓ P1' (SEQ ID NO: 157), wherein P3 is P, V or A; P2 is Q or D; P1 is A or N; and P1' is L, I or M. In some embodiments, the cleavable linker contains the general formula P3 P2 P1 ↓ P1' (SEQ ID NO: 158), wherein P3 is P; P2 is Q or D; P1 is A or N; and P1' is L or I. In some embodiments, the substrate for MMP comprises the amino acid sequence PAGL (SEQ ID NO: 24).

In some embodiments, the cleavable linker comprises a combination of an amino acid sequence that is a substrate for granzyme B and an amino acid sequence that is a substrate for matriptase. In some embodiments, the cleavable linker comprises a combination of the amino acid sequence LEAD (SEQ ID NO: 22) and the amino acid sequence RQAR (SEQ ID NO: 23).

In some embodiments, the cleavable linker comprises a combination of an amino acid sequence that is a substrate for granzyme B and an amino acid sequence that is a substrate for MMP. In some embodiments, the cleavable linker comprises a combination of the amino acid sequence LEAD (SEQ ID NO: 22) and the amino acid sequence PAGL (SEQ ID NO: 24).

In some embodiments, the cleavable linker comprises a combination of an amino acid sequence that is a substrate for matriptase and an amino acid sequence that is a substrate for MMP. In some embodiments, the cleavable linker comprises a combination of the amino acid sequence RQAR (SEQ ID NO: 23) and the amino acid sequence PAGL (SEQ ID NO: 24).

In some embodiments, the cleavable linker comprises a combination of an amino acid sequence that is a substrate for granzyme B, an amino acid sequence that is a substrate for matriptase, and an amino acid sequence that is a substrate for MMP. In some embodiments, the cleavable linker comprises a combination of an amino acid sequence that is a substrate for granzyme B and an amino acid sequence that is a substrate for MMP. In some embodiments, the cleavable linker comprises a combination of the amino acid sequence LEAD (SEQ ID NO: 22), the amino acid sequence RQAR (SEQ ID NO: 23), and the amino acid sequence PAGL (SEQ ID NO: 24).

The cleavable linker can include any known linkers. Examples of cleavable linkers are described in Be'liveau et al. (2009) FEBS Journal, 276; U.S. published application Nos. US20160194399; US20150079088; US20170204139; US20160289324; US20160122425; US20150087810; US20170081397; U.S. Pat. No. 9,644,016.

In some embodiments, the cleavable linker comprises an amino acid sequence selected from the group consisting of TGLEADGSPAGLGRQARVG (SEQ ID NO: 25); TGLEADGSRQARVGPAGLG (SEQ ID NO: 26); TGSPAGLEADGSRQARVGS (SEQ ID NO: 27); TGPAGLGLEADGSRQARVG (SEQ ID NO: 28); TGRQARVGLEADGSPAGLG (SEQ ID NO: 29); TGSRQARVGPAGLEADGS (SEQ ID NO: 30); and TGPAGLGSRQARVGLEADGS (SEQ ID NO: 31); GPAGLGLEPDGSRQARVG (SEQ ID NO: 104); GGSGGGGIEPDIGGSGGS (SEQ ID NO: 105); GGSGGGGLEADTGGSGGS (SEQ ID NO: 106); GSIEPDIGS (SEQ ID NO: 107); GSLEADTGS (SEQ ID NO: 108); GGSGGGGIEPDGGGSGGS (SEQ ID NO: 109); GGSGGGGIEPDVGGSGGS (SEQ ID NO: 110); GGSGGGGIEPDSGGSGGS (SEQ ID NO: 111); GGSGGGGIEPDTGGSGGS (SEQ ID NO: 112); GGGSLEPDGSGS (SEQ ID NO: 113); and GPAGLGLEADGSRQARVG (SEQ ID NO: 114), GGEGGGGSGGSGGGS (SEQ ID NO: 115); GSSAGSEAGGSGQAGVGS (SEQ ID NO: 116); GGSGGGGLEAEGSGGGGS (SEQ ID NO: 117); GGSGGGGIEPDPGGSGGS(SEQ ID NO: 118); TGGSGGGGIEPDIGGSGGS (SEQ ID NO: 148).

4. Antigen Binding Domains:

The multispecific polypeptide constructs of the present disclosure include at least one antigen binding domain, such as at least a first antigen binding domain and a second antigen binding domain. In some aspects, the antigen binding domain, or independently each of the antigen binding domains, is selected from an antibody or antigen binding fragment, a natural cognate binding partner, an Anticalin (engineered lipocalin), a Darpin, a Fynomer, a Centyrin (engineered fibroneticin III domain), a cystine-knot domain, an Affilin, an Affibody, or an engineered CH3 domain. In some embodiments, the natural cognate binding partner comprises an extracellular domain or binding fragment thereof of the native cognate binding partner of the TAA, or a variant thereof that exhibits binding activity to the TAA.

In some embodiments, the antigen binding domain, or independently each of the antigen binding domains, such as the first antigen-binding domain and the second antigen binding domains, includes one or more copies of an antibody or an antigen-binding fragment thereof. In some embodiments, the antigen binding domain or independently each of the antigen binding domains, such as the first antigen-binding domain and the second antigen binding domains, includes one or more copies of an antibody or an antigen-binding fragment thereof selected from the group consisting of a Fab fragment, a F(ab')$_2$ fragment, an Fv fragment, a scFv, a scAb, a dAb, a single domain heavy chain antibody, and a single domain light chain antibody. In some embodiments, the antigen binding domain or independently each of the antigen binding domains, such as the first antigen-binding domain and the second antigen binding domains, includes one or more single domain antibody (sdAb) fragments, for example $V_H$H, $V_{NAR}$, engineered $V_H$ or $V_K$ domains. $V_H$Hs can be generated from natural camelid heavy chain only antibodies, genetically modified rodents that produce heavy chain only antibodies, or naïve/synthetic camelid or humanized camelid single domain antibody libraries. $V_{NAR}$s can be generated from cartilaginous fish heavy chain only antibodies. Various methods have been implemented to generate monomeric sdAbs from conventionally heterodimeric $V_H$ and $V_K$ domains, including interface engineering and selection of specific germline families. In some embodiments, the antigen binding domain or independently each of the antigen binding domains, such as the first antigen-binding domain and/or the second antigen binding domains, of the multispecific polypeptide constructs contains VH and VL sequences assembled as FABs or scFvs. In some embodiments, the antigen binding domain or independently each of the antigen binding domains, such as the first antigen-binding domain and/or the second antigen binding domains, of the multispecific polypeptide constructs contains binding domains as single domain antibodies (sdAbs).

In some embodiments, the antigen binding domain, or independently each of the antigen binding domains, is or includes an extracellular domain or binding fragment thereof of the native cognate binding partner of the TAA, or a variant thereof that exhibits binding activity to the TAA.

In some embodiments, the antigen binding domain or independently each of the antigen binding domains, such as the first antigen-binding domain and the second antigen binding domains, bind the same antigen. In some embodiments, the antigen binding domain or independently each of the antigen binding domains, such as the first antigen-binding domain and the second antigen binding domains, bind a different antigen. In some embodiments, the antigen binding domain or independently each of the antigen binding domains, such as the first antigen-binding domain and the second antigen binding domains, bind the same tumor associated antigen (TAA). In some embodiments, the antigen binding domain or independently each of the antigen binding domains, such as the first antigen-binding domain and the second antigen binding domains, bind a different TAA. In some embodiments, the antigen binding domain or independently each of the antigen binding domains, such as the first antigen-binding domain and the second antigen binding domains bind a different epitope on the same TAA. In some embodiments, the antigen binding domain or independently each of the antigen binding domains, such as the first antigen-binding domain and the second antigen binding domains, bind the same epitope on the same TAA.

In some embodiments, the antigen binding domain, or independently each of the antigen binding domains that binds TAA results in monovalent, bivalent, trivalent, or tetravalent binding to the TAA.

In some embodiments, the TAA is selected from the group consisting of 1-92-LFA-3, 5T4, Alpha-4 integrin, Alpha-V integrin, alpha4beta1 integrin, alpha4beta7 integrin, AGR2, Anti-Lewis-Y, Apelin J receptor, APRIL, B7-H3, B7-H4, BAFF, BTLA, C5 complement, C-242, CA9, CA19-9, (Lewis a), Carbonic anhydrase 9, CD2, CD3, CD6, CD9, CD11a, CD19, CD20, CD22, CD24, CD25, CD27, CD28, CD30, CD33, CD38, CD40, CD40L, CD41, CD44, CD44v6, CD47, CD51, CD52, CD56, CD64, CD70, CD71, CD74, CD80, CD81, CD86, CD95, CD117, CD123, CD125, CD132, (IL-2RG), CD133, CD137, CD138, CD166, CD172A, CD248, CDH6, CEACAM5 (CEA), CEACAM6 (NCA-90), CLAUDIN-3, CLAUDIN-4, cMet, Collagen, Cripto, CSFR, CSFR-1, CTLA-4, CTGF, CXCL10, CXCL13, CXCR1, CXCR2, CXCR4, CYR61, DL44, DLK1, DLL3, DLL4, DPP-4, DSG1, EDA, EDB, EGFR, EGFRviii, Endothelin B receptor (ETBR), ENPP3, EpCAM, EPHA2, EPHB2, ERBB3, F protein of RSV, FAP, FGF-2, FGF8, FGFR1, FGFR2, FGFR3, FGFR4, FLT-3, Folate receptor alpha (FRα), GAL3ST1, G-CSF, G-CSFR, GD2, GITR, GLUT1, GLUT4, GM-CSF, GM-CSFR, GP IIb/IIIa receptors, Gp130, GPIIB/IIIA, GPNMB, GRP78, HER2/neu, HER3, HER4, HGF, hGH, HVEM, Hyaluronidase, ICOS, IFNalpha, IFNbeta, IFNgamma, IgE, IgE Receptor (FceRI), IGF, IGF1R, IL1B, IL1R, IL2, IL11, IL12, IL12p40, IL-12R, IL-12Rbeta1, IL13, IL13R, IL15, IL17, IL18, IL21, IL23, IL23R, IL27/IL27R (wsx1), IL29, IL-31R, IL31/IL31R, IL2R, IL4, IL4R, IL6, IL6R, Insulin Receptor, Jagged Ligands, Jagged 1, Jagged 2, KISS1-R, LAG-3, LIF-R, Lewis X, LIGHT, LRP4, LRRC26, Ly6G6D, LyPD1, MCSP, Mesothelin, MRP4, MUC1, Mucin-16 (MUC16, CA-125), Na/K ATPase, NGF, Nicastrin, Notch Receptors, Notch 1, Notch 2, Notch 3, Notch 4, NOV, OSM-R, OX-40, PAR2, PDGF-AA, PDGF-BB, PDGFRalpha, PDGFRbeta, PD-1, PD-L1, PD-L2, Phosphatidylserine, P1GF, PSCA, PSMA, PSGR, RAAG12, RAGE, SLC44A4, Sphingosine 1 Phosphate, STEAP1, STEAP2, TAG-72, TAPA1, TEM-8, TGFbeta, TIGIT, TIM-3, TLR2, TLR4, TLR6, TLR7, TLR8, TLR9, TMEM31, TNFalpha, TNFR, TNFRS12A, TRAIL-R1, TRAIL-R2, Transferrin, Transferrin receptor, TRK-A, TRK-B, uPAR, VAP1, VCAM-1, VEGF, VEGF-A, VEGF-B, VEGF-C, VEGF-D, VEGFR1, VEGFR2, VEGFR3, VISTA, WISP-1, WISP-2, and WISP-3.

In some embodiments, at least one antigen binding domain, or independently each antigen binding domain, binds the tumor associated antigen (TAA) folate receptor alpha (FRα). For example, the antigen binding domain contains the binding domain as an sdAb that binds FRα. Exemplary FRα-binding sdAbs are set forth in SEQ ID NOS: 120, 121, and 122.

In some embodiments, at least one antigen binding domain, or independently each antigen binding domain, binds the tumor associated antigen (TAA) cMET. For example, the antigen binding domain contains the binding domain as a sdAb that binds cMET. An exemplary cMET-binding sdAb is set forth in SEQ ID NO: 123 (U.S. Pat. No. 9,346,884).

In some embodiments, at least one antigen binding domain, or independently each antigen binding domain, binds the tumor associated antigen (TAA) B7H3. For example, the antigen binding domain contains the binding domain as an scFv that binds B7H3. An exemplary B7H3-binding scFv is set forth in SEQ ID NO: 124. In some embodiments, the antigen binding domain is or contains a Fab antibody fragment comprising a VH-CH1 (Fd) and LC. An exemplary B7H3 Fd is set forth in SEQ ID NO: 127 and an exemplary B7H3 LC is set forth in SEQ ID NO: 128 (PCT Publication No, WO2017/030926).

In some embodiments, at least one antigen binding domain, or independently each antigen binding domain, binds the tumor associated antigen (TAA) CD20. For example, the antigen binding domain contains the binding domain as an scFv that binds CD20. Exemplary CD20-binding scFvs are set forth in SEQ ID NO: 125, 189, and 190 (U.S. Pub. No. US 2005/0123546).

In some embodiments, at least one antigen binding domain, or independently each antigen binding domain, binds the tumor associated antigen (TAA) DLL3. For example, the antigen binding domain contains the binding domain as an scFv that binds DLL3. Exemplary DLL3-binding scFv is set forth in SEQ ID NO: 126 and 189 (U.S. Pub. No. US 2017/0037130). In some embodiments, the antigen binding domain is or contains a Fab antibody fragment comprising a Fd and LC that binds DLL3. An exemplary DLL3 Fd is set forth in SEQ ID NO: 133 and an exemplary DLL3 LC is set forth in SEQ ID NO: 134 (U.S. Pat. No. 8,044,178).

In some embodiments, at least one antigen binding domain, or independently each antigen binding domain, binds the tumor associated antigen (TAA) 5T4. An exemplary 5T4 Fd is set forth in SEQ ID NO: 129 and an exemplary 5T4 LC is set forth in SEQ ID NO: 130. In some embodiments, the antibody binding domain comprises a VH-CH1 (Fd) or VL-CL as set forth in SEQ ID NOS: 167 and 168 (U.S. Pat. No. 8,044,178).

In some embodiments, at least one antigen binding domain, or independently each antigen binding domain, binds the tumor associated antigen (TAA) gpNMB. In some embodiments, the antigen binding domain is or contains a Fab fragment comprising a Fd and LC chain. An exemplary gpNMB Fd is set forth in SEQ ID NO: 131 and an exemplary gpNMB LC is set forth in SEQ ID NO: 132.

In some embodiments, the antigen binding domain is linked, directly or indirectly via a linker, to the Fc region and/or to the CD3 binding region. In some embodiments, linkage is via a linker. In some embodiments, the linker is a linking peptide (LP), which can include any flexible or rigid linker as described in Section 11.3, although generally peptides linking the antigen binding domain or domains is not a cleavable liker.

In some embodiments, the multispecific polypeptide construct comprises a first linking peptide (LP1) between the first antigen binding domain and the Fc region. In some embodiments, the multispecific polypeptide construct comprises a second linking peptide (LP2) between the CD3 binding region and the second antigen binding domain. In some embodiments, the multispecific polypeptide construct comprises a first linking peptide (LP1) between the first antigen binding domain and the Fc region and a second linking peptide (LP2) between the CD3 binding region and the second antigen binding domain. In some aspects, the multispecific polypeptide construct has the structural arrangement from N-terminus to C-terminus as follows: first antigen binding domain-LP1-Fc region-linker-CD3 binding region-LP2-second antigen binding domain. In some embodiments, the two linking peptides are not identical to each other.

In some embodiments, the LP1 or LP2 is independently a peptide of about 1 to 20 amino acids in length. In some embodiments, the LP1 or LP2 is independently a peptide that is or comprises any Gly-Ser linker as set forth in SEQ ID NOs: 10-13, 119, 135, 147, 149 or GGS.

III. Pharmaceutical Composition

Provided herein are compositions of any of the provided multispecific polypeptide constructs. It will be appreciated that administration of therapeutic entities in accordance with the disclosure will be administered with suitable carriers, excipients, and other agents that are incorporated into formulations to provide improved transfer, delivery, tolerance, and the like. A multitude of appropriate formulations can be found in the formulary known to all pharmaceutical chemists: Remington's Pharmaceutical Sciences (15th ed., Mack Publishing Company, Easton, PA (1975)), particularly Chapter 87 by Blaug, Seymour, therein. These formulations include, for example, powders, pastes, ointments, jellies, waxes, oils, lipids, lipid (cationic or anionic) containing vesicles (such as Lipofectin™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. Any of the foregoing mixtures may be appropriate in treatments and therapies in accordance with the present disclosure, provided that the active ingredient in the formulation is not inactivated by the formulation and the formulation is physiologically compatible and tolerable with the route of administration. See also Baldrick P. "Pharmaceutical excipient development: the need for preclinical guidance." Regul. Toxicol Pharmacol. 32(2):210-8 (2000), Wang W. "Lyophilization and development of solid protein pharmaceuticals." Int. J. Pharm. 203 (1-2):1-60 (2000), Charman W N "Lipids, lipophilic drugs, and oral drug delivery-some emerging concepts." J Pharm Sci. 89(8):967-78 (2000), Powell et al. "Compendium of excipients for parenteral formulations" PDA J Pharm Sci Technol. 52:238-311 (1998) and the citations therein for additional information related to formulations, excipients and carriers well known to pharmaceutical chemists.

In some embodiments, the multispecific polypeptide constructs, conjugated multispecific polypeptide constructs, and compositions thereof—referred to collectively herein as the Therapeutic(s) and derivatives, fragments, analogs and homologs thereof, can be incorporated into pharmaceutical compositions suitable for administration. Principles and considerations involved in preparing such compositions, as well as guidance in the choice of components are provided, for example, in Remington's Pharmaceutical Sciences: The Science And Practice Of Pharmacy 19th ed. (Alfonso R. Gennaro, et al., editors) Mack Pub. Co., Easton, Pa.: 1995; Drug Absorption Enhancement: Concepts, Possibilities, Limitations, And Trends, Harwood Academic Publishers, Langhorne, Pa., 1994; and Peptide And Protein Drug Delivery (Advances In Parenteral Sciences, Vol. 4), 1991, M. Dekker, New York.

Such compositions typically comprise the multispecific polypeptide construct or a conjugated thereof and a pharmaceutically acceptable carrier. Where a multispecific polypeptide construct includes a fragment of an antibody, the smallest fragment of the antibody that specifically binds to the target protein can be used. For example, based upon the variable-region sequences of an antibody, peptide molecules can be designed that retain the ability of the antibody to bind the target protein sequence. Such peptides can be synthesized chemically and/or produced by recombinant DNA technology. (See, e.g., Marasco et al., Proc. Natl. Acad. Sci. USA, 90: 7889-7893 (1993)).

As used herein, the term "pharmaceutically acceptable carrier" is intended to include any and all solvents, dispersion media, coatings, antibacterial and antifungal agents, isotonic and absorption delaying agents, and the like, compatible with pharmaceutical administration. Suitable carriers are described in the most recent edition of Remington's Pharmaceutical Sciences, a standard reference text in the field, which is incorporated herein by reference. Suitable examples of such carriers or diluents include, but are not limited to, water, saline, ringer's solutions, dextrose solution, and 5% human serum albumin. Liposomes and non-aqueous vehicles such as fixed oils may also be used. The use of such media and agents for pharmaceutically active substances is well known in the art. Except insofar as any conventional media or agent is incompatible with the active compound, use thereof in the compositions is contemplated.

The formulations to be used for in vivo administration must be sterile. This is readily accomplished by filtration through sterile filtration membranes.

A pharmaceutical composition of the disclosure is formulated to be compatible with its intended route of administration. Examples of routes of administration include parenteral, e.g., intravenous, intradermal, subcutaneous, oral (e.g., inhalation), transdermal (i.e., topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid (EDTA); buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be suitable to include isotonic agents, for example, sugars, polyalcohols such as manitol, sorbitol, sodium chloride in the composition. Prolonged absorption of the injectable compositions can be brought about by including in the composition an agent that delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof. Where the composition is lyophilized, sterilization using this method may be conducted either prior to or following lyophilization and reconstitution. The composition for parenteral administration may be stored in lyophilized form or in solution. In addition, parenteral compositions generally are placed into a container having a sterile access port, for example, an intravenous solution bag or vial having a stopper pierceable by a hypodermic injection needle.

In some embodiments, the pharmaceutical composition is administered to a subject through any route, including orally, transdermally, by inhalation, intravenously, intra-arterially, intramuscularly, direct application to a wound site, application to a surgical site, intraperitoneally, by suppository, subcutaneously, intradermally, transcutaneously, by nebulization, intrapleurally, intraventricularly, intra-articularly, intraocularly, or intraspinally.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the multispecific polypeptide construct are delivered in the form of an aerosol spray from pressured container or dispenser that contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the Therapeutics are prepared with carriers that will protect the compound against rapid elimination from the body, such as sustained/controlled release formulations, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art.

For example, the Therapeutics can be entrapped in microcapsules prepared, for example, by coacervation techniques or by interfacial polymerization, for example, hydroxymethylcellulose or gelatin-microcapsules and poly-(methylmethacrylate) microcapsules, respectively, in colloidal drug delivery systems (for example, liposomes, albumin microspheres, microemulsions, nano-particles, and nanocapsules) or in macroemulsions.

In some embodiments, the pharmaceutical composition comprises a pharmaceutically-acceptable excipient, for example a filler, binder, coating, preservative, lubricant, flavoring agent, sweetening agent, coloring agent, a solvent, a buffering agent, a chelating agent, or stabilizer. Examples of pharmaceutically-acceptable fillers include cellulose, dibasic calcium phosphate, calcium carbonate, microcrystalline cellulose, sucrose, lactose, glucose, mannitol, sorbitol, maltol, pregelatinized starch, corn starch, or potato starch. Examples of pharmaceutically-acceptable binders include polyvinylpyrrolidone, starch, lactose, xylitol, sorbitol, maltitol, gelatin, sucrose, polyethylene glycol, methyl cellulose, or cellulose. Examples of pharmaceutically-acceptable coatings include hydroxypropyl methylcellulose (HPMC), shellac, corn protein zein, or gelatin. Examples of pharmaceutically-acceptable disintegrants include polyvinylpyrrolidone, carboxymethyl cellulose, or sodium starch glycolate. Examples of pharmaceutically-acceptable lubricants include polyethylene glycol, magnesium stearate, or stearic acid. Examples of pharmaceutically-acceptable preservatives include methyl parabens, ethyl parabens, propyl paraben, benzoic acid, or sorbic acid. Examples of pharmaceutically-acceptable sweetening agents include sucrose, saccharine, aspartame, or sorbitol. Examples of pharmaceutically-acceptable buffering agents include carbonates, citrates, gluconates, acetates, phosphates, or tartrates.

Sustained-release preparations can be prepared. Suitable examples of sustained-release preparations include semipermeable matrices of solid hydrophobic polymers containing the antibody, which matrices are in the form of shaped articles, e.g., films, or microcapsules. In some embodiments, the pharmaceutical composition further comprises an agent for the controlled or sustained release of the product, such as injectable microspheres, bio-erodible particles, polymeric compounds (polylactic acid, polyglycolic acid), beads, or liposomes. Examples of sustained-release matrices include polyesters, hydrogels (for example, poly(2-hydroxyethylmethacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods.

The materials can also be obtained commercially from Alza Corporation and Nova Pharmaceuticals, Inc. Liposomal suspensions (including liposomes targeted to infected cells with monoclonal antibodies to viral antigens) and can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the disclosure are dictated by and directly dependent on the unique characteristics of the active compound and the particular therapeutic effect to be achieved, and the limitations inherent in the art of compounding such an active compound for the treatment of individuals.

Further provided are kits comprising the pharmaceutical compositions (or articles of manufacture) described herein. The pharmaceutical compositions can be included in a container, pack, or dispenser together with instructions for administration. The kits described herein may also include other materials desirable from a commercial and user standpoint, including other buffers, diluents, filters, needles, syringes, and package inserts with instructions for performing any methods described herein.

The formulation can also contain more than one multispecific polypeptide construct as necessary for the particular indication being treated, for example, those with complementary activities that do not adversely affect each other. In some embodiments, or in addition, the composition can comprise an agent that enhances its function, such as, for example, a cytotoxic agent, cytokine, chemotherapeutic agent, or growth-inhibitory agent. Such molecules are suitably present in combination in amounts that are effective for the purpose intended.

In some embodiments, the dosage of the pharmaceutical composition is a single dose or a repeated dose. In some embodiments, the doses are given to a subject once per day, twice per day, three times per day, or four or more times per day. In some embodiments, about 1 or more (such as about 2 or more, about 3 or more, about 4 or more, about 5 or more, about 6 or more, or about 7 or more) doses are given in a week. In some embodiments, multiple doses are given over the course of days, weeks, months, or years. In some embodiments, a course of treatment is about 1 or more doses (such as about 2 or more does, about 3 or more doses, about 4 or more doses, about 5 or more doses, about 7 or more doses, about 10 or more doses, about 15 or more doses, about 25 or more doses, about 40 or more doses, about 50 or more doses, or about 100 or more doses).

In some embodiments, the pharmaceutical composition is administered to a subject. Generally, dosages and routes of administration of the pharmaceutical composition are determined according to the size and condition of the subject, according to standard pharmaceutical practice. For example, the therapeutically effective dose can be estimated initially either in cell culture assays or in animal models such as mice, rats, rabbits, dogs, pigs, or monkeys. An animal model may also be used to determine the appropriate concentration range and route of administration. Such information can then be used to determine useful doses and routes for administration in humans. The exact dosage will be determined in light of factors related to the subject requiring treatment. Dosage and administration are adjusted to provide sufficient levels of the active compound or to maintain the desired effect. Factors that may be taken into account include the severity of the disease state, the general health of the subject, the age, weight, and gender of the subject, time and frequency of administration, drug combination(s), reaction sensitivities, and response to therapy. The optimal dosage and treatment regime for a particular patient can readily be determined by one skilled in the art of medicine by monitoring the patient for signs of disease and adjusting the treatment accordingly.

IV. Methods of Use and Therapeutic Administration

Also provided are methods for using and uses of the multispecific polypeptide constructs. Such methods and uses include therapeutic methods and uses, for example, involving administration of the molecules or compositions containing the same, to a subject having a disease, condition, or disorder, such as a tumor or cancer. In some embodiments, the molecule and/or composition is administered in an effective amount to effect treatment of the disease or disorder. Uses include uses of the multispecific polypeptide constructs in such methods and treatments, and in the preparation of a medicament in order to carry out such therapeutic methods. In some embodiments, the methods are carried out by administering the multispecific polypeptide constructs, or compositions comprising the same, to the subject having or suspected of having the disease or condition. In some embodiments, the methods thereby treat the disease or condition or disorder in the subject.

In one embodiment, a multispecific polypeptide construct of the disclosure may be used as therapeutic agents. Such agents will generally be employed to diagnose, prognose, monitor, treat, alleviate, and/or prevent a disease or pathology in a subject. A therapeutic regimen is carried out by identifying a subject, e.g., a human patient or other mammal suffering from (or at risk of developing) a disorder using standard methods. A multispecific polypeptide construct is administered to the subject. A multispecific polypeptide construct is administered to the subject and will generally have an effect due to its binding with the target(s).

In some embodiments, provided herein is a method of modulating an immune response in a subject by administering a therapeutically effective amount of any of the provided multispecific conjugates or pharmaceutical compositions. In some embodiments, the method of modulating an immune response increases or enhances an immune response in a subject. For example, the increase or enhanced response may be an increase in cell-mediated immunity. In some examples, the method increases T-cell activity, such as cytolytic T-cell (CTL) activity. In some embodiments, the modulated (e.g., increased) immune response is against a tumor or cancer.

Administration of the multispecific polypeptide construct may activate innate immune cells via engagement of FcγRs through the Fc-region of the multispecific polypeptide construct. Administration of the multispecific polypeptide construct may agonize, stimulate, activate, and/or augment innate immune cell effector functions, including ADCC, cytokine release, degranulation and/or ADCP. Administration of the multispecific polypeptide construct may activate T-cell once the linker(s) joining the first and second component is cleaved by a protease thereby allowing the anti-CD3 binding portion to bind CD3ε on the T cells. Administration of the multispecific polypeptide construct may agonize, stimulate, activate, and/or augment CD3-mediated T cell activation, cytotoxicity, cytokine release and/or proliferation.

In some embodiments, the provided methods are for treating a disease or condition in a subject by administering a therapeutically effective amount of any of the provided multispecific conjugates or pharmaceutical compositions. In some embodiments, the disease or condition is a tumor or a cancer. Generally, alleviation or treatment of a disease or disorder involves the lessening of one or more symptoms or medical problems associated with the disease or disorder. For example, in the case of cancer, the therapeutically effective amount of the drug can accomplish one or a combination of the following: reduce the number of cancer cells; reduce the tumor size; inhibit (i.e., to decrease to some extent and/or stop) cancer cell infiltration into peripheral organs; inhibit tumor metastasis; inhibit, to some extent, tumor growth; and/or relieve to some extent one or more of the symptoms associated with the cancer. In some embodiments, a composition of this disclosure can be used to prevent the onset or reoccurrence of the disease or disorder in a subject, e.g., a human or other mammal, such as a non-human primate, companion animal (e.g., cat, dog, horse), farm animal, work animal, or zoo animal. The terms subject and patient are used interchangeably herein.

In some embodiments, the pharmaceutical composition can be used to inhibit growth of mammalian cancer cells (such as human cancer cells). A method of treating cancer can include administering an effective amount of any of the pharmaceutical compositions described herein to a subject with cancer. The effective amount of the pharmaceutical composition can be administered to inhibit, halt, or reverse progression of cancers. Human cancer cells can be treated in vivo, or ex vivo. In ex vivo treatment of a human patient, tissue or fluids containing cancer cells are treated outside the body and then the tissue or fluids are reintroduced back into the patient. In some embodiments, the cancer is treated in a human patient in vivo by administration of the therapeutic composition into the patient.

Non-liming examples of disease include: all types of cancers (breast, lung, colorectal, prostate, melanomas, head and neck, pancreatic, etc.), rheumatoid arthritis, Crohn's disuse, SLE, cardiovascular damage, ischemia, etc. For example, indications would include leukemias, including T-cell acute lymphoblastic leukemia (T-ALL), lymphoblastic diseases including multiple myeloma, and solid tumors, including lung, colorectal, prostate, pancreatic, and breast, including triple negative breast cancer. For example, indications include bone disease or metastasis in cancer, regardless of primary tumor origin; breast cancer, including by way of non-limiting example, ER/PR+ breast cancer, Her2+ breast cancer, triple-negative breast cancer; colorectal cancer; endometrial cancer; gastric cancer; glioblastoma; head and neck cancer, such as esophageal cancer; lung cancer, such as by way of non-limiting example, non-small cell lung cancer; multiple myeloma ovarian cancer; pancreatic cancer; prostate cancer; sarcoma, such as osteosarcoma; renal cancer, such as by way of nonlimiting example, renal cell carcinoma; and/or skin cancer, such as by way of nonlimiting example, squamous cell cancer, basal cell carcinoma, or melanoma. In some embodiments, the cancer is a squamous cell cancer. In some embodiments, the cancer is a skin squamous cell carcinoma. In some embodiments, the cancer is an esophageal squamous cell carcinoma. In some embodiments, the cancer is a head and neck squamous cell carcinoma. In some embodiments, the cancer is a lung squamous cell carcinoma.

A therapeutically effective amount of a multispecific polypeptide construct of the disclosure relates generally to the amount needed to achieve a therapeutic objective. As noted above, this may be a binding interaction between the multispecific polypeptide construct and its target antigen(s) that, in certain cases, agonize, stimulate, activate, and/or augment FcγR-mediated innate immune cell activation or CD3-mediated T cell activation. The amount required to be administered will furthermore depend on the binding affinity of the multispecific polypeptide construct for its specific antigen(s), and will also depend on the rate at which an administered multispecific polypeptide construct is depleted from the free volume other subject to which it is administered. Common ranges for therapeutically effective dosing of a multispecific polypeptide construct may be, by way of nonlimiting example, from about 0.01 µg/kg body weight to about 10 mg/kg body weight. In some embodiments, the therapeutically effective dosing of a multispecific polypeptide construct of the disclosure may be, by way of nonlimiting example, from about 0.01 mg/kg body weight to about 5-10 mg/kg body weight. Common dosing frequencies may range, for example, from twice daily to once a week.

Efficaciousness of treatment is determined in association with any known method for diagnosing or treating the particular disorder. Methods for the screening of multispecific polypeptide construct that possess the desired specificity include, but are not limited to, enzyme linked immunosorbent assay (ELISA) and other immunologically mediated techniques known within the art. A variety of means are known for determining if administration of the provided multispecific polypeptide constructs sufficiently modulates immunological activity by eliminating, sequestering, or inactivating immune cells mediating or capable of mediating an undesired immune response; inducing, generating, or turning on immune cells that mediate or are capable of mediating a protective immune response; changing the physical or functional properties of immune cells; or a combination of these effects. Examples of measurements of the modulation of immunological activity include, but are not limited to, examination of the presence or absence of immune cell populations (using flow cytometry, immunohistochemistry, histology, electron microscopy, polymerase chain reaction (PCR)); measurement of the functional capacity of immune cells including ability or resistance to proliferate or divide in response to a signal (such as using T-cell proliferation assays and pepscan analysis based on 3H-thymidine incorporation following stimulation with anti-CD3 antibody, anti-T-cell receptor antibody, anti-CD28 antibody, calcium ionophores, PMA (phorbol 12-myristate 13-acetate) antigen presenting cells loaded with a peptide or protein antigen; B cell proliferation assays); measurement of the ability to kill or lyse other cells (such as cytotoxic T cell assays); measurements of the cytokines, chemokines, cell surface molecules, antibodies and other products of the cells (e.g., by flow cytometry, enzyme-linked immunosorbent assays, Western blot analysis, protein microarray analysis, immunoprecipitation analysis); measurement of biochemical markers of activation of immune cells or signaling pathways within immune cells (e.g., Western blot and immunoprecipitation analysis of tyrosine, serine or threonine phosphorylation, polypeptide cleavage, and formation or dissociation of protein complexes; protein array analysis; DNA transcriptional, profiling using DNA arrays or subtractive hybridization); measurements of cell death by apoptosis, necrosis, or other mechanisms (e.g., annexin V staining, TUNEL assays, gel electrophoresis to measure DNA laddering, histology; fluorogenic caspase assays, Western blot analysis of caspase substrates); measurement of the genes, proteins, and other molecules produced by immune cells (e.g., Northern blot analysis, polymerase chain reaction, DNA microarrays, protein microarrays, 2-dimensional gel electrophoresis, Western blot analysis, enzyme linked immunosorbent assays, flow cytometry); and measurement of clinical symptoms or outcomes such as improvement of autoimmune, neurodegenerative, and other diseases involving self-proteins or self-polypeptides (clinical scores, requirements for use of additional therapies, functional status, imaging studies) for example, by measuring relapse rate or disease severity.

The multispecific polypeptide construct are also useful in a variety of diagnostic and prophylactic formulations. In one embodiment, a multispecific polypeptide construct is administered to patients that are at risk of developing one or more of the aforementioned disorders. A patient's or organ's predisposition to one or more of the disorders can be determined using genotypic, serological or biochemical markers.

In another embodiment of the disclosure, a multispecific polypeptide construct is administered to human individuals diagnosed with a clinical indication associated with one or more of the aforementioned disorders. Upon diagnosis, a multispecific polypeptide construct is administered to mitigate or reverse the effects of the clinical indication.

Combination Therapies

In some embodiments, the multispecific polypeptide constructs, conjugated multispecific polypeptide constructs, and compositions thereof—referred to collectively herein as the Therapeutic(s)—are administered in conjunction with one or more additional agents, or a combination of additional agents. Suitable additional agents include current pharmaceutical and/or surgical therapies for an intended application. For example, the Therapeutic(s) can be used in conjunction with an additional chemotherapeutic or antineoplastic agent. For example, the Therapeutic(s) and additional agent are formulated into a single therapeutic composition, and the Therapeutic(s) and additional agent are administered simultaneously. In some embodiments, the Therapeutic(s) and additional agent are separate from each other, e.g., each is formulated into a separate therapeutic composition, and the Therapeutic(s) and the additional agent are administered simultaneously, or the Therapeutic(s) and the additional agent are administered at different times during a treatment regimen. For example, the Therapeutic(s) is administered prior to the administration of the additional agent, the Therapeutic(s) is administered subsequent to the administration of the additional agent, or the Therapeutic(s) and the additional agent are administered in an alternating fashion. As described herein, the Therapeutic(s) and additional agent are administered in single doses or in multiple doses. In some embodiments, the additional agent is coupled or otherwise attached to the Therapeutic(s). Suitable additional agents are selected according to the purpose of the intended application (i.e., killing, prevention of cell proliferation, hormone therapy or gene therapy). Such agents may include but is not limited to, for example, pharmaceutical agents, toxins, fragments of toxins, alkylating agents, enzymes, antibiotics, antimetabolites, antiproliferative agents, hormones, neurotransmitters, DNA, RNA, siRNA, oligonucleotides, antisense RNA, aptamers, diagnostics, radiopaque dyes, radioactive isotopes, fluorogenic compounds, magnetic labels, nanoparticles, marker compounds, lectins, compounds that alter cell membrane permeability, photochemical compounds, small molecules, liposomes, micelles, gene therapy vectors, viral vectors, and the like. Finally, combinations of agents or combinations of different classes of agents may be used.

In one embodiment, the multispecific polypeptide constructs are administered in combination therapy, i.e., combined with other agents, e.g., therapeutic agents, that are useful for treating pathological conditions or disorders, such as autoimmune disorders and inflammatory diseases. The term "in combination" in this context means that the agents are given substantially contemporaneously, either simultaneously or sequentially. If given sequentially, at the onset of administration of the second compound, the first of the two compounds is still detectable at effective concentrations at the site of treatment.

For example, the combination therapy can include one or more multispecific polypeptide constructs of the disclosure co-formulated with, and/or co-administered with, one or more additional therapeutic agents, e.g., one or more cytokine and growth factor inhibitors, immunosuppressants, anti-inflammatory agents, metabolic inhibitors, enzyme inhibitors, and/or cytotoxic or cytostatic agents, as described in more detail below. Furthermore, one or more multispecific polypeptide constructs described herein may be used in combination with two or more of the therapeutic agents described herein. Such combination therapies may advantageously utilize lower dosages of the administered therapeutic agents, thus avoiding possible toxicities or complications associated with the various monotherapies.

In other embodiments, one or more multispecific polypeptide constructs of the disclosure can be co-formulated with, and/or co-administered with, one or more anti-inflammatory drugs, immunosuppressants, or metabolic or enzymatic inhibitors. Nonlimiting examples of the drugs or inhibitors that can be used in combination with the antibodies described herein, include, but are not limited to, one or more of: nonsteroidal anti-inflammatory drug(s) (NSAIDs), e.g., ibuprofen, tenidap, naproxen, meloxicam, piroxicam, diclofenac, and indomethacin; sulfasalazine; corticosteroids such as prednisolone; cytokine suppressive anti-inflammatory drug(s) (CSAIDs); inhibitors of nucleotide biosynthesis, e.g., inhibitors of purine biosynthesis, folate antagonists (e.g., methotrexate (N-[4-[[(2,4-diamino-6-pteridinyl) methyl]methylamino]benzoyl]-L-glutamic acid); and inhibitors of pyrimidine biosynthesis, e.g., dihydroorotate dehydrogenase (DHODH) inhibitors. Suitable therapeutic agents for use in combination with the antibodies of the disclosure include NSAIDs, CSAIDs, (DHODH) inhibitors (e.g., leflunomide), and folate antagonists (e.g., methotrexate).

Examples of additional inhibitors include one or more of: corticosteroids (oral, inhaled and local injection); immunosuppressants, e.g., cyclosporin, tacrolimus (FK-506); and mTOR inhibitors, e.g., sirolimus (rapamycin—RAPAMUNE™ or rapamycin derivatives, e.g., soluble rapamycin derivatives (e.g., ester rapamycin derivatives, e.g., CCI-779); agents that interfere with signaling by proinflammatory cytokines such as TNFα or IL-1 (e.g. IRAK, NIK, IKK, p38 or MAP kinase inhibitors); COX2 inhibitors, e.g., celecoxib, rofecoxib, and variants thereof; phosphodiesterase inhibitors, e.g., R973401 (phosphodiesterase Type IV inhibitor); phospholipase inhibitors, e.g., inhibitors of cytosolic phospholipase 2 (cPLA2) (e.g., trifluoromethyl ketone analogs); inhibitors of vascular endothelial cell growth factor or growth factor receptor, e.g., VEGF inhibitor and/or VEGF-R inhibitor; and inhibitors of angiogenesis. Suitable therapeutic agents for use in combination with the antibodies of the disclosure are immunosuppressants, e.g., cyclosporin, tacrolimus (FK-506); mTOR inhibitors, e.g., sirolimus (rapamycin) or rapamycin derivatives, e.g., soluble rapamycin derivatives (e.g., ester rapamycin derivatives, e.g., CCI-779); COX2 inhibitors, e.g., celecoxib and variants thereof; and phospholipase inhibitors, e.g., inhibitors of cytosolic phospholipase 2 (cPLA2), e.g., trifluoromethyl ketone analogs. Additional examples of therapeutic agents that can be combined with a multispecific polypeptide construct include one or more of: 6-mercaptopurines (6-MP); azathioprine sulphasalazine; mesalazine; olsalazine; chloroquine/hydroxychloroquine (PLAQUENIL®); pencillamine; aurothiornalate (intramuscular and oral); azathioprine; coichicine; beta-2 adrenoreceptor agonists (salbutamol, terbutaline, salmeteral); xanthines (theophylline, aminophylline); cromoglycate; nedocromil; ketotifen; ipratropium and oxitropium; mycophenolate mofetil; adenosine agonists; antithrombotic agents; complement inhibitors; and adrenergic agents.

V. Exemplary Embodiments

Among the provided embodiments are:

1. A multispecific polypeptide construct, the multispecific polypeptide construct comprising a first component comprising an immunoglobulin Fc region and a second component comprising a CD3-binding region, wherein:
the first and second components are coupled by a linker, wherein the Fc region is positioned N-terminal to the CD3-binding region; and
one or both of the first and second components comprises an antigen binding domain that binds a tumor associated antigen (TAA).

2. The multispecific polypeptide construct of embodiment 1, wherein the CD3-binding region binds CD3 (CD3c).

3. The multispecific construct of embodiment 1 or embodiment 2, wherein the antigen binding domain is positioned amino-terminally relative to the Fc region and/or carboxy-terminally relative to the CD3 binding region of the multispecific polypeptide construct.

4. The multispecific polypeptide construct of any of embodiments 1-3, wherein the first component comprises a first antigen binding domain and the second component comprises a second antigen binding domain, wherein each of the antigen binding domains bind a tumor associated antigen (TAA).

5. The multispecific polypeptide construct of embodiment 4, wherein the first antigen binding domain is positioned amino-terminally relative to the Fc region of the multispecific construct and the second antigen binding domain is positioned carboxy-terminally relative to the CD3 binding region of the multispecific construct.

6. A multispecific polypeptide construct, wherein the multispecific construct comprises in order, from N-terminus to C-terminus:
a first antigen binding domain that binds to a tumor-associated antigen (TAA);
an immunoglobulin Fc region;
a linker;
a CD3 binding region that binds CD3 (CD3c); and
a second antigen binding domain that binds a tumor-associated antigen (TAA).

7. A multispecific polypeptide construct, wherein the multispecific construct comprises in order, from N-terminus to C-terminus:
an immunoglobulin Fc region;
a linker;
a CD3 binding region that binds CD3 (CD3c); and
an antigen binding domain that binds a tumor-associated antigen (TAA).

8. A multispecific polypeptide construct, wherein the multispecific construct comprises in order, from N-terminus to C-terminus:
an antigen binding domain that binds to a tumor-associated antigen (TAA);
an immunoglobulin Fc region;
a linker; and
a CD3 binding region that binds CD3 (CD3c).

9. The multispecific polypeptide construct of any of embodiments 1-8, wherein the Fc region is a homodimeric Fc region.

10. The multispecific polypeptide construct of any of embodiments 1-9, wherein the Fc region is an Fc region of a human IgG1, a human IgG2, a human IgG3, or a human IgG4, or is an immunologically active fragment thereof.

11. The multispecific polypeptide construct of any of embodiments 1-10, wherein the Fc region comprises a polypeptide comprises the amino acid sequence set forth in SEQ ID NO: 1 or a sequence of amino acids that has at least 90%, 91%, 92%, 93%, 94%, 95%, 96%, 97%, 98%, 99% sequence identity to SEQ ID NO:1.

12. The multispecific polypeptide construct of any of embodiments 1-10, wherein the Fc region comprises a polypeptide comprises the amino acid sequence set forth in SEQ ID NO: 2 or a sequence of amino acids that has at least 90%, 91%, 92%, 93%, 94%, 95%, 96%, 97%, 98%, 99% sequence identity to SEQ ID NO:2;
the Fc region comprises a polypeptide comprises the amino acid sequence set forth in SEQ ID NO: 4 or a sequence of amino acids that has at least 90%, 91%, 92%, 93%, 94%, 95%, 96%, 97%, 98%, 99% sequence identity to SEQ ID NO:4; or
the Fc region comprises a polypeptide comprises the amino acid sequence set forth in SEQ ID NO: 5 or a sequence of amino acids that has at least 90%, 91%, 92%, 93%, 94%, 95%, 96%, 97%, 98%, 99% sequence identity to SEQ ID NO:5.

13. The multispecific polypeptide construct of any of embodiments 1-6, 9 and 12, wherein the Fc region is a heterodimeric Fc region.

14. The multispecific polypeptide construct of embodiment 13, wherein one or both Fc polypeptides of the heterodimeric Fc region comprises at least one modification to induce heterodimerization compared to a polypeptide of a homodimeric Fc region, optionally compared to the Fc polypeptide set forth in SEQ ID NO:1 or an immunologically active fragment thereof.

15. The multispecific polypeptide construct of embodiment 14, wherein each of the Fc polypeptides of the heterodimeric Fc independently comprise at least one amino acid modification.

16. The multispecific polypeptide construct of embodiment 15, wherein each of the Fc polypeptides of the heterodimeric Fc comprise a knob-into-hole modification or comprise a charge mutation to increase electrostatic complementarity of the polypeptides.

17. The multispecific polypeptide construct of embodiment 16, wherein the amino acid modification is a knob-into-hole modification.

18. The multispecific fusion polypeptide of any of embodiments 13-17, wherein the first Fc polypeptide of the heterodimeric Fc comprises the modification selected from among Thr366Ser, Leu368Ala, Tyr407Val, and combinations thereof and the second Fc polypeptide of the heterodimeric Fc comprises the modification T366W.

19. The multispecific fusion polypeptide of embodiment 18, wherein the first and second Fc polypeptides further comprises a modification of a non-cysteine residue to a cysteine residue, wherein the modification of the first polypeptide is at one of the position Ser354 and Y349 and the modification of the second Fc polypeptide is at the other of the position Ser354 and Y349.

20. The multispecific polypeptide construct of embodiment 16, wherein the amino acid modification is a charge mutation to increase electrostatic complementarity of the polypeptides.

21. The multispecific polypeptide construct of any of embodiments 13-16 and 20, wherein the first and/or second Fc polypeptides or each of the first and second Fc polypeptide comprise a modification in complementary positions, wherein the modification is replacement with an amino acid having an opposite charge to the complementary amino acid of the other polypeptide.

22. The multispecific polypeptide construct of any of embodiments 14-21, wherein one of the first or second Fc polypeptide of the heterodimeric Fc further comprises a modification at residue Ile253.

23. The multispecific polypeptide construct of embodiment 22, wherein the modification is Ile253Arg.

24. The multispecific polypeptide construct of any of embodiments 14-23, wherein one of the first or second Fc polypeptide of the heterodimeric Fc further comprises a modification at residue His435.

25. The multispecific polypeptide construct of embodiment 24, wherein the modification is His435Arg.

26. The multispecific polypeptide construct of any of embodiments 1-25, wherein the Fc region comprises a polypeptide that lacks Lys447.

27. The multispecific polypeptide construct of any of embodiments 1-26, wherein the Fc region comprises a polypeptide comprising at least one modification to enhance FcRn binding.

28. The multispecific fusion polypeptide of embodiment 27, wherein the modification is at a position selected from the group consisting of Met252, Ser254, Thr256, Met428, Asn434, and combinations thereof.

29. The multispecific fusion polypeptide of embodiment 28, wherein the modification is at a position selected from the group consisting of Met252Y, Ser254T, Thr256E, Met428L, Met428V, Asn434S, and combinations thereof.

30. The multispecific fusion polypeptide of embodiment 28, wherein the modification is at position Met252 and at position Met428.

31. The multispecific fusion polypeptide of embodiment 30, wherein the modification is Met252Y and Met428L.

32. The multispecific fusion polypeptide of embodiment 30, wherein the modification is Met252Y and Met428V.

33. The multispecific polypeptide construct of any of embodiments 13-32, wherein the first polypeptide of the heterodimeric Fc comprises the sequence of amino acids set forth in any of SEQ ID NOS:82, 86, 94 or 96, and the second polypeptide of the heterodimeric Fc comprises the sequence of amino acids set forth in any of SEQ ID NOS:83, 87, 90, 92, 98 or 100.

34. The multispecific polypeptide construct of any of embodiments 1-33, wherein the Fc region comprises a polypeptide comprising at least one amino acid modification that reduces effector function and/or reduces binding to an effector molecule selected from an Fc gamma receptor or C1q.

35. The multispecific polypeptide construct of embodiment 34, wherein the one or more amino acid modification is deletion of one or more of Glu233, Leu234 or Leu235.

36. The multispecific polypeptide construct of any of embodiments 13-32, 34 and 35, wherein the first polypeptide of the heterodimeric Fc comprises the sequence of amino acids set forth in any of SEQ ID NOS: 84, 88, 95 or 97 and the second polypeptide of the heterodimeric Fc comprises the sequence of amino acids set forth in any of SEQ ID NOS: 85, 89, 91, 93, 99 or 101.

37. The multispecific polypeptide construct of any of embodiments 1-32, wherein the Fc region comprises a polypeptide comprising at least one modification to enhance FcγR binding.

38. The multispecific polypeptide construct of embodiment 37, wherein the modification is modification at Ser239 or Ile332.

39. The multispecific polypeptide construct of any of embodiments 1-32 and 37, wherein the glycosylation of the Fc region is modified to enhance FcγR binding as compared to an unmodified Fc region.

40. The multispecific polypeptide construct of embodiment 39, wherein the Fc region lacks or has reduced fucose content.

41. The multispecific polypeptide construct of any of embodiments 1-40, wherein the CD3 binding region is an anti-CD3 antibody or antigen-binding fragment.

42. The multispecific polypeptide construct of embodiment 41, wherein the anti-CD3 antibody or antigen binding fragment comprises a variable heavy chain region (VH) and a variable light chain region (VL).

43. The multispecific polypeptide construct of any of embodiments 1-42, wherein the CD3 binding region is monovalent.

44. The multispecific polypeptide construct of any of embodiments 41-43, wherein the anti-CD3 antibody or antigen binding fragment is not a single chain antibody, optionally is not a single chain variable fragment (scFv).

45. The multispecific polypeptide construct of embodiment 42 or embodiment 44, wherein the Fc is a heterodimeric Fc and the VH and VL that comprise the anti-CD3 antibody or antigen binding fragment are linked to opposite polypeptides of the heterodimeric Fc.

46. The multispecific polypeptide construct of any of embodiments 1-45, wherein the CD3 binding region is not able to, or is not substantially able to, bind or engage CD3 unless at least one of the antigen binding domain is bound to its TAA.

47. The multispecific polypeptide construct of any of embodiments 1-46, wherein the CD3 binding region is not able to, or is not substantially able, to bind or engage CD3 unless at least two of the antigen binding domain is bound to its TAA.

48. The multispecific polypeptide construct of any of embodiments 1-47, wherein the linker is a polypeptide linker.

49. The multispecific polypeptide construct of embodiment 48, wherein the linker is a polypeptide of up to 25 amino acids in length.

50. The multispecific polypeptide construct of embodiment 48 or embodiment 49, wherein the linker is a polypeptide of from or from about 2 to 24 amino acids, 2 to 20 amino acids, 2 to 18 amino acids, 2 to 14 amino acids, 2 to 12 amino acids, 2 to 10 amino acids, 2 to 8 amino acids, 2 to 6 amino acids, 6 to 24 amino acids, 6 to 20 amino acids, 6 to 18 amino acids, 6 to 14 amino acids, 6 to 12 amino acids, 6 to 10 amino acids, 6 to 8 amino acids, 8 to 24 amino acids, 8 to 20 amino acids, 8 to 18 amino acids, 8 to 14 amino acids, 8 to 12 amino acids, 8 to 10 amino acids, 10 to 24 amino acids, 10 to 20 amino acids, 10 to 18 amino acids, 10 to 14 amino acids, 10 to 12 amino acids, 12 to 24 amino acids, 12 to 20 amino acids, 12 to 18 amino acids, 12 to 14 amino acids, 14 to 24 amino acids, 14 to 20 amino acids, 14 to 18 amino acids, 18 to 24 amino acids, 18 to 20 amino acids or 20 to 24 amino acids.

51. The multispecific polypeptide construct of any of embodiments 48-50, wherein the linker is a polypeptide that is 3, 4, 5, 6, 7, 8, 9, 10, 11, 12, 13, 14, 15, 16, 17, 18, 19 or 20 amino acids in length.

52. The multispecific polypeptide construct of any of embodiments 1-51, wherein the linker is a cleavable linker.

53. A multispecific polypeptide construct, the multispecific polypeptide construct comprising a first component comprising a heterodimeric Fc region and a second component comprising an anti-CD3 antibody or antigen-binding fragment comprising a variable heavy chain region (VH) and a variable light chain region (VL), wherein:
the VH and VL that comprise the anti-CD3 antibody or antigen binding fragment are linked to opposite polypeptides of the heterodimeric Fc;
the first and second components are coupled by a cleavable linker, wherein the heterodimeric Fc region is positioned N-terminal to the anti-CD3 antibody; and
one or both of the first and second components comprises an antigen binding domain that binds a tumor associated antigen (TAA).

54. The multispecific polypeptide construct of embodiment 52 or embodiment 53, wherein binding of the CD3-binding region to CD3 is substantially reduced when the multispecific polypeptide construct is in an uncleaved state compared to a cleaved state.

55. The multispecific polypeptide of any of embodiments 52-54, wherein in a cleaved state the first and second components are not linked.

56. The multispecific polypeptide construct of any of embodiments 52-55, wherein the cleavable linker is a polypeptide that functions as a substrate for a protease.

57. The multispecific polypeptide construct of embodiment 56, wherein the protease is produced by an immune effector cell, by a tumor, or by cells present in the tumor microenvironment.

58. The multispecific polypeptide construct of embodiment 57, wherein the protease is produced by an immune effector cell and the immune effector cell is an activated T cell, a natural killer (NK) cell, or an NK T cell.

59. The multispecific polypeptide construct of any of embodiments 56-58, wherein the protease is selected from among matriptase, a matrix metalloprotease (MMP), granzyme B, and combinations thereof.

60. The multispecific polypeptide construct of embodiment 59, wherein the protease is granzyme B.

61. The multispecific polypeptide construct of any of embodiments 52-60, wherein the cleavable linker comprises an amino acid sequence of the general formula P4 P3 P2 P1 ↓ P1' (SEQ ID NO: 150), wherein P4 is amino acid I, L, Y, M, F, V, or A; P3 is amino acid A, G, S, V, E, D, Q, N, or Y; P2 is amino acid H, P, A, V, G, S, or T; P1 is amino acid D or E; and P1' is amino acid I, L, Y, M, F, V, T, S, G or A.

62. The multispecific polypeptide construct of any of embodiments 52-61, wherein the cleavable linker comprises an amino acid sequence of the general formula P4 P3 P2 P1 ↓ P1' (SEQ ID NO: 151), wherein P4 is amino acid I or L; P3 is amino acid E; P2 is amino acid P or A; P1 is amino acid D; and P1' is amino acid I, V, T, S, or G.

63. The multispecific polypeptide construct of any of embodiments 52-62, wherein the cleavable linker comprises the amino acid sequence IEPDI (SEQ ID NO:136), LEPDG (SEQ ID NO:152, LEADT (SEQ ID NO:137), IEPDG (SEQ ID NO:138), IEPDV (SEQ ID NO:139), IEPDS (SEQ ID NO:140), IEPDT (SEQ ID NO:141) or LEADG (SEQ ID NO:153).

64. The multispecific polypeptide construct of any of embodiments 52-63, wherein the cleavable linker comprises an amino acid sequence selected from the group consisting of SEQ ID NOs:22, 105-112, 136-141, 148, 150-153.

65. The multispecific polypeptide construct of embodiment 59, wherein the protease is matriptase.

66. The multispecific polypeptide construct of any of embodiments 52-65, wherein:
the cleavable linker comprises the sequence P1QAR↓(A/V) (SEQ ID NO: 154), wherein P1 is any amino acid; or
the cleavable linker comprises the sequence RQAR(A/V) (SEQ ID NO: 155).

67. The multispecific polypeptide construction of any of embodiments 52-66, wherein the cleavable linker comprises the sequence RQARV (SEQ ID NO: 156).

68. The multispecific polypeptide construct of any of embodiments 52-67, wherein the cleavable linker comprises an amino acid sequence selected from the group consisting of SEQ ID NOs: 23, 154-156.

69. The multispecific polypeptide construct of embodiment 59, wherein the protease is an MMP.

70. The multispecific polypeptide construct of embodiment 69, wherein the MMP is MMP-2.

71. The multispecific polypeptide construct of any of embodiments 52-70, wherein the cleavable linker comprises the general formula P3 P2 P1 ↓ P1' (SEQ ID NO: 157), wherein P3 is P, V or A; P2 is Q or D; P1 is A or N; and P1' is L, I or M.

72. The multispecific polypeptide construct of any of embodiments 52-71, wherein the cleavable linker comprises the general formula P3 P2 P1 ↓ P1' (SEQ ID NO: 158), wherein P3 is P; P2 is Q or D; P1 is A or N; and P1' is L or I.

73. The multispecific polypeptide construct of any of embodiments 52-72, wherein the cleavable linker comprises the sequence PAGL (SEQ ID NO:24).

74. The multispecific polypeptide construct of any of embodiments 52-73, wherein the cleavable linker comprises an amino acid sequence selected from the group consisting of SEQ ID NOs:22-31, 104-114, 117-118, 136-144, 148, 150-158.

75. The multispecific polypeptide construct of any of embodiments 45-74, wherein the multispecific polypeptide construct comprises at least (i) a first polypeptide comprising the first Fc polypeptide of the heterodimeric Fc region, the linker and the VH domain of the anti-CD3 antibody or antigen binding fragment; and (ii) a second polypeptide comprising the second Fc polypeptide of the heterodimeric Fc region, the linker and the VL domain of the anti-CD3 antibody or antigen binding fragment, wherein one or both of the first and second polypeptide comprise at least one antigen-binding domain that binds to a tumor associated antigen (TAA).

76. The multispecific polypeptide construct of any of embodiments 1-75, wherein one or more antigen binding domain that binds TAA results in monovalent, bivalent, trivalent, or tetravalent binding to the TAA.

77. The multispecific polypeptide construct of embodiment 75, wherein only one of the first or second polypeptide comprises the at least one antigen-binding domain that binds a TAA.

78. The multispecific polypeptide construct of embodiment 75 or embodiment 77, wherein the at least one antigen binding domain is positioned amino-terminally relative to the Fc region and/or is positioned carboxy-terminally relative to the CD3 binding region of one of the first or second polypeptide of the multispecific polypeptide construct.

79. The multispecific polypeptide construct of embodiment 75 or embodiment 77, wherein the at least one antigen binding domain is positioned amino-terminally relative to the Fc region of the multispecific construct and the second antigen binding domain is positioned carboxy-terminally relative to the CD3 binding region of the multispecific construct.

80. The multispecific polypeptide construct of any of embodiments 1-79, wherein the antigen binding domain, or independently each of the antigen binding domains, comprises an extracellular domain or binding fragment thereof of the native cognate binding partner of the TAA, or a variant thereof that exhibits binding activity to the TAA.

81. The multispecific polypeptide construct of any of embodiments 1-79, wherein the antigen binding domain, or independently each of the antigen binding domains, is an antibody or antigen-binding fragment thereof selected from the group consisting of a Fab fragment, a F(ab')2 fragment, an Fv fragment, a scFv, a scAb, a dAb, a single domain heavy chain antibody, and a single domain light chain antibody.

82. The multispecific polypeptide construct of embodiment 81, wherein the antibody or antigen-binding fragment thereof is a Fv, a scFv, a Fab, a single domain antibody (sdAb), a VNAR, or a VHH.

83. The multispecific polypeptide construct of embodiment 81 or embodiment 82, wherein the antibody or antigen-binding fragment is an sdAb.

84. The multispecific polypeptide construct of embodiment 83, wherein the sdAb is a human or humanized sdAb.

85. The multispecific polypeptide construct of embodiment 83 or embodiment 84, wherein the sdAb is VHH, VNAR, an engineered VH domain or an engineered VK domain.

86. The multispecific polypeptide construct of embodiment 81 or embodiment 82, wherein the antibody or antigen-binding fragment thereof is an scFv.

87. The multispecific polypeptide construct of embodiment 81 or embodiment 82, wherein the antibody or antigen-binding fragment thereof is a Fab.

88. The multispecific polypeptide construct of embodiment 87, wherein the multispecific polypeptide construct comprises:
(i) a first polypeptide comprising the first Fc polypeptide of the heterodimeric Fc region, the linker and the VH domain of the anti-CD3 antibody or antigen binding fragment;
(ii) a second polypeptide comprising the second Fc polypeptide of the heterodimeric Fc region, the linker and the VL domain of the anti-CD3 antibody or antigen binding fragment, and (iii) a third polypeptide comprising a VH-CH1 (Fd) or VL-CL of a Fab antibody fragment that binds to a tumor-associated antigen, wherein the first and/or second polypeptide further comprises the other of the VH-CH1 (Fd) or VL-CL of the Fab antibody fragment.

89. The multispecific polypeptide construct of embodiment 88, wherein only one of the first or second polypeptide comprises the other of the VH-CH1 (Fd) or VL-CL of the Fab antibody fragment.

90. The multispecific polypeptide construct of embodiment 89, wherein both the first or second polypeptide comprises the other of the VH-CH1 (Fd) or VL-CL of the Fab antibody fragment.

91. The multispecific polypeptide construct of embodiment 89 or embodiment 90, wherein the other of the VH-CH1 (Fd) or VL-CL of the Fab antibody fragment is positioned amino-terminally relative to the Fc region and/or at the carboxy-terminally relative to the CD3 binding region of one of the first or second polypeptide of the multispecific polypeptide construct.

92. The multispecific polypeptide construct of any of embodiments 89-91, wherein the other of the VH-CH1 (Fd) or VL-CL of the Fab antibody fragment is positioned amino-terminally relative to the Fc region of the first polypeptide or second polypeptide and at the carboxy-terminally relative to the CD3 binding region of the other of the first or second polypeptide.

93. The multispecific polypeptide construct of any of embodiments 1-92, wherein the antigen binding domain, or independently each of the antigen binding domains, binds to a tumor antigen selected from among 1-92-LFA-3, 5T4, Alpha-4 integrin, Alpha-V integrin, alpha4beta1 integrin, alpha4beta7 integrin, AGR2, Anti-Lewis-Y, Apelin J receptor, APRIL, B7-H3, B7-H4, BAFF, BTLA, C5 complement, C-242, CA9, CA19-9, (Lewis a), Carbonic anhydrase 9, CD2, CD3, CD6, CD9, CD11a, CD19, CD20, CD22, CD24, CD25, CD27, CD28, CD30, CD33, CD38, CD40, CD40L, CD41, CD44, CD44v6, CD47, CD51, CD52, CD56, CD64, CD70, CD71, CD74, CD80, CD81, CD86, CD95, CD117, CD123, CD125, CD132, (IL-2RG), CD133, CD137, CD138, CD166, CD172A, CD248, CDH6, CEACAM5 (CEA), CEACAM6 (NCA-90), CLAUDIN-3, CLAUDIN-4, cMet, Collagen, Cripto, CSFR, CSFR-1, CTLA-4, CTGF, CXCL10, CXCL13, CXCR1, CXCR2, CXCR4, CYR61, DL44, DLK1, DLL3, DLL4, DPP-4, DSG1, EDA, EDB, EGFR, EGFRviii, Endothelin B receptor (ETBR), ENPP3, EpCAM, EPHA2, EPHB2, ERBB3, F protein of RSV, FAP, FGF-2, FGF8, FGFR1, FGFR2, FGFR3, FGFR4, FLT-3, Folate receptor alpha (FRα), GAL3ST1, G-CSF, G-CSFR, GD2, GITR, GLUT1, GLUT4, GM-CSF, GM-CSFR, GP IIb/IIIa receptors, Gp130, GPIIB/IIIA, GPNMB, GRP78, HER2/neu, HER3, HER4, HGF, hGH, HVEM, Hyaluronidase, ICOS, IFNalpha, IFNbeta, IFNgamma, IgE, IgE Receptor (FceRI), IGF, IGF1R, IL1B, IL1R, IL2, IL11, IL12, IL12p40, IL-12R, IL-12Rbeta1, IL13, IL13R, IL15, IL17, IL18, IL21, IL23, IL23R, IL27/IL27R (wsx1), IL29, IL-31R, IL31/IL31R, IL2R, IL4, IL4R, IL6, IL6R, Insulin Receptor, Jagged Ligands, Jagged 1, Jagged 2, KISS1-R, LAG-3, LIF-R, Lewis X, LIGHT, LRP4, LRRC26, Ly6G6D, LyPD1, MCSP, Mesothelin, MRP4, MUC1, Mucin-16 (MUC16, CA-125), Na/K ATPase, NGF, Nicastrin, Notch Receptors, Notch 1, Notch 2, Notch 3, Notch 4, NOV, OSM-R, OX-40, PAR2, PDGF-AA, PDGF-BB, PDGFRalpha, PDGFRbeta, PD-1, PD-L1, PD-L2, Phosphatidylserine, P1GF, PSCA, PSMA, PSGR, RAAG12, RAGE, SLC44A4, Sphingosine 1 Phosphate, STEAP1, STEAP2, TAG-72, TAPA1, TEM-8, TGFbeta, TIGIT, TIM-3, TLR2, TLR4, TLR6, TLR7, TLR8, TLR9, TMEM31, TNFalpha, TNFR, TNFRS12A, TRAIL-R1, TRAIL-R2, Transferrin, Transferrin receptor, TRK-A, TRK-B, uPAR, VAP1, VCAM-1, VEGF, VEGF-A, VEGF-B, VEGF-C, VEGF-D, VEGFR1, VEGFR2, VEGFR3, VISTA, WISP-1, WISP-2, and WISP-3.

94. The multispecific polypeptide construct of any of embodiments 1-93, wherein multispecific antigen binding domain comprises at least a first antigen binding domain and a second antigen binding domain, wherein the first antigen binding domain and second antigen binding domain bind to the same TAA.

95. The multispecific polypeptide construct of embodiment 94, wherein the first antigen binding domain and the second antigen binding domain binds a different epitope of the same TAA.

96. The multispecific polypeptide construct of embodiment 94, wherein the first antigen binding domain and the second antigen binding domain binds the same epitope of the same TAA.

97. The multispecific polypeptide construct of any of embodiments 1-96, wherein multispecific antigen binding domain comprises at least a first antigen binding domain and a second antigen binding domain wherein the first antigen binding domain and the second antigen binding domain bind a different TAA.

98. The multispecific polypeptide construct of any of embodiments 5-97, wherein the multispecific polypeptide construct comprises a first linking peptide (LP1) between the first antigen binding domain and the Fc region.

99. The multispecific polypeptide construct of any of embodiments 5-98, wherein the multispecific polypeptide construct comprises a second linking peptide (LP2) between the CD3 binding region and the second antigen binding domain.

100. The multispecific polypeptide construct of any of embodiments 5-99, wherein the multispecific polypeptide construct comprises a first linking peptide (LP1) between the first antigen binding domain and the Fc region and a second linking peptide (LP2) between the CD3 binding region and the second antigen binding domain, and wherein the multispecific polypeptide construct has the structural arrangement from N-terminus to C-terminus as follows: first antigen binding domain-LP1-Fc region-linker-CD3 binding region-LP2-second antigen binding domain.

101. The multispecific polypeptide construct of embodiment 100, wherein the linker is a cleavable linker.

102. The multispecific polypeptide construct of embodiment 100 and embodiment 101, wherein the two linking peptides are not identical to each other.

103. The multispecific polypeptide construct of any of embodiments 98-102, wherein LP1 or LP2 is independently a peptide of about 1 to 20 amino acids in length.

104. The multispecific polypeptide of embodiment 103, wherein LP1 or LP2 independently comprise a peptide that is or comprises any Gly-Ser linker as set forth in SEQ ID NOs: 10-13, 119, 135, 147, 149 or GGS.

105. The multispecific polypeptide construct of any of embodiments 41-104, wherein the anti-CD3 antibody or antigen binding fragment is an Fv antibody fragment.

106. The multispecific polypeptide construct of embodiment 105, wherein the Fv antibody fragment comprises a disulfide stabilized anti-CD3 binding Fv fragment (dsFv).

107. The multispecific polypeptide construct of any of embodiments 41-106, wherein the anti-CD3 antibody or antigen-binding fragment comprises a VH CDR1 comprising the amino acid sequence TYAMN (SEQ ID NO: 16); a VH CD2 comprising the amino acid sequence RIRSKYNNYATYYADSVKD (SEQ ID NO: 17); a VH CDR3 comprising the amino acid sequence HGNFGNSYVSWFAY (SEQ ID NO: 18), a VL CDR1 comprising the amino acid sequence RSSTGAVTTSNYAN (SEQ ID NO: 19); a VL CDR2 comprising the amino acid sequence GTNKRAP (SEQ ID NO: 20); and a VL CDR3 comprising the amino acid sequence ALWYSNLWV (SEQ ID NO: 21).

108. The multispecific polypeptide construct of embodiment 106 or embodiment 107, wherein the anti-CD3 dsFv comprises:
a VH having the amino acid sequence of any of SEQ ID NOS: 14 and 32-62 or a sequence that exhibits at least 90%, 91%, 92%, 93%, 94%, 95%, 96%, 97%, 98% or 99% sequence identity to any of SEQ ID NOS: 14 and 32-62; and
a VL having the amino acid sequence of any of SEQ ID NOS: 15 and 63-81 or a sequence that exhibits at least 90%, 91%, 92%, 93%, 94%, 95%, 96%, 97%, 98% or 99% sequence identity to any of SEQ ID NOS: 14 and 32-62.

109. The multispecific polypeptide construct of any of embodiments 106-108, wherein the anti-CD3 dsFv comprises the amino acid sequence of SEQ ID NO: 14 and the amino acid sequence of SEQ ID NO: 15.

110. The multispecific polypeptide construct of any of embodiments 102-104, wherein the anti-CD3 dsFv comprises the amino acid sequence of SEQ ID NO: 44 and the amino acid sequence of SEQ ID NO: 72.

111. The multispecific polypeptide construct of any of embodiments 1-109, wherein the multispecific polypeptide construct is conjugated to an agent.

112. The multispecific polypeptide construct of embodiment 111, wherein the agent is a therapeutic agent, an antineoplastic agent, a toxin or fragment thereof, a detectable moiety or a diagnostic agent.

113. The multispecific polypeptide construct of embodiment 112, wherein the agent is conjugated to the multispecific polypeptide construct via a linker.

114. A polynucleotide(s) encoding the multispecific polypeptide constructs of any of embodiments 1-113.

115. A polynucleotide encoding a polypeptide chain of any of the multispecific polypeptide constructs of any of embodiments 1-113.

116. A polynucleotide, comprising a first nucleic acid sequence encoding a first polypeptide of a multispecific construct of any of embodiments 1-115 and a second nucleic acid sequence encoding a second polypeptide of the multispecific construct, wherein the first and second nucleic acid sequence are separated by an internal ribosome entry site (IRES), or a nucleic acid encoding a self-cleaving peptide or a peptide that causes ribosome skipping.

117. The polynucleotide of embodiment 116, wherein the first nucleic acid sequence and second nucleic acid sequence are operably linked to the same promoter.

118. The polynucleotide of embodiment 116 or embodiment 117, wherein the multispecific polypeptide construct comprises a third polypeptide chain, and the polynucleotide further comprises a third nucleic acid encoding the third polypeptide of the multispecific construct.

119. The polynucleotide of embodiment 118, wherein the third nucleic acid is separated from the first and/or second polypeptide by an internal ribosome entry site (IRES), or a nucleic acid encoding a self-cleaving peptide or a peptide that causes ribosome skipping and/or the third nucleic acid sequence is operably linked to the same promoter as the first and/or second nucleic acid sequence.

120. The polynucleotide of any of embodiments 116-119, wherein the nucleic acid encoding a self-cleaving peptide or a peptide that causes ribosome skipping is selected from a T2A, a P2A, a E2A or a F2A.

121. A vector, comprising the polynucleotide of any of embodiments 114-120.

122. The vector of embodiment 121 that is an expression vector.

123. The vector of embodiment 121 or 122 that is a viral vector or a eukaryotic vector, optionally wherein the eukaryotic vector is a mammalian vector.

124. A cell, comprising polynucleotide or polynucleotides of embodiments 114-120, or a vector or vectors of any of embodiments 121-123.

125. The cell of embodiment 124, wherein the cell is recombinant or isolated.

126. The cell of embodiment 125, wherein the cell is a mammalian cell.

127. The cell of embodiment 126, wherein the cell is a HEK293 or CHO cell.

128. A method of producing a multispecific polypeptide construct, the method comprising introducing into a cell a polynucleotide or polynucleotides of any of embodiments 114-120 or a vector or vectors of any of embodiments 121-123 and culturing the cell under conditions to produce the multispecific polypeptide construct.

129. A method of producing a multispecific polypeptide construct, the method comprising culturing the cell of any of embodiments 124-127 under conditions in which the multispecific polypeptide is produced by the cell.

130. The cell of embodiment 128 or 129, wherein the cell is a mammalian cell.

131. The cell of embodiment 130, wherein the cell is a HEK293 or CHO cell.

132. The method of embodiment 128 or embodiment 129, further comprising isolating or purifying the multispecific polypeptide construct from the cell.

133. The method of any of embodiments 128-132, wherein the multispecific polypeptide construct is a heterodimer.

134. A multispecific polypeptide construct produced by the method of any of embodiments 128-133.

135. A pharmaceutical composition comprising the multispecific polypeptide construct of any of embodiments 1-113 or embodiment 134 and a pharmaceutically acceptable carrier.

136. The pharmaceutical composition of embodiment 135 that is sterile.

137. A method of stimulating or inducing an immune response, the method comprising contacting a target cell and a T cell with the multispecific polypeptide construct of any of embodiments 1-113 or embodiment 134 or the pharmaceutical composition of embodiments 109 or embodiment 110, said target cell expressing a tumor associated antigen recognized by the multispecific polypeptide construct.

138. The method of embodiment 137, wherein the target cell is a tumor cell expressing the tumor associated antigen (TAA).

139. The method of embodiment 138 or embodiment 138, wherein the multispecific polypeptide construct comprises a cleavage linker that functions as a substrate for a protease and the inducing or stimulating the immune response is increased in the presence of the protease.

140. The method of embodiment 139, wherein the protease is produced by an immune effector cell, by a tumor, or by cells present in the tumor microenvironment.

141. The method of embodiment 139 or embodiment 140, wherein the protease is produced by an immune effector cell and the immune effector cell is an activated T cell, a natural killer (NK) cell, or an NK T cell.

142. The method of embodiment 141, wherein the immune effector cell is in proximity to cells that express the antigen.

143. The method of any of embodiments 137-142, wherein the protease is produced by a tumor that is in proximity to cells that express the TAA in a tissue and/or produced by a tumor that is co-localized with TAA in a tissue, and wherein the protease cleaves the cleavable linker in the multispecific polypeptide construct when the multispecific polypeptide construct is exposed to the protease.

144. The method of any of embodiments 137-143, wherein the protease is selected from among matriptase, a matrix metalloprotease (MMP), granzyme B, and combinations thereof.

145. The method of embodiment 144, wherein the protease is granzyme B.

146. The method of any of embodiments 137-145, wherein the contacting is carried out ex vivo or in vitro.

147. The method of any of embodiments 137-145, wherein the contacting is carried out in vivo in a subject.

148. A method of stimulating or inducing an immune response in a subject, the method comprising administering, to a subject in need thereof, a therapeutically effective amount of the multispecific conjugate of any of embodiments 1-113 or embodiment 134 or the pharmaceutical composition of embodiments 109 or embodiment 110.

149. The method of embodiment, 137-147, and 148, which increases cell-mediated immunity.

150. The method of any of embodiments 137-147, 148, and 149, which increases T-cell activity.

151. The method of any of embodiments 137-147, 148-150, which increases cytolytic T-cell (CTL) activity.

152. The method of any of embodiments 137-147, 148-151, wherein the immune response is increased against a tumor or cancer.

153. The method of any of embodiments 137-147, 148-152, wherein the method treats a disease or condition in the subject.

154. A method of treating a disease or condition in a subject, the method comprising administering, to a subject in need thereof, a therapeutically effective amount of the multispecific conjugate of any of embodiments 1-113 or the pharmaceutical composition of embodiments 135 or embodiment 136.

155. The method of embodiment 153 or embodiment 154, wherein the disease or condition is a tumor or a cancer.

156. The method of any of embodiments 147, 148-155, wherein said subject is a human.

157. A multispecific polypeptide construct that, in an inactive state, comprises a first component and a second component, wherein the first and second components are operably linked, wherein each of the first and second components comprises an antigen binding domain that binds a tumor associated antigen (TAA), wherein the first component comprises an Fc region, wherein the second component comprises a CD3-binding region, and wherein the first and second components are coupled by a cleavable linker.

158. The multispecific polypeptide of embodiment 157, wherein, in an inactive state, binding of the CD3-binding region to CD3 is inhibited or substantially reduced.

159. The multispecific polypeptide of embodiment 157, wherein in an activated state, the first and second components are not operably linked.

160. The multispecific polypeptide of embodiment 157, wherein in an activated state, the second component binds the epsilon chain of CD3 (CD3ε) and a tumor associated antigen (TAA).

161. A multispecific polypeptide construct that, in an activated state binds the epsilon chain of CD3 (CD3ε) and a tumor associated antigen (TAA), the multispecific polypeptide construct comprising:
- a first antigen binding domain that binds a first epitope on the TAA;
- an antibody or antigen binding fragment thereof that binds to CD3ε;
- an immunoglobulin Fc polypeptide region;
- a second antigen binding domain that binds a second epitope on the TAA; and
- a cleavable linker coupled to the immunoglobulin Fc polypeptide region and the second antigen binding domain, wherein the cleavable linker is a polypeptide that functions as a substrate for a protease.

162. The multispecific polypeptide construct of embodiment 161, wherein the protease is produced by an immune effector cell.

163. The multispecific polypeptide construct of embodiment 162, wherein the immune effector cell is in proximity to cells that express the TAA.

164. The multispecific polypeptide construct of any one of embodiments 161 to 163, wherein the protease cleaves the cleavable linker in the multispecific polypeptide construct when the multispecific polypeptide construct is exposed to the protease.

165. The multispecific polypeptide construct of embodiment 161, wherein the protease is produced by a tumor that is in proximity to cells that express the TAA in a tissue and/or produced by a tumor that is co-localized with TAA in a tissue, and wherein the protease cleaves the cleavable linker in the multispecific polypeptide construct when the multispecific polypeptide construct is exposed to the protease.

166. The multispecific polypeptide construct of embodiment 161, wherein the cleavable linker is a polypeptide of up to 25 amino acids in length.

167. The multispecific polypeptide construct of embodiment 161, wherein the cleavable linker is a substrate for matriptase, a matrix metalloprotease (MMP), granzyme B, and combinations thereof.

168. The multispecific polypeptide construct of embodiment 161, wherein the cleavable linker comprises an amino acid sequence selected from the group consisting of SEQ ID NOs: 24-31.

169. The multispecific polypeptide construct of embodiment 161, wherein each of the first antigen binding domain and the second antigen binding domain is an antibody or antigen-binding fragment thereof selected from the group consisting of a Fab fragment, a F(ab')$_2$ fragment, an Fv fragment, a scFv, a scAb, a dAb, a single domain heavy chain antibody, and a single domain light chain antibody.

170. The multispecific fusion polypeptide of embodiment 169, wherein the antibody or antigen-binding fragment thereof is a Fv, a scFv, a Fab, a single domain antibody (sdAb), a $V_{NAR}$, or a VHH.

171. The multispecific fusion polypeptide of embodiment 169, wherein the antibody or antigen-binding fragment is an sdAb.

172. The multispecific fusion polypeptide of embodiment 171, wherein the sdAb is a human or humanized sdAb.

173. The multispecific fusion polypeptide of embodiment 171, wherein the sdAb is VHH, $V_{NAR}$, an engineered VH domain or an engineered VK domain.

174. The multispecific fusion polypeptide of embodiment 161, wherein the immunoglobulin Fc region polypeptide comprises an amino acid sequence selected from the group consisting of SEQ ID NOs: 1-2.

175. The multispecific fusion polypeptide of embodiment 174, wherein the immunoglobulin Fc region polypeptide comprises at least one modification to enhance FcγR binding.

176. The multispecific fusion polypeptide of embodiment 175, wherein the modification is modification at Ser239 or Ile332.

177. The multispecific fusion polypeptide of embodiment 174, wherein the immunoglobulin Fc glycosylation is modified to enhance FcγR binding as compared to an unmodified Fc region.

178. The multispecific fusion polypeptide of embodiment 177, wherein the immunoglobulin Fc glycosylation lacks or has reduced fucose content.

179. The multispecific fusion polypeptide of embodiment 174, wherein the immunoglobulin Fc region polypeptide comprises at least one modification to induce heterodimerization.

180. The multispecific fusion polypeptide of embodiment 179, wherein the modification is at a position selected from the group consisting of Thr366, Leu368, and Tyr407, and combinations thereof.

181. The multispecific fusion polypeptide of embodiment 180, wherein the modification is selected from the group consisting of Thr366Ser, Leu368Ala, Tyr407Val, and combinations thereof.

182. The multispecific fusion polypeptide of embodiment 181, further comprising a modification of a non-cysteine residue to a cysteine residue at a position selected from the group consisting of Ser354, Y349, and combinations thereof.

183. The multispecific fusion polypeptide of embodiment 181, further comprising a modification at residue Ile235.

184. The multispecific fusion polypeptide of embodiment 183, wherein the modification is Ile235Arg.

185. The multispecific fusion polypeptide of embodiment 174, wherein the immunoglobulin Fc region polypeptide comprises a modification at residue Ile235.

186. The multispecific fusion polypeptide of embodiment 185, wherein the modification is Ile235Arg.

187. The multispecific fusion polypeptide of embodiment 174, wherein the immunoglobulin Fc region polypeptide comprises at least one modification to enhance FcRn binding.

188. The multispecific fusion polypeptide of embodiment 187, wherein the modification is at a position selected from the group consisting of Met252, Ser254, Thr256, Met428, Asn434, and combinations thereof.

189. The multispecific fusion polypeptide of embodiment 188, wherein the modification is at a position selected from the group consisting of Met252Y, Ser254T, Thr256E, Met428L, Met428V, Asn434S, and combinations thereof.

190. The multispecific fusion polypeptide of embodiment 187, wherein the modification is at position Met252 and at position Met428.

191. The multispecific fusion polypeptide of embodiment 190, wherein the modification is Met252Y and M428L.

192. The multispecific fusion polypeptide of embodiment 190, wherein the modification is Met252Y and M428V.

193. The multispecific polypeptide construct of embodiment 161, wherein the multispecific polypeptide construct comprises a first linking peptide (LP1) between the first antigen binding domain and the immunoglobulin Fc polypeptide region.

194. The multispecific polypeptide construct of embodiment 161, wherein the multispecific polypeptide construct comprises a second linking peptide (LP2) between the anti-CD3 binding domain and the second antigen binding domain.

195. The multispecific polypeptide construct of embodiment 161, wherein the multispecific polypeptide construct comprises a first linking peptide (LP1) between the first antigen binding domain and the immunoglobulin Fc polypeptide region and a second linking peptide (LP2) between the anti-CD3 binding domain and the second antigen binding domain, and wherein the multispecific polypeptide construct in the uncleaved state has the structural arrangement from N-terminus to C-terminus as follows: first antigen binding domain-LP1-immunoglobulin Fc polypeptide linker region-cleavable linker-anti-CD3 binding domain-LP2-second antigen binding domain.

196. The multispecific polypeptide construct of embodiment 195, wherein the two linking peptides are not identical to each other.

197. The multispecific polypeptide construct of embodiment 195, wherein each of LP1 and LP2 is a peptide of about 1 to 20 amino acids in length.

198. The multispecific polypeptide construct of embodiment 161, wherein the antibody or antigen binding fragment thereof that binds to CD3ε is an Fv antibody fragment.

199. The multispecific polypeptide construct of embodiment 198, wherein the Fv antibody fragment comprises a disulfide stabilized anti-CD3 binding Fv fragment (dsFv).

200. The multispecific polypeptide construct of embodiment 199, wherein anti-CD3 dsFv comprises a VH CDR1 comprising the amino acid sequence TYAMN (SEQ ID NO: 16); a VH CD2 comprising the amino acid sequence RIRSKYNNYATYYADSVKD (SEQ ID NO: 17); a VH CDR3 comprising the amino acid sequence HGNFGNSYVSWFAY (SEQ ID NO: 18), a VL CDR1 comprising the amino acid sequence RSSTGAVTTSNYAN (SEQ ID NO: 19); a VL CDR2 comprising the amino acid sequence GTNKRAP (SEQ ID NO: 20); and a VL CDR3 comprising the amino acid sequence ALWYSNLWV (SEQ ID NO: 21).

201. The multispecific polypeptide construct of embodiment 198, wherein the VH and VL that comprise the anti-CD3 binding Fv are linked to opposite sides of a heterodimeric Fc.

202. The multispecific polypeptide construct of embodiment 200, wherein anti-CD3 dsFv comprises the amino acid sequence of SEQ ID NO: 14.

203. The multispecific polypeptide construct of embodiment 200, wherein anti-CD3 dsFv comprises the amino acid sequence of SEQ ID NO: 15.

204. The multispecific polypeptide construct of embodiment 200, wherein anti-CD3 dsFv comprises the amino acid sequence of SEQ ID NO: 14 and the amino acid sequence of SEQ ID NO: 15.

205. The multispecific polypeptide construct of embodiment 204, wherein anti-CD3 dsFv comprises an amino acid sequence selected from the group consisting of SEQ ID NO: 32-81.

206. The multispecific polypeptide construct of embodiment 204, wherein anti-CD3 dsFv comprises a combination of an amino acid sequence selected from the group consisting of SEQ ID NO: 32-62 and an amino acid sequence selected from the group consisting of SEQ ID NO: 63-81.

207. The multispecific polypeptide construct of any one of embodiments 1 to 206, wherein the multispecific polypeptide construct is conjugated to an agent.

208. The multispecific polypeptide construct of embodiment 207, wherein the agent is a therapeutic agent, an antineoplastic agent, a toxin or fragment thereof, a detectable moiety or a diagnostic agent.

209. The multispecific polypeptide construct of embodiment 207, wherein the agent is conjugated to the multispecific polypeptide construct via a linker.

210. A pharmaceutical composition comprising the multispecific polypeptide construct of any of one of embodiments 1 to 209 and a carrier.

211. A method of treating or alleviating a symptom of a clinical indication associated with a disorder in a subject, the method comprising administering the multispecific polypeptide construct of any one of embodiments 157 to 209 or the pharmaceutical composition of embodiment 210 to a subject in need thereof in an amount sufficient to alleviate the symptom of the clinical indication associated with the disorder.

212. The method of embodiment 211, wherein said subject is a human. 213. The method of embodiment 211, wherein the disorder is cancer.

VI. Examples

The following examples are included for illustrative purposes only and are not intended to limit the scope of the invention.

Example 1. Method of Producing Constrained CD3 Binding Proteins

Example 1 describes the generation and expression of multispecific polypeptide constructs containing a CD3 binding region that exhibits constrained CD3 binding. The multispecific constructs were generated in various configurations, as shown in FIG. 1, FIG. 2, FIG. 3, FIGS. 4A-4C, FIGS. 5A-5E, FIGS. 6A-6B, FIG. 7, FIG. 8 and FIG. 9 to contain a heterodimeric Fc region of an immunoglobulin coupled by a linker (e.g. a cleavable linker) to the CD3 binding region, and one or more antigen binding domain that binds a tumor associated antigen (TAA) positioned amino-terminally relative to the Fc region and/or carboxy-terminally relative to the CD3 binding region of the multispecific polypeptide construct. Exemplary representative constructs with different TAA antigen binding domains and linkers were generated.

Polynucleotides encoding at least a first polypeptide chain and a second polypeptide chain of the heterodimeric multispecific polypeptide construct were generated and cloned into a plasmid for expression. The first polypeptide chain generally included in order, from the N-terminus to C-terminus, an Fc hole polypeptide (e.g. set forth in SEQ ID NO:83); a cleavable linker, such as one containing one or more substrate recognition sites for a protease; and a variable light (VL) domain of a dsFv anti-CD3 antibody (e.g. set forth in SEQ ID NO:72). The second polypeptide chain generally included in order, from the N-terminus to C-terminus, an Fc knob polypeptide (e.g. set forth in SEQ ID NO: 82); the same cleavable linker as the first polypeptide chain; and a variable heavy domain of a dsFv anti-CD3 antibody (e.g. set forth in SEQ ID NO:44). Except as noted, the exemplary cleavable linker, GGSGGGGIEPDIGGSGGS (SEQ ID NO:105) containing a substrate recognition site for granzyme B was used in exemplary constructs. A similar linker, TGGSGGGIEPDIGGSGGS (SEQ ID NO:148), was used in exemplary construct cx1547 containing FRα. For the exemplary construct cx309, the exemplary cleavable linker GSPAGLEADGSRQARVGS (SEQ ID NO: 166) was used. Similar constructs can be generated using other heterodimeric Fc configurations, including other knob-into-hole configurations, such as any as described; other linkers, including other cleavable linkers, particularly polypeptide linkers that include a substrate recognition site for a protease, such as granzyme B, matriptase and/or an MMP; and other CD3-binding regions, including other anti-CD3 antibodies, including dsFv or other monovalent fragments; or other TAA antigen-binding fragments, such as scFv, sdAb or Fab formats.

In some cases, similar constructs were generated, except containing a non-cleavable linker. The non-cleavable linker included linkers ranging from 3-18 amino acids in size. Examples of non-cleavable linker used in exemplary generated molecules were GGS (e.g. contained in exemplary construct cx1356), GGSGGS (SEQ ID NO:10, contained in exemplary construct cx1357), GGSGGSGGS (SEQ ID NO:11, contained in exemplary construct cx1358), GGSGGSGGSGGS (SEQ ID NO:12, contained in exemplary construct cx1359), GGSGGSGGSGGSGGS (SEQ ID NO:13, contained in exemplary construct cx1360), and GGGGGSGGGGGSGGGGS (SEQ ID NO:119) or GGSGGGGSGGGGSGGGGS (SEQ ID NO: 147, contained in exemplary construct cx681).

One or both of the polypeptide chains additionally encoded one or more TAA antigen binding domain amino terminal to the Fc domain and/or carboxy terminal to the CD3 binding region, in various configurations. When the TAA was provided as a single chain fragment, e.g. sdAb or scFv, the TAA antigen binding domain was linked at the N-terminus to one or both polypeptide chains of the Fc heterodimer (e.g. hole and/or knob) by a peptide linker, e.g. PGGGG (SEQ ID NO:102) and/or was linked at the C-terminus to one or both domains (e.g. VH and/or VL) of the CD3 binding region by a peptide linker, e.g. GGGG (SEQ ID NO:103). Other similar peptide linkers can be employed. When the TAA was provided as a Fab, such as in the exemplary construct designated cx3313 or cx3315, an additional polynucleotide encoding the light chain of the Fab was cloned into a plasmid. In this example, the encoded polypeptides included one or more polypeptide chains in which the VH-CH1 (Fd) of the Fab was linked at the N-terminus of one or both polypeptide chains of the Fc heterodimer and/or linked at the C-terminus of one or both domains of the CD3 binding region, similar to above. The third polynucleotide encoded the VL-CL of the Fab. Any antigen binding domain that binds to a TAA can be employed in the provided multispecific polypeptide constructs.

Exemplary generated proteins contained an antigen binding domain that binds one of the following tumor associated antigens: Folate Receptor Alpha (FRα), B7H3, EGFR, 5T4, CD20, and DLL3. The generated proteins were either composed of VH and VL sequences assembled as Fabs or scFvs, or were generated to contain the binding domains as single domain antibodies (sdAbs). Various TAA-binding domains where used herein including sdAb, scFv and Fab, including from the following sources: cMet sdAb as set forth in SEQ ID NO: 123 (U.S. Pat. No. 9,346,884); B7H3 Fab and scFv as set forth in SEQ ID NOS: 127 and 128 and scFv as set forth in SEQ ID NO: 124 (PCT Pub. No. WO2017030926); 5T4 scFv as set forth in SEQ ID NO: 129, 130, 167, and 168 (U.S. Pat. No. 8,044,178); DLL3 scFv as set forth in SEQ ID NO: 189 (U.S. Pub. No. US 2017/0037130); CD20 GA101 as set forth in SEQ ID NO: 125, 189, and 190 (U.S. Pub. No. US 2005/0123546). Multispecific polypeptide constructs were generated containing 1, 2, 3 or 4 TAA antigen binding domain, such as to provide for monovalent, bivalent, trivalent, or tetravalent binding. In some cases, the TAA antigen binding domains were the same. In some cases, the TAA antigen binding domains were different, such that the generated multispecific polypeptide constructs exhibited specificity for at least two different TAAs, to different epitopes of the same TAA or the same epitopes of the same TAA. For example, exemplary dual targeted multispecific polypeptide constructs were generated containing an antigen binding domain with specificity for EGFR and cMet (see e.g. FIG. 5C and exemplary constructs designated cx2973, cx2979 and cx2977). Further, exemplary multispecific polypeptide constructs were generated containing different TAA antigen binding domains specific for the same epitope of B7H3 or for two different epitopes of B7H3 (e.g. FIG. 6A and exemplary constructs designated cx2846 and cx3094, respectively) or for the same epitope of 5T4 (e.g. FIG. 7, exemplary construct cx3252).

Figure 3:
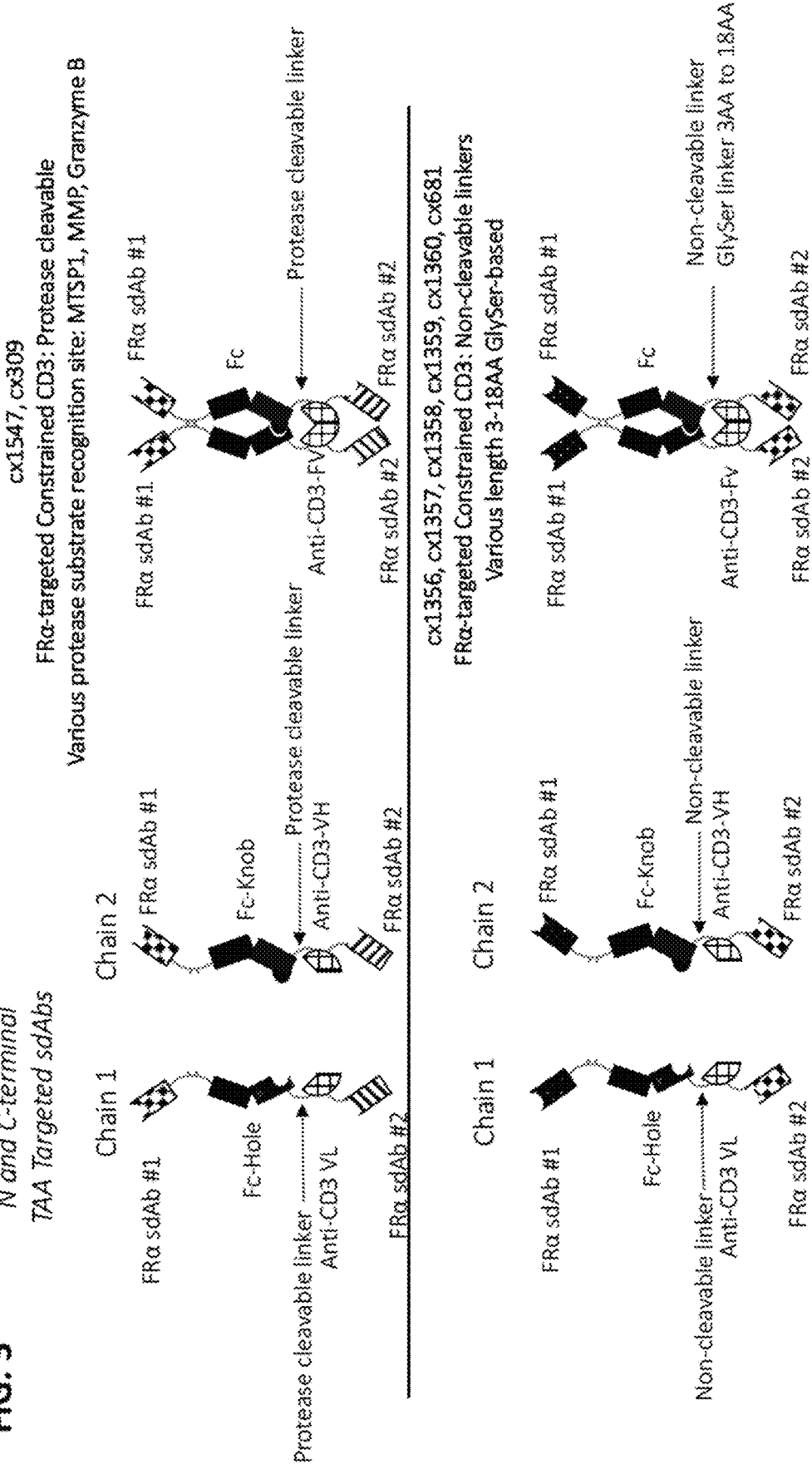
FIG. 3 is a schematic of various FRa-targeting constrained CD3 construct composed of two polypeptides, Chain 1 and Chain 2. The top panel provides an exemplary depiction of a cleavable multispecific polypeptide construct having a cleavable linker containing a protease substrate recognition site or sites, e.g. for one or more of MTSP1, MMP and/or granzyme B. Chain 1 contains a FRa sdAb (antigen binding domain), linked to a heterodimeric Fc "hole", linked via the protease cleavable linker (cx1547: granzyme B only, cx309: MTSP1, MMP and granzyme B) to anti-CD3 VL domain, linked to a second FRa sdAb Chain 2 contains a FRa sdAb, linked to a complementary heterodimeric Fc "knob", linked via the same protease linker as above to anti-CD3 VH domain, linked to second FRa sdAb. The bottom panel of FIG. 3 depicts a similar configuration as the top panel, except that the linker is a non-cleavable linker (ranging from 3 amino acids in cx1356 to 18 amino acids in cx681). When co-expressed the CD3 binding domain is properly assembled via the association of the VL:VH on the hole and knob, respectively.
Figure 4A:
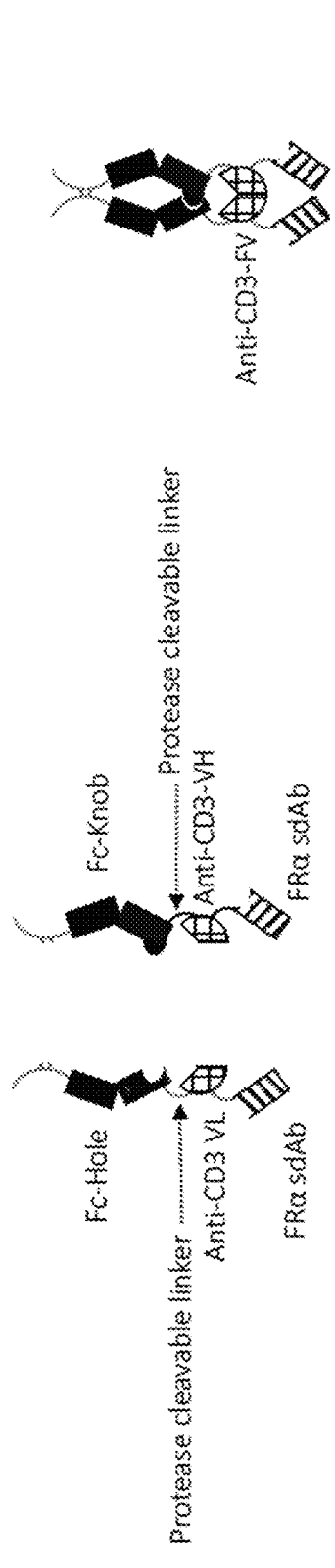
FIG. 4A-4C depicts constructs that were generated to compare the effect of the linker to constrain CD3 binding in the generated constructs.
Figure 4B:
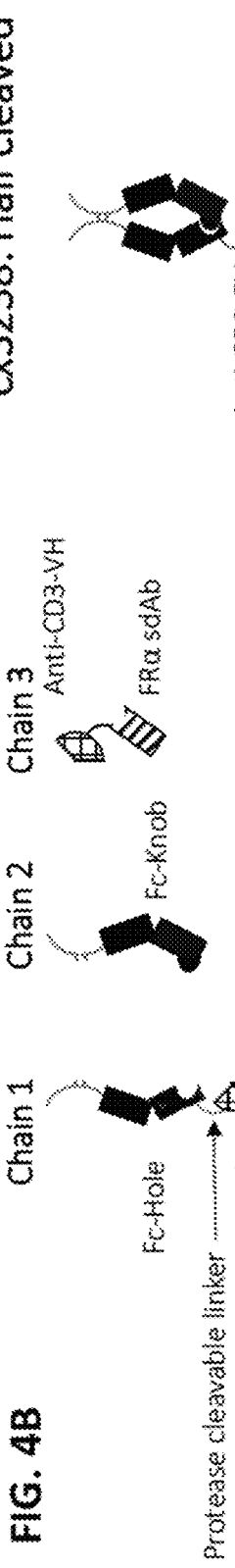
Figure 4C:
Figure 5B:
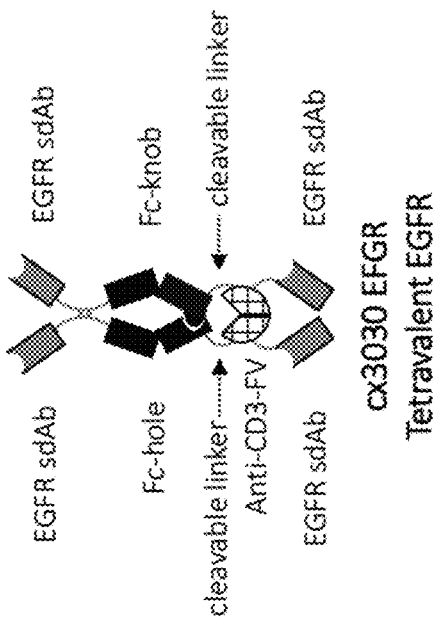
FIG. 5A-5E depicts representative EGFR-targeted and EGFR/cMET-dual targeted constrained CD3 engagers.
Figure 5A:
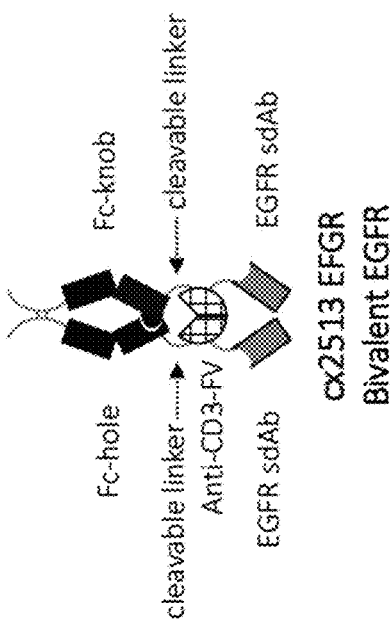
Figure 5C:
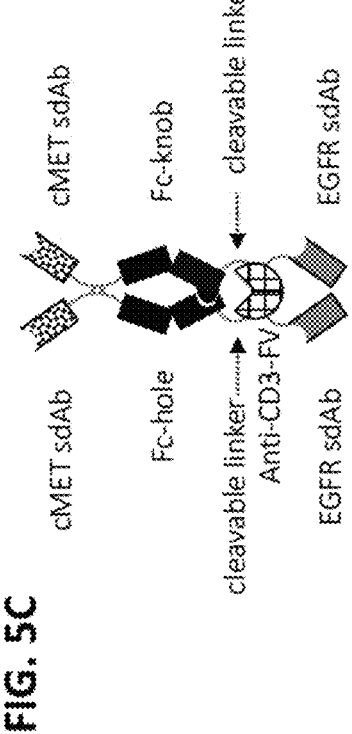
Figure 5E:
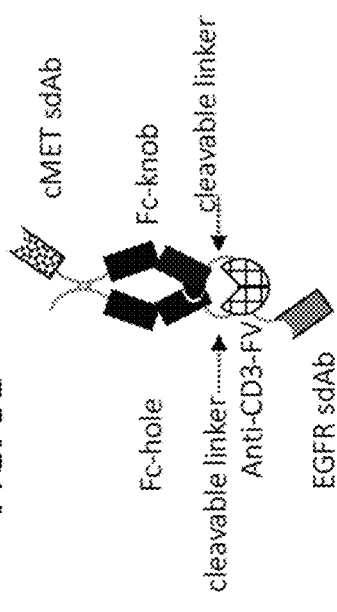
Figure 5D:
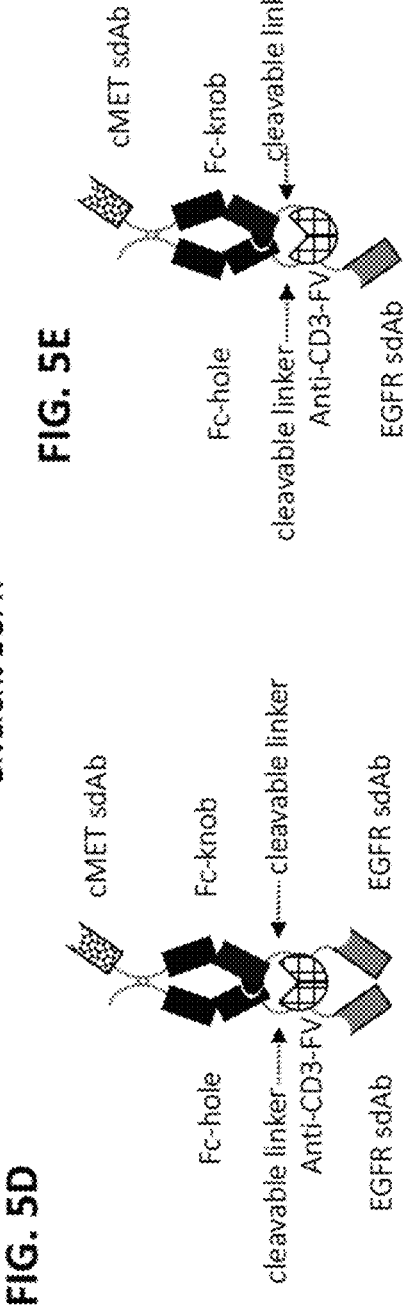
Figure 6A:
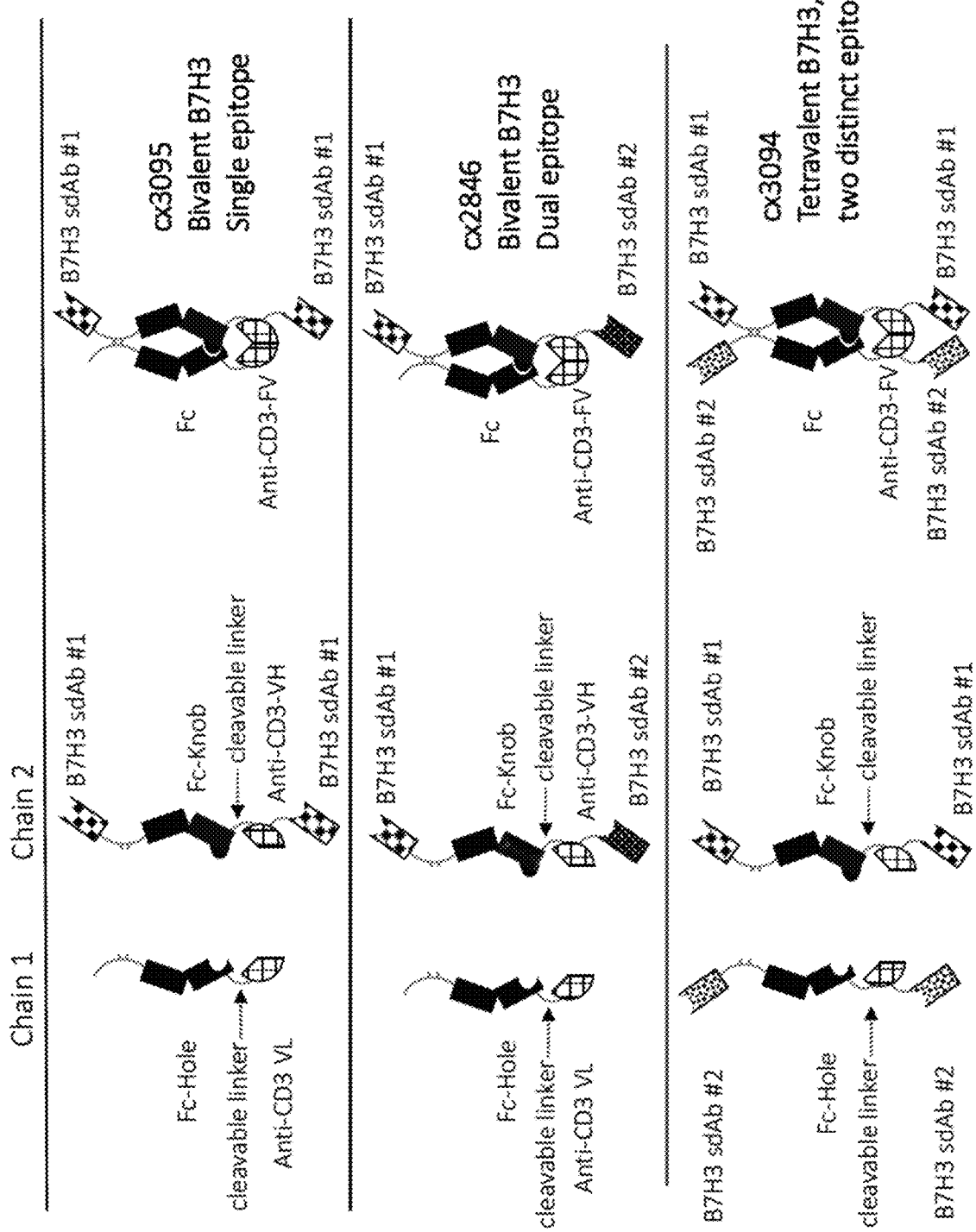
FIGS. 6A and 6B are schematics of the component chains to assemble exemplary B7H3-targeted constrained CD3 engagers. B7H3-binding domains utilized in these representative constructs included sdAb, scFv or FAB. Generally, sdAb and scFv containing constructs were composed as two heterodimeric chains, whereas FAB containing constructs included a third chain for the cognate light chain (VL-CL).
Figure 6B:
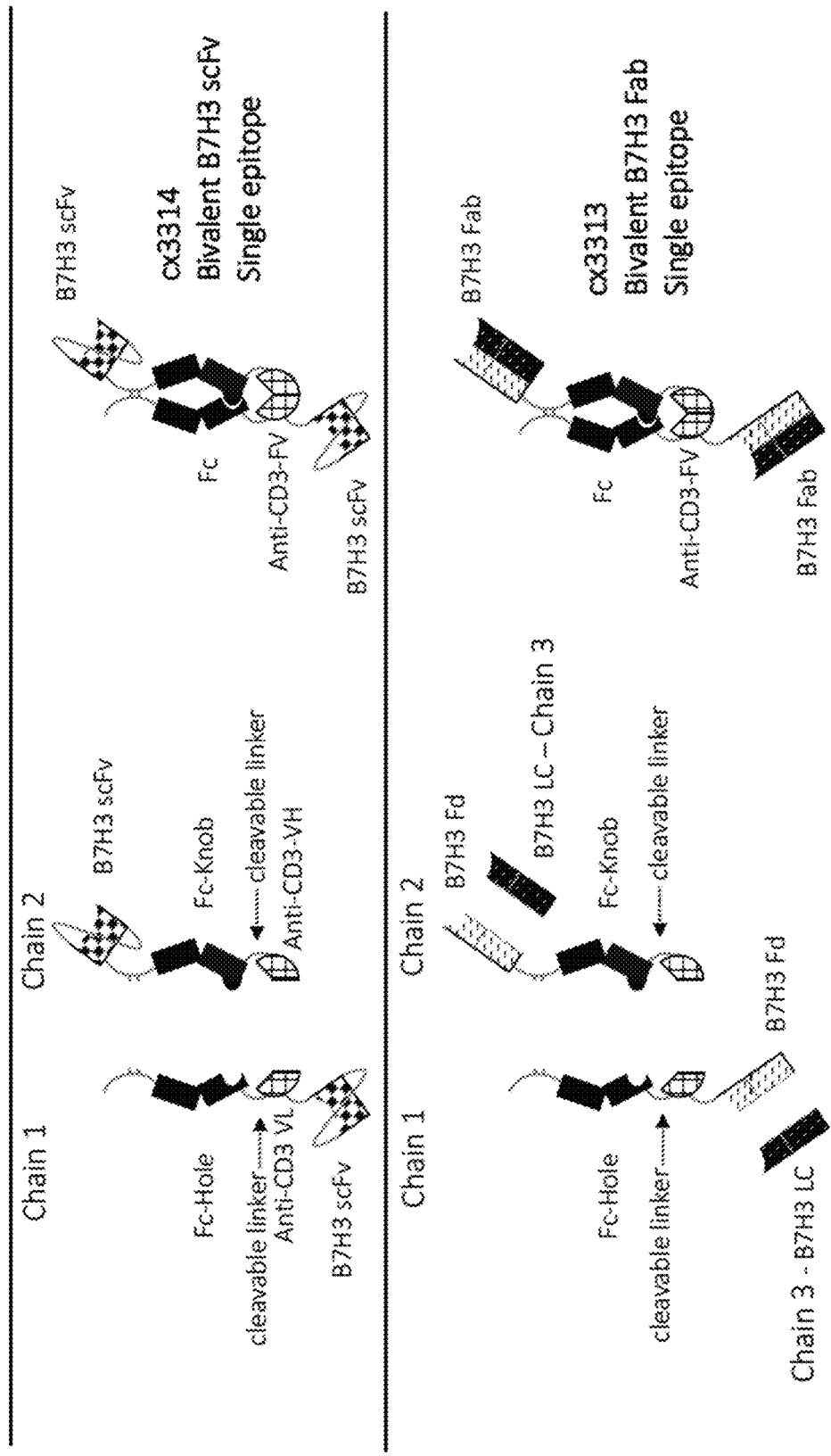
Figure 7:
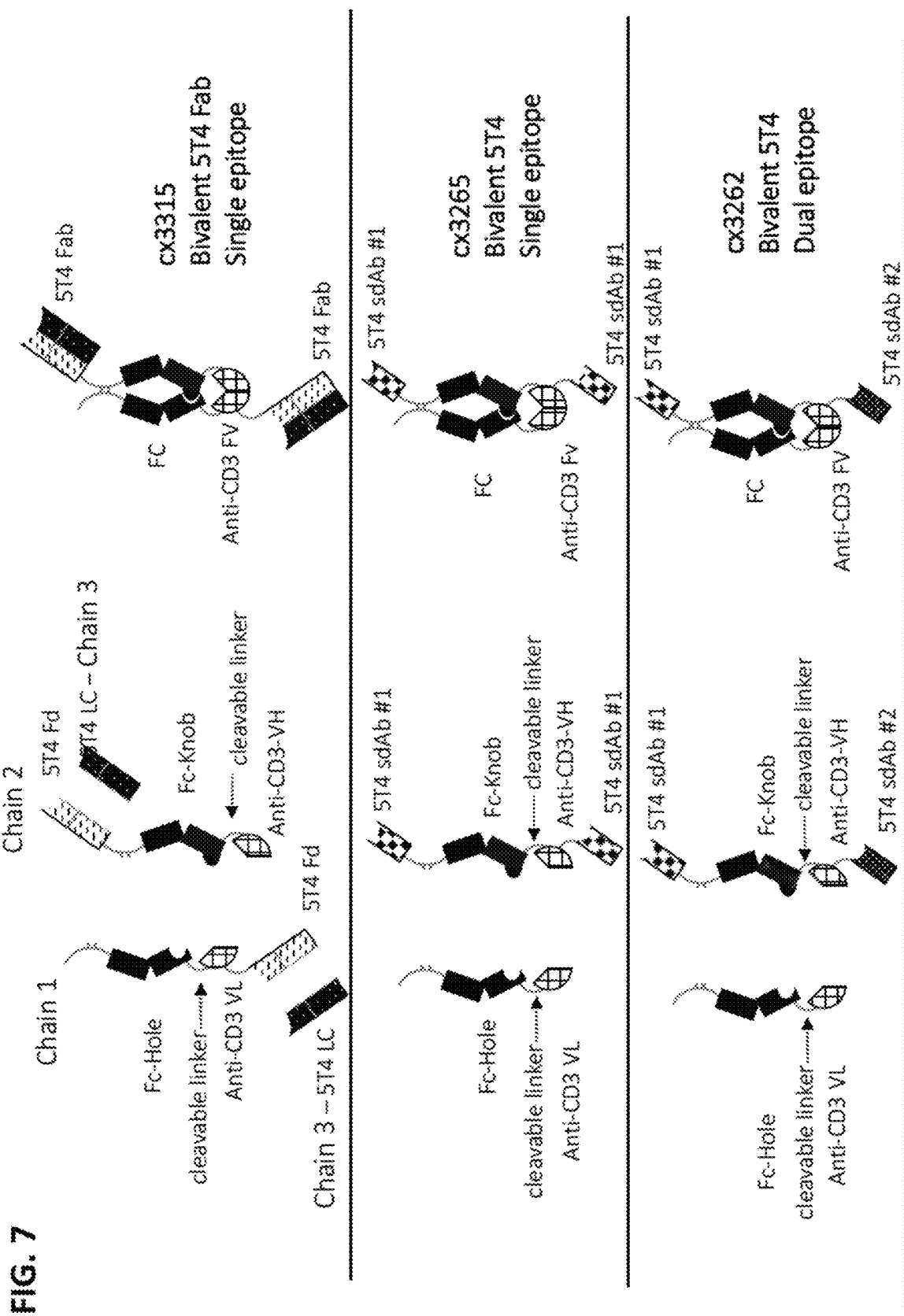
FIG. 7 depicts 5T4-targeting constrained CD3 engagers. The core of the molecule was generated to contain a heterodimeric Fc followed by cleavable linkers and a disulfide stabilized anti-CD3 Fv. The TAA binding portion of these molecules was placed on the N- or C-termini of either heterodimeric Fc chain. In the top row, the TAA binding unit is a Fab, being composed of a Fd (VH-CH1) on N-terminus of the knob polypeptide, and C-terminus of the hole polypeptide. In the case of a Fab being the binding unit, a third chain (the light chain—VL-CL) was expressed to associate with the Fd. In the middle and bottom row, the TAA binding units are single domain antibodies that were both positioned on the knob polypeptide at the N- and C-terminus. In the middle row, the TAA binding sdAbs of the generated construct are the same, and in the bottom row, the TAA binding sdAbs of the generated construct are different sequences with different epitopes.
Figure 8:
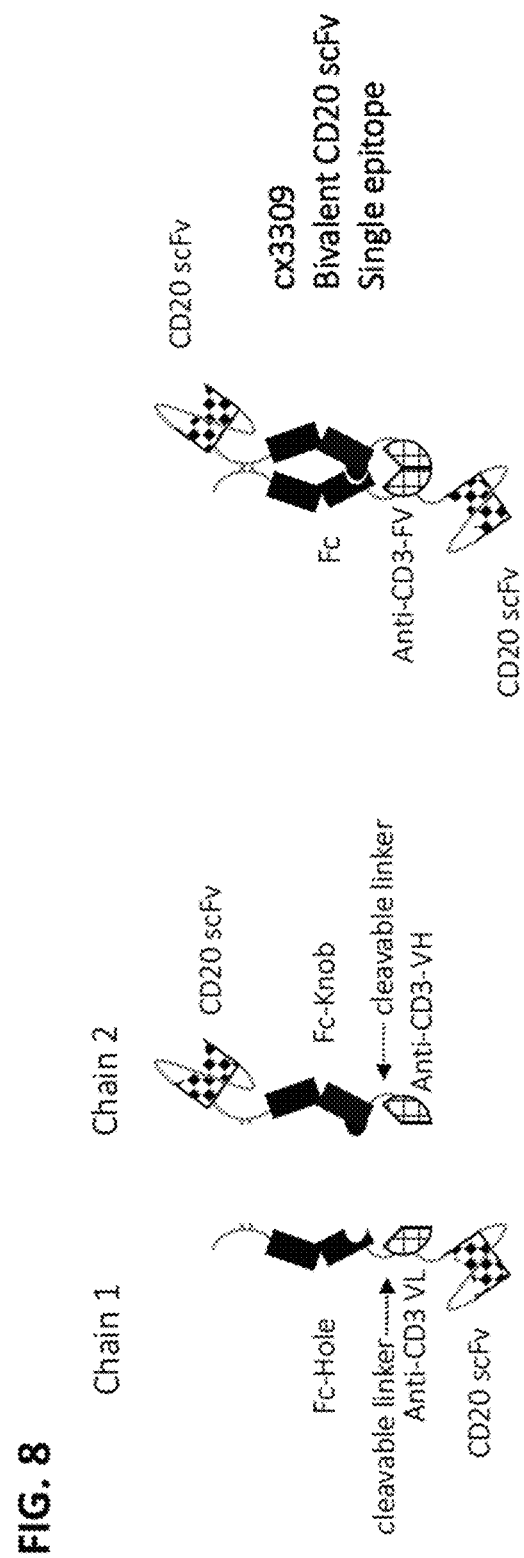
FIG. 8 is a schematic of a representative CD20-targeted constrained CD3 engaging construct, cx3309, wherein the CD20 binding domains are scFvs derived from the CD20 antibody GA101.
Figure 9:
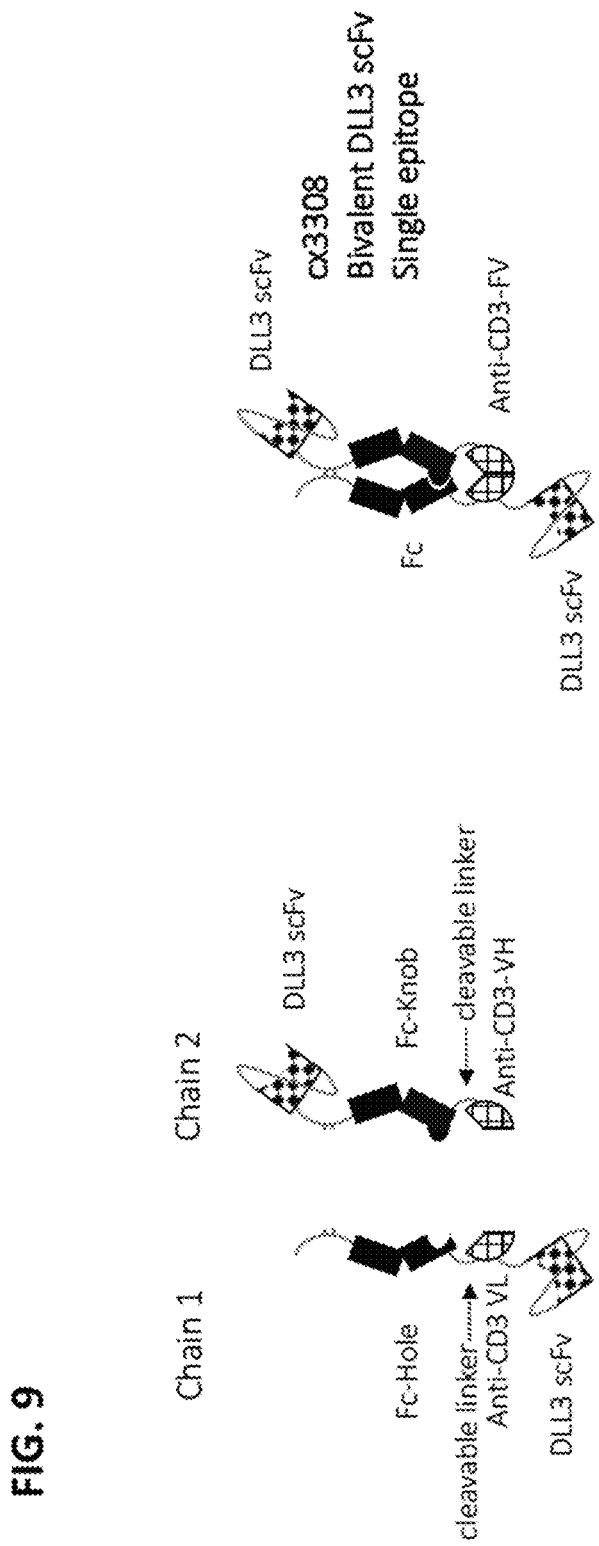
FIG. 9 is schematic of a representative DLL3-targeted constrained CD3 engaging construct, cx3308, wherein the DLL3 binding domains are scFvs. This exemplary construct is comprised of two chains each with a complementary component of a heterodimeric Fc linked to one component of the CD3 binding domain and a DLL3 binding scFv. In the assembled form the construct is bivalent to DLL3 and has the CD3 binding domain positioned C-terminal to the Fc heterodimer.

Polynucleotides were generated to encode polypeptide chains of exemplary multispecific polypeptide constructs designated cx1547, cx309, cx1356, cx1357, cx1358, cx1359, cx1360, cx681 and cx1762 (each targeting FRα); cx2513 and cx3030 (each targeting EGFR); cx2973, cx2979, cx2977 (each targeting cMET and EGFR); cx3095, cx2846, cx3094, cx3314 and cx3313 (each targeting B7H3); cx3315, cx3265 and cx3262 (each targeting 5T4); cx3309 (targeting CD20); and cx3308 (targeting DLL3), including constructs as depicted in FIGS. 3, 4A(top panel)-4C, 5A-5E, 6A-6B, 7, 8, and 9. The constructs were generated to contain a cleavable or non-cleavable linker.

Separate plasmids encoding each chain of the heterodimeric constrained CD3 binding protein were transiently transfected at an equimolar ratio into mammalian cells (either HEK293 or CHO) using polyethylenimine. Recombinant protein secreted into the supernatant was collected after 3-7 days, and purified by protein A chromatography, followed by either preparative size exclusion chromatography (SEC) or flow-through hydrophobic interaction chromatography (HIC). Heterodimeric protein was selectively purified owing to a mutation designed into one chain of the heterodimeric Fc at position I253R or H435R (usually the hole-Fc) such that it did not bind protein A. The second chromatography step on SEC (AKTA with Superdex-200 resin) or FT-HIC (AKTA with butyl/phenyl sepharose) was used to remove undesired cross-paired species containing two heterodimeric Fcs that were more hydrophobic and twice the expected molecular weight.

The method favored production of heterodimeric multispecific polypeptide constructs, containing properly paired species of heterodimeric Fc and the disulfide stabilized anti-CD3 Fv as described (anti-CD3 VH with the mutation G44C as set forth in SEQ ID NO: 44 and VL with the mutation G100C as set forth in SEQ ID NO: 72). Purified heterodimeric constrained CD3 binding protein was stable and did not accumulate cross-paired species upon prolonged incubation at 4° C. or increased protein concentration.

Figure 10A:
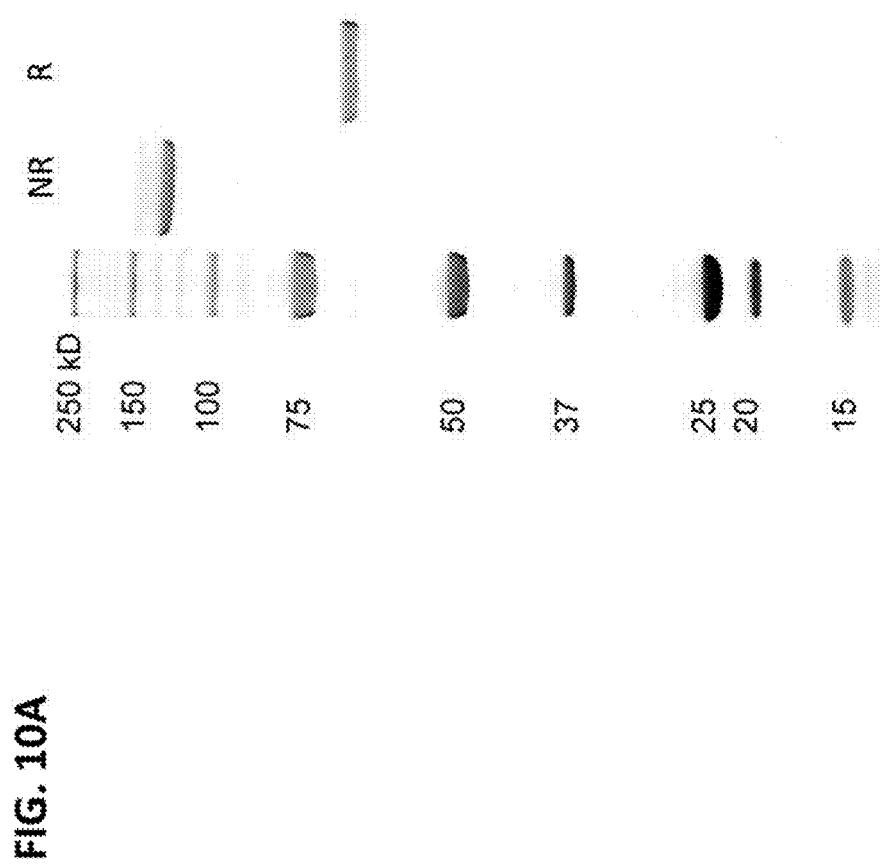
FIG. 10A is an image of a SDS-PAGE of a representative FRa-targeted constrained CD3 engaging construct, cx1547, reducing (R) and non-reducing (NR) conditions. Expected molecular weight 135 kDa.
Figure 10B:
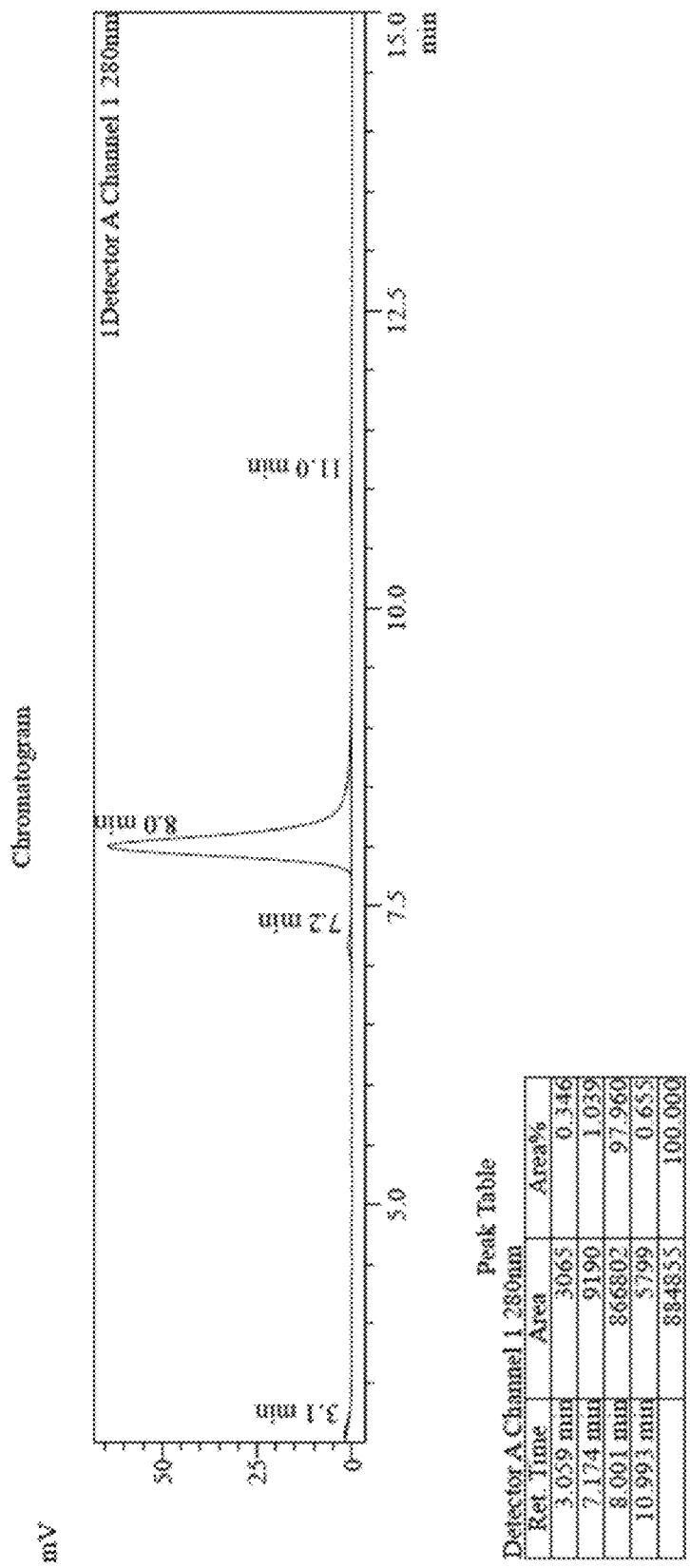
FIGS. 10B and 10C are graphs of chromatogram from size-exclusion analysis of cx1547, demonstrating that it is single species with a determined molecular weight of 137.9 kDa.
Figure 10C:
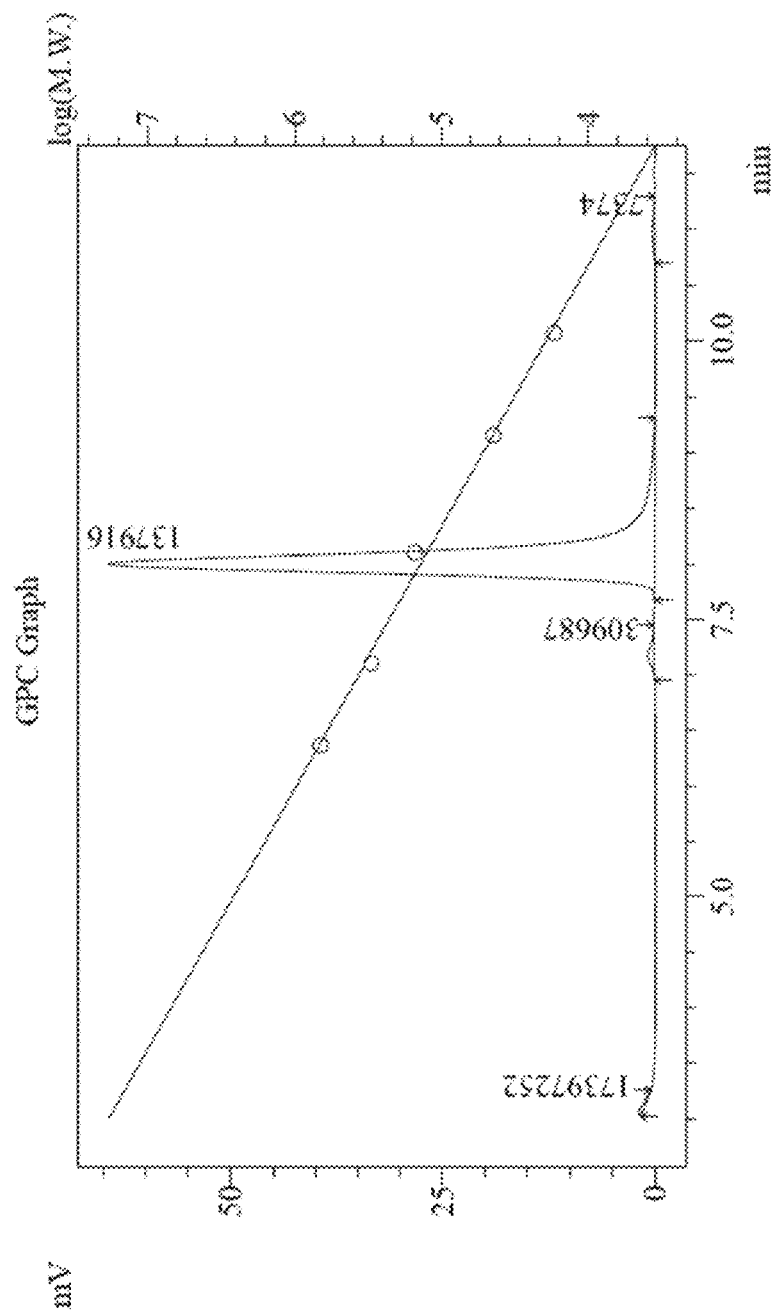

FIG. 10A shows an image of a SDS-PAGE of the FRα-targeted constrained CD3 engaging construct, cx1547, reducing (R) and non-reducing (NR) conditions (expected molecular weight 135 kDa). FIGS. 10B and 10C shows a chromatogram from size-exclusion analysis of cx1547, demonstrating that a single species with a determined molecular weight of 137.9 kDa was observed.

Example 2. Binding to Cancer Cells and Primary T Cells by Flow Cytometry

This Example describes studies assessing binding of exemplary constructs to T cells or to cancer cells. These studies were carried out in single cultures containing either only the T cells or only the cancer cells in isolation from each other.

1. Binding to Primary T Cells in Cleaved and Uncleaved State

Binding of an exemplary multispecific polypeptide construct of the disclosure, referred to herein as cx309, to CD3 on the surface of primary T cells was assessed following proteolytic cleavage of its cleavable linker, GSPAGLEAD-GSRQARVGS (SEQ ID NO:27), which contains substrate recognition sites for matriptase, granzyme B, and MMP-2. The tumor antigen binding domains of cx309 binds the Folate Receptor Alpha (FRα), which is not expressed on the primary T cells.

Primary T cells were negatively enriched from PBMCs isolated from healthy human donor leukopaks. Where noted, cx309 was pre-cleaved prior to addition to cells, with cleavage confirmed by SDS-PAGE. Specifically, cx309 was exposed to matriptase (FIG. 11A) or matrix metalloprotease 2 (MMP-2) (FIG. 11B) (cleaved) or was not exposed to protease (uncleaved). The cx309 construct, either cleaved or uncleaved, was titrated onto cells or added at a single, saturating concentration. Bound cx309 was detected with fluorophore-conjugated secondary antibodies specific for either human Fc or humanized vhh, and binding was measured by flow cytometry. Cells incubated with secondary antibody only served as negative controls.

Figure 11A:
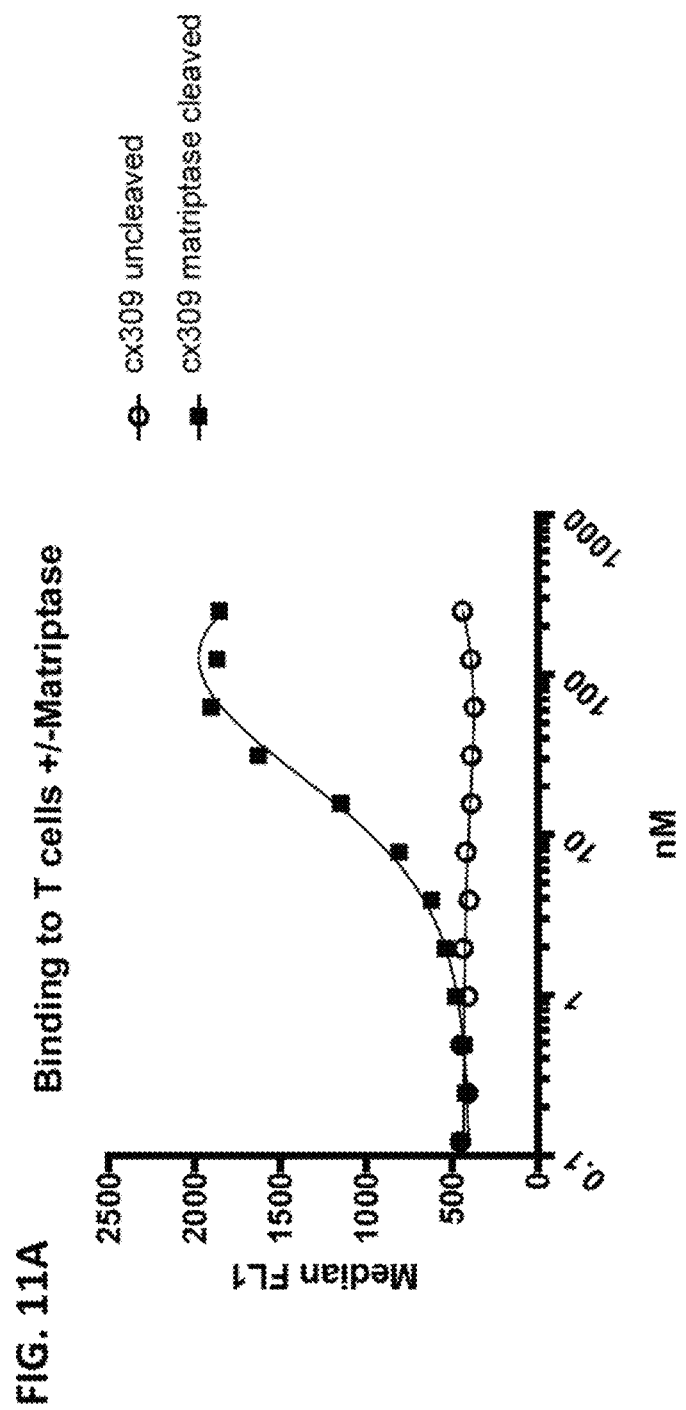
FIGS. 11A and 11B are a pair of graphs demonstrating the binding capacity of an exemplary multispecific polypeptide construct of the disclosure, referred to herein as cx309, to bind human T-cell in the uncleaved or proteolytically cleaved state. Matriptase and MMP-2 were used to cleave cx309 in FIG. 11A and FIG. 11B, respectively.
Figure 11B:
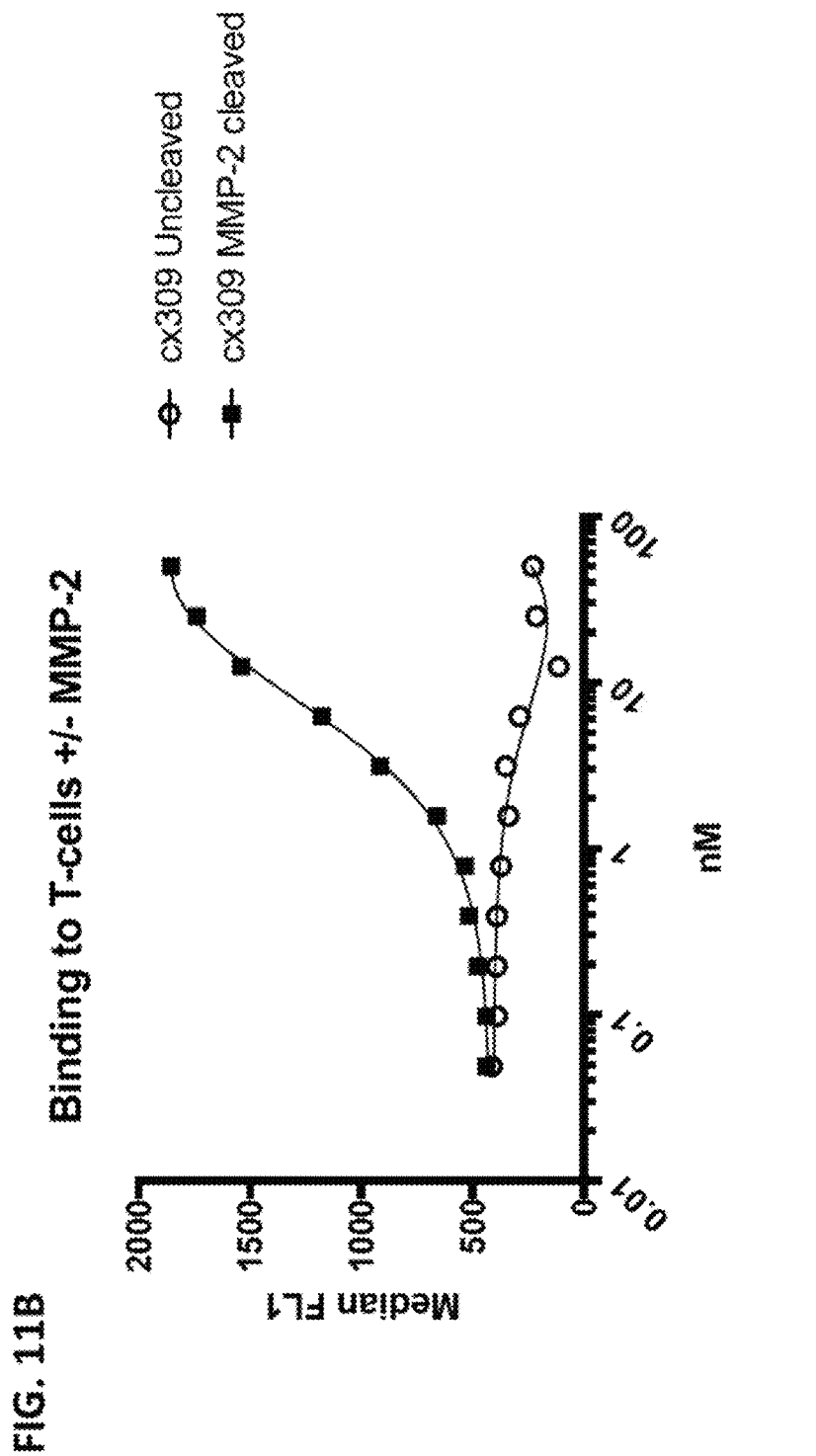

As shown in FIGS. 11A and 11B, cx309 bound to T cells after the construct was cleaved, by either matriptase or MMP-2 within the linker between the Fc and the CD3 binding domain prior to initiation of the binding assay. No binding to T cells was observed with the uncleaved construct, showing that cx309 was able to bind to T-cells in the cleaved, i.e., active state but displayed undetectable T-cell binding in the uncleaved form.

2. Comparison of Binding to T Cells Vs. Antigen-Expressing Cancer Cells

Figure 12B:
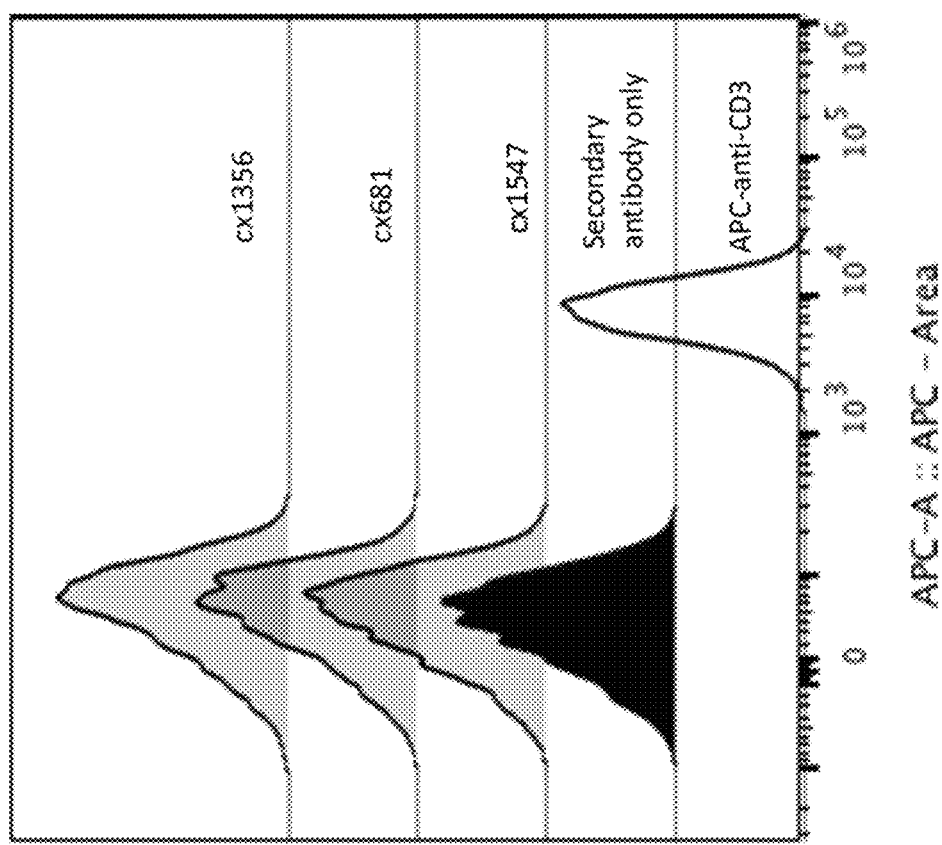
FIG. 12A-12D depicts cellular binding by representative FRa-targeting constrained CD3 engaging constructs, cx1356, cx681 and cx1547.
Figure 12A:
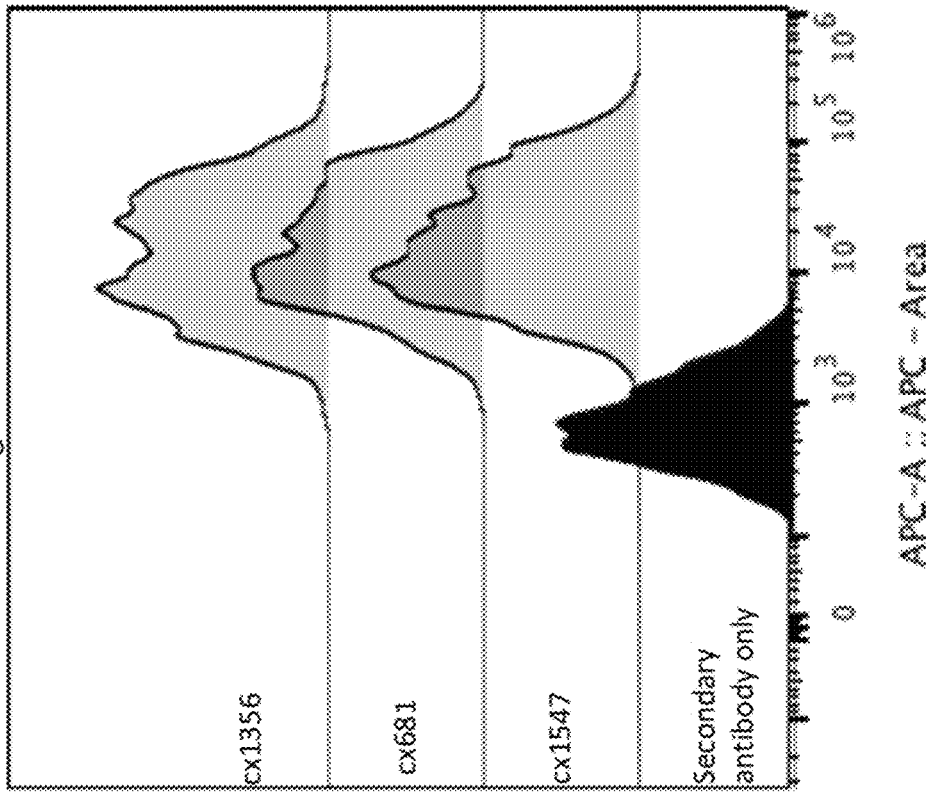
Figure 12D:
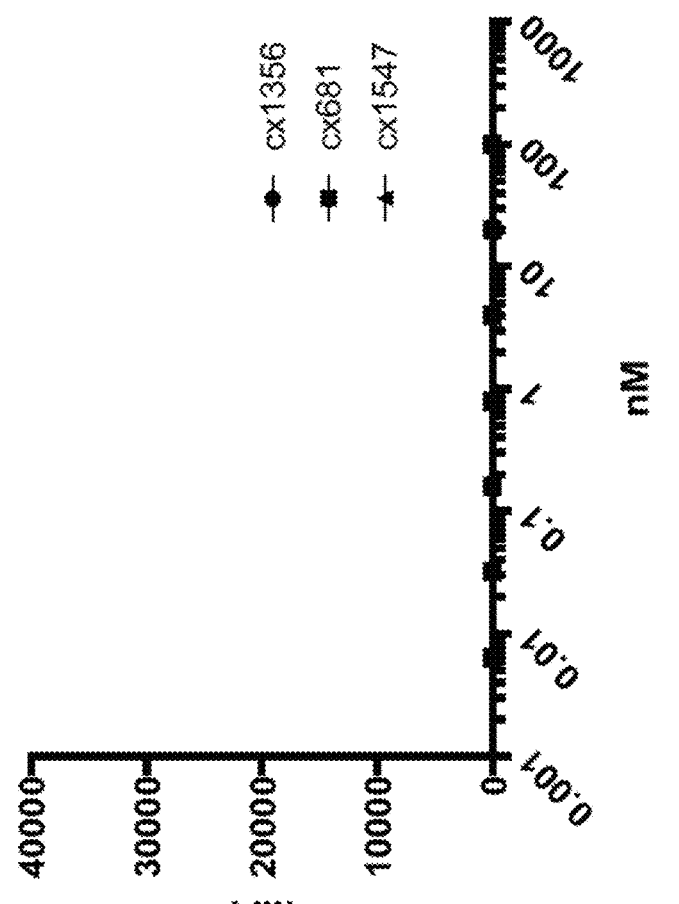
Figure 12C:
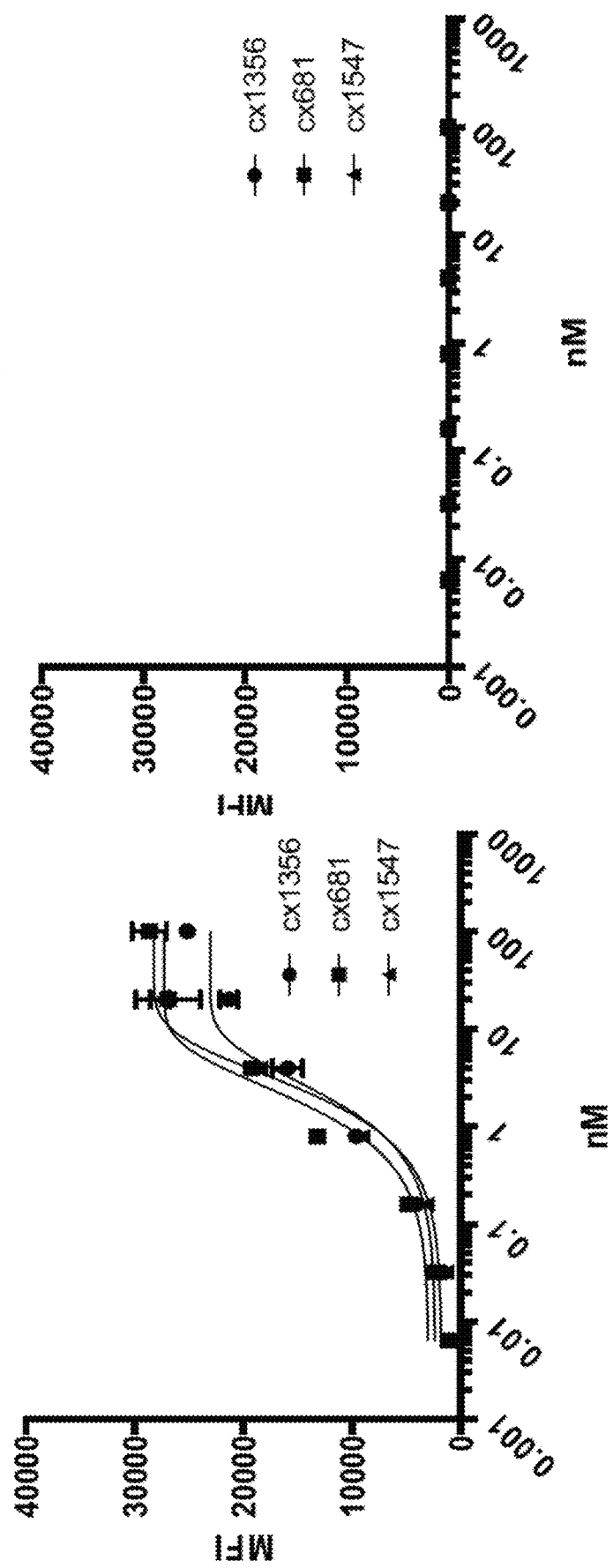

Additional representative FRα-targeting constrained CD3 engaging constructs with various linkers between the Fc and the component of the CD3 binding domains were assessed for binding to T cells as described above and to FRα expressing cells (Ovcar-5). For the studies, 100 nM of each construct, cx1356, cx681 or cx1547, was used. The additional representative FRα-targeting constrained CD3 engaging constructs with various linkers between the Fc and the component of the CD3 binding domains were found to bind FRα expressing cells (Ovcar-5) (FIGS. 12A and 12C), but lacked the capacity to bind T-cells (FIGS. 12B and 12D).

Figure 13B:
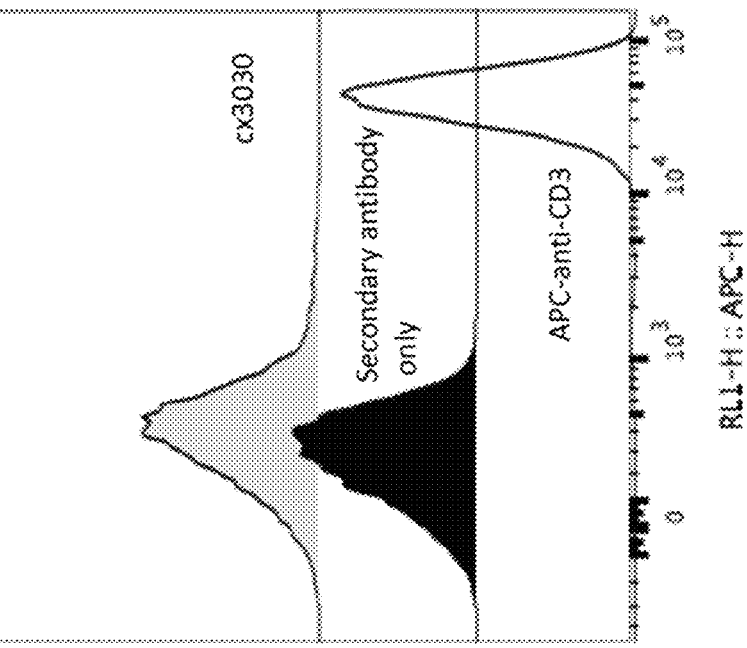
FIG. 13A-13B depicts cellular binding by a representative EFGR-targeting constrained CD3 engaging construct, cx3030.
Figure 13A:
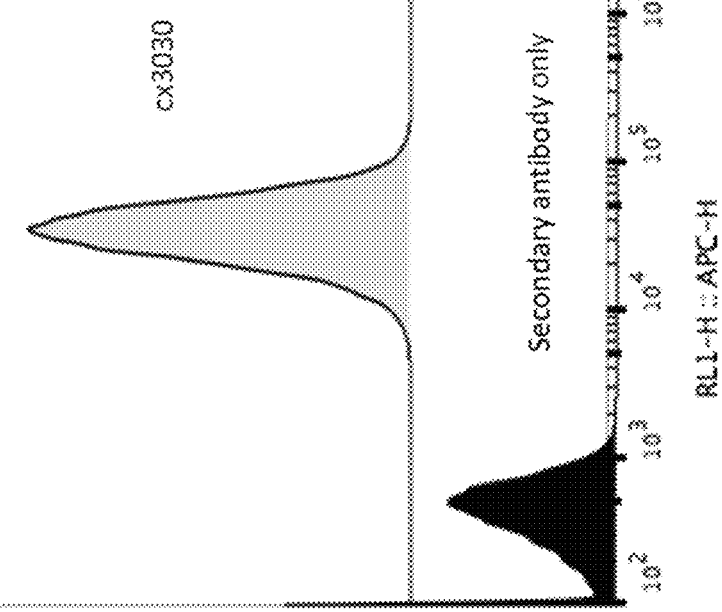

In a similar study, a representative EGFR-targeting constrained CD3 engaging construct generated as substantially described in Example 1, cx3030, was found to bind EGFR expressing cells (Colo-205) (FIG. 13A), yet lacked the capacity to bind T-cells (FIG. 13B). 400 nM of each construct was used. This observation further demonstrates that the constrained CD3 engaging constructs display attenuated T-cell binding in isolation.

Figure 14B:
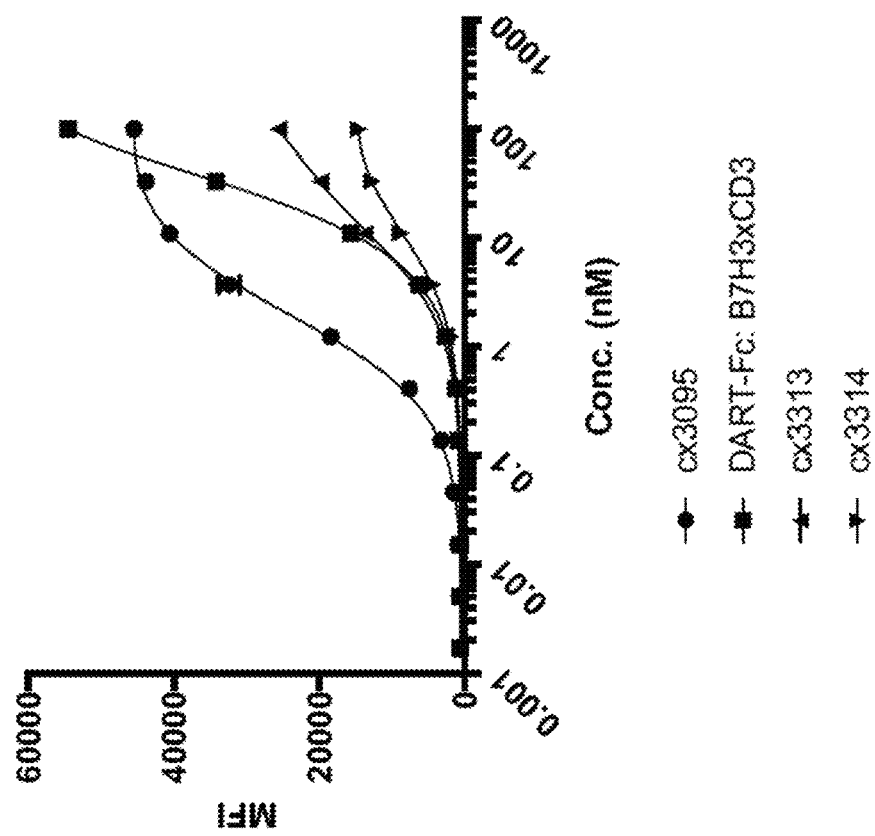
FIG. 14A-14D depicts binding to B7H3 positive A375 (FIGS. 14A and 14B) and the lack of binding to CD3 on T-cells (FIGS. 14C and 14D) by the B7H3-targeted constrained CD3 engagers. The alternative format DART-Fc targeting B7H3 and CD3 displayed strong binding to both B7H3 and CD3 on T-cells. Various B7H3 antigen binding domains were used herein including cx3095 sdAb, cx3313 FAB, and cx3314 scFv. The scFv and FAB contain the same anti-B7H3 VH and VL sequences used in the DART-Fc format.
Figure 14A:
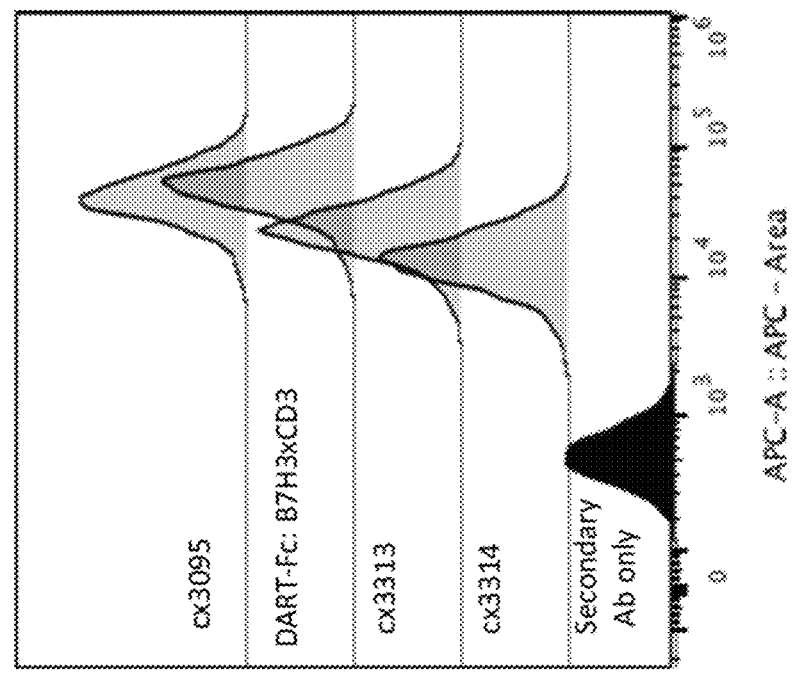
Figure 14D:
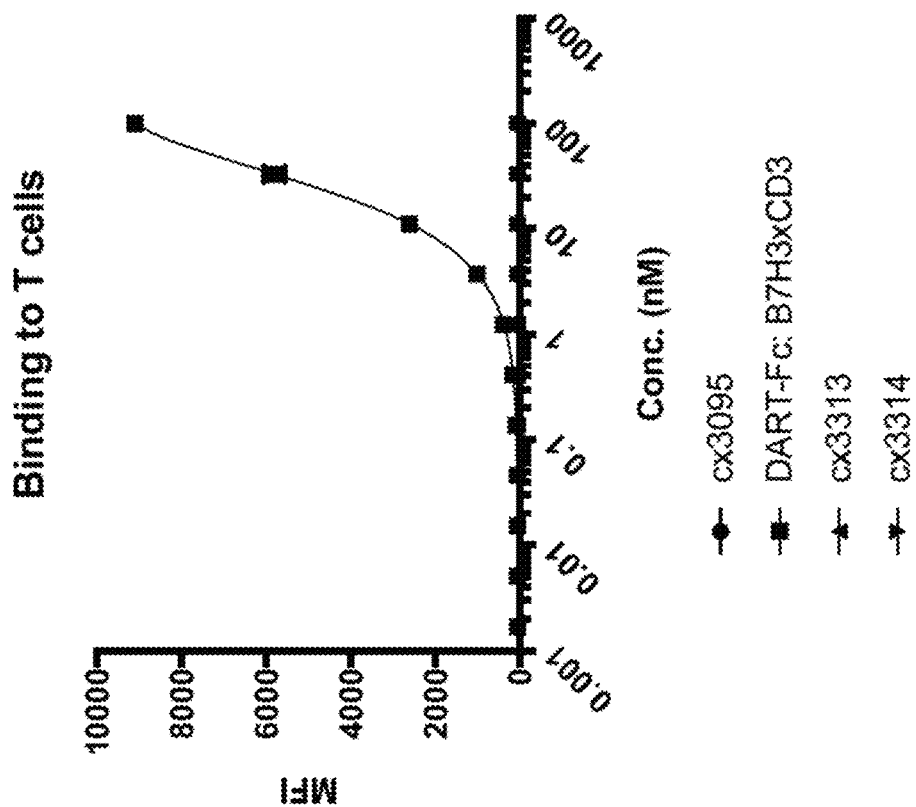
Figure 14C:
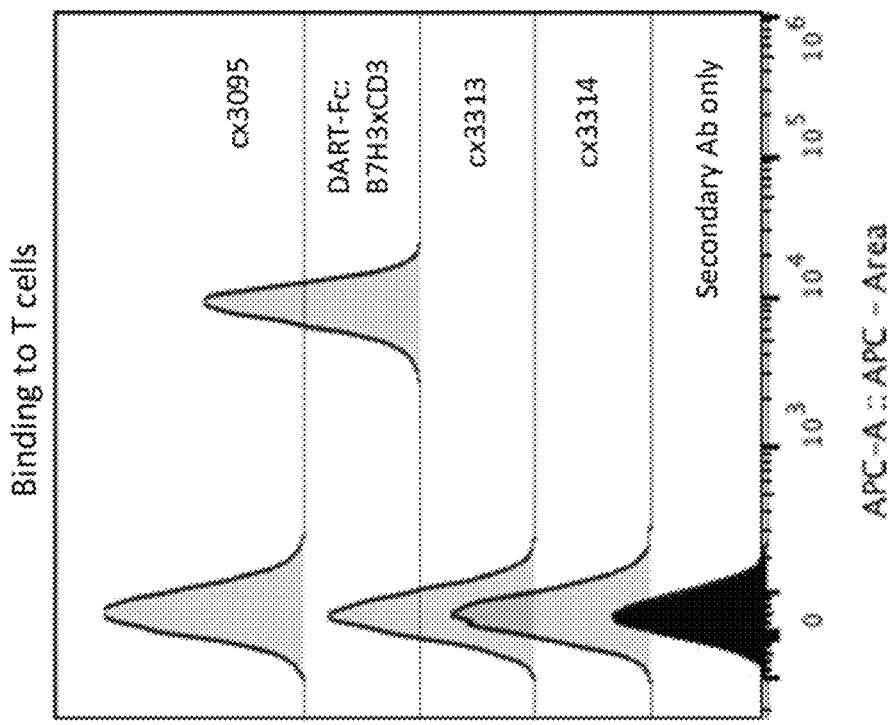

As shown in FIGS. 14A-14D, similar results were observed for representative B7H3-targeting constrained CD3 engagers, cx3313, cx3314 and cx3095. Cx3313 and cx3314 were generated as substantially described in Example 1 and were composed of the same B7H3 VH and VL sequences assembled as Fabs or scFvs, respectively, as described in Example 1. cx3095 contained a B7H3 binding domains that was a single domain antibody. As shown in FIGS. 14A and 14B, representative B7H3-targeting constrained CD3 engagers were found to bind A375 cells expressing B7H3. However, as shown in FIGS. 14C and 14D, the same constructs were not able to bind to T cells in isolation. In these studies, the binding of the representative B7H3-targeting constrained CD3 engagers, cx3313, cx3314 and cx3095 was compared to Dual-affinity Re-targeting Antibody (DART®)-monomeric Fc format targeting B7H3 and CD3 (DART-Fc B7H3×CD3; see e.g. WO2017030926A1). The DART-Fc B7H3×CD3 contained a B7H3 sequence as set forth in SEQ ID NO: 169, 145, or 146. Notably only the DART-Fc format was observed to allow for T-cell binding in the absence of B7H3 engagement (FIGS. 14C and 14D), whereas, all formats displayed binding to B7H3-expressing cells (FIGS. 14A and 14B).

Figure 15B:
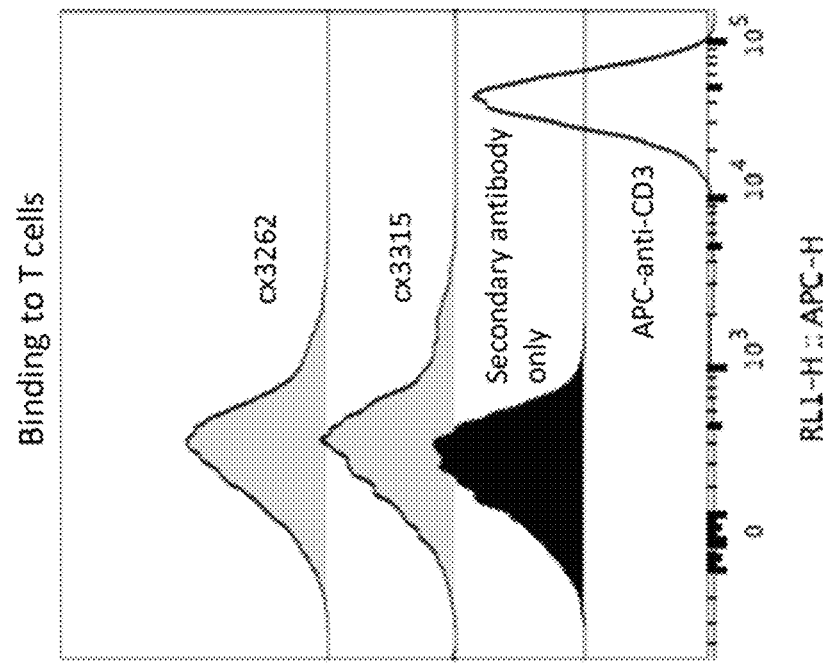
FIG. 15A-15B depicts cellular binding by representative 5T4-targeting constrained CD3 engaging constructs, cx3262 and cx3315.
Figure 15A:
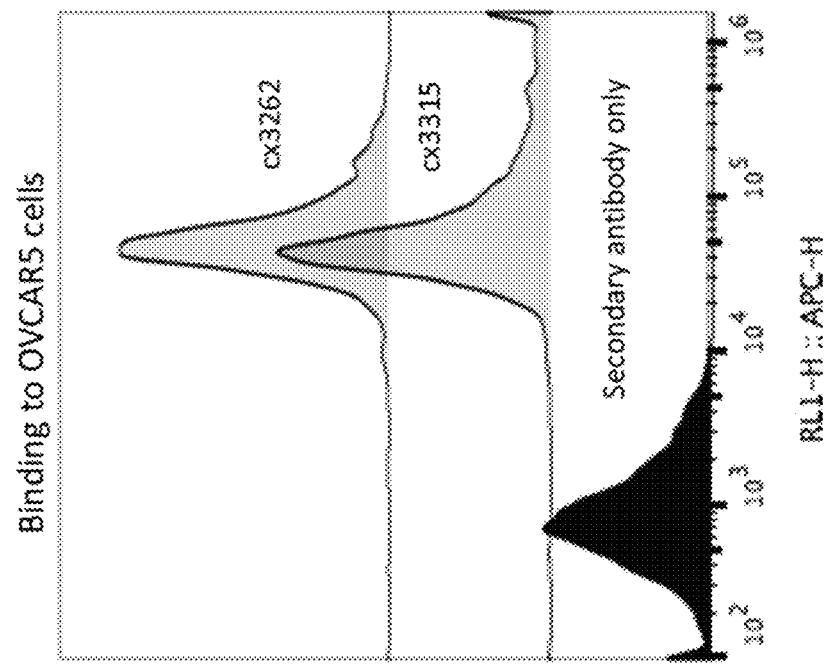
Figure 16B:
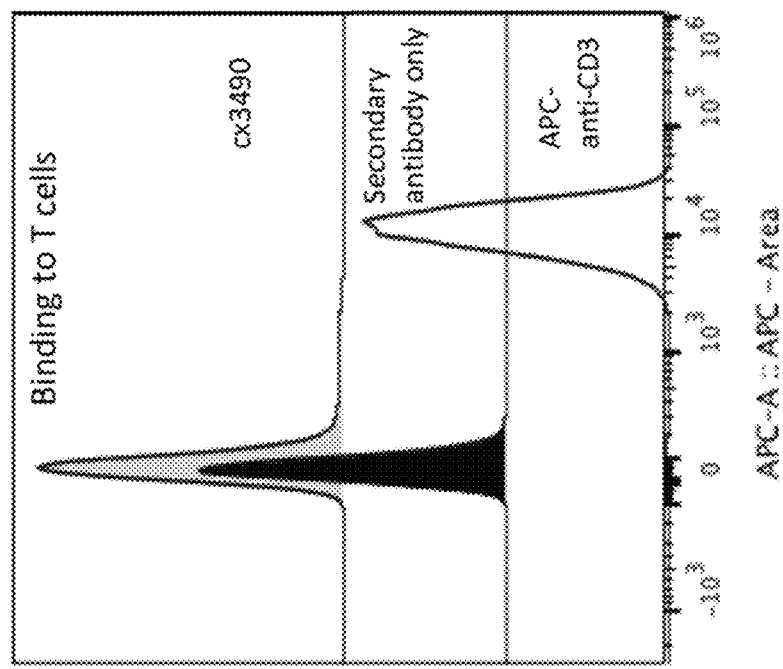
FIG. 16A-16D depicts cellular binding by a representative CD20-targeting constrained CD3 engaging construct, cx3309.
Figure 16A:
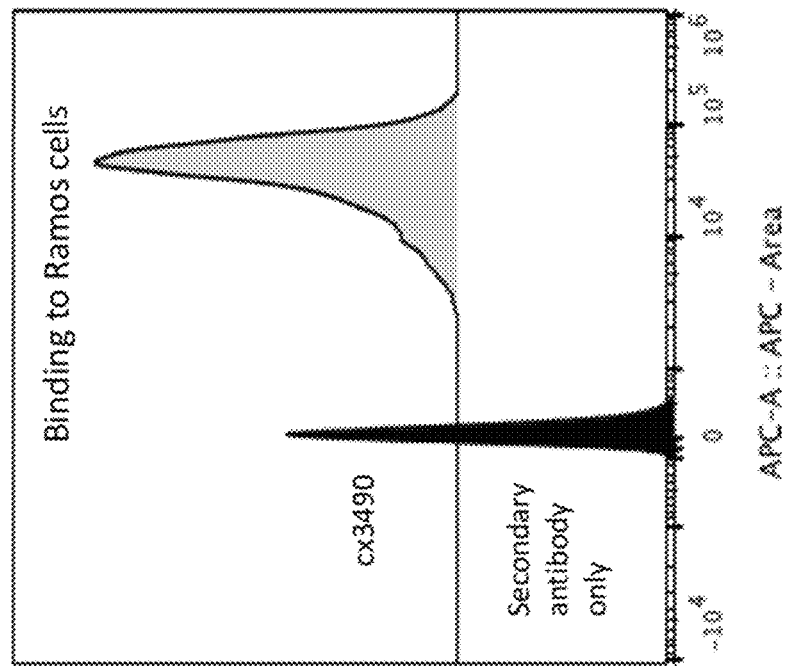
Figure 16D:
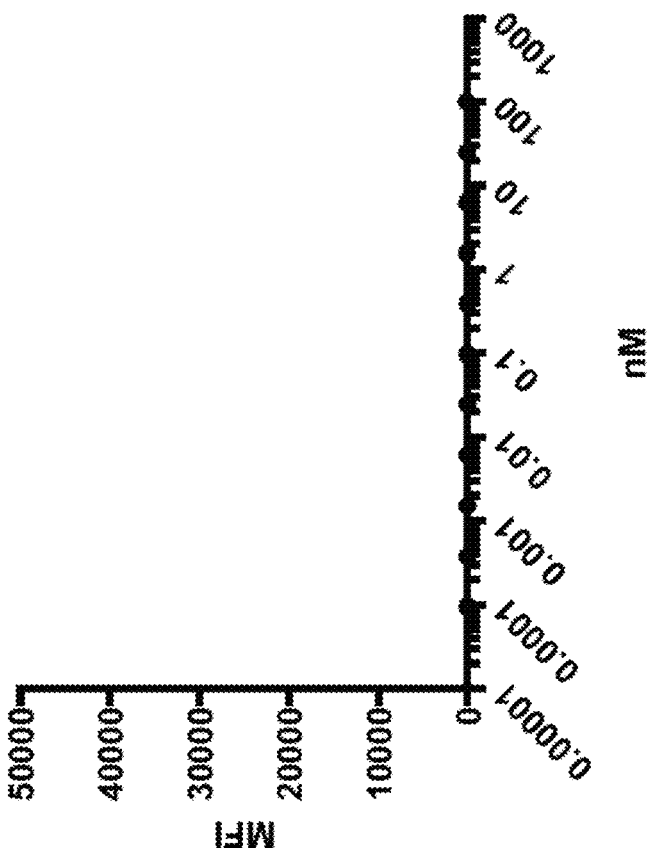
Figure 16C:
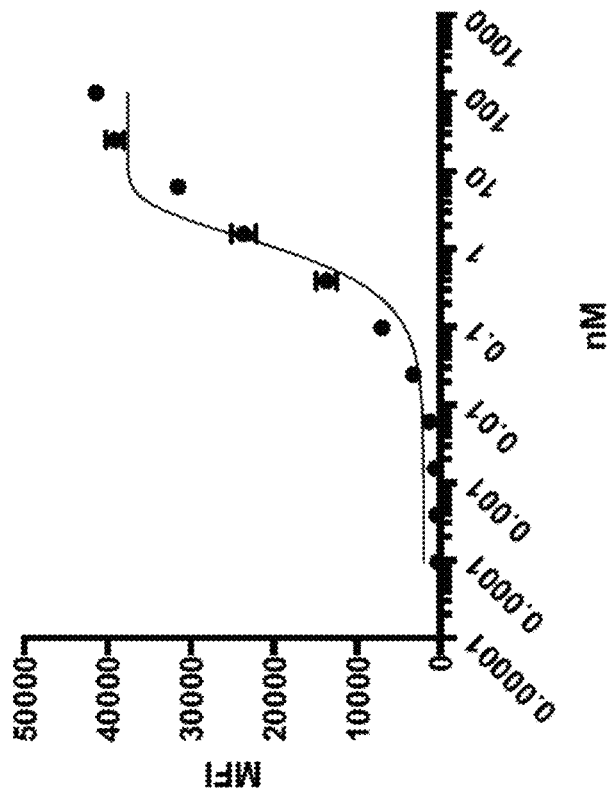

In a further study, similar constrained binding was observed for representative 5T4-targeting constrained CD3 engaging constructs generated as substantially described in Example 1, cx3262 and cx3315. The 5T4 binding domains of cx3262 were generated as single domain antibodies, whereas, the 5T4 binding domain of cx3315 was generated with an scFv derived as set forth in SEQ ID NO: 167 and 168 (See U.S. Pat. No. 8,044,178). Both representative 5T4-targeting constrained CD3 engaging constructs were found to bind 5T4 expressing cells (Ovcar-5) (FIG. 15A), yet lacked T-cell binding capacities (FIG. 15B). 400 nM of each construct was used. This observation further demonstrates that the constrained CD3 engaging constructs described herein display attenuated T-cell binding in isolation.

As shown in FIG. 16A-16D, a representative CD20-targeting constrained CD3 engaging construct, cx3490, was found to bind CD20 expressing cells (Ramos), yet lacks T-cell binding capacities. 100 nM of cx3490 construct was used. The CD20 binding domains of cx3490 were scFvs derived from VH and VL of the CD20 antibody GA101 as described in Example 1.

Example 3. Assessment of CD3 Reporter T Cell Activation Using a Reporter Assay

This example describes assessment of the ability of various constructs to activate a CD3 NFAT reporter Jurkat cell line in co-cultures with target antigen-expressing cells. These assays were used to demonstrate that while T-cell binding via the CD3-binding domain is restricted or inhibited on isolated T-cells (as shown in Example 2), once the multispecific polypeptides provided herein are bound to a cognate antigen they are capable of engaging T-cells and mediating T-cell activation.

1. Luciferase Reporter Assay

Antigen targeting constrained CD3 engaging constructs were titrated onto co-cultures of target cells and genetically engineered Jurkat cells that express an NFAT-driven luciferase reporter (Promega, USA). In this assay, engagement of CD3 results in NFAT signaling and production of intracellular luciferase. Assay plates were incubated at 37° C. for approximately 6 hours and then equilibrated to room temperature. Bio-Glo™ reagent was added to sample wells and luminescence of supernatants was measured using a SpectraMax® L microplate reader.

Figure 17:
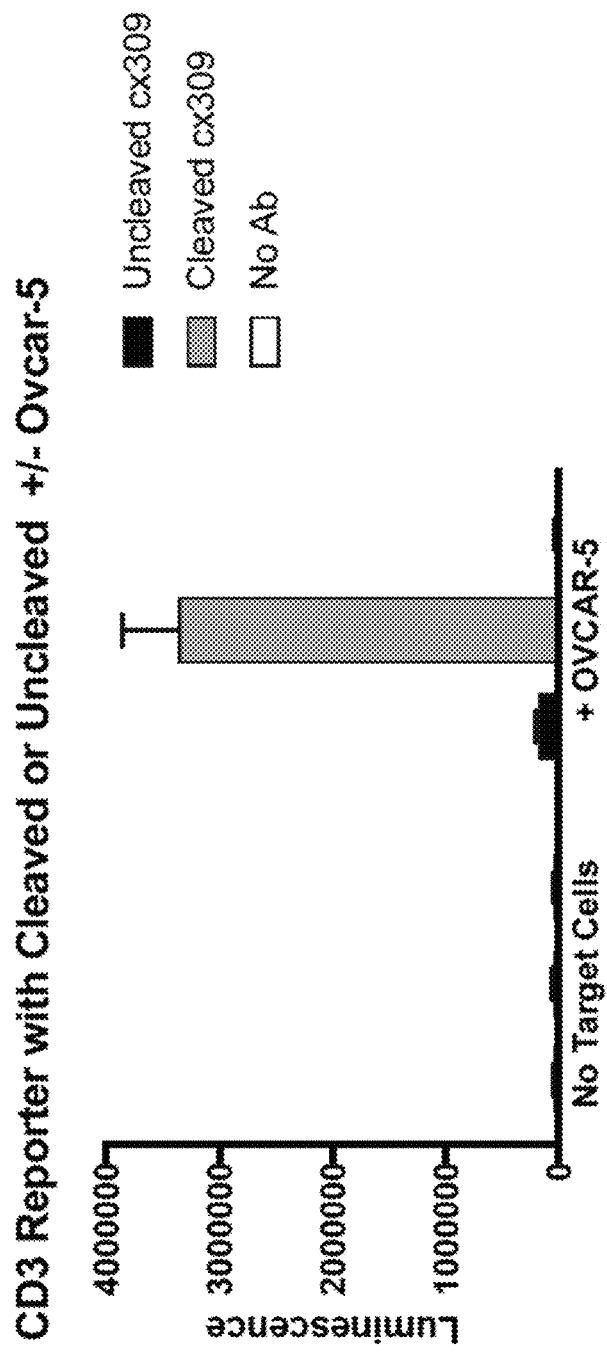
FIG. 17 is a graph demonstrating the ability of cleaved or uncleaved cx309 to activate a CD3 NFAT reporter Jurkat cell line (Promega, USA) in the presence or absence of FRa expressing cells, Ovcar5.
Figure 18:
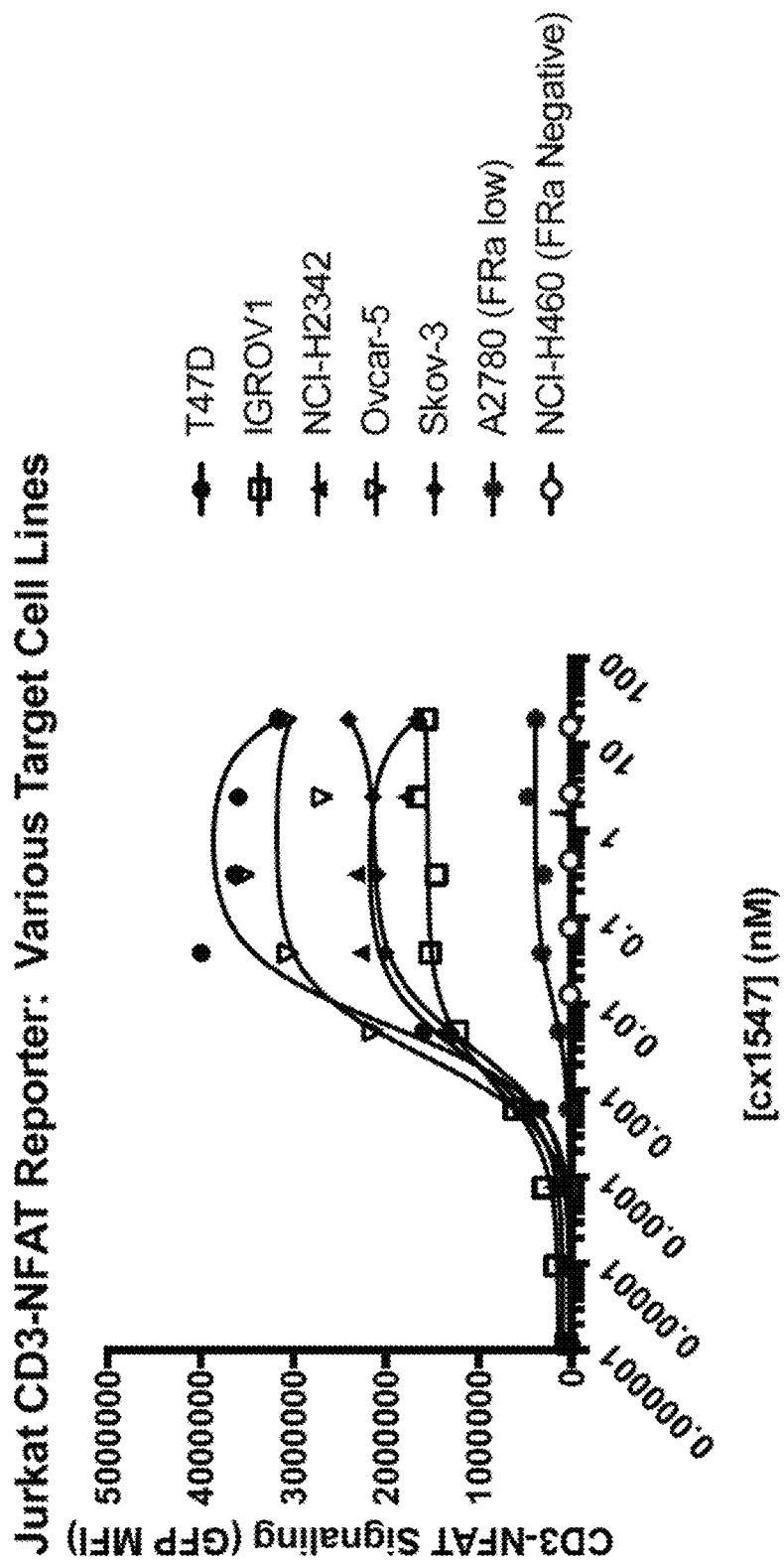
FIG. 18 depicts antigen dependent T-cell activation by cx1547. Various cell lines being either FRa positive (T47D, IGROV1, NCI-H2342, Ovcar-5, Skov-3, and A2780) or negative (NCI-H460), were co-incubated in with a Jurkat CD3 NFAT-GFP reporter cell line and fluorescence was measured at 6 hours. This demonstrates the capacity of the constrained CD3 constructs to activate T-cells in an antigen manner.
Figure 19B:
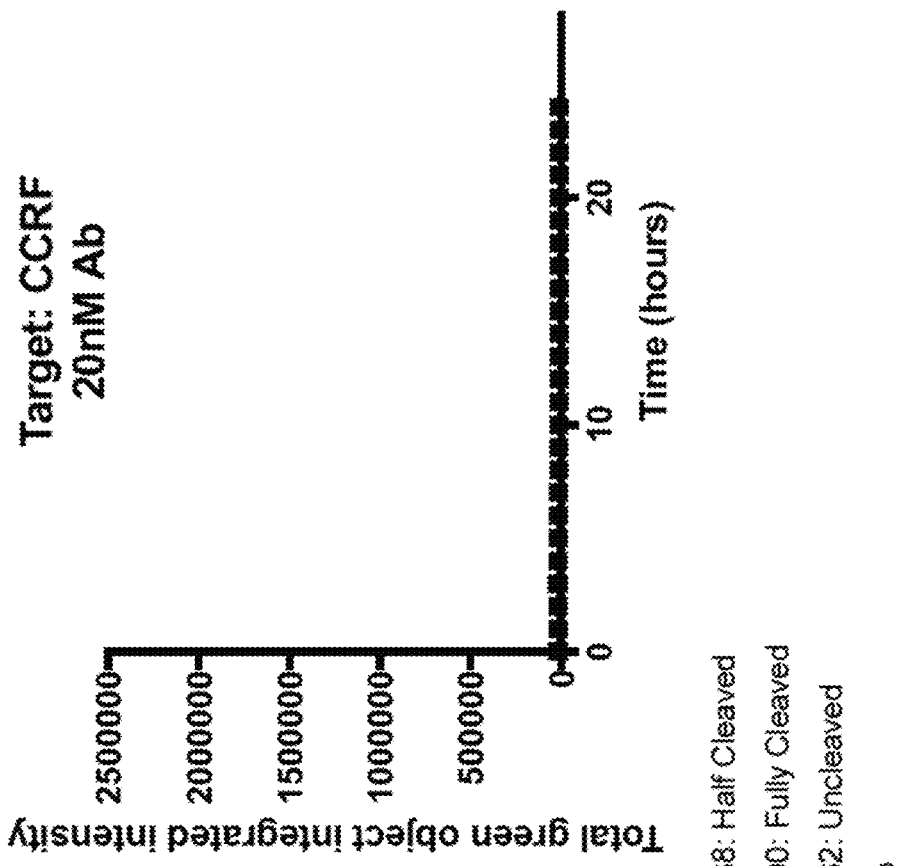
FIG. 19A-19D depicts the enhancement of T-cell activating capacity of the constrained CD3 engagers if proteolysis were to occur within the linker between the Fc domain and the CD3 binding domain. Shown here are the kinetics of T-cell activation mediated by 20 nM of cx1762, cx3238 or cx2190 in the presence of FRa positive Ovcar-5 cells (FIG. 19A) or FRa negative CCRF-CEM cells (FIG. 19B). Also shown here is the potency of T-cell activation mediated by cx1762, cx3238 or cx2190 in the presence of FRa positive Ovcar-5 cells (FIG. 19C) or FRa negative CCRF-CEM cells (FIG. 19D). A Jurkat CD3 NFAT-GFP reporter was used to monitor CD3 signaling over a 24 hour period using an Incucyte ZOOM imager. Notably T-cell activation is dependent on antigen expression on the target cell line and is greatly enhanced by removal of the Fc domain N-terminal to the CD3 binding domain on one or both sides of the CD3 binding VH:VL domains.
Figure 19A:
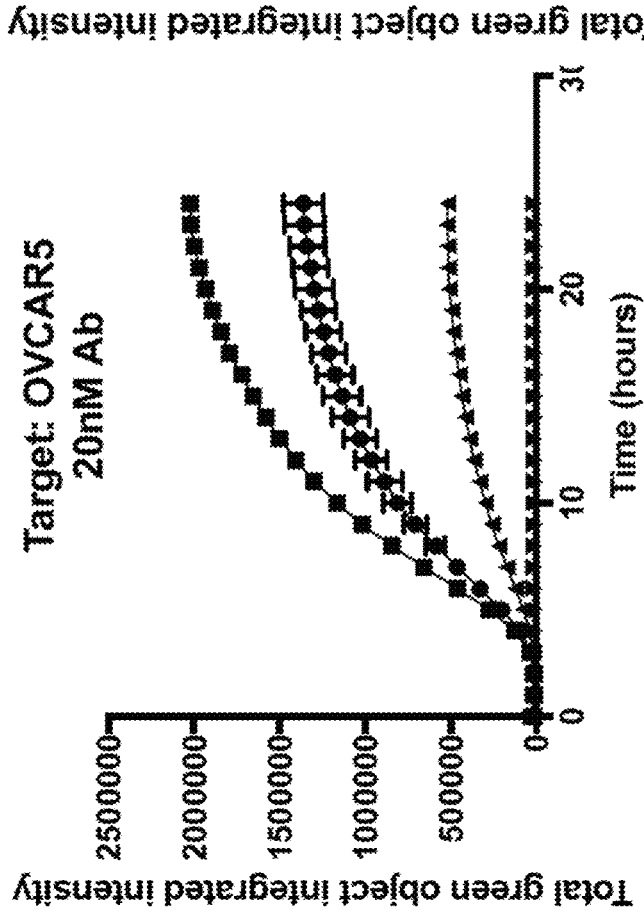
Figure 19C:
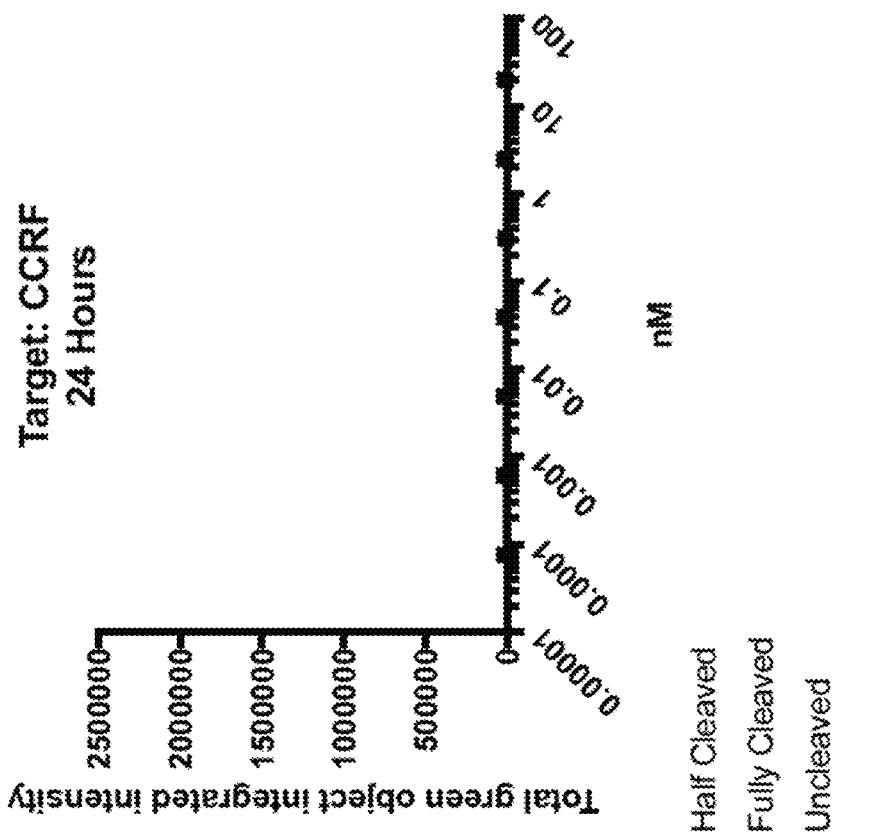
Figure 19D:
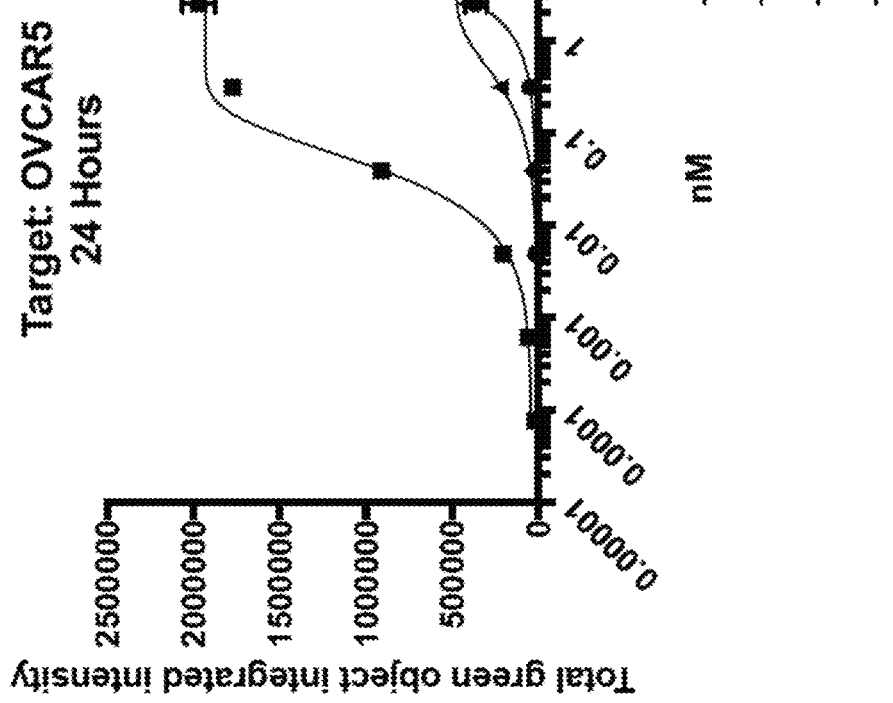
Figure 20A:
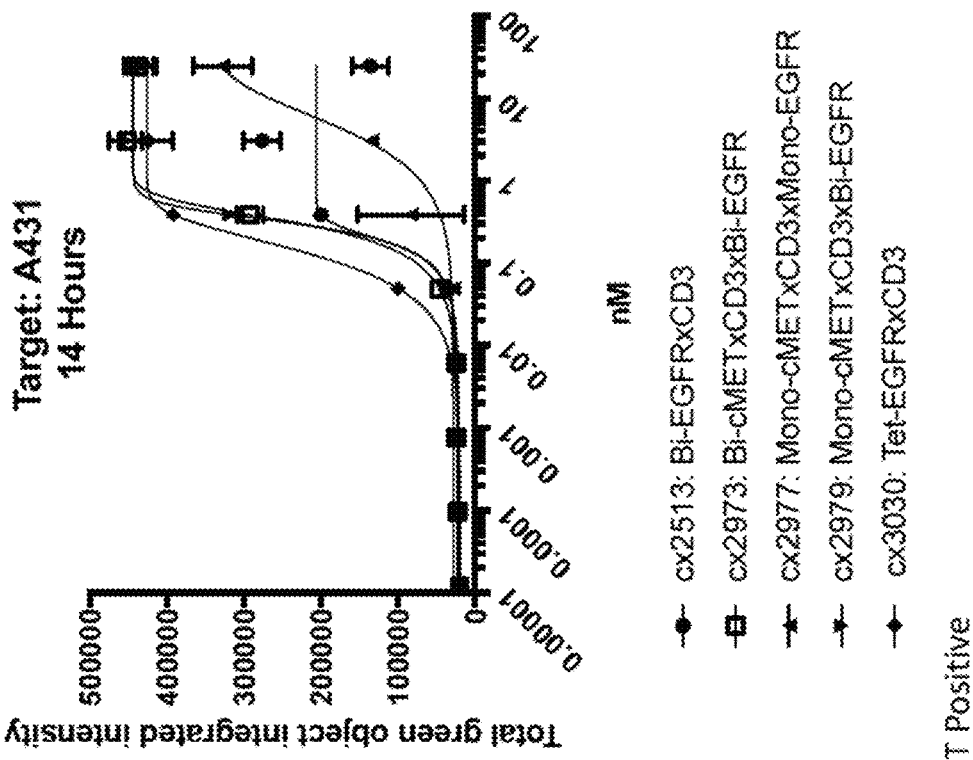
Figure 20B:
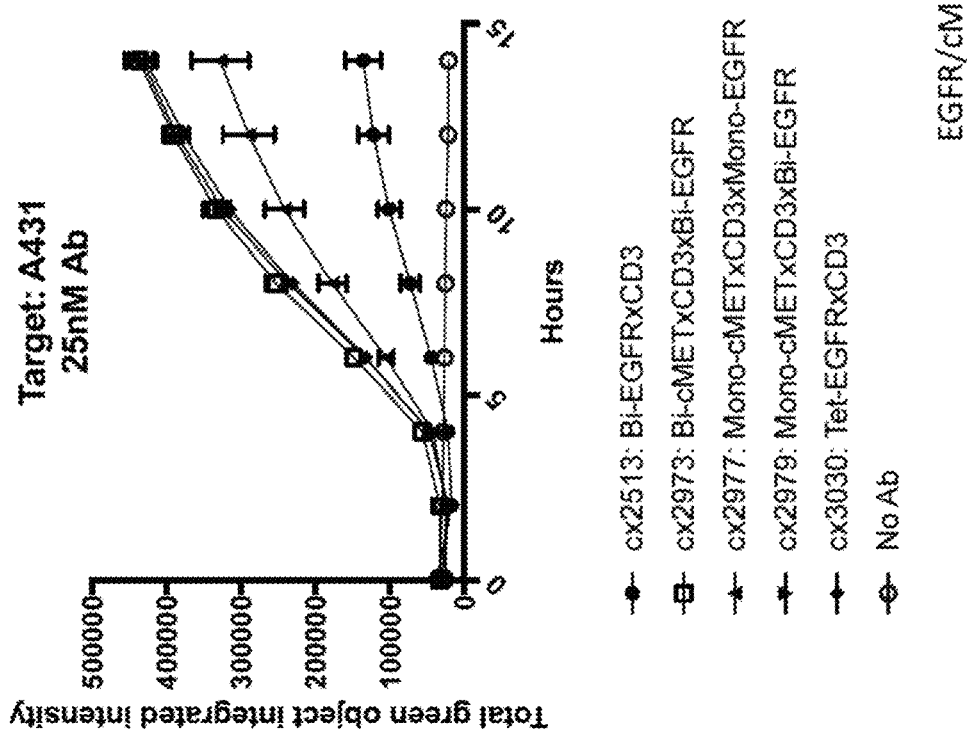

As shown in FIG. 17, a representative FRα-targeting constrained CD3 engaging construct, cx309, displayed significantly enhanced capacity to activate T-cells when cleaved at the linker between the Fc and the CD3 binding domain. Herein, cx309 was pre-cleaved with matriptase prior to assay initiation. Notably T-cell activation was only observed in the presence of the FRα positive Ovcar-5 cell line. Some T-cell activation was observed with the uncleaved cx309. This result is consistent with the ability of the constrained CD3 engaging constructs to exhibit CD3 binding upon binding to its antigen, with increased CD3 engagement after proteolytic cleavage.

2. GFP Reporter Assay

Antigen targeting constrained CD3 engaging constructs were titrated onto co-cultures of target cells and engineered Jurkat cells that express NFAT-driven green fluorescence protein (GFP). Engagement of CD3 results in NFAT signaling and production of green fluorescence. For reporter assays utilizing adherent target cells, target cells were seeded, allowed to settle at room temperature for uniform distribution, and incubated for several hours at 37° C. to permit adherence prior to addition of reporter cells and antigen targeting constrained CD3 engaging constructs. Assay plates were serially imaged using an IncuCyte® ZOOM system and CD3 reporter cell activation was determined by measuring total green object integrated intensity.

Figures 23A, 23B:
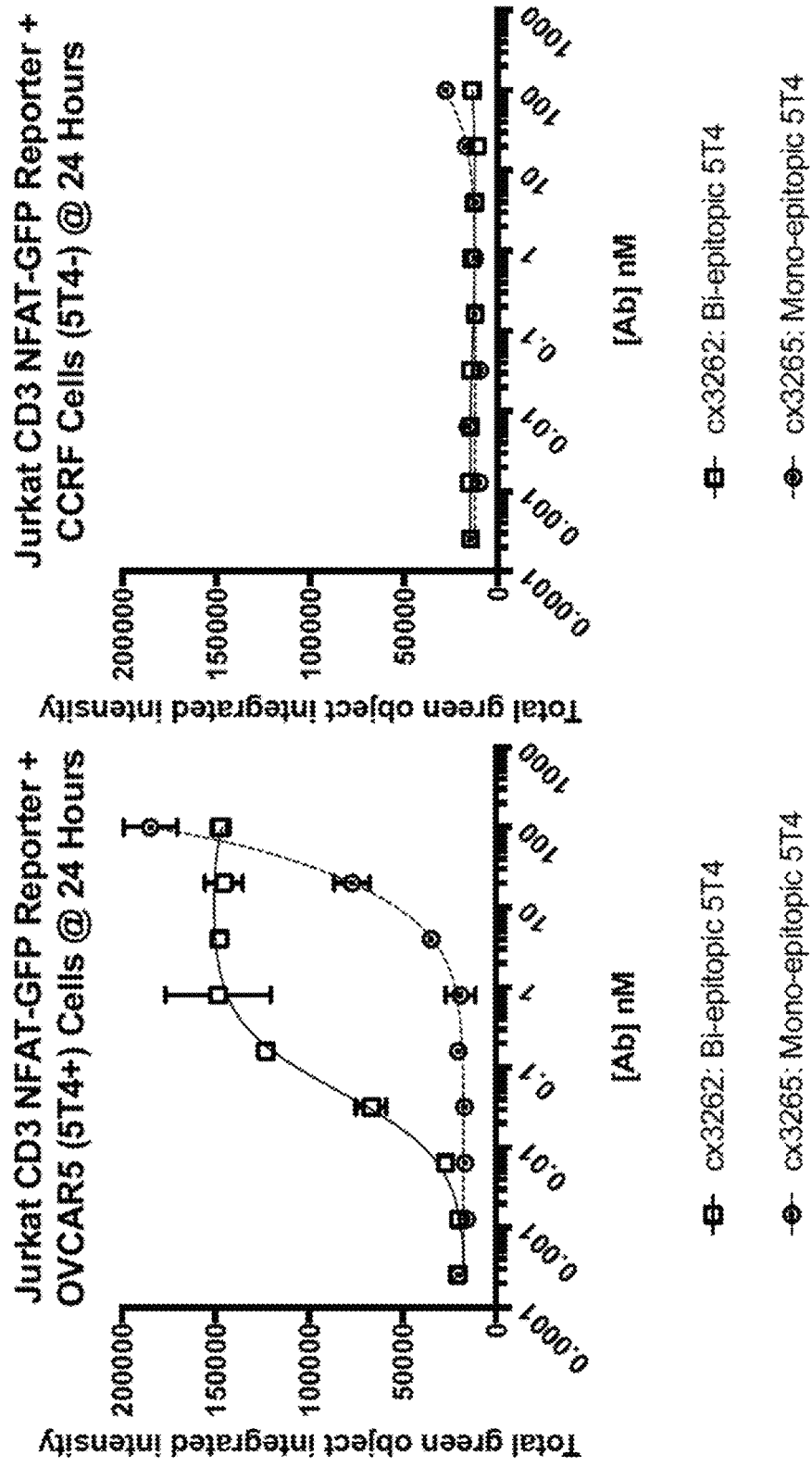
FIG. 23A-23B is a series of graphs showing the T cell activating capacity of 5T4-targeted constrained CD3 engaging constructs. This example shows how bivalent biepitopic TAA targeting can increase the activity of constrained CD3 engager over a bivalent monoepitopic protein on TAA positive cells (OVCAR5). Neither construct induced T cell activation in the presence of TAA negative cells (CCRF).
Figure 24:
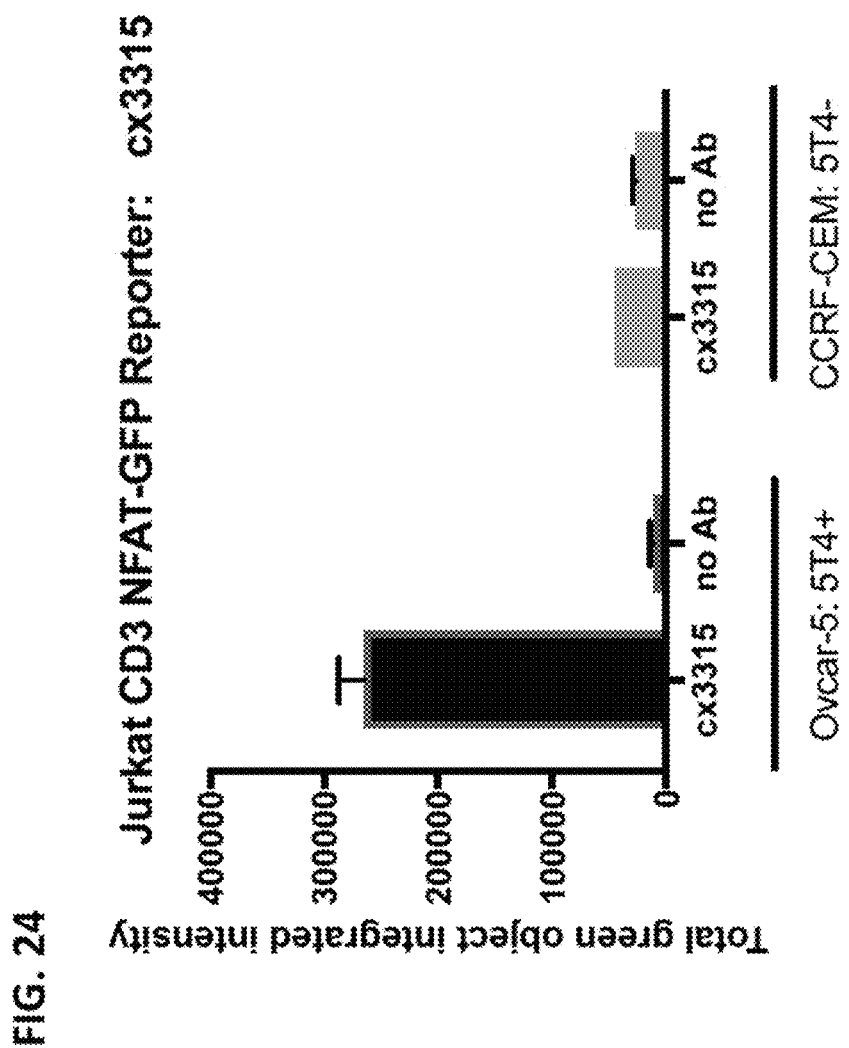
FIG. 24 is a graph showing the ability to induce antigen dependent T-cell activation by a representative 5T4-targeted constrained CD3 engaging construct, cx3315. A Jurkat CD3 NFAT-GFP reporter cell line was used to monitor T-cell activation by cx3315 in the presence of a 5T4 positive cell line (OVCAR5), and a 5T4 negative cell line (CCRF-CEM).
Figure 25:
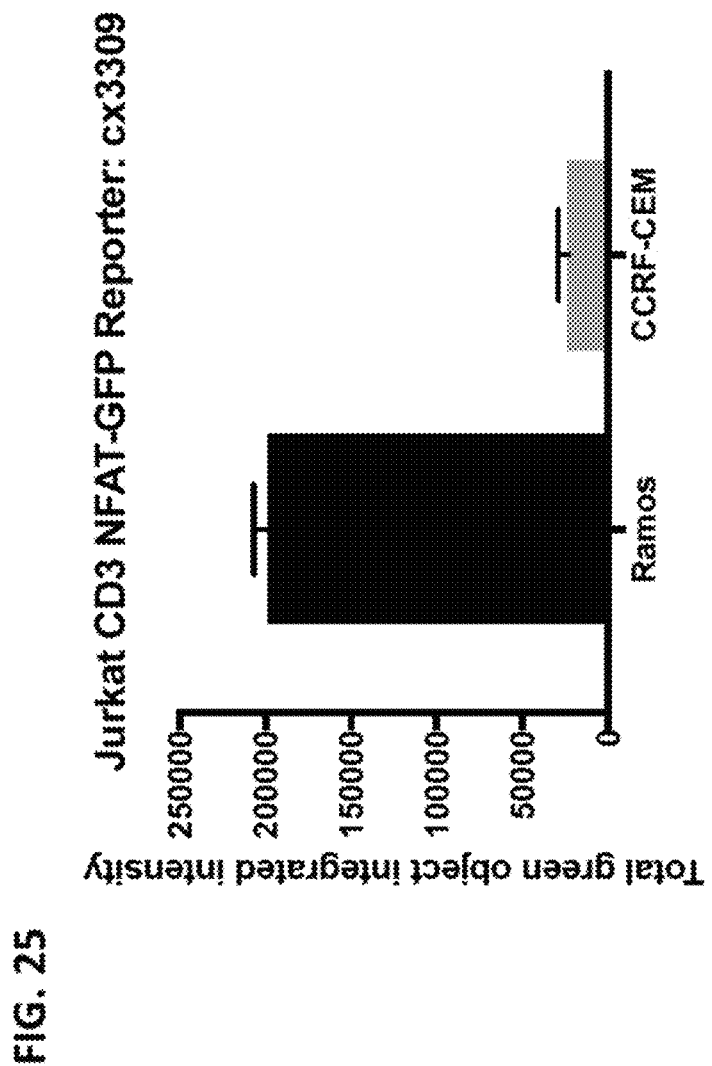
FIG. 25 depicts the ability to induce antigen dependent T-cell activation by a representative CD20-targeted constrained CD3 engaging construct, cx3309. A Jurkat CD3 NFAT-GFP reporter cell line was used to monitor T-cell activation by cx3309 in the presence of a CD20 positive cell line: Ramos and a cell CD20 negative cell line: CCRF-CEM.
Figure 26:
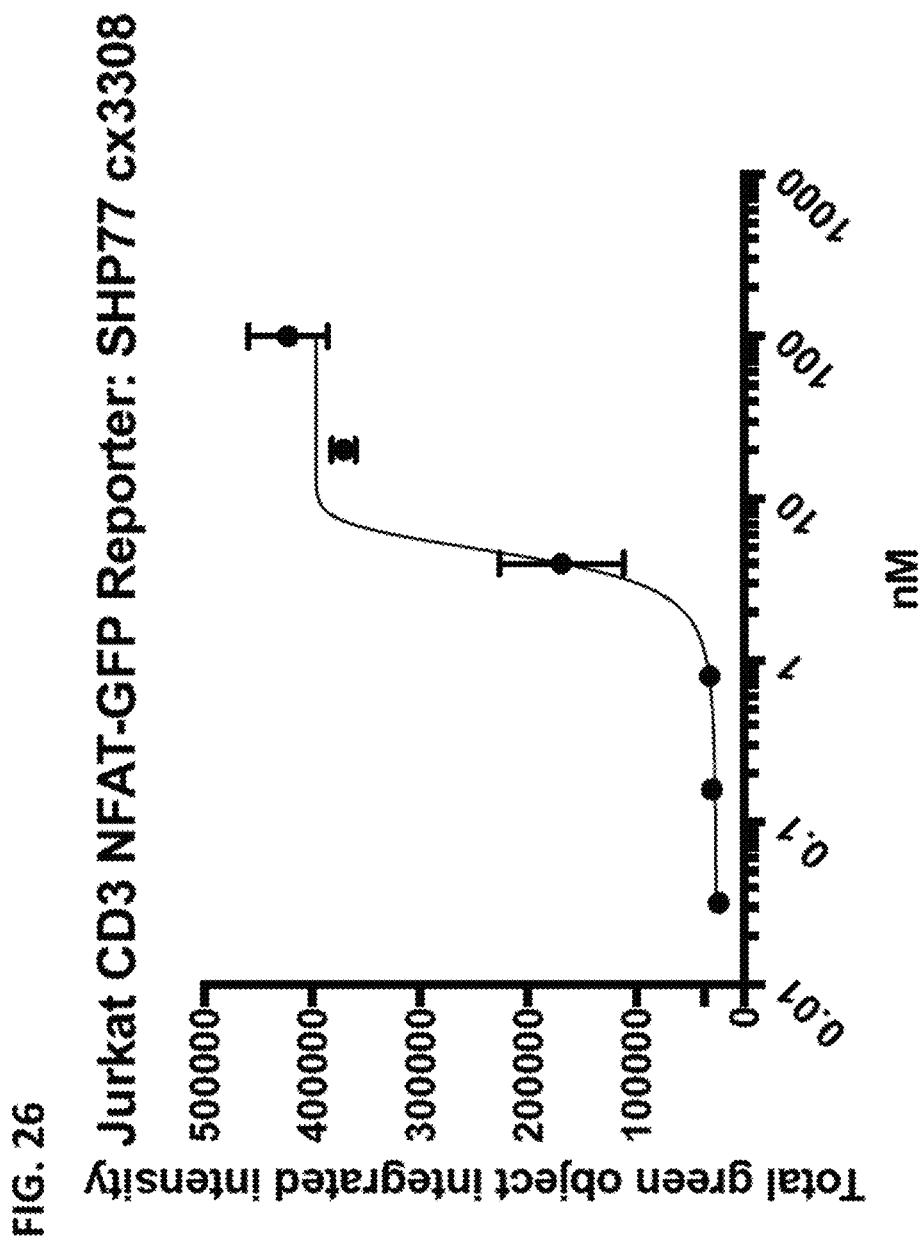
FIG. 26 is a graph showing the ability to induce T-cell activation by a representative DLL3-targeted constrained CD3 engaging construct, cx3308. A Jurkat CD3 NFAT-GFP reporter cell line was used to monitor T-cell activation by cx3309 in the presence of SHP-77 cells, which are DLL3 positive. This demonstrates that scFv moieties can be used to target TAAs in the constrained CD3 format and effectively activate T-cells when bound to a cognate TAA positive cell line.
Figures 27A, 27B:
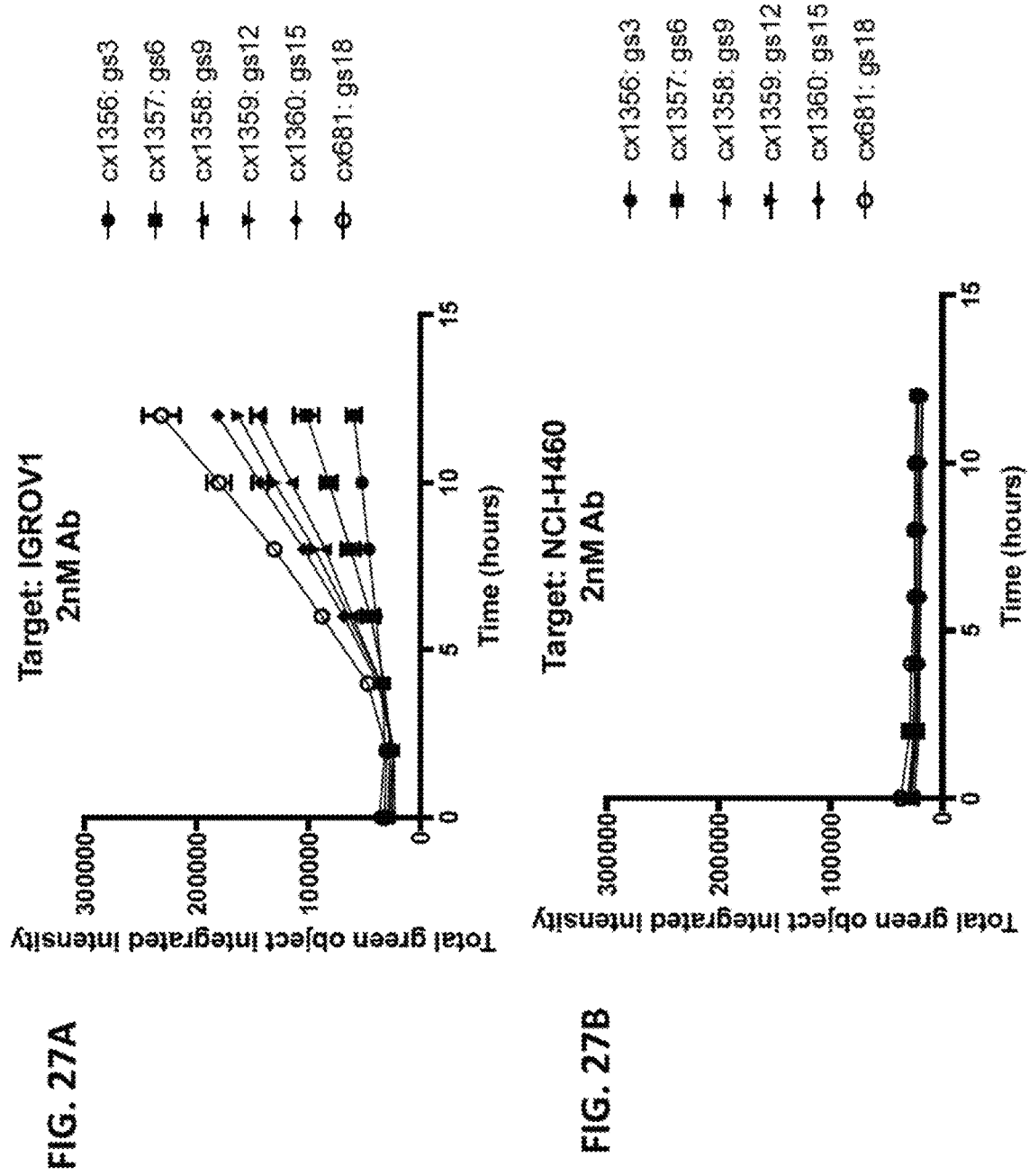
FIG. 27A-27F depicts the impact of linker length on the capacity to activate T-cells in the presence of FRα positive cells—IGROV1 (FIG. 27A, 27C, 27E), or FRa negative NCI-H460 (FIG. 27B, 27D, 27F).
Figures 27C, 27D:
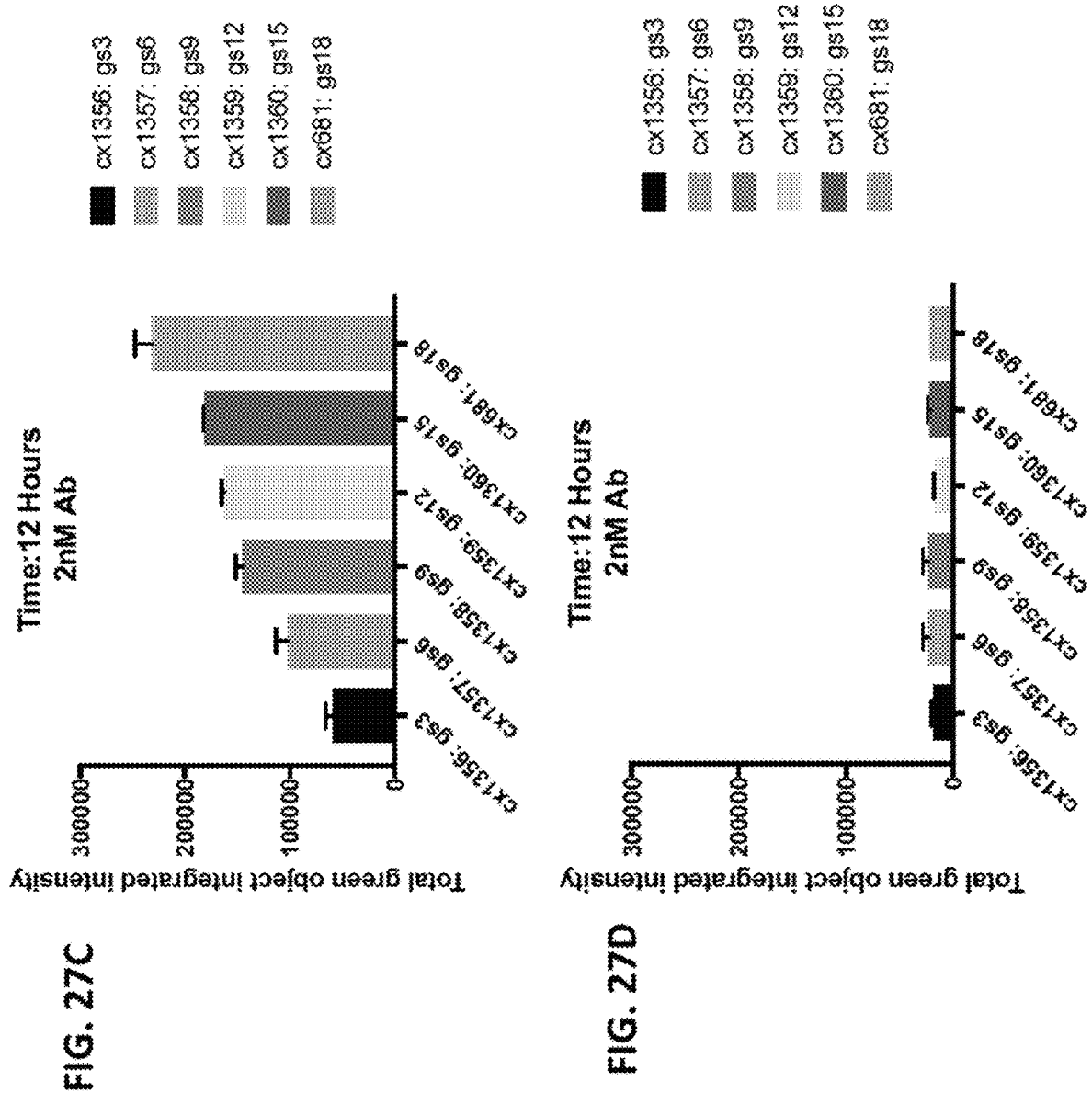
Figures 27E, 27F:
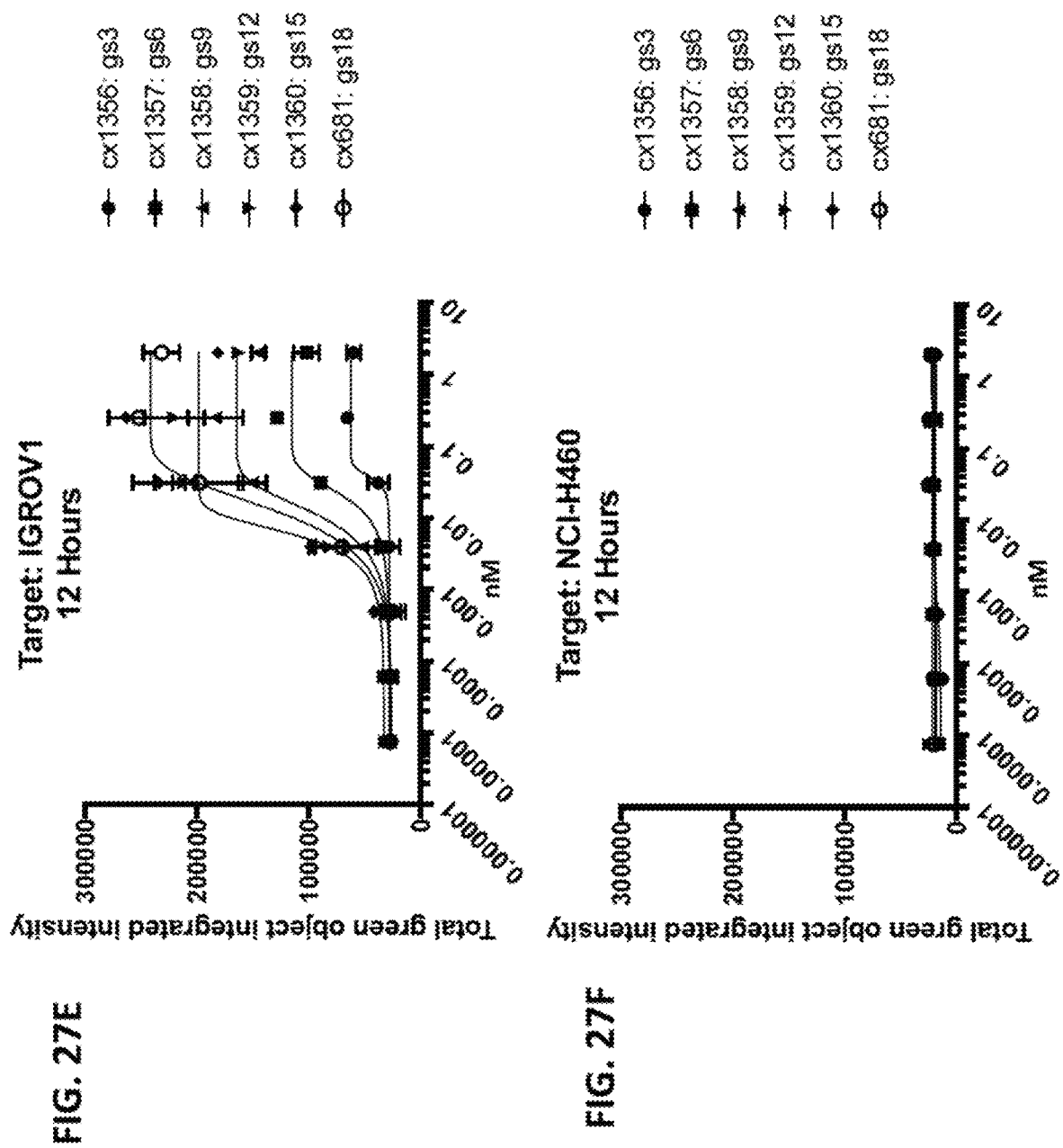

FIGS. 18 and 19A-19D show constructs targeting Folate Receptor (FRα); FIG. 20A-20D shows constructs targeting EGFR or EGFR and cMET; FIGS. 21A-21B and 22A-22F show constructs targeting B7H3; FIGS. 23A-23B and 24 show constructs targeting 5T4; FIG. 25 shows a construct targeting CD20; and FIG. 26 shows a construct targeting DLL3. As shown in all figures, each of the tested representative constructs were able to induce antigen dependent T-cell activation in the presence of a target-expressing cells as shown by increased GFP signal. FIGS. 22A-F show that the degree of activation is similar to or, in some cases, greater than the comparator molecule DART-Fc: B7H3×CD3 described in Example 2.

Notably FIG. 19A-19D demonstrate the enhanced T-cell activating capacity that is achieved when the Fc portion of the constrained CD3 engaging constructs is removed, allowing unrestricted T-cell engagement. The Fc of these constrained CD3 engaging constructs may be removed via proteolysis if proteolytic cleavable linkers are included between the Fc and the CD3 binding domain. cx3238 represents the fully cleaved C-terminal portion and was produced via co-expression of two plasmids encoding 1) the anti-CD3 VH linked to a C-terminal FRα-binding sdAb and 2) the anti-CD3 VL linked to a C-terminal FRα-binding sdAb. This result is consistent with the positioning of the Fc domain as constraining the ability of the CD3 binding region to bind CD3.

Example 4. Assessment of Linker Length on Activity

The effect of various length linkers between the Fc and the component domains (VH and VL) that comprise the CD3 binding region on T-cell activating capacity was tested using the Jurkat reporter assay described in Example 3. FRα-targeting constrained CD3 engaging constructs, generated as described in Example 1 containing GlySer-based linkers of varying lengths as listed in Table E1 were used in these assays.

TABLE E1

Tested Linker Lengths

| SEQ ID NO | Linker |
|---|---|
| — | gs3: GGS |
| 10 | gs6: GGSGGS |
| 11 | gs9: GGSGGSGGS |
| 12 | gs12: GGSGGSGGSGGS |
| 13 | gs15: GGSGGSGGSGGSGGS |
| 119 | gs18: GGGGGSGGGGSGGGGS |
| 147 | gs18: GGSGGGGSGGGGSGGGGS |

As shown in FIGS. 27A-27F the length of the linker and T-cell activating capacity were positively correlated. T-cell activating capacity was shown to directly relate to linker length, indicating shorter linkers restrict CD3 binding to a greater extent. Importantly, T-cell engagement of the constructs is dependent on TAA-binding, as these constructs did not demonstrate a T-cell binding capacity in isolation (e.g. solution form when unbound to target TAA) as shown above in Example 2 (FIG. 12A-12D). Together, these constructs displayed restricted or inhibited binding to CD3, yet were capable of activating T-cells in a target dependent manner.

Example 5. Assessment of Functional Activity

This Example describes the assessment and characterization of the tested constrained CD3 engaging constructs in human primary T cell in vitro assays.

1. T Cell-Mediated Cytotoxicity

Target cells were fluorescently labeled with CytoID® red. For cytotoxicity assays utilizing adherent target cells, target cells were seeded, allowed to settle at room temperature for uniform distribution, and incubated for several hours at 37° C. to permit adherence prior to addition of other assay components. Primary T cells were negatively enriched from PBMCs isolated from healthy human donor leukopaks and added at a 10:1-40:1 T cell-to-target cell ratio. Green caspase-3/7 reagent was added, which fluorescently labeled nuclear DNA of cells undergoing apoptosis. Antibodies were titrated onto the co-culture and assay plates were serially imaged using an IncuCyte® ZOOM system. Target cell death was determined by measuring total red/green overlap object area.

Figure 28B:
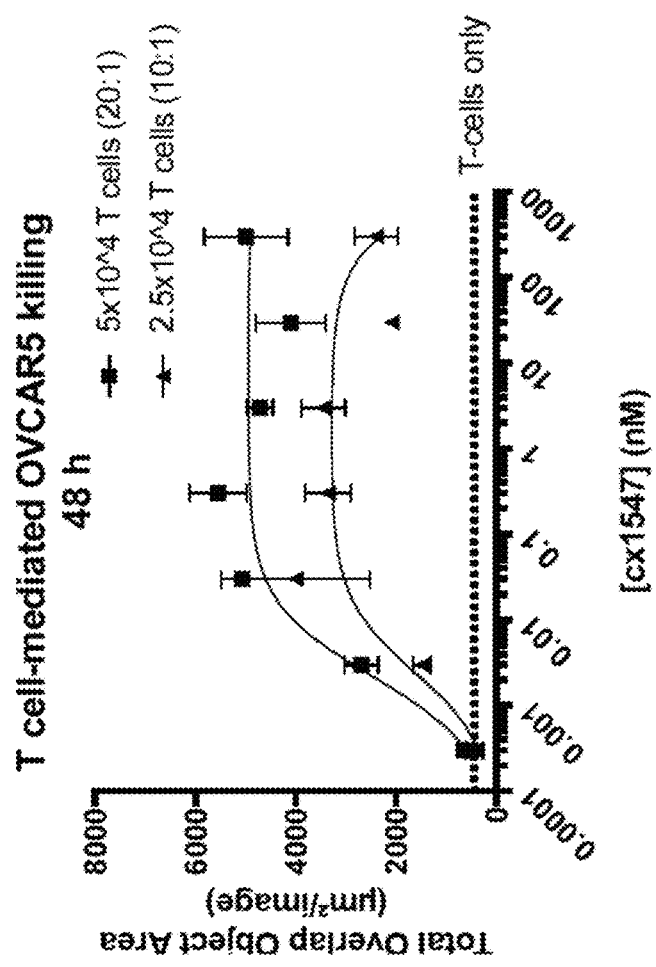
FIG. 28A-28C depicts FRa-dependent T-cell mediated cytotoxicity by cx1547.
Figure 28A:
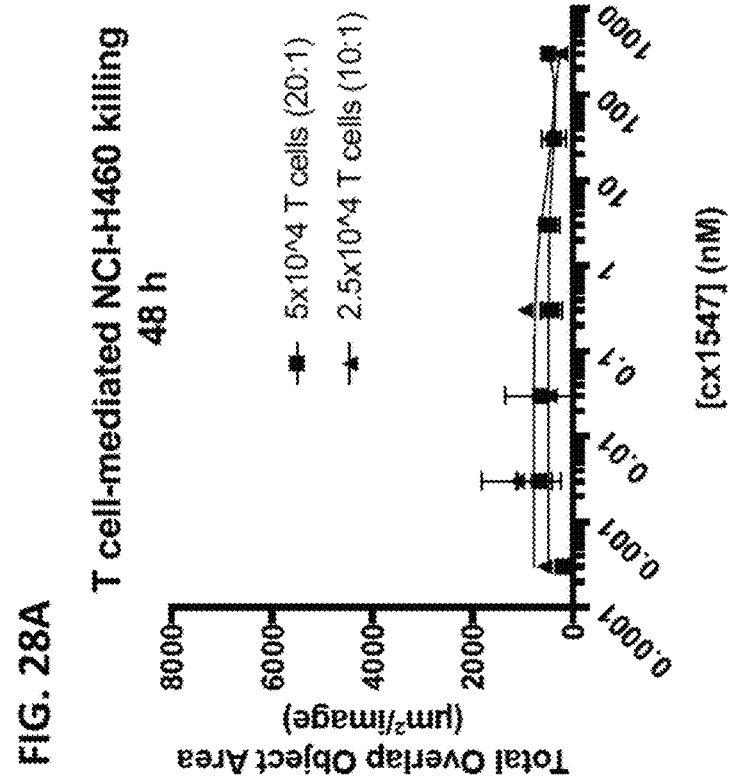
Figure 28C:
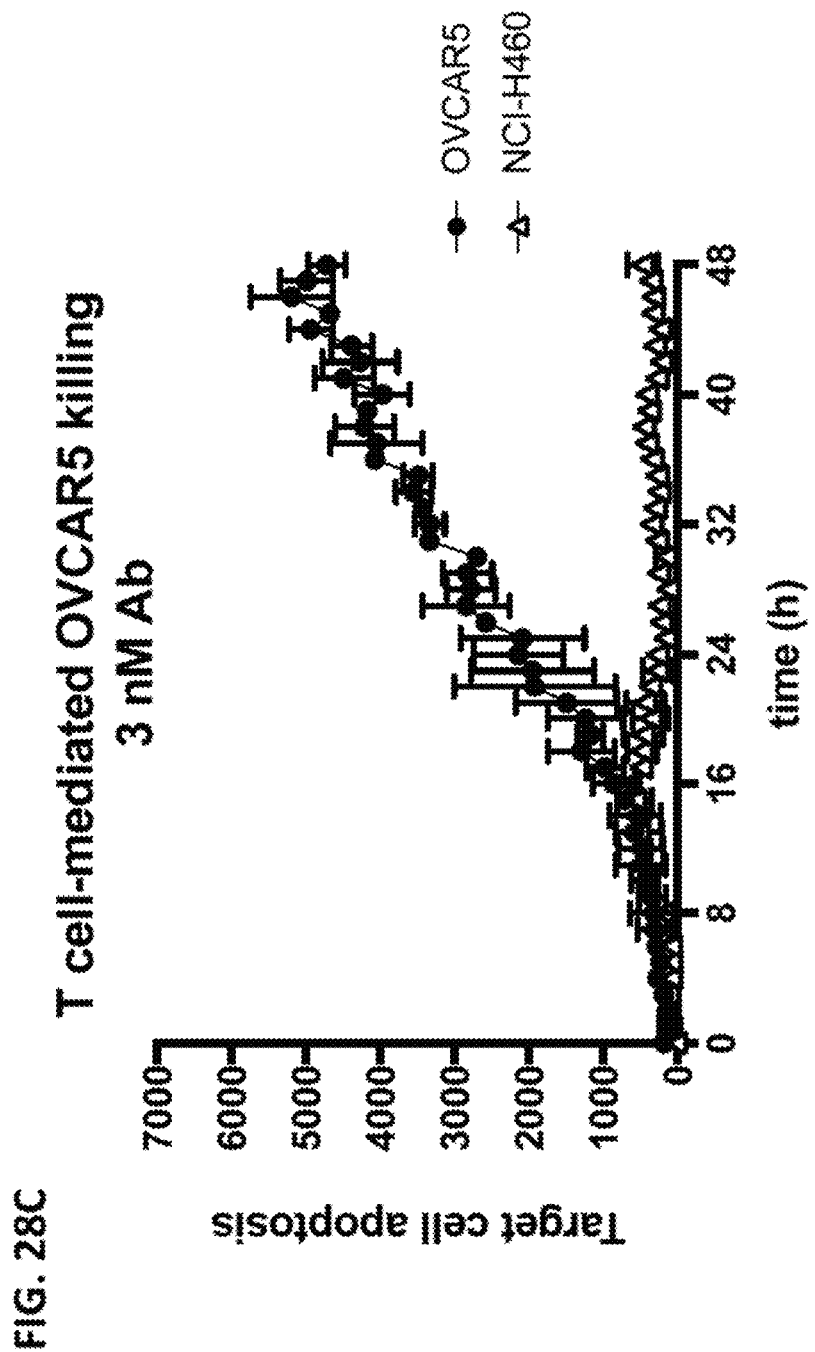
Figure 29A:
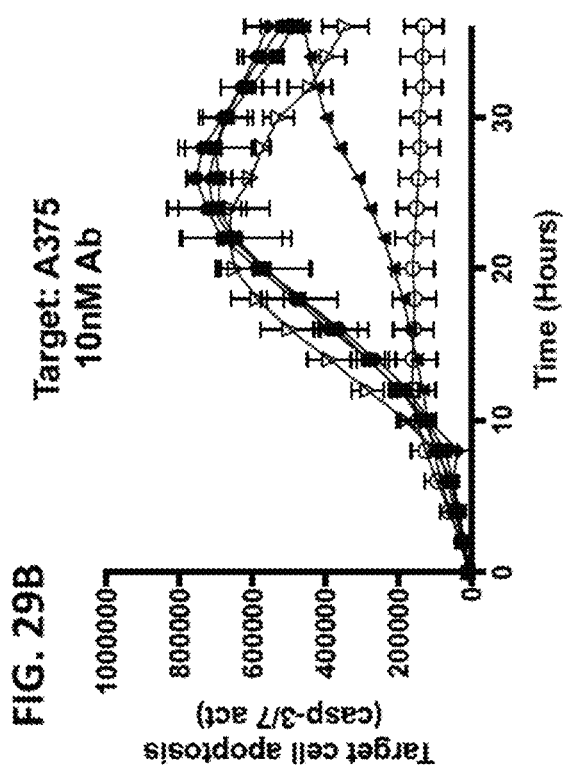
FIG. 29A-29F depicts the kinetics of T-cell-mediated cytotoxicity driven by representative B7H3-targeted constrained CD3 engaging constructs and an alternative DART-Fc format targeting B7H3 and CD3. A titration range of 50 nM to 80 pM of the CD3 engaging constructs on the B7H3 positive A375 cell line are shown in FIG. 29A-29E.
Figure 29B:
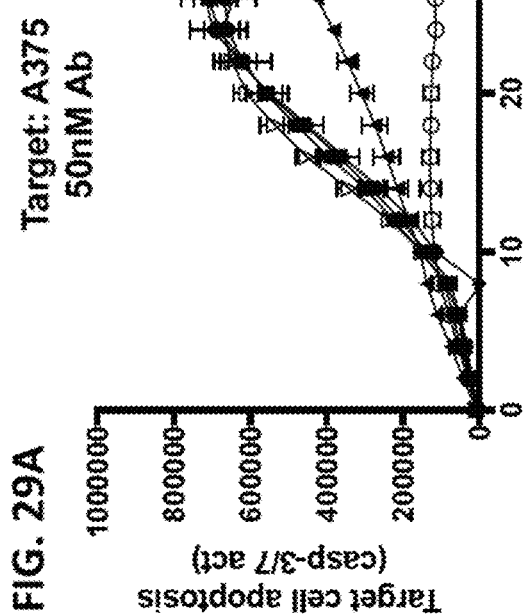
Figure 29C:
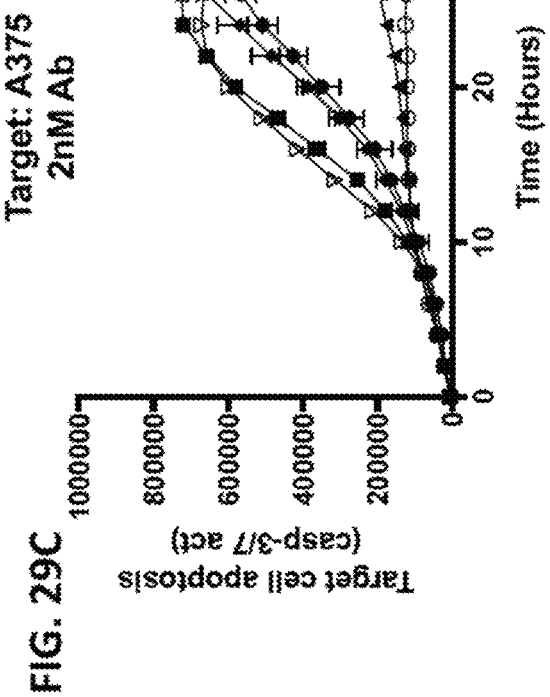
Figure 29E:
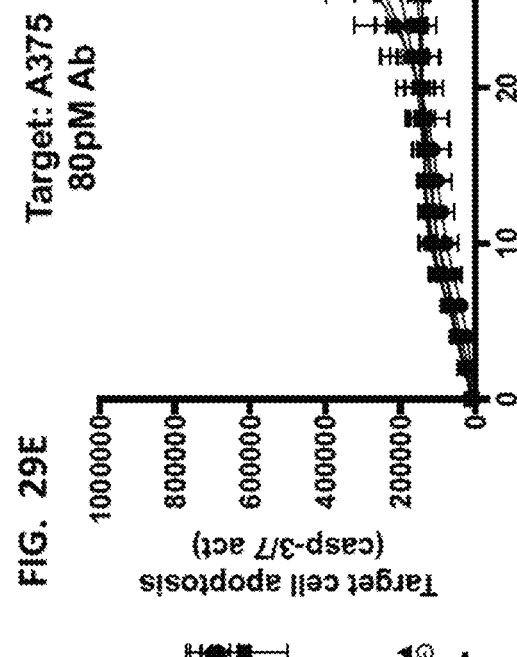
Figure 29D:
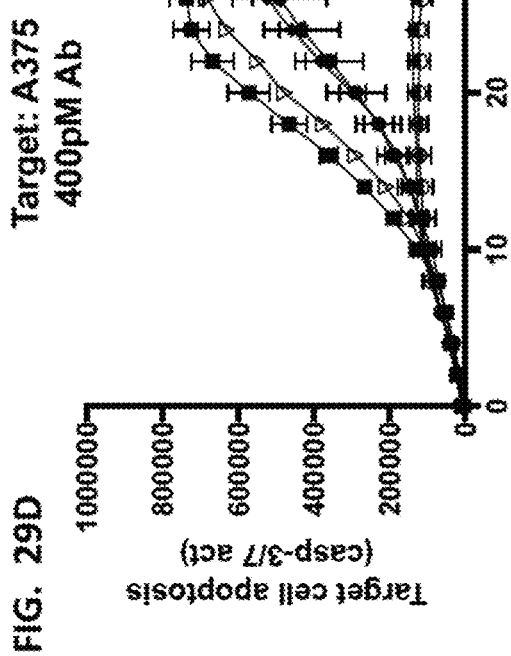
Figure 29F:
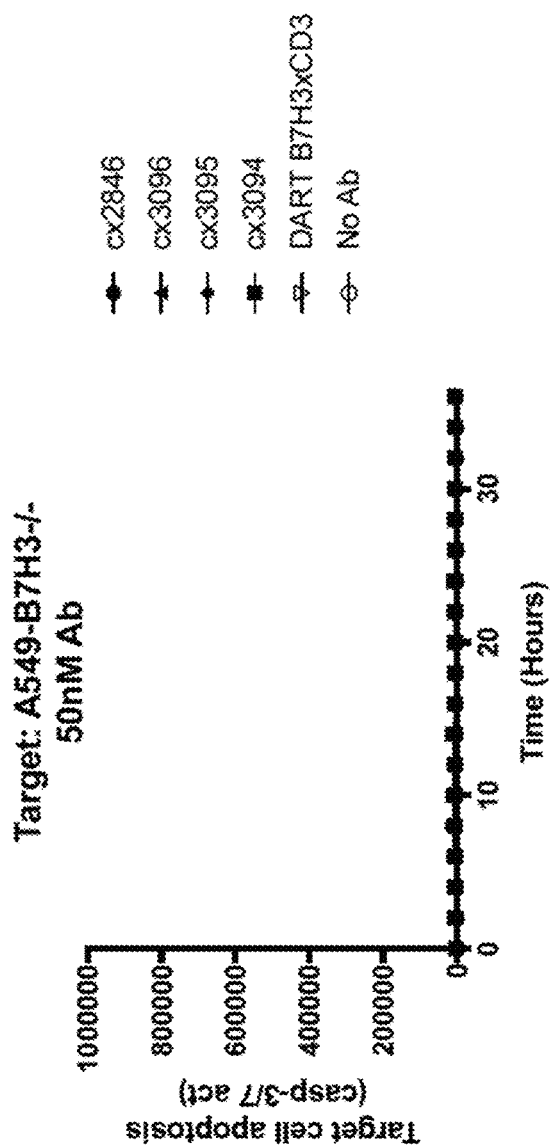
Figure 30:
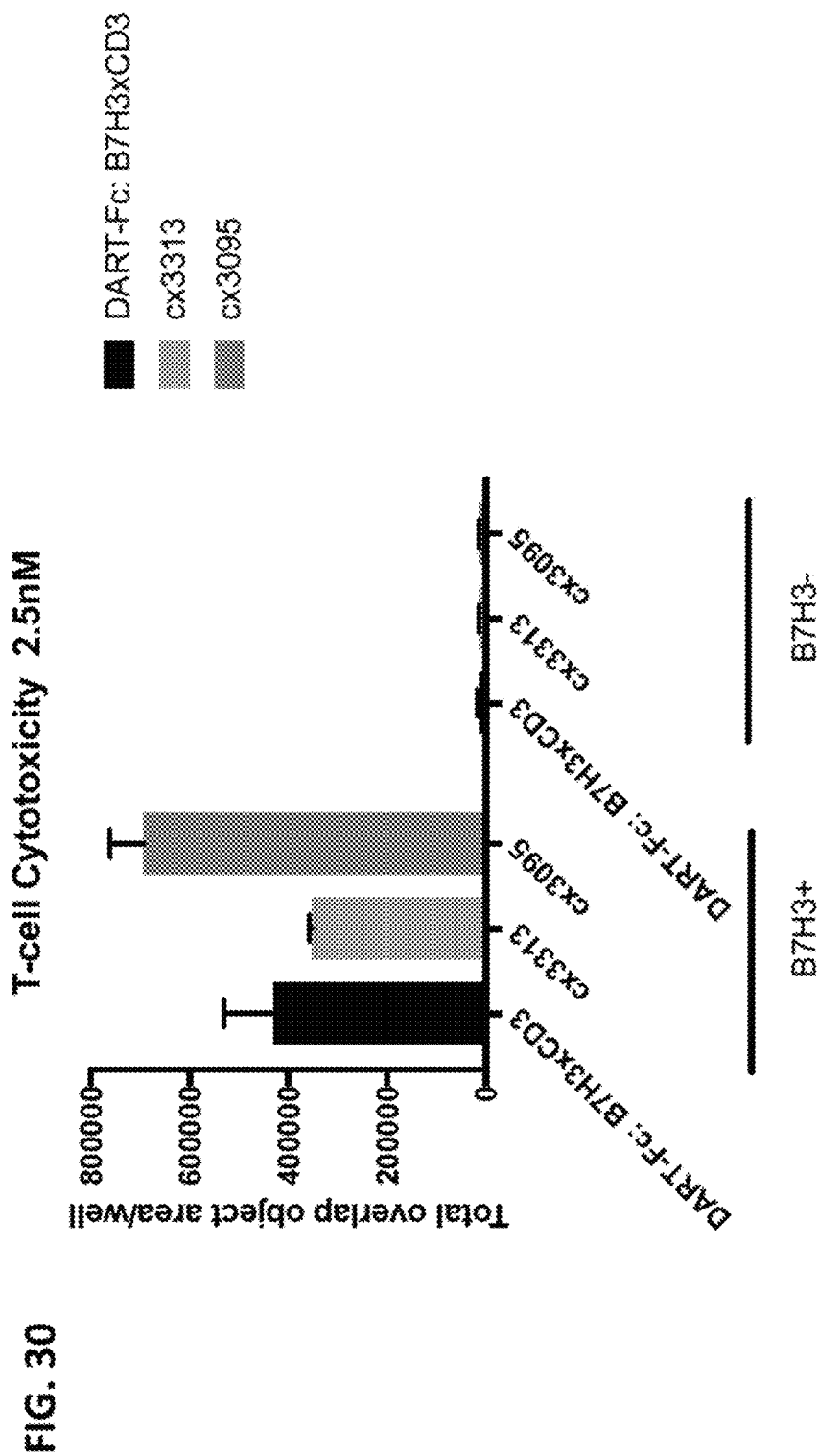
FIG. 30 depicts the magnitude of induced T-cell mediated cytotoxicity by 2.5 nM of B7H3-targeted constrained CD3 engaging constructs and the DART-Fc B7H3×CD3 format on antigen positive (A375) and negative (A549-B7H3 knock-down) cell lines.
Figure 31A:
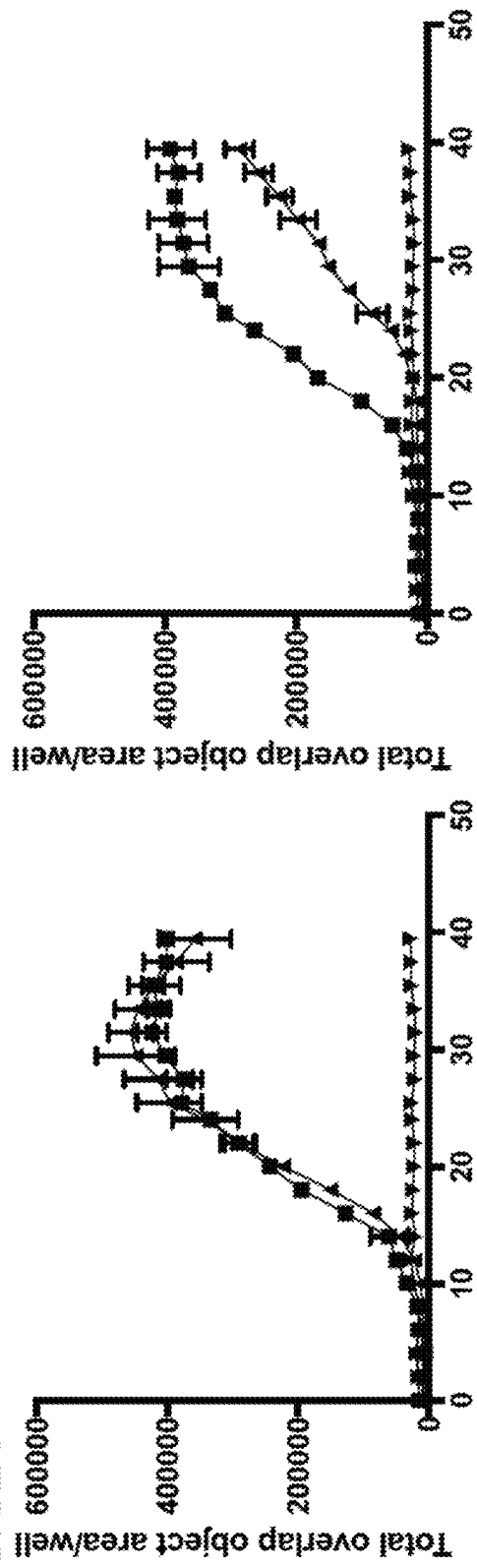
FIG. 31A-31F depicts the comparative potency of two formats FRa-targeted CD3 engagers at inducing mediated T-cell cytotoxicity toward FRa positive Ovcar-5 cells (FIG. 31A-31E) and FRα negative NCI-H60 cells (FIG. 31F). cx2190 is a representative C-terminal product that would be derived from granzyme B proteolytic processing of cx1762. Notably cx2190 displays superior potency compared to cx1792, demonstrating the substantial enhancement in CD3 binding mediated by proteolysis within the linker region between the Fc and CD3 binding domain. The kinetics of T-cell mediated cytotoxicity on FRα positive cells at 20 nM, 32 pM and 6 pM are depicted in FIGS. 31A, 31B, and 31C, respectively.
Figure 31B:
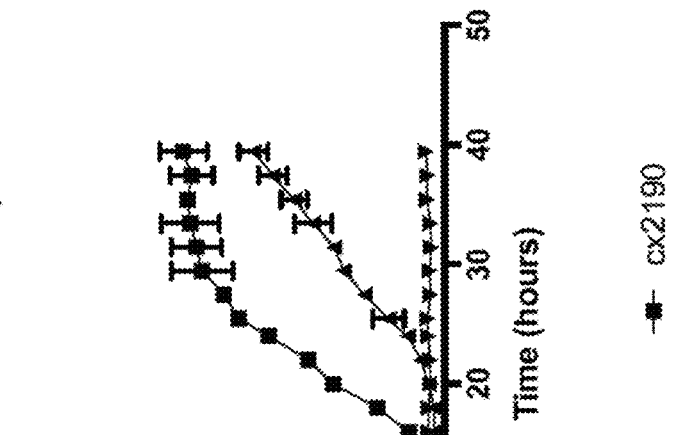
Figure 31C:
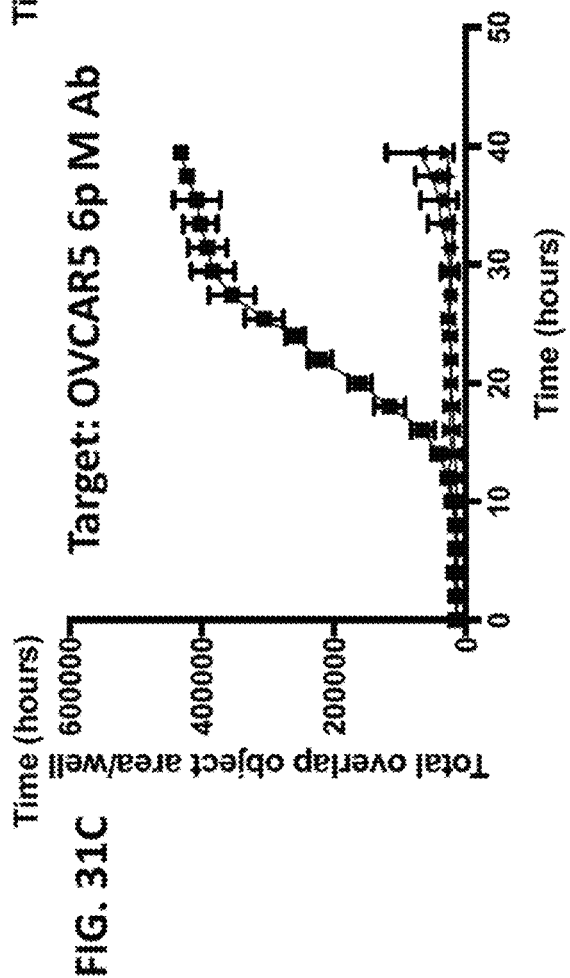
Figure 31E:
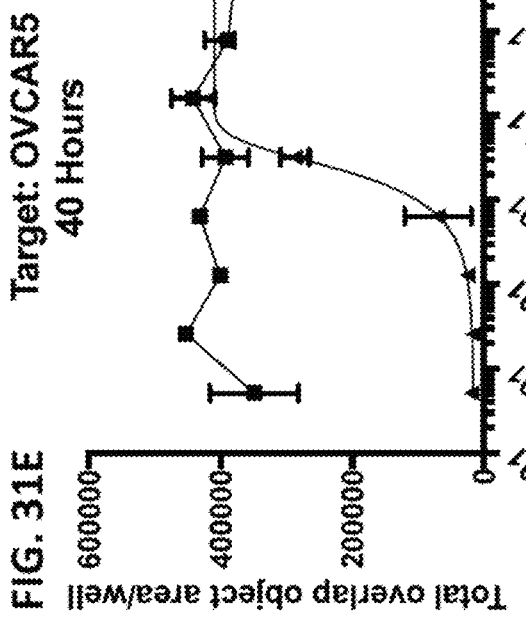
Figure 31D:
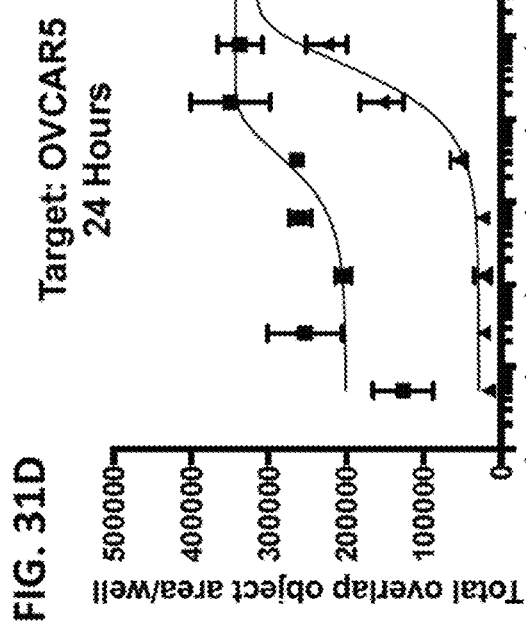
Figure 31F:

As shown in FIG. 28A-28C, cx1547, a FRα-targeted constrained CD3 engaging construct induced potent T-cell-mediated cytotoxicity of antigen positive but not antigen negative cell lines, consistent with the capacity to potently induce antigen-dependent T-cell activation. Similarly, B7H3-targeting constrained CD3 engaging constructs induced potent T-cell-mediated cytotoxicity of antigen positive but not antigen negative cell lines, as shown in FIGS. 29A-29F and 30. These constructs displayed similar potencies to an alternative format, DART-Fc B7H3×CD3. These observations support that the antigen-targeted constrained CD3 format provided herein compared to other CD3 engaging formats known in the art, lack or exhibit reduced T-cell binding in isolation while maintaining potent antigen-dependent T-cell cytotoxicity inducing capacities.

As shown in FIG. 31A-31F, a construct representative of a C-terminal proteolytic product containing only the CD3 binding domain operably linked to TAA-binding domains, designated cx2190 (see FIG. 4C) displayed enhanced antigen-dependent T-cell cytotoxicity inducing capacity compared to the uncleaved FRα-targeted constrained CD3 engaging construct, designated cx1762 (see FIG. 4A).

Figure 32:
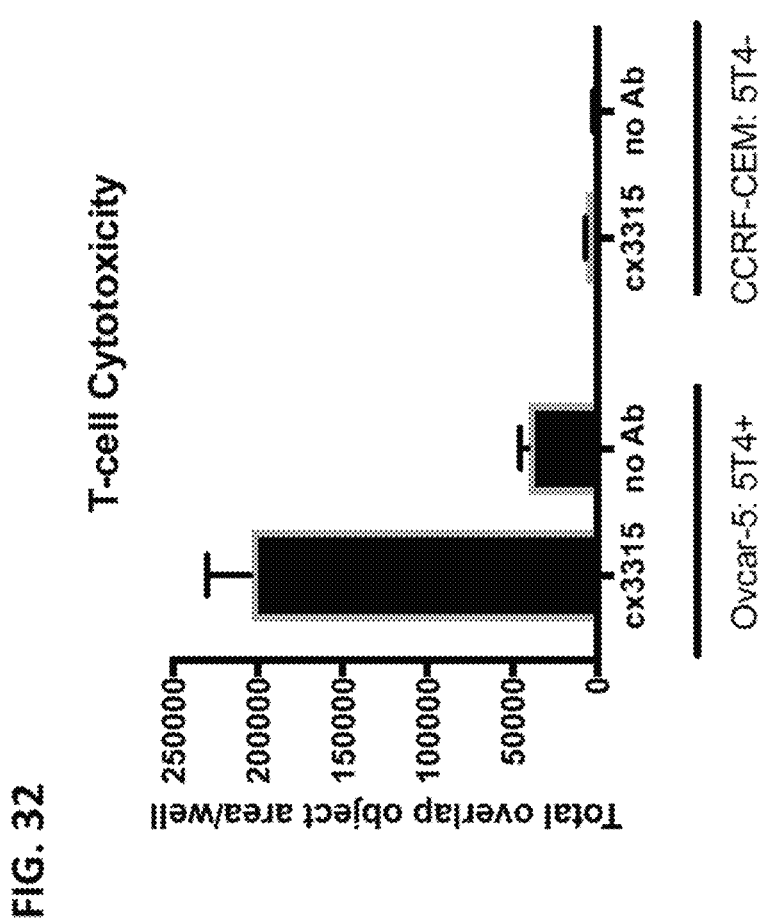
FIG. 32 depicts T-cell-mediated cytotoxicity mediated by a representative 5T4-targeted constrained CD3 engaging construct, cx3315. cx3315 induced specific T-cell cytotoxicity toward a 5t4 expressing cell line, Ovcar-5, but not toward a 5T4 negative cell line, CCRF-CEM. 20 nM cx3315 was used in this assay.

As shown in FIG. 32, a representative 5T4-targeted constrained CD3 engaging construct, cx3315 induced specific T-cell cytotoxicity toward a 5t4 expressing cell line, Ovcar-5, but not toward a 5T4 negative cell line, CCRF-CEM.

2. T Cell Activation

To assess T cell activation, suspension cells from T cell-mediated cytotoxicity assays were collected and stained with a live/dead stain and fluorophore-conjugated anti-CD4, anti-CD8, anti-CD25, and/or anti-CD71 antibodies. Cells were analyzed using a SONY® SA3800 spectral analyzer and CD4+ or CD8+ T cell activation was determined by measuring expression levels of CD25 or CD71 or percent CD25- or CD71-positive.

Figure 33:
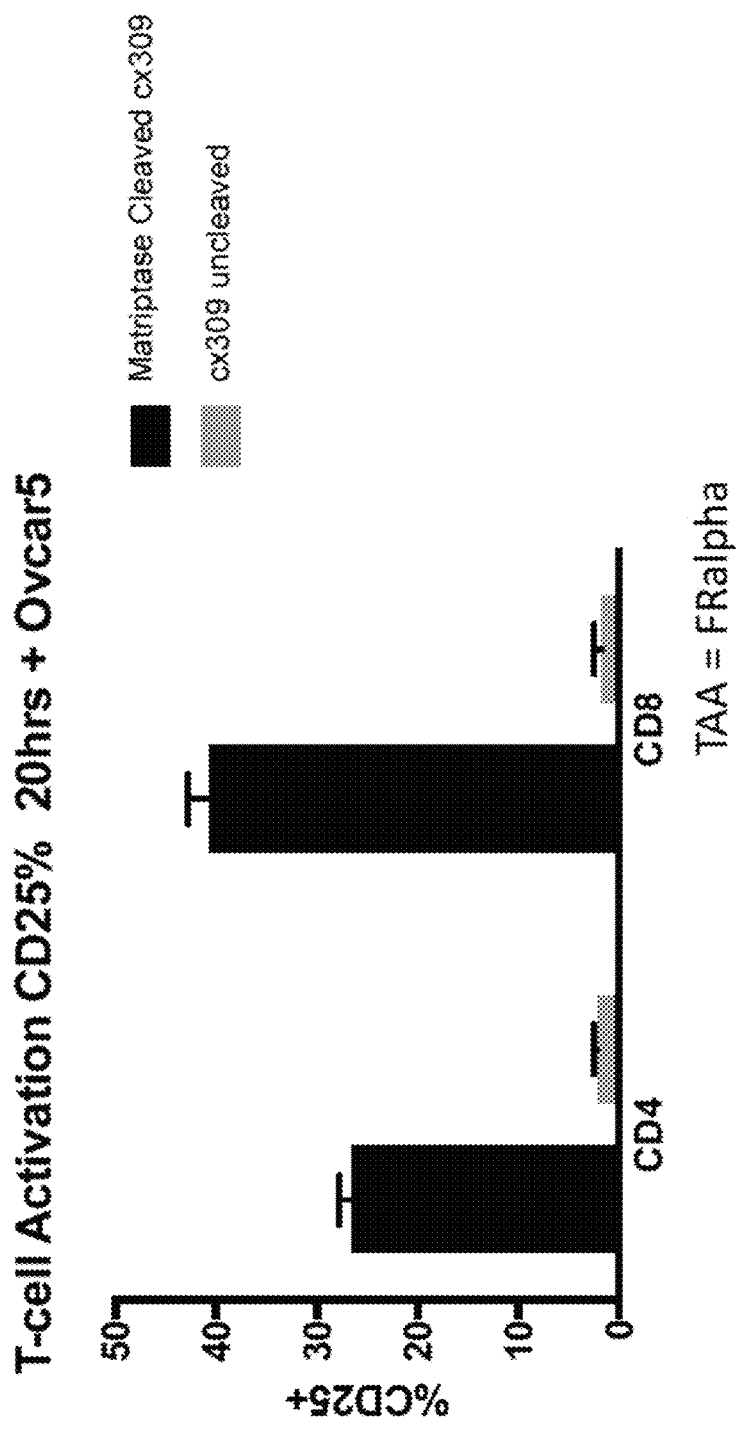
FIG. 33 is a graph demonstrating the activation of T-cells following a 20 hr co-culture of T-cells and Ovcar5 cell in the presence of cleaved or uncleaved cx309. Only cleaved cx309 was capable of mediating FRa-dependent T-cell activation via CD3 binding. T-cell activation was monitored by flow cytometric analysis of the CD25% of CD4 and CD8 populations.
Figure 34A:
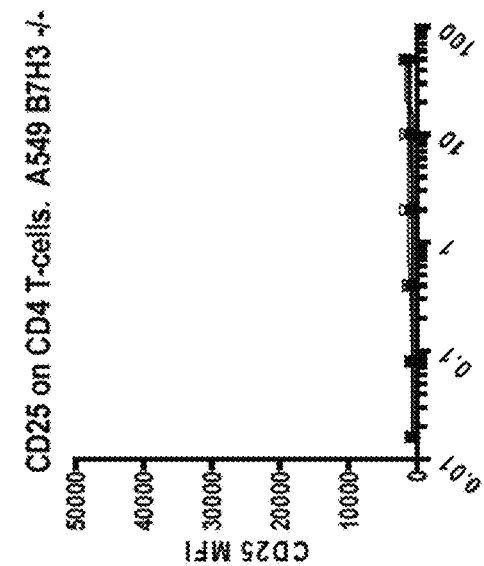
Figure 34C:
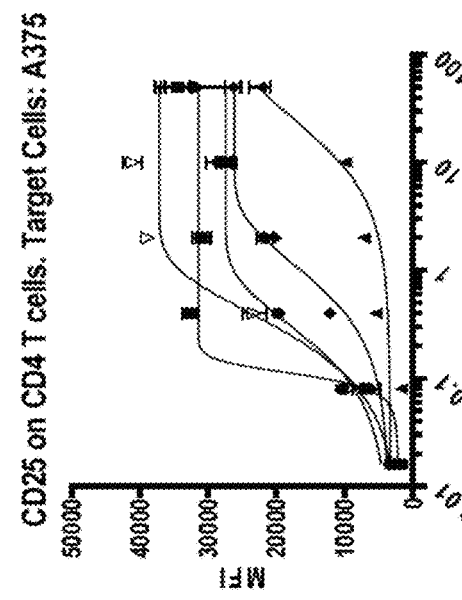
Figure 34B:
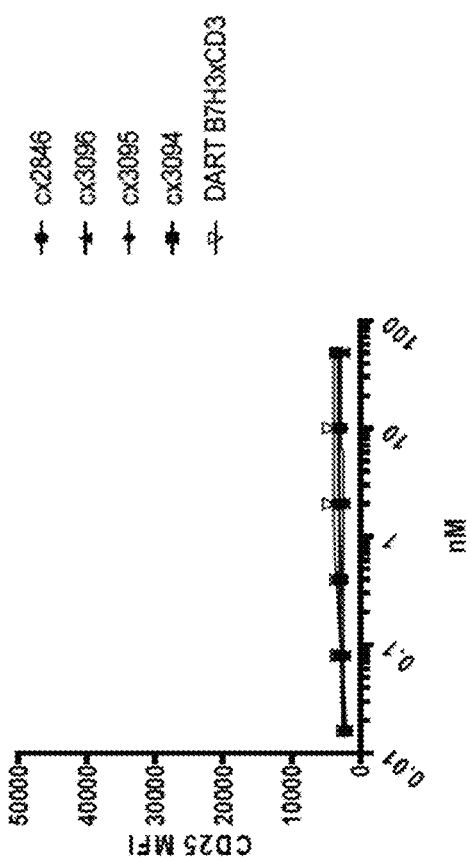
Figure 34D:
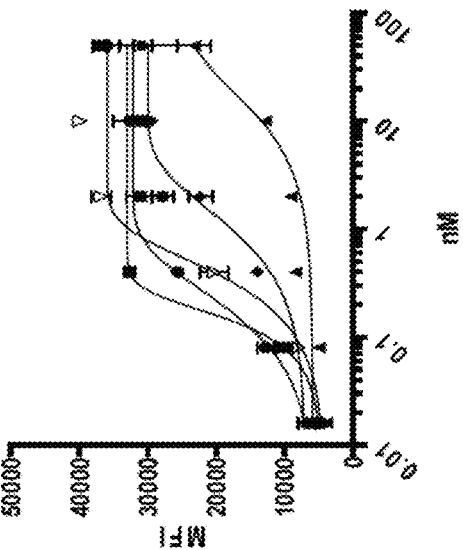

FIG. 33 shows T cell activation as measured by incubating cleaved cx309 and uncleaved, i.e., inactive cx309 constructs for 20 hours in a co-culture of T-cells and Ovcar5 cells. As shown, only cleaved cx309 was capable of mediating FRα-dependent T-cell activation via CD3 binding. T-cell activation was monitored by flow cytometric analysis of the CD25% of CD4 and CD8 populations.

Additionally, a construct containing B7H3 TAA was also tested. As shown in FIG. 34A-34H, B7H3-targeting constrained CD3 engaging construct also mediated B7H3-dependent T-cell activation via CD3 binding. Similar potencies of T-cell activation by the constrained CD3 engaging constructs and the DART-Fc format were observed despite the significant differences in T-cell binding by these two formats (FIG. 14A-14D).

Thus, the results demonstrated that the antigen-target constrained CD3 engaging constructs tested induced potent antigen-dependent activation of both CD4 and CD8 T-cells.

3. T Cell Cytokine Production (ELISA)

Figure 35:
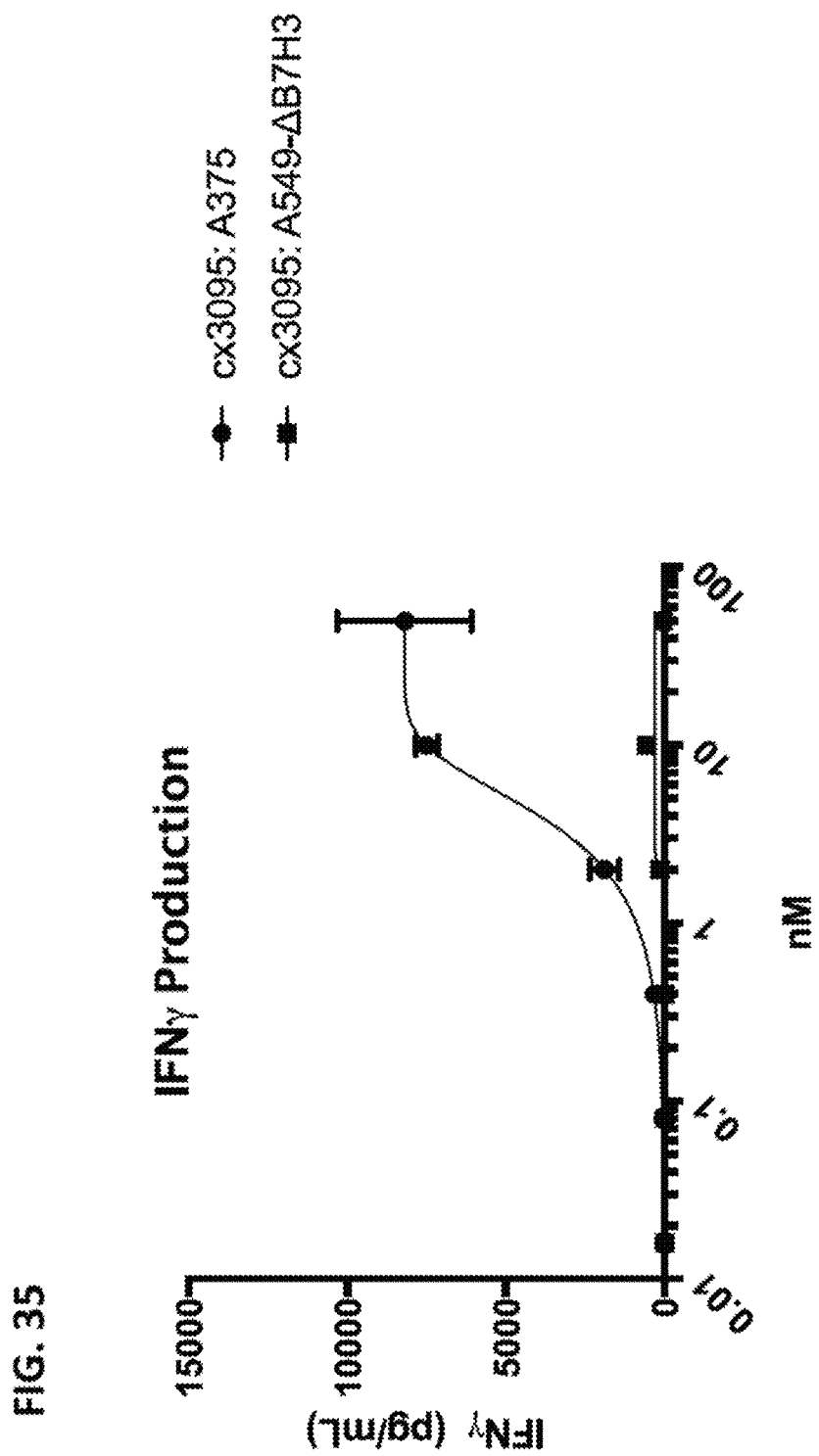
FIG. 35 depicts the ability of a B7H3-targeted constrained CD3 engaging construct, cx3095, to mediate antigen-dependent INFγ production. Cytokine production was quantitated using an INFγ ELISA. A375 was used as B7H3 positive cell line, whereas a B7H3 knock-down A549 cell line was used as negative cell line.

Supernatants from T cell-mediated cytotoxicity assays were analyzed for IFNγ content by sandwich ELISA (BioLegend®, USA). The manufacturer's instructions were followed and a standard curve was generated from which cytokine concentration values of supernatant samples were interpolated. Samples that had absorbance values below the lower limit of detection were assigned a cytokine concentration equal to half that of the lowest standard concentration. FIG. 35 shows that a representative B7H3-targeted constrained CD3 engaging construct was observed to elicit IFNγ production by T-cells in an antigen dependent manner.

4. T Cell Cytokine Production (FluoroSpot)

Figure 36A:
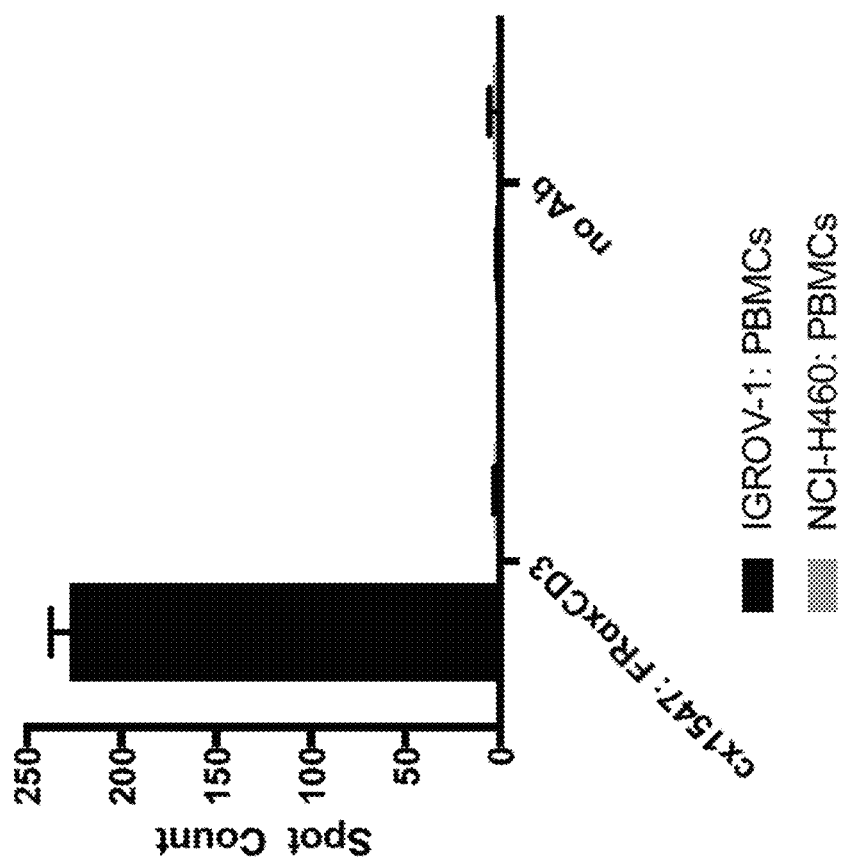
FIG. 36A-36B depicts the ability of a representative FRa-targeted constrained CD3 engaging construct, cx1547, to induce FRa-dependent IFNγ (FIG. 36A) and IL-2 (FIG. 36B) from human PBMCs. Cytokine production was measured using a FluoroSpot cytokine capture assay. The IGROV-1 and NCI-H460 were used as the FRα positive and negative cell lines, respectively.
Figure 36B:
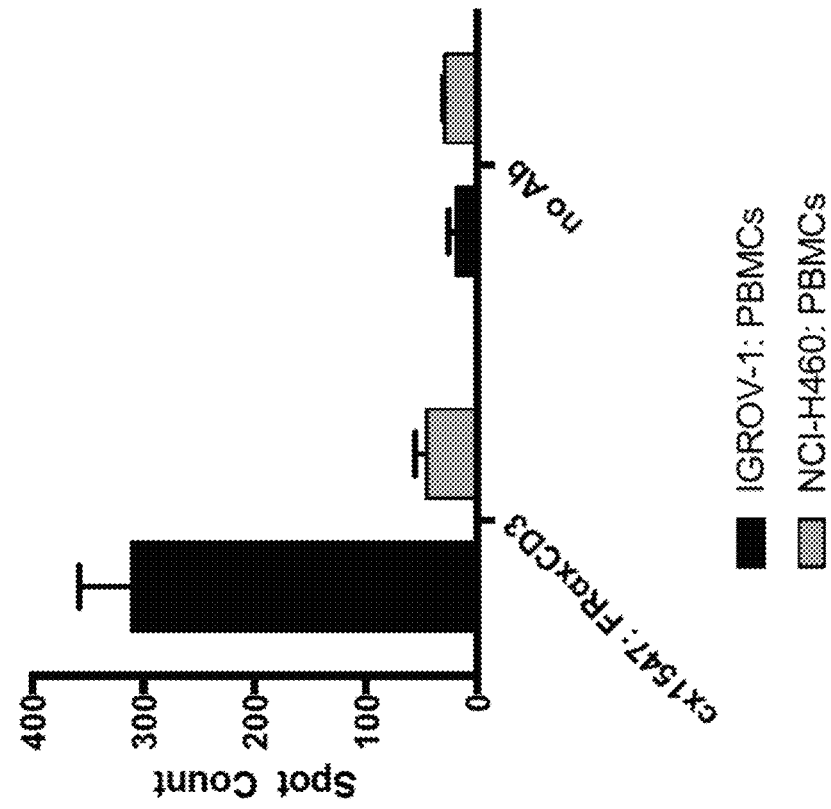
Figure 37:
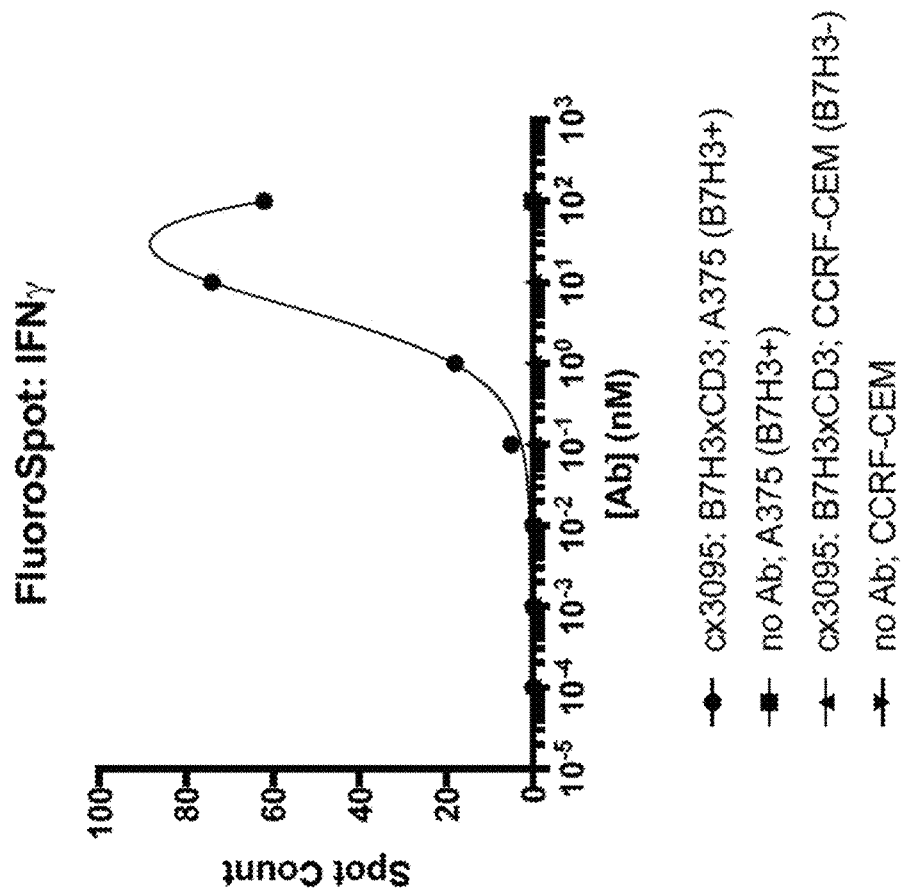
FIG. 37 depicts the ability of a B7H3-targeted constrained CD3 engaging construct, cx3095, to mediate antigen-dependent INFγ production. Cytokine production was monitored using a FluoroSpot assay. A375 and CCRF-CEM cell line were used as B7H3 positive and negative cell lines, respectively.
Figure 38A:
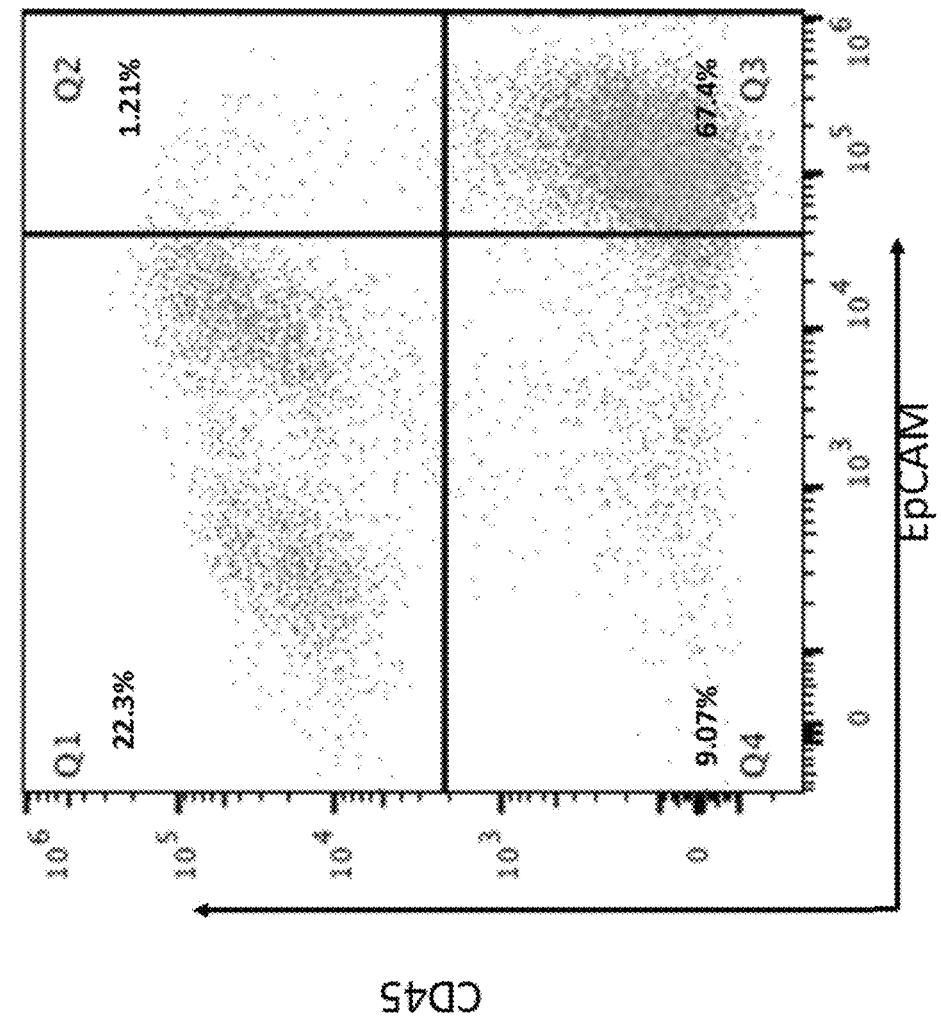
FIG. 38A-38D depicts the ability of the FRa-targeting constrained CD3 construct, cx1547, to activate T-cells present in a dissociated primary human ovarian tumor sample and elicit cytotoxicity.
Figure 38C:
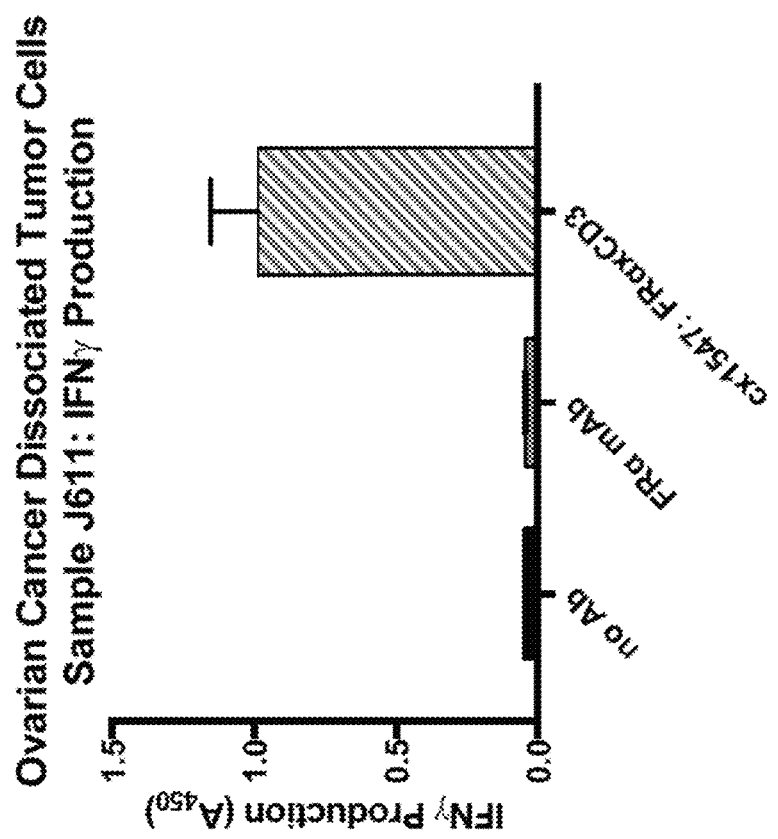
Figure 38B:
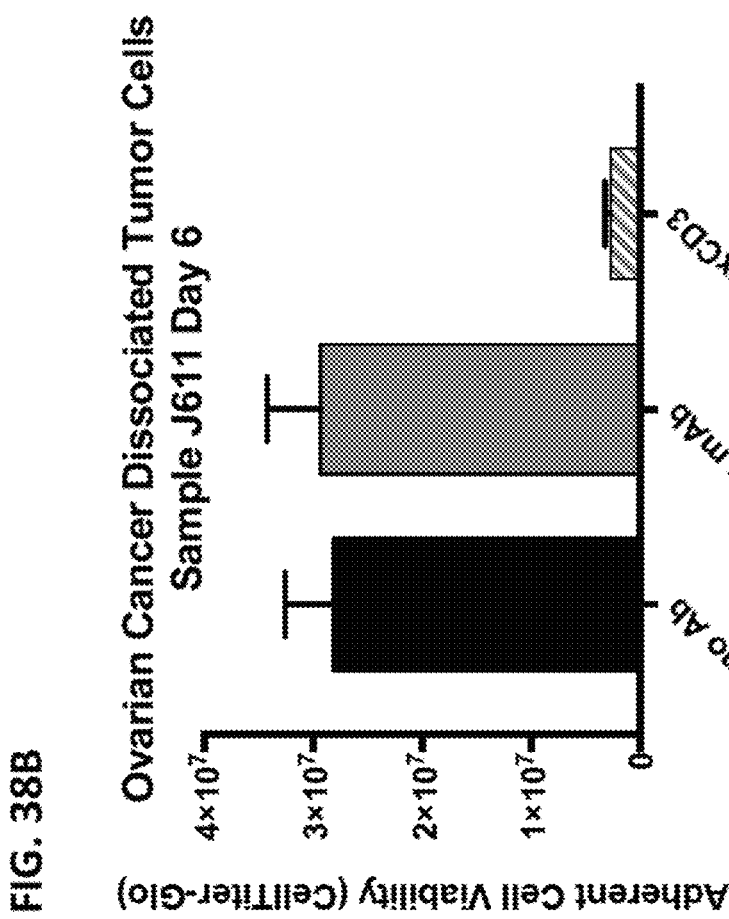
Figure 38D:
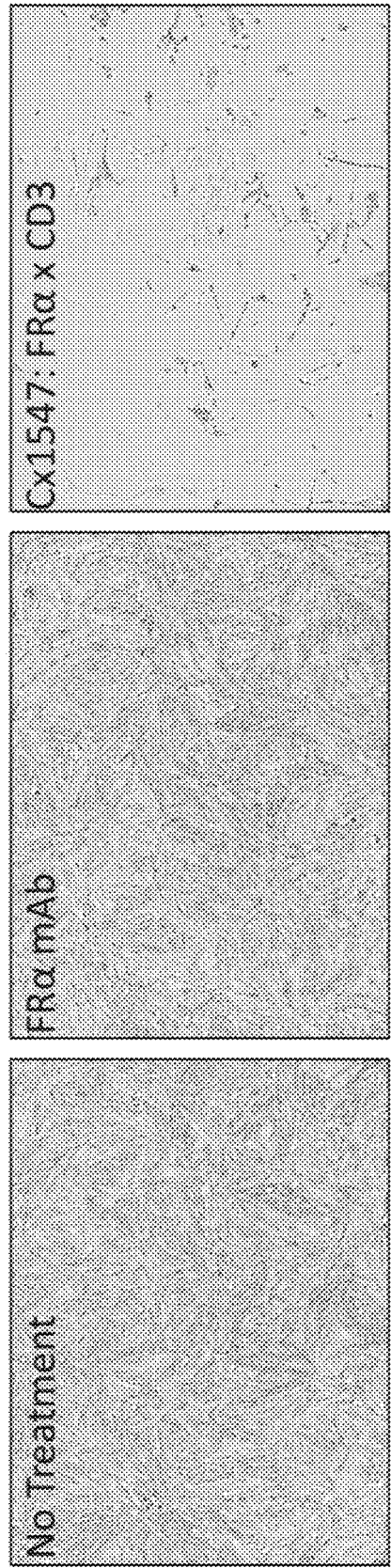

FluoroSpot membranes were coated with IFNγ and IL-2 capture antibodies overnight at 4° C. Membranes were washed with PBS and antibody titrations, target cells, and PBMCs or T cells negatively enriched from PBMCs were added. For target cell: PBMC co-culture, cells were seeded at a 1:20 ratio. For target cell:T cell co-culture, cells were seeded at a 1:10 ratio. Assay plates were incubated for ~24 h at 37° C. and membranes were prepared according to the manufacturer's (C.T.L.) instructions. Membranes were imaged using a CTL-ImmunoSpot S6 Universal Analyzer. Cytokine spot count was measured using uniform exposure time and intensity settings among assay wells. FIGS. 36A-36B and 37 depicts the ability of the antigen-targeted constrained CD3 engaging construct to elicit cytokine production from T-cells in FRα or B7H3-dependent manner, respectively.

5. Dissociated Tumor Cell Killing

An ovarian cancer dissociated tumor cell sample (Conversant) was stained with Zombie Red™ and fluorophore-conjugated anti-CD45 and anti-EpCAM antibodies to identify tumor cells (CD45–/EpCAM+) and tumor infiltrating immune cells (CD45+/EpCAM–) by flow cytometry. Unstained cells were seeded in a 96-well tissue culture plate and representative FRα-constrained CD3 engaging constructs and recombinant human IL-2 were added at 20 nM and 10 ng/mL final concentrations. Following culture at 37° C. for 6 days, supernatant aliquots were collected for analysis of IFNγ content by sandwich ELISA (described above) and remaining supernatants containing non-adherent cells were removed. Adherent cells were gently washed with PBS to remove residual suspension cells and debris, media was added to cells, and assay wells were imaged using an IncuCyte® ZOOM system to visualize tumor cell confluency. An equal volume of CellTiter-Glo® viability reagent was added to sample wells and luminescence was measured using a SpectraMax® L microplate reader. FIG. 38A-38D depicts the capacity of the antigen-targeted constrained CD3 engaging construct to activate T-cells that had previously infiltrated a tumor sample and mediate cytotoxicity and tumor cell elimination.

Other Embodiments

While the invention has been described in conjunction with the detailed description thereof, the foregoing description is intended to illustrate and not limit the scope of the disclosure, which is defined by the scope of the appended claims. Other aspects, advantages, and modifications are within the scope of the following claims.

SEQUENCE TABLE

| SEQ ID NO | SEQUENCE | | | | | DESCRIPTION |
|---|---|---|---|---|---|---|
| 1 | PAPELLGGPS | VFLFPPKPKD | TLMISRTPEV | TCVVVDVSHE | DPEVKFNWYV | IgG1 Fc |
|   | DGVEVHNAKT | KPREEQYNST | YRVVSVLTVL | HQDWLNGKEY | | |
|   | KCKVSNKALP | APIEKTISKA | KGQPREPQVY | TLPPSRDELT | KNQVSLTCLV | |
|   | KGFYPSDIAV | EWESNGQPEN | NYKTTPPVLD | SDGSFFLYSK | LTVDKSRWQQ | |
|   | GNVFSCSVMH | EALHNHYTQK | SLSLSPGK | | | |
| 2 | PAPGGPSVFL | FPPKPKDTLM | ISRTPEVTCV | VVDVSHEDPE | VKFNWYVDGV | IgG2 Fc |
|   | EVHNAKTKPR | EEQYNSTYRV | VSVLTVLHQD | WLNGKEYKCK | | |
|   | VSNKALPAPI | EKTISKAKGQ | PREPQVYTLP | PSRDELTKNQ | VSLTCLVKGF | |
|   | YPSDIAVEWE | SNGQPENNYK | TTPPVLDSDG | SFFLYSKLTV | DKSRWQQGNV | |
|   | FSCSVMHEAL | HNHYTQKSLS | LSPGK | | | |
| 3 | PAPPVAGPSV | FLFPPKPKDT | LMISRTPEVT | CVVVDVSHED | PEVQFNWYVD | IgG2 Fc |
|   | GVEVHNAKTK | PREEQFNSTF | RVVSVLTVVH | QDWLNGKEYK | | |
|   | CKVSNKGLPA | PIEKTISKTK | GQPREPQVYT | LPPSREEMTK | NQVSLTCLVK | |

| SEQ ID NO | SEQUENCE | DESCRIPTION |
|---|---|---|
| | GFYPSDISVE WESNGQPENN YKTTPPMLDS DGSFFLYSKL TVDKSRWQQG NVFSCSVMHE ALHNHYTQKS LSLSPGK | |
| 4 | PAPELLGGPS VFLFPPKPKD TLMISRTPEV TCVVVDVSHE DPEVQFKWYV DGVEVHNAKT KPREEQYNST FRVVSVLTVL HQDWLNGKEY KCKVSNKALP APIEKTISKT KGQPREPQVY TLPPSREEMT KNQVSLTCLV KGFYPSDIAV EWESSGQPEN NYNTTPPMLD SDGSFFLYSK LTVDKSRWQQ GNIFSCSVMH EALHNRFTQK SLSLSPGK | IgG3 Fc |
| 5 | PAPEFLGGPS VFLFPPKPKD TLMISRTPEV TCVVVDVSQE DPEVQFNWYV DGVEVHNAKT KPREEQFNST YRVVSVLTVL HQDWLNGKEY KCKVSNKGLP SSIEKTISKA KGQPREPQVY TLPPSQEEMT KNQVSLTCLV KGFYPSDIAV EWESNGQPEN NYKTTPPVLD SDGSFFLYSR LTVDKSRWQE GNVFSCSVMH EALHNHYTQK SLSLSLGK | IgG4 Fc |
| 6 | PAPELLGGPS VFLFPPKPKD TLMISRTPEV TCVVVDVSQE DPEVQFNWYV DGVEVHNAKT KPREEQFNST YRVVSVLTVL HQDWLNGKEY KCKVSNKGLP SSIEKTISKA KGQPREPQVY TLPPSQEEMT KNQVSLTCLV KGFYPSDIAV EWESNGQPEN NYKTTPPVLD SDGSFFLYSR LTVDKSRWQE GNVFSCSVMH EALHNHYTQK SLSLSLGK | IgG4 Fc |
| 7 | EPKSSDKTHTCPPC | Hinge |
| 8 | DKTHTCPPC | Hinge |
| 9 | ESKYGPPCPPC | Hinge |
| 10 | GGSGGS | (GGS)2 |
| 11 | GGSGGSGGS | (GGS)3 |
| 12 | GGSGGSGGSGGS | (GGS)4 |
| 13 | GGSGGSGGSGGSGGS | (GGS)5 |
| 14 | EVQLVESGGGLVQPKGSLKLSCAASGFTFNTYAMNWVRQAPGKGLEWVARI RSKYNNYATYYADSVKDRFTISRDDSQSILYLQMNNLKTEDTAMYYCVRHG NFGNSYVSWFAYWGQGTLVTVSA | anti-CD3 Hv |
| 15 | QAVVTQESALTTSPGETVTLTCRSSTGAVTTSNYANWVQEKPDHLFTGLIGG TNKRAPGVPARFSGSLIGDKAALTITGAQTEDEAIYFCALWYSNLWVFGGGT KLTVL | anti-CD3 Lv |
| 16 | TYAMN | anti-CD3 VH CDR1 |
| 17 | RIRSKYNNYATYYADSVKD | anti-CD3 VH CDR2 |
| 18 | HGNFGNSYVSWFAY | anti-CD3 VH CDR3 |
| 19 | RSSTGAVTTSNYAN | anti-CD3 VL CDR1 |
| 20 | GTNKRAP | anti-CD3 VL CDR2 |
| 21 | ALWYSNLWV | anti-CD3 VL CDR3 |
| 22 | LEAD | Granzyme B substrate |
| 23 | RQAR | Granzyme B substrate |
| 24 | PAGL | MMP substrate |
| 25 | TGLEADGSPAGLGRQARVG | Linker |
| 26 | TGLEADGSRQARVGPAGLG | Linker |
| 27 | TGSPAGLEADGSRQARVGS | Linker |

SEQUENCE TABLE

| SEQ ID NO | SEQUENCE | DESCRIPTION |
|---|---|---|
| 28 | TGPAGLGLEADGSRQARVG | Linker |
| 29 | TGRQARVGLEADGSPAGLG | Linker |
| 30 | TGSRQARVGPAGLEADGS | Linker |
| 31 | TGPAGLGSRQARVGLEADGS | Linker |
| 32 | EVQLVESGGGLVQPGGSLRLSCAASGFTFSTYAMNWVRQAPGKGLEWVGRIRSKYNNYATYYADSVKDRFTISRDDSKNSLYLQMNSLKTEDTAVYYCVRHGNFGNSYVSWFAYWGQGTLVTVSS | anti-CD3 VH1 |
| 33 | EVKLVESGGGLVQPGGSLRLSCAASGFTFNTYAMNWVRQAPGKGLEWVARIRSKYNNYATYYADSVKDRFTISRDDSKSSLYLQMNNLKTEDTAMYYCVRHGNFGNSYVSWFAYWGQGTLVTVSS | anti-CD3 VH2 |
| 34 | EVKLVESGGGLVKPGRSLRLSCAASGFTFNTYAMNWVRQAPGKGLEWVARIRSKYNNYATYYADSVKDRFTISRDDSKSILYLQMNNLKTEDTAMYYCVRHGNFGNSYVSWFAYWGQGTLVTVSS | anti-CD3 VH3 |
| 35 | EVKLVESGGGLVKPGRSLRLSCAASGFTFNTYAMNWVRQAPGKGLEWVARIRSKYNNYATYYADSVKDRFTISRDDSKSILYLQMNSLKTEDTAMYYCVRHGNFGNSYVSWFAYWGQGTLVTVSS | anti-CD3 VH4 |
| 36 | EVKLVESGGGLVKPGRSLRLSCAASGFTFNTYAMNWVRQAPGKGLEWVARIRSKYNNYATYYADSVKDRFTISRDDSKSILYLQMNSLKTEDTAMYYCVRHGNFGNSYVSWFAYWGQGTLVTVSS | anti-CD3 VH5 |
| 37 | EVQLLESGGGLVQPGGSLRLSCAASGFTFSTYAMNWVRQAPGKGLEWVSRIRSKYNNYATYYADSVKGRFTISRDDSKNTLYLQMNSLRAEDTAVYYCVRHGNFGNSYVSWFAYWGQGTLVTVSS | anti-CD3 VH6 |
| 38 | EVQLVESGGGLVQPGGSLRLSCAASGFTFSTYAMSWVRQAPGKGLEWVGRIRSKYNNYATYYADSVKGRFTISRDDSKNTLYLQMNSLRAEDTAVYYCVRHGNFGDSYVSWFAYWGQGTLVTVSS | anti-CD3 VH7 |
| 39 | EVQLVESGGGLVQPGGSLKLSCAASGFTFNKYAMNWVRQAPGKGLEWVARIRSKYNNYATYYADSVKDRFTISRDDSKNTAYLQMNNLKTEDTAVYYCVRHGNFGNSYISYWAYWGQGTLVTVS | anti-CD3 VH8 |
| 40 | EVQLVESGGGLVQPGGSLRLSCAASGFTFNTYAMNWVRQAPGKGLEWVARIRSKYNNYATYYADSVKGRFTISRDDSKNTLYLQMNSLRAEDTAVYYCVRHGNFGNSYVSWFAYWGQGTTVTVSS | anti-CD3 VH9 |
| 41 | EVQLVESGGGLVQPGGSLRLSCAASGFTFNTYAMNWVRQAPGKGLEWVARIRSKYNNYATYYADSVKGRFTISRDDSKNTLYLQMNSLRAEDTAVYYCVRHGNFGNSYVSYFAYWGQGTTVTVSS | anti-CD3 VH10 |
| 42 | EVQLVESGGGLVQPKGSLKLSCAASGFTFNTYAMNWVRQAPGKGLEWVARIRSKYNNYATYYADSVKDRFTISRDDQSILYLQMNNLKTEDTAMYYCVRHGNFGNSYVSWFAYWGQGTLVTVSS | anti-CD3 VH11 |
| 43 | EVQLVESGGGLVQPGGSLRLSCAASGFTFNTYAMNWVRQAPGKGLEWVARIRSKYNNYATYYADSVKGRFTISRDDAKNTLYLQMSSLRAEDTAVYYCVRHGNFGNSYVSWFAYWGQGTLVTVKP | anti-CD3 VH12 |
| 44 | EVQLVESGGGLVQPGGSLRLSCAASGFTFNTYAMNWVRQAPGKCLEWVARIRSKYNNYATYYADSVKGRFTISRDDAKNTLYLQMSSLRAEDTAVYYCVRHGNFGNSYVSWFAYWGQGTLVTVKP | anti-CD3 VH13 |
| 45 | EVQLVESGGGLVQPGGSLRLSCAASGFTFNTYAMNWVRQAPGKGLEWVARIRSKYNNYATYYADSVKGRFTISRDDAKNTLYLQMSSLRAEDTAVYYCVRHGNFGNSYVSWFAYWGCGTLVTVKP | anti-CD3 VH14 |
| 46 | EVQLVESGGGLVQPGGSLRLSCAASGFTFSTYAMNWVRQAPGKGLEWVARIRSKYNNYATYYADSVKGRFTISRDDAKNTLYLQMSSLRAEDTAVYYCVRHGNFGNSYVSWFAYWGQGTLVTVSS | anti-CD3 VH15 |
| 47 | EVQLVESGGGLVQPGGSLRLSCAASGFTFNTYAMNWVRQAPGKGLEWVSRIRSKYNNYATYYADSVKGRFTISRDDAKNTLYLQMSSLRAEDTAVYYCVRHGNFGNSYVSWFAYWGQGTLVTVSS | anti-CD3 VH16 |

-continued

SEQUENCE TABLE

| SEQ ID NO | SEQUENCE | DESCRIPTION |
|---|---|---|
| 48 | EVQLVESGGGLVQPGGSLRLSCAASGFTFSTYAMNWVRQAPGKGLEWVSRIRSKYNNYATYYADSVKGRFTISRDDAKNTLYLQMSSLRAEDTAVYYCVRHGNFGNSYVSWFAYWGQGTLVTVSS | anti-CD3 VH17 |
| 49 | EVQLVESGGGLVQPGGSLRLSCAASGFTFSTYAMNWVRQAPGKCLEWVARIRSKYNNYATYYADSVKGRFTISRDDAKNTLYLQMSSLRAEDTAVYYCVRHGNFGNSYVSWFAYWGQGTLVTVSS | anti-CD3 VH18 |
| 50 | EVQLVESGGGLVQPGGSLRLSCAASGFTFNTYAMNWVRQAPGKCLEWVSRIRSKYNNYATYYADSVKGRFTISRDDAKNTLYLQMSSLRAEDTAVYYCVRHGNFGNSYVSWFAYWGQGTLVTVSS | anti-CD3 VH19 |
| 51 | EVQLVESGGGLVQPGGSLRLSCAASGFTFSTYAMNWVRQAPGKCLEWVSRIRSKYNNYATYYADSVKGRFTISRDDAKNTLYLQMSSLRAEDTAVYYCVRHGNFGNSYVSWFAYWGQGTLVTVSS | anti-CD3 VH20 |
| 52 | EVQLVESGGGLVQPGGSLRLSCAASGFTFSTYAMNWVRQAPGKCLEWVGRIRSKYNNYATYYADSVKDRFTISRDDSKNSLYLQMNSLKTEDTAVYYCVRHGNFGNSYVSWFAYWGQGTLVTVSS | anti-CD3 VH21 |
| 53 | EVKLVESGGGLVQPGGSLRLSCAASGFTFNTYAMNWVRQAPGKCLEWVARIRSKYNNYATYYADSVKDRFTISRDDSKSSLYLQMNNLKTEDTAMYYCVRHGNFGNSYVSWFAYWGQGTLVTVSS | anti-CD3 VH22 |
| 54 | EVKLVESGGGLVKPGRSLRLSCAASGFTFNTYAMNWVRQAPGKCLEWVARIRSKYNNYATYYADSVKDRFTISRDDSKSILYLQMNNLKTEDTAMYYCVRHGNFGNSYVSWFAYWGQGTLVTVSS | anti-CD3 VH23 |
| 55 | EVKLVESGGGLVKPGRSLRLSCAASGFTFNTYAMNWVRQAPGKCLEWVARIRSKYNNYATYYADSVKDRFTISRDDSKSILYLQMNSLKTEDTAMYYCVRHGNFGNSYVSWFAYWGQGTLVTVSS | anti-CD3 VH24 |
| 56 | EVKLVESGGGLVKPGRSLRLSCAASGFTFNTYAMNWVRQAPGKCLEWVARIRSKYNNYATYYADSVKDRFTISRDDSKSILYLQMNSLKTEDTAMYYCVRHGNFGNSYVSWFAYWGQGTLVTVSS | anti-CD3 VH25 |
| 57 | EVQLLESGGGLVQPGGSLRLSCAASGFTFSTYAMNWVRQAPGKCLEWVSRIRSKYNNYATYYADSVKGRFTISRDDSKNTLYLQMNSLRAEDTAVYYCVRHGNFGNSYVSWFAYWGQGTLVTVSS | anti-CD3 VH26 |
| 58 | EVQLVESGGGLVQPGGSLRLSCAASGFTFSTYAMSWVRQAPGKCLEWVGRIRSKYNNYATYYADSVKGRFTISRDDSKNTLYLQMNSLRAEDTAVYYCVRHGNFGDSYVSWFAYWGQGTLVTVSS | anti-CD3 VH27 |
| 59 | EVQLVESGGGLVQPGGSLKLSCAASGFTFNKYAMNWVRQAPGKCLEWVARIRSKYNNYATYYADSVKDRFTISRDDSKNTAYLQMNNLKTEDTAVYYCVRHGNFGNSYISYWAYWGQGTLVTVS | anti-CD3 VH28 |
| 60 | EVQLVESGGGLVQPGGSLRLSCAASGFTFNTYAMNWVRQAPGKCLEWVARIRSKYNNYATYYADSVKGRFTISRDDSKNTLYLQMNSLRAEDTAVYYCVRHGNFGNSYVSWFAYWGQGTTVTVSS | anti-CD3 VH29 |
| 61 | EVQLVESGGGLVQPGGSLRLSCAASGFTFNTYAMNWVRQAPGKCLEWVARIRSKYNNYATYYADSVKGRFTISRDDSKNTLYLQMNSLRAEDTAVYYCVRHGNFGNSYVSYFAYWGQGTTVTVSS | anti-CD3 VH30 |
| 62 | EVQLVESGGGLVQPKGSLKLSCAASGFTFNTYAMNWVRQAPGKCLEWVARIRSKYNNYATYYADSVKGRFTISRDDSQSILYLQMNNLKTEDTAMYYCVRHGNFGNSYVSWFAYWGQGTLVTVSS | anti-CD3 VH31 |
| 63 | QAVVTQESALTTSPGETVTLTCRSSTGAVTTSNYANWVQEKPDHLFTGLIGGTNKRAPGVPARFSGSLIGDKAALTITGAQTEDEAIYFCALWYSNLWVFGGGTKLTVL | anti-CD3 VL1 |
| 64 | QAVVTQEPSLTVSPGGTVTLTCGSSTGAVTTSNYANWVQQKPGKSPRGLIGGTNKRAPGVPARFSGSLLGGKAALTISGAQPEDEADYYCALWYSNHWVFGCGTKLEIK | anti-CD3 VL2 |
| 65 | QAVVTQEPSLTVSPGGTVTLTCRSSTGAVTTSNYANWVQQKPGQAPRGLIGGTNKRAPWTPARFSGSLLGGKAALTITGAQAEDEADYYCALWYSNLWVFGGGTKLTVL | anti-CD3 VL3 |

-continued

SEQUENCE TABLE

| SEQ ID NO | SEQUENCE | DESCRIPTION |
| --- | --- | --- |
| 66 | QAVVTQEPSFSVSPGGTVTLTCRSSTGAVTTSNYANWVQQTPGQAFRGLIGG<br>TNKRAPGVPARFSGSLIGDKAALTITGAQADDESIYFCALWYSNLWVFGGGT<br>KLTVL | anti-CD3 VL4 |
| 67 | QAVVTQEPSFSVSPGGTVTLTCRSSTGAVTTSNYANWVQQTPGQAFRGLIGG<br>TNKRAPGVPARFSGSILGNKAALTITGAQADDESIYFCALWYSNLWVFGGGT<br>KLTVL | anti-CD3 VL5 |
| 68 | QAVVTQEPSFSVSPGGTVTLTCRSSTGAVTTSNYANWVQQTPGQAFRGLIGG<br>TNKRAPGVPARFSGSILGNKAALTITGAQADDESDYYCALWYSNLWVFGGG<br>TKLTVL | anti-CD3 VL6 |
| 69 | QAVVTQEPSLTVSPGGTVTLTCSSTGAVTTSNYANWVQEKPGQAFRGLIGG<br>TNKRAPGTPARFSGSLLGGKAALTLSGAQPEDEAEYYCALWYSNLWVFGGG<br>TKLTVL | anti-CD3 VL7 |
| 70 | QTVVTQEPSLTVSPGGTVTLTCSSTGAVTSGNYPNWVQQKPGQAPRGLIGG<br>TKFLAPGTPARFSGSLLGGKAALTLSGVQPEDEAEYYCVLWYSNRWVFGGG<br>TKLTVL | anti-CD3 VL8 |
| 71 | QAVVTQEPSLTVSPGGTVTLTCSSTGAVTTSNYANWVQQKPGQAPRGLIGG<br>TNKRAPGVPARFSGSLLGGKAALTISGAQPEDEADYYCALWYSNHWVFGGG<br>TKLEIK | anti-CD3 VL9 |
| 72 | QAVVTQEPSLTVSPGGTVTLTCSSTGAVTTSNYANWVQQKPGQAPRGLIGG<br>TNKRAPGVPARFSGSLLGGKAALTISGAQPEDEADYYCALWYSNHWVFGCG<br>TKLEIK | anti-CD3 VL10 |
| 73 | QAVVTQEPSLTVSPGGTVTLTCSSTGAVTTSNYANWVQQKPGQCFRGLIGG<br>TNKRAPGVPARFSGSLLGGKAALTISGAQPEDEADYYCALWYSNHWVFGEG<br>TKLEIK | anti-CD3 VL11 |
| 74 | QAVVTQESALTTSPGETVTLTCRSSTGAVTTSNYANWVQEKPDHLFTGLIGG<br>TNKRAPGVPARFSGSLIGDKAALTITGAQTEDEAIYFCALWYSNLWVFGCGT<br>KLTVL | anti-CD3 VL12 |
| 75 | QAVVTQEPSLTVSPGGTVTLTCSSTGAVTTSNYANWVQQKPGKSPRGLIGG<br>TNKRAPGVPARFSGSLLGGKAALTISGAQPEDEADYYCALWYSNHWVFGGG<br>TKLEIK | anti-CD3 VL13 |
| 76 | QAVVTQEPSLTVSPGGTVTLTCRSSTGAVTTSNYANWVQQKPGQAPRGLIGG<br>TNKRAPWTPARFSGSLLGGKAALTITGAQAEDEADYYCALWYSNLWVFGC<br>GTKLTVL | anti-CD3 VL14 |
| 77 | QAVVTQEPSFSVSPGGTVTLTCRSSTGAVTTSNYANWVQQTPGQAFRGLIGG<br>TNKRAPGVPARFSGSLIGDKAALTITGAQADDESIYFCALWYSNLWVFGGGT<br>KLTVL | anti-CD3 VL15 |
| 78 | QAVVTQEPSFSVSPGGTVTLTCRSSTGAVTTSNYANWVQQTPGQAFRGLIGG<br>TNKRAPGVPARFSGSILGNKAALTITGAQADDESIYFCALWYSNLWVFGCGT<br>KLTVL | anti-CD3 VL16 |
| 79 | QAVVTQEPSFSVSPGGTVTLTCRSSTGAVTTSNYANWVQQTPGQAFRGLIGG<br>TNKRAPGVPARFSGSILGNKAALTITGAQADDESDYYCALWYSNLWVFGCG<br>TKLTVL | anti-CD3 VL17 |
| 80 | QAVVTQEPSLTVSPGGTVTLTCSSTGAVTTSNYANWVQEKPGQAFRGLIGG<br>TNKRAPGTPARFSGSLLGGKAALTLSGAQPEDEAEYYCALWYSNLWVFGCG<br>TKLTVL | anti-CD3 VL18 |
| 81 | QTVVTQEPSLTVSPGGTVTLTCSSTGAVTSGNYPNWVQQKPGQAPRGLIGG<br>TKFLAPGTPARFSGSLLGGKAALTLSGVQPEDEAEYYCVLWYSNRWVFGCG<br>TKLTVL | anti-CD3 VL19 |
| 82 | DKTHTCPPCPAPELLGGPSVFLFPPKPKDTLMISRTPEVTCVVVDVSHEDPEV<br>KFNWYVDGVEVHNAKTKPREEQYNSTYRVVSVLTVLHQDWLNGKEYKCK<br>VSNKALPAPIEKTISKAKGQPREPQVYTLPPCRDELTKNQVSLWCLVKGFYPS<br>DIAVEWESNGQPENNYKTTPPVLDSDGSFFLYSKLTVDKSRWQQGNVFSCSV<br>MHEALHNHYTQKSLSLSPT | Knob Fc |
| 83 | DKTHTCPPCPAPELLGGPSVFLFPPKPKDTLMRSRTPEVTCVVVDVSHEDPEV<br>KFNWYVDGVEVHNAKTKPREEQYNSTYRVVSVLTVLHQDWLNGKEYKCK<br>VSNKALPAPIEKTISKAKGQPREPQVCTLPPSRDELTKNQVSLSCAVKGFYPS | Hole Fc |

| SEQ ID NO | SEQUENCE | DESCRIPTION |
|---|---|---|
|  | DIAVEWESNGQPENNYKTTPPVLDSDGSFFLVSKLTVDKSRWQQGNVFSCSV MHEALHNHYTQKSLSLSPT | |
| 84 | DKTHTCPPCPAPGGPSVFLFPPKPKDTLMISRTPEVTCVVVDVSHEDPEVKFN WYVDGVEVHNAKTKPREEQYNSTYRVVSVLTVLHQDWLNGKEYKCKVSN KALPAPIEKTISKAKGQPREPQVYTLPPCRDELTKNQVSLWCLVKGFYPSDIA VEWESNGQPENNYKTTPPVLDSDGSFFLYSKLTVDKSRWQQGNVFSCSVMH EALHNHYTQKSLSLSPT | Knob Fc |
| 85 | DKTHTCPPCPAPGGPSVFLFPPKPKDTLMRSRTPEVTCVVVDVSHEDPEVKFN WYVDGVEVHNAKTKPREEQYNSTYRVVSVLTVLHQDWLNGKEYKCKVSN KALPAPIEKTISKAKGQPREPQVCTLPPSRDELTKNQVSLSCAVKGFYPSDIAV EWESNGQPENNYKTTPPVLDSDGSFFLVSKLTVDKSRWQQGNVFSCSVMHE ALHNHYTQKSLSLSPT | Hole Fc |
| 86 | DKTHTCPPCPAPELLGGPSVFLFPPKPKDTLMISRTPEVTCVVVDVSHEDPEV KFNWYVDGVEVHNAKTKPREEQYNSTYRVVSVLTVLHQDWLNGKEYKCK VSNKALPAPIEKTISKAKGQPREPQVYTLPPCRDELTKNQVSLWCLVKGFYPS DIAVEWESNGQPENNYKTTPPVLDSDGSFFLYSKLTVDKSRWQQGNVFSCSV MHEALHNHYTQKSLSLSPG | Knob Fc |
| 87 | DKTHTCPPCPAPELLGGPSVFLFPPKPKDTLMRSRTPEVTCVVVDVSHEDPEV KFNWYVDGVEVHNAKTKPREEQYNSTYRVVSVLTVLHQDWLNGKEYKCK VSNKALPAPIEKTISKAKGQPREPQVCTLPPSRDELTKNQVSLSCAVKGFYPS DIAVEWESNGQPENNYKTTPPVLDSDGSFFLVSKLTVDKSRWQQGNVFSCSV MHEALHNHYTQKSLSLSPG | Hole Fc |
| 88 | DKTHTCPPCPAPGGPSVFLFPPKPKDTLMISRTPEVTCVVVDVSHEDPEVKFN WYVDGVEVHNAKTKPREEQYNSTYRVVSVLTVLHQDWLNGKEYKCKVSN KALPAPIEKTISKAKGQPREPQVYTLPPCRDELTKNQVSLWCLVKGFYPSDIA VEWESNGQPENNYKTTPPVLDSDGSFFLYSKLTVDKSRWQQGNVFSCSVMH EALHNHYTQKSLSLSPG | Knob Fc |
| 89 | DKTHTCPPCPAPGGPSVFLFPPKPKDTLMRSRTPEVTCVVVDVSHEDPEVKFN WYVDGVEVHNAKTKPREEQYNSTYRVVSVLTVLHQDWLNGKEYKCKVSN KALPAPIEKTISKAKGQPREPQVCTLPPSRDELTKNQVSLSCAVKGFYPSDIAV EWESNGQPENNYKTTPPVLDSDGSFFLVSKLTVDKSRWQQGNVFSCSVMHE ALHNHYTQKSLSLSPG | Hole Fc |
| 90 | DKTHTCPPCPAPELLGGPSVFLFPPKPKDTLMISRTPEVTCVVVDVSHEDPEV KFNWYVDGVEVHNAKTKPREEQYNSTYRVVSVLTVLHQDWLNGKEYKCK VSNKALPAPIEKTISKAKGQPREPQVCTLPPSRDELTKNQVSLSCAVKGFYPS DIAVEWESNGQPENNYKTTPPVLDSDGSFFLVSKLTVDKSRWQQGNVFSCSV MHEALHNRYTQKSLSLSPT | Hole Fc |
| 91 | DKTHTCPPCPAPGGPSVFLFPPKPKDTLMISRTPEVTCVVVDVSHEDPEVKFN WYVDGVEVHNAKTKPREEQYNSTYRVVSVLTVLHQDWLNGKEYKCKVSN KALPAPIEKTISKAKGQPREPQVCTLPPSRDELTKNQVSLSCAVKGFYPSDIAV EWESNGQPENNYKTTPPVLDSDGSFFLVSKLTVDKSRWQQGNVFSCSVMHE ALHNRYTQKSLSLSPT | Hole Fc |
| 92 | DKTHTCPPCPAPELLGGPSVFLFPPKPKDTLMISRTPEVTCVVVDVSHEDPEV KFNWYVDGVEVHNAKTKPREEQYNSTYRVVSVLTVLHQDWLNGKEYKCK VSNKALPAPIEKTISKAKGQPREPQVCTLPPSRDELTKNQVSLSCAVKGFYPS DIAVEWESNGQPENNYKTTPPVLDSDGSFFLVSKLTVDKSRWQQGNVFSCSV MHEALHNRYTQKSLSLSPG | Hole Fc |
| 93 | DKTHTCPPCPAPGGPSVFLFPPKPKDTLMISRTPEVTCVVVDVSHEDPEVKFN WYVDGVEVHNAKTKPREEQYNSTYRVVSVLTVLHQDWLNGKEYKCKVSN KALPAPIEKTISKAKGQPREPQVCTLPPSRDELTKNQVSLSCAVKGFYPSDIAV EWESNGQPENNYKTTPPVLDSDGSFFLVSKLTVDKSRWQQGNVFSCSVMHE ALHNRYTQKSLSLSPG | Hole Fc |
| 94 | DKTHTCPPCPAPELLGGPSVFLFPPKPKDTLYISRTPEVTCVVVDVSHEDPEVK FNWYVDGVEVHNAKTKPREEQYNSTYRVVSVLTVLHQDWLNGKEYKCKVS NKALPAPIEKTISKAKGQPREPQVYTLPPCRDELTKNQVSLWCLVKGFYPSDI AVEWESNGQPENNYKTTPPVLDSDGSFFLYSKLTVDKSRWQQGNVFSCSVV HEALHNHYTQKSLSLSPT | Knob Fc |
| 95 | DKTHTCPPCPAPGGPSVFLFPPKPKDTLYISRTPEVTCVVVDVSHEDPEVKFN WYVDGVEVHNAKTKPREEQYNSTYRVVSVLTVLHQDWLNGKEYKCKVSN KALPAPIEKTISKAKGQPREPQVYTLPPCRDELTKNQVSLWCLVKGFYPSDIA VEWESNGQPENNYKTTPPVLDSDGSFFLYSKLTVDKSRWQQGNVFSCSVVH EALHNHYTQKSLSLSPT | Knob Fc |

SEQUENCE TABLE

| SEQ ID NO | SEQUENCE | DESCRIPTION |
|---|---|---|
| 96 | DKTHTCPPCPAPELLGGPSVFLFPPKPKDTLYISRTPEVTCVVVDVSHEDPEVK FNWYVDGVEVHNAKTKPREEQYNSTYRVVSVLTVLHQDWLNGKEYKCKVS NKALPAPIEKTISKAKGQPREPQVYTLPPCRDELTKNQVSLWCLVKGFYPSDI AVEWESNGQPENNYKTTPPVLDSDGSFFLYSKLTVDKSRWQQGNVFSCSVV HEALHNHYTQKSLSLSPG | Knob Fc |
| 97 | DKTHTCPPCPAPGGPSVFLFPPKPKDTLYISRTPEVTCVVVDVSHEDPEVKFN WYVDGVEVHNAKTKPREEQYNSTYRVVSVLTVLHQDWLNGKEYKCKVSN KALPAPIEKTISKAKGQPREPQVYTLPPCRDELTKNQVSLWCLVKGFYPSDIA VEWESNGQPENNYKTTPPVLDSDGSFFLYSKLTVDKSRWQQGNVFSCSVVH EALHNHYTQKSLSLSPG | Knob Fc |
| 98 | DKTHTCPPCPAPELLGGPSVFLFPPKPKDTLYISRTPEVTCVVVDVSHEDPEVK FNWYVDGVEVHNAKTKPREEQYNSTYRVVSVLTVLHQDWLNGKEYKCKVS NKALPAPIEKTISKAKGQPREPQVCTLPPSRDELTKNQVSLSCAVKGFYPSDIA VEWESNGQPENNYKTTPPVLDSDGSFFLVSKLTVDKSRWQQGNVFSCSVVH EALHNRYTQKSLSLSPT | Hole Fc |
| 99 | DKTHTCPPCPAPGGPSVFLFPPKPKDTLYISRTPEVTCVVVDVSHEDPEVKFN WYVDGVEVHNAKTKPREEQYNSTYRVVSVLTVLHQDWLNGKEYKCKVSN KALPAPIEKTISKAKGQPREPQVCTLPPSRDELTKNQVSLSCAVKGFYPSDIAV EWESNGQPENNYKTTPPVLDSDGSFFLVSKLTVDKSRWQQGNVFSCSVVHE ALHNRYTQKSLSLSPT | Hole Fc |
| 100 | DKTHTCPPCPAPELLGGPSVFLFPPKPKDTLYISRTPEVTCVVVDVSHEDPEVK FNWYVDGVEVHNAKTKPREEQYNSTYRVVSVLTVLHQDWLNGKEYKCKVS NKALPAPIEKTISKAKGQPREPQVCTLPPSRDELTKNQVSLSCAVKGFYPSDIA VEWESNGQPENNYKTTPPVLDSDGSFFLVSKLTVDKSRWQQGNVFSCSVVH EALHNRYTQKSLSLSPG | Hole Fc |
| 101 | DKTHTCPPCPAPGGPSVFLFPPKPKDTLYISRTPEVTCVVVDVSHEDPEVKFN WYVDGVEVHNAKTKPREEQYNSTYRVVSVLTVLHQDWLNGKEYKCKVSN KALPAPIEKTISKAKGQPREPQVCTLPPSRDELTKNQVSLSCAVKGFYPSDIAV EWESNGQPENNYKTTPPVLDSDGSFFLVSKLTVDKSRWQQGNVFSCSVVHE ALHNRYTQKSLSLSPG | Hole Fc |
| 102 | PGGGG | Peptide Linker |
| 103 | GGGG | Peptide Linker |
| 104 | GPAGLGLEPDGSRQARVG | Linker |
| 105 | GGSGGGGIEPDIGGSGGS | Linker |
| 106 | GGSGGGGLEADTGGSGGS | Linker |
| 107 | GSIEPDIGS | Linker |
| 108 | GSLEADTGS | Linker |
| 109 | GGSGGGGIEPDGGGSGGS | Linker |
| 110 | GGSGGGGIEPDVGGSGGS | Linker |
| 111 | GGSGGGGIEPDSGGSGGS | Linker |
| 112 | GGSGGGGIEPDTGGSGGS | Linker |
| 113 | GGGSLEPDGSGS | Linker |
| 114 | GPAGLGLEADGSRQARVG | Linker |
| 115 | GGEGGGGSGGSGGGS | Linker |
| 116 | GSSAGSEAGGSGQAGVGS | Linker |
| 117 | GGSGGGGLEAEGSGGGGS | Linker |
| 118 | GGSGGGGIEPDPGGSGGS | Linker |
| 119 | GGGGGSGGGGSGGGGS | Linker |

-continued

SEQUENCE TABLE

| SEQ ID NO | SEQUENCE | DESCRIPTION |
|---|---|---|
| 120 | QLQLQESGGGLVQPGGSLRLSCAASGFTLDNYAIGWFRQAPGKEREGVSCIS SSDGSTYYADSVKGRFTISRNNAKGTVYLLMNSLKPEDTAVYYCATELVPAC TYSNGRGPLDGMDYWGKGTQVTVKP | FR alpha sdAb |
| 121 | EVQLLESGGGEVQPGGSLRLSCAASGSIFSIDATAWYRQAPGKQRELVAIITSS GSTNYPESVKGRFTISRDNAKNTVYLQMSSLRAEDTAVYYCNAITRYGGSTY DFWGQGTLVTVKP | FR alpha sdAb |
| 122 | EVQPGGSLRLSCAASETFGVVFTLGWYRQAPGKGREFVARVTGTDTVDYAE SVKGRFTISSDFARNTVYLQMNSLRAEDTAVYYCNTGAYWGQGTLVTVKP | FR alpha sdAb |
| 123 | EVQLVESGGGLVQPGGSLRLSCAASGFILDYYAIGWFRQAPGKEREGVLCID ASDDITYYADSVKGRFTISRDNAKNTVYLQMNSLKPEDTGVYYCATPIGLSSS CLLEYDYDYWGQGTLVTVKP | cMET sdAb |
| 124 | EVQLVESGGGLVQPGGSLRLSCAASGFTFSSFGMHWVRQAPGKGLEWVAYI SSDSSAIYYADTVKGRFTISRDNAKNSLYLQMNSLRDEDTAVYYCGRGRENI YYGSRLDYWGQGTTVTVSSSGGGGSGGGGSGGGGSDIQLTQSPSFLSASVGD RVTITCKASQNVDTNVAWYQQKPGKAPKALIYSASYRYSGVPSRFSGSGSGT DFTLTISSLQPEDFATYYCQQYNNYPFTFGQGTKLEIK | B7H3 scFv |
| 125 | QVQLVQSGAEVKKPGSSVKVSCKASGYAFSYSWINWVRQAPGQGLEWMGR IFPGDGDTDYNGKFKGRVTITADKSTSTAYMELSSLRSEDTAVYYCARNVFD GYWLVYWGQGTLVTVSGSGGGGSGGGGTGGGGSDIVMTQTPLSLPVTPGEP ASISCRSSKSLLHSNGITYLYWYLQKPGQSPQLLIYQMSNLVSGVPDRFSGSG SGTDFTLKISRVEAEDVGVYYCAQNLELPYTFGGGTKVEIK | CD20 scFv |
| 126 | QVQLQESGPGLVKPSETLSLTCTVSGGSISSYYWSWIRQPPGKGLEWIGYVYY SGTTNYNPSLKSRVTISVDTSKNQFSLKLSSVTAADTAVYYCASIAVTGFYFD YWGQGTLVTVSSGGGGSGGGGSGGGGSEIVLTQSPGTLSLSPGERVTLSCRA SQRVNNNYLAWYQQRPGQAPRLLIYGASSRATGIPDRFSGSGSGTDFTLTISR LEPEDFAVYYCQQYDRSPLTFGGGTKLEIK | DLL3 scFv |
| 127 | EVQLVESGGGLVQPGGSLRLSCAASGFTFSSFGMHWVRQAPGKGLEWVAYI SSDSSAIYYADTVKGRFTISRDNAKNSLYLQMNSLRDEDTAVYYCGRGRENI YYGSRLDYWGQGTTVTVSSASTKGPSVFPLAPSSKSTSGGTAALGCLVKDYF PEPVTVSWNSGALTSGVHFPAVLQSSGLYSLSSVVTVPSSSLGTQTYICNVN HKPSNTKVDKKVEPKSC | B7H3 Fd |
| 128 | DIQLTQSPSFLSASVGDRVTITCKASQNVDTNVAWYQQKPGKAPKALIYSAS YRYSGVPSRFSGSGSGTDFTLTISSLQPEDFATYYCQQYNNYPFTFGQGTKLEI KRTVAAPSVFIFPPSDEQLKSGTASVVCLLNNFYPREAKVQWKVDNALQSGN SQESVTEQDSKDSTYSLSSTLTLSKADYEKHKVYACEVTHQGLSSPVTKSFNR GEC | B7H3 LC |
| 129 | EVQLVESGGGLVQPKGSLKLSCAASGFTFNTYAMNWVRQAPGKGLEWVARI RSKSNNYATYYADSVKDRFTISRDDSQSMLYLQMNNLKTEDTAMYYCVRQ WDYDVRAMNYWGQGTSVTVSSASTKGPSVFPLAPSSKSTSGGTAALGCLVK DYFPEPVTVSWNSGALTSGVHTFPAVLQSSGLYSLSSVVTVPSSSLGTQTYIC NVNHKPSNTKVDKKVEPKSC | 5T4 Fd |
| 130 | DIVMTQSHIFMSTSVGDRVSITCKASQDVDTAVAWYQQKPGQSPKLLIYWAS TRLTGVPDRFTGSGSGTDFTLTISNVQSEDLADYFCQQYSSYPYTFGGGTKLE IKRTVAAPSVFIFPPSDEQLKSGTASVVCLLNNFYPREAKVQWKVDNALQSG NSQESVTEQDSKDSTYSLSSTLTLSKADYEKHKVYACEVTHQGLSSPVTKSF NRGEC | 5T4 LC |
| 131 | QVQLQESGPGLVKPSQTLSLTCTVSGGSISSFNYYWSWIRHHPGKGLEWIGYI YYSGSTYSNPSLKSRVTISVDTSKNQFSLTLSSVTAADTAVYYCARGYNWNY FDYWGQGTLVTVSSASTKGPSVFPLAPSSKSTSGGTAALGCLVKDYFPEPVT VSWNSGALTSGVHTFPAVLQSSGLYSLSSVVTVPSSSLGTQTYICNVNHKPSN TKVDKKVEPKSC | gpNMB Fd |
| 132 | EIVMTQSPATLSVSPGERATLSCRASQSVDNNLVWYQQKPGQAPRLLIYGAS TRATGIPARFSGSGSGTEFTLTISSLQSEDFAVYYCQQYNNWPPWTFGQGTKV EIKRTVAAPSVFIFPPSDEQLKSGTASVVCLLNNFYPREAKVQWKVDNALQS GNSQESVTEQDSKDSTYSLSSTLTLSKADYEKHKVYACEVTHQGLSSPVTKS FNRGEC | gpNMB LC |
| 133 | QIQLVQSGPELKKPGETVKISCKASGYTFTNYGMNWVKQAPGKGLKWMAW INTYTGEPTYADDFKGRFAFSLETSASTASLQIINLKNEDTATYFCARIGDSSPS DYWGQGTTLTVSSSASTKGPSVFPLAPSSKSTSGGTAALGCLVKDYFPEPVT VSWNSGALTSGVHTFPAVLQSSGLYSLSSVVTVPSSSLGTQTYICNVNHKPSN TKVDKKVEPKSC | DLL3 Fd |

SEQUENCE TABLE

| SEQ ID NO | SEQUENCE | DESCRIPTION |
|---|---|---|
| 134 | SIVMTQTPKFLLVSAGDRVTITCKASQSVSNDVVWYQQKPGQSPKLLIYYAS NRYTGVPDRFAGSGYGTDFSFTISTVQAEDLAVYFCQQDYTSPWTFGGGTKL EIRRTVAAPSVFIFPPSDEQLKSGTASVVCLLNNFYPREAKVQWKVDNALQS GNSQESVTEQDSKDSTYSLSSTLTLSKADYEKHKVYACEVTHQGLSSPVTKS FNRGEC | DLL3 LC |
| 135 | GGGGGS | Peptide Linker |
| 136 | IEPDI | Linker |
| 137 | LEADT | Linker |
| 138 | IEPDG | Linker |
| 139 | IEPDV | Linker |
| 140 | IEPDS | Linker |
| 141 | IEPDT | Linker |
| 142 | LEPD | Linker |
| 143 | LEAE | Linker |
| 144 | IEPDP | Linker |
| 145 | QAVVTQEPSLTVSPGGTVTLTCRSSTGAVTTSNYANWVQQKPGQAPRGLIGG TNKRAPWTPARFSGSLLGGKAALTITGAQAEDEADYYCALWYSNLWVFGG GTKLTVLGGGGSGGGGEVQLVESGGGLVQPGGSLRLSCAASGFTFSSFGMH WVRQAPGKGLEWVAYISSDSSAIYYADTVKGRFTISRDNAKNSLYLQMNSL RDEDTAVYYCGRGRENIYYGSRLDYWGQGTTVTVSSGGCGGGKVAALKEK VAALKEKVAALKEKVAALKE | Second Polypeptide Chain of B7-H3 x CD3 Bispecific DART-A Diabody |
| 146 | DKTHTCPPCPAPEAAGGPSVFLFPPKPKDTLMISRTPEVTCVVVDVSHEDPEV KFNWYVDGVEVHNAKTKPREEQYNSTYRVVSVLTVLHQDWLNGKEYKCK VSNKALPAPIEKTISKAKGQPREPQVYTLPPSREEMTKNQVSLSCAVKGFYPS DIAVEWESNGQPENNYKTTPPVLDSDGSFFLVSKLTVDKSRWQQGNVFSCSV MHEALHNRYTQKSLSLSPGK | Third Polypeptide Chain of B7-H3 x CD3 Bispecific DART-A Diabody |
| 147 | GGSGGGGSGGGGSGGGGS | Linker |
| 148 | TGGSGGGGIEPDIGGSGGS | Linker |
| 149 | GGGGS | Linker |
| 150 | $X_1 X_2 X_3 X_4 X_5$ (P4 P3 P2 P1 ↓ P1')<br>X1 = I, L, Y, M, F, V, or A; (P4 = I, L, Y, M, F, V, or A)<br>X2 = A, G, S, V, E, D, Q, N, or Y; (P3 = A, G, S, V, E, D, Q, N, or Y)<br>X3 = H, P, A, V, G, S, or T; (P2 = H, P, A, V, G, S, or T)<br>X4 = D or E; (P1 = D or E)<br>X5 = I, L, Y, M, F, V, T, S, G or A (P1' = I, L, Y, M, F, V, T, S, G or A) | Linker consensus |
| 151 | X1 E X3 D X5 (P4 P3 P2 P1 ↓ P1')<br>X1= I or L; (P4 = I or L)<br>(P3 = E)<br>X3 = P or A; (P2 = P or A)<br>X5 = I, V, T, S, or G (P1' = I, V, T, S, or G) | Linker consensus |
| 152 | LEPDG | Linker |
| 153 | LEADG | Linker |
| 154 | $X_1QARX_5$ (P1QAR↓(A/V))<br>X1 = any amino acid; (P1 is any amino acid)<br>X5 = A or V | Linker consensus |
| 155 | $RQARX_5$(RQAR(A/V))<br>X5 = A or V | Linker consensus |
| 156 | RQARV | Linker |

-continued

SEQUENCE TABLE

| SEQ ID NO | SEQUENCE | DESCRIPTION |
|---|---|---|
| 157 | X1 X2 X3 X4 (P3 P2 P1 ↓ P1')<br>X1 = P, V or A; (P3 = P =, V or A)<br>X2 = Q or D; (P2 = Q or D)<br>X3 = A or N; (P1 = A or N)<br>X4 = L, I or M (P1' = L, I or M) | Linker consensus |
| 158 | PX2X3X4 (P3 P2 P1 ↓ P1')<br>(P3 = P)<br>X2 = Q or D; (P2 = Q or D)<br>X3 = A or N; (P1 is A or N)<br>X4 = L or I (P1' is L or I) | Linker consensus |
| 159 | GSGATNFSLLKQAGDVEENPGP | P2A |
| 160 | ATNFSLLKQAGDVEENPGP | P2A |
| 161 | QCTNYALLKLAGDVESNPGP | E2A |
| 162 | VKQTLNFDLLKLAGDVESNPGP | F2A |
| 163 | EGRGSLLTCGDVEENPGP | T2A |
| 164 | LEGGGEGRGSLLTCGDVEENPGPR | T2A |
| 165 | GGATCTGGAGCAACAAACTTCTCACTACTCAAACAAGCAGGTGACGTGGA GGAGAATCCCGGACCC | P2A DNA |
| 166 | GSPAGLEADGSRQARVGS | Linker |
| 167 | EVQLVESGGGL VQPKGSLKLS CAASGFTFNT YAMNWVRQAP GKGLEWVARI RSKSNNYATY YADSVKDRFT ISRDDSQSML YLQMNNLKTE DTAMYXCVRQ WDYDVRAMNY WGQGTSVTVS S | anti-5T4 VH |
| 168 | DIVMTQSHIF MSTSVGDRVS ITCKASQDVD TAVAWYQQKP GQSPKLLIYW ASTRLTGVPD RFTGSGSGTD FTLTISNVQS EDLADYFCQQ YSSYPYTFGG GTKLEIK | anti-5T4 VL |
| 169 | DIQLTQSPSF LSASVGDRVT ITCKASQNVD TNVAWYQQKP GKAPKALIYS ASYRYSGVPS RFSGSGSGTD FTLTISSLQP EDFATYYCQQ YNNYPFTFGQ GTKLEIKGGG SGGGGEVQLV ESGGGLVQPG GSLRLSCAAS GFTFSTYAMN WVRQAPGKGL EWVGRIRSKY NNYATYYADS VKDRFTISRD DSKNSLYLQM NSLKTEDTAV YYCVRHGNFG NSYVSWFAYW GQGTLVTVSS GGCGGGEVAA LEKEVAALEK EVAALEKEVA ALEKGGGDKT HTCPPCPAPE AAGGPSVFLF PPKPKDTLMI SRTPEVTCVV VDVSHEDPEV KFNWYVDGVE VHNAKTKPRE EQYNSTYRVV SVLTVLHQDW LNGKEYKCKV SNKALPAPIE KTISKAKGQP REPQVYTLPP SREEMTKNQV SLWCLVKGFY PSDIAVEWES NGQPENNYKT TPPVLDSDGS FFLYSKLTVD KSRWQQGNVF SCSVMHEALH NHYTQKSLSL SPGK | First Polypeptide Chain of B7-H3 x CD3 Bispecific DART-A Diabody |
| 170 | GGGGSGGGGSGGGGS | Linker |
| 171 | GGS(GGS)n<br>wherein n is 0 to 10 | Linker |
| 172 | (GGGGGS)n<br>wherein n is 1 to 4 | Linker |
| 173 | (GGGGS)n<br>wherein n is 1 to 5 | Linker |
| 174 | Gly$_x$Xaa-Gly$_y$-Xaa-Gly$_z$<br>Xaa is independently selected from A, V, L, I, M, F, W, P, G, S, T, C, Y, N,Q, K, R, H, D, or E<br>x, y, and z are each integers in the range from 1-5 | Linker |
| 175 | Gly-Gly-Gly-Xaa-Gly-Gly-Gly-Xaa-Gly-Gly-Gly<br>Xaa is independently selected from A, V, L, I, M, F, W, P, G, S, T, C, Y, N,Q, K, R, H, D, or E | Linker |
| 176 | ATTTGSSPGPT | Linker |
| 177 | GGGGG-C-GGGGG | Linker |

SEQUENCE TABLE

| SEQ ID NO | SEQUENCE | DESCRIPTION |
|---|---|---|
| 178 | (EAAAK)n<br>n = 2-20 | Linker |
| 179 | AS-(AP)n-GT<br>n = 2-20 | Linker |
| 180 | AS-(EAAAK)n-GT<br>n = 2-20 | Linker |
| 181 | (GGGGA)n<br>n = 2-20 | Linker |
| 182 | (PGGGS)n<br>n = 2-20 | Linker |
| 183 | (AGGGS)n<br>n = 2-20 | Linker |
| 184 | GGS-(EGKSSGSGSESKST)n-GGS<br>n = 2-20 | Linker |
| 185 | (SSSSG)n<br>n = 1-9 | Linker |
| 186 | SSSASASSA | Linker |
| 187 | GSPGSPG | Linker |
| 188 | QVQLQESGPG LVKPSETLSL TCTVSGGSIS SYYWSWIRQP PGKGLEWIGY<br>VYYSGTTNYN PSLKSRVTIS VDTSKNQFSL KLSSVTAADT AVYYCASIAV<br>TGFYFDYWGQ GTLVTVSSGG GGSGGGGSGG GGSEIVLTQS PGTLSLSPGE<br>RVTLSCRASQ RVNNNYLAWY QQRPGQAPRL LIYGASSRAT GIPDRFSGSG<br>SGTDFTLTIS RLEPEDFAVY YCQQYDRSPL TFGGGTKLEI K | DLL3 scFv |
| 189 | QVQLVQSGAE VKKPGSSVKV SCKASGYAFS YSWINWVRQA<br>PGQGLEWMGR<br>IFPGDGDTDY NGKFKGRVTI TADKSTSTAY MELSSLRSED TAVYYCARNV<br>FDGYWLVYWG QGTLVTVSS | CD20 VH |
| 190 | DIVMTQTPLS LPVTPGEPAS ISCRSSKSLL HSNGITYLYW YLQKPGQSPQ<br>LLIYQMSNLV SGVPDRFSGS GSGTDFTLKI SRVEAEDVGV YYCAQNLELP<br>YTFGGGTKVE IKRTV | CD20 VL |

What is claimed is:

1. A multispecific polypeptide construct, the multispecific polypeptide construct comprising a first component comprising a heterodimeric immunoglobulin Fc region and a second component comprising a CD3-binding region wherein:

the first and second components are coupled by a first linker that is a polypeptide of 2-18 amino acids in length composed of at least 50% Glycine residues, wherein the Fc region is amino-terminal to the CD3-binding region;

the CD3-binding region is an anti-CD3 disulfide stabilized Fv antibody fragment (dsFv) comprising a variable heavy chain (VH) and a variable light chain (VL), wherein the VH has the amino acid sequence of SEQ ID NO: 44 or a sequence that exhibits at least 90% sequence identity to SEQ ID NO: 44, and the VL has the amino acid sequence of SEQ ID NO: 72 or a sequence that exhibits at least 90% sequence identity to SEQ ID NO: 72, wherein the VH and VL are each linked to opposite polypeptides of the heterodimeric Fc by the first linker;

each of the Fc polypeptides of the heterodimeric Fc region comprises a knob-into-hole modification or a charge mutation to increase electrostatic complementarity of the Fc polypeptides;

the first component comprises at least one antigen binding domain that is a single domain antibody (sdAb) and binds a tumor associated antigen (TAA), wherein each of the at least one antigen binding domain of the first component is linked amino-terminal to the Fc region by a second linker that is a polypeptide of 2-6 amino acids in length composed of at least 50% Glycine residues; and the second component further comprises at least one antigen binding domain that is a sdAb and binds to the same TAA as the first component, wherein each of the at least one antigen binding domain of the second component is linked carboxy-terminal to the CD3-binding region by a third linker that is a polypeptide of 2-6 amino acids in length composed of at least 50% Glycine residues, wherein (i) each of the sdAbs is a camelid $V_HH$ or a humanized camelid $V_HH$; and (ii) the CD3-binding region is not able to bind cell surface CD3 as determined by flow cytometry, unless the at least one antigen binding domain is bound to its TAA.

2. The multispecific polypeptide construct of claim 1, wherein the TAA is selected from the group consisting of 5T4, B7H3, Carbonic anhydrase 9, CD3, CD20, CD38, CD47, CEACAM5 (CEA), cMet, CXCL10, CXCR4, DLL3, EGFR, Folate receptor alpha (FRα), HER2, HGF, IL-6R, IL-23, Mesothelin, MUC1, PD-1, PD-L1, PSMA, TAG-72, TIM-3, Tumor necrosis factor alpha (TNFα), VCAM-1, and VEGFR2.

3. The multispecific polypeptide construct of claim 1, wherein the TAA is selected from the group consisting of 5T4, B7H3, cMET, EGFR, and Folate receptor alpha (FRα).

4. The multispecific polypeptide construct of claim 1, wherein the TAA is 5T4.

5. The multispecific polypeptide construct of claim 1, wherein the TAA is B7H3.

6. The multispecific polypeptide construct of claim 1, wherein the TAA is EGFR.

7. The multispecific polypeptide construct of claim 1, wherein the TAA is Folate receptor alpha (FRα).

8. The multispecific polypeptide construct of claim 1, wherein the first linker, the second linker and the third linker independently comprise amino acid residues selected from the group consisting of Glycine (Gly), Serine (Ser), Alanine (Ala), and Threonine (Thr).

9. The multispecific polypeptide construct of claim 1, wherein the first linker, the second linker and the third linker independently comprise Glycine (Gly) and Serine (Ser) amino acid residues.

10. A pharmaceutical composition comprising the multispecific polypeptide construct of claim 1 and a pharmaceutically acceptable carrier.

\* \* \* \* \*

SEQUENCE LISTING

<160> NUMBER OF SEQ ID NOS: 190

<210> SEQ ID NO 1
<211> LENGTH: 218
<212> TYPE: PRT
<213> ORGANISM: Artificial Sequence
<220> FEATURE:
<223> OTHER INFORMATION: IgG1 Fc

<400> SEQUENCE: 1

```
Pro Ala Pro Glu Leu Leu Gly Gly Pro Ser Val Phe Leu Phe Pro Pro
1               5                   10                  15

Lys Pro Lys Asp Thr Leu Met Ile Ser Arg Thr Pro Glu Val Thr Cys
            20                  25                  30

Val Val Val Asp Val Ser His Glu Asp Pro Glu Val Lys Phe Asn Trp
        35                  40                  45

Tyr Val Asp Gly Val Glu Val His Asn Ala Lys Thr Lys Pro Arg Glu
    50                  55                  60

Glu Gln Tyr Asn Ser Thr Tyr Arg Val Val Ser Val Leu Thr Val Leu
```

```
                65                  70                  75                  80
His Gln Asp Trp Leu Asn Gly Lys Glu Tyr Lys Cys Lys Val Ser Asn
                    85                  90                  95

Lys Ala Leu Pro Ala Pro Ile Glu Lys Thr Ile Ser Lys Ala Lys Gly
                100                 105                 110

Gln Pro Arg Glu Pro Gln Val Tyr Thr Leu Pro Pro Ser Arg Asp Glu
                115                 120                 125

Leu Thr Lys Asn Gln Val Ser Leu Thr Cys Leu Val Lys Gly Phe Tyr
    130                 135                 140

Pro Ser Asp Ile Ala Val Glu Trp Glu Ser Asn Gly Gln Pro Glu Asn
145                 150                 155                 160

Asn Tyr Lys Thr Thr Pro Pro Val Leu Asp Ser Asp Gly Ser Phe Phe
                165                 170                 175

Leu Tyr Ser Lys Leu Thr Val Asp Lys Ser Arg Trp Gln Gln Gly Asn
                180                 185                 190

Val Phe Ser Cys Ser Val Met His Glu Ala Leu His Asn His Tyr Thr
                195                 200                 205

Gln Lys Ser Leu Ser Leu Ser Pro Gly Lys
    210                 215

<210> SEQ ID NO 2
<211> LENGTH: 215
<212> TYPE: PRT
<213> ORGANISM: Artificial Sequence
<220> FEATURE:
<223> OTHER INFORMATION: IgG2 Fc

<400> SEQUENCE: 2

Pro Ala Pro Gly Gly Pro Ser Val Phe Leu Phe Pro Pro Lys Pro Lys
1               5                   10                  15

Asp Thr Leu Met Ile Ser Arg Thr Pro Glu Val Thr Cys Val Val Val
                20                  25                  30

Asp Val Ser His Glu Asp Pro Glu Val Lys Phe Asn Trp Tyr Val Asp
            35                  40                  45

Gly Val Glu Val His Asn Ala Lys Thr Lys Pro Arg Glu Glu Gln Tyr
    50                  55                  60

Asn Ser Thr Tyr Arg Val Val Ser Val Leu Thr Val Leu His Gln Asp
65                  70                  75                  80

Trp Leu Asn Gly Lys Glu Tyr Lys Cys Lys Val Ser Asn Lys Ala Leu
                85                  90                  95

Pro Ala Pro Ile Glu Lys Thr Ile Ser Lys Ala Lys Gly Gln Pro Arg
                100                 105                 110

Glu Pro Gln Val Tyr Thr Leu Pro Pro Ser Arg Asp Glu Leu Thr Lys
                115                 120                 125

Asn Gln Val Ser Leu Thr Cys Leu Val Lys Gly Phe Tyr Pro Ser Asp
    130                 135                 140

Ile Ala Val Glu Trp Glu Ser Asn Gly Gln Pro Glu Asn Asn Tyr Lys
145                 150                 155                 160

Thr Thr Pro Pro Val Leu Asp Ser Asp Gly Ser Phe Phe Leu Tyr Ser
                165                 170                 175

Lys Leu Thr Val Asp Lys Ser Arg Trp Gln Gln Gly Asn Val Phe Ser
                180                 185                 190

Cys Ser Val Met His Glu Ala Leu His Asn His Tyr Thr Gln Lys Ser
                195                 200                 205

Leu Ser Leu Ser Pro Gly Lys
```

<210> SEQ ID NO 3
<211> LENGTH: 217
<212> TYPE: PRT
<213> ORGANISM: Artificial Sequence
<220> FEATURE:
<223> OTHER INFORMATION: IgG2 Fc

<400> SEQUENCE: 3

Pro Ala Pro Pro Val Ala Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Gln Phe Asn Trp Tyr
        35                  40                  45

Val Asp Gly Val Glu Val His Asn Ala Lys Thr Lys Pro Arg Glu Glu
    50                  55                  60

Gln Phe Asn Ser Thr Phe Arg Val Val Ser Val Leu Thr Val Val His
65                  70                  75                  80

Gln Asp Trp Leu Asn Gly Lys Glu Tyr Lys Cys Lys Val Ser Asn Lys
                85                  90                  95

Gly Leu Pro Ala Pro Ile Glu Lys Thr Ile Ser Lys Thr Lys Gly Gln
            100                 105                 110

Pro Arg Glu Pro Gln Val Tyr Thr Leu Pro Pro Ser Arg Glu Glu Met
        115                 120                 125

Thr Lys Asn Gln Val Ser Leu Thr Cys Leu Val Lys Gly Phe Tyr Pro
    130                 135                 140

Ser Asp Ile Ser Val Glu Trp Glu Ser Asn Gly Gln Pro Glu Asn Asn
145                 150                 155                 160

Tyr Lys Thr Thr Pro Pro Met Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215

<210> SEQ ID NO 4
<211> LENGTH: 218
<212> TYPE: PRT
<213> ORGANISM: Artificial Sequence
<220> FEATURE:
<223> OTHER INFORMATION: IgG3 Fc

<400> SEQUENCE: 4

Pro Ala Pro Glu Leu Leu Gly Gly Pro Ser Val Phe Leu Phe Pro Pro
1               5                   10                  15

Lys Pro Lys Asp Thr Leu Met Ile Ser Arg Thr Pro Glu Val Thr Cys
            20                  25                  30

Val Val Val Asp Val Ser His Glu Asp Pro Glu Val Gln Phe Lys Trp
        35                  40                  45

Tyr Val Asp Gly Val Glu Val His Asn Ala Lys Thr Lys Pro Arg Glu
    50                  55                  60

Glu Gln Tyr Asn Ser Thr Phe Arg Val Val Ser Val Leu Thr Val Leu
65                  70                  75                  80

```
His Gln Asp Trp Leu Asn Gly Lys Glu Tyr Lys Cys Lys Val Ser Asn
                85                  90                  95

Lys Ala Leu Pro Ala Pro Ile Glu Lys Thr Ile Ser Lys Thr Lys Gly
            100                 105                 110

Gln Pro Arg Glu Pro Gln Val Tyr Thr Leu Pro Pro Ser Arg Glu Glu
        115                 120                 125

Met Thr Lys Asn Gln Val Ser Leu Thr Cys Leu Val Lys Gly Phe Tyr
    130                 135                 140

Pro Ser Asp Ile Ala Val Glu Trp Glu Ser Gly Gln Pro Glu Asn
145                 150                 155                 160

Asn Tyr Asn Thr Thr Pro Pro Met Leu Asp Ser Asp Gly Ser Phe Phe
                165                 170                 175

Leu Tyr Ser Lys Leu Thr Val Asp Lys Ser Arg Trp Gln Gln Gly Asn
            180                 185                 190

Ile Phe Ser Cys Ser Val Met His Glu Ala Leu His Asn Arg Phe Thr
        195                 200                 205

Gln Lys Ser Leu Ser Leu Ser Pro Gly Lys
    210                 215
```

<210> SEQ ID NO 5
<211> LENGTH: 218
<212> TYPE: PRT
<213> ORGANISM: Artificial Sequence
<220> FEATURE:
<223> OTHER INFORMATION: IgG4 Fc

<400> SEQUENCE: 5

```
Pro Ala Pro Glu Phe Leu Gly Gly Pro Ser Val Phe Leu Phe Pro Pro
1               5                   10                  15

Lys Pro Lys Asp Thr Leu Met Ile Ser Arg Thr Pro Glu Val Thr Cys
            20                  25                  30

Val Val Val Asp Val Ser Gln Glu Asp Pro Glu Val Gln Phe Asn Trp
        35                  40                  45

Tyr Val Asp Gly Val Glu Val His Asn Ala Lys Thr Lys Pro Arg Glu
    50                  55                  60

Glu Gln Phe Asn Ser Thr Tyr Arg Val Val Ser Val Leu Thr Val Leu
65                  70                  75                  80

His Gln Asp Trp Leu Asn Gly Lys Glu Tyr Lys Cys Lys Val Ser Asn
                85                  90                  95

Lys Gly Leu Pro Ser Ser Ile Glu Lys Thr Ile Ser Lys Ala Lys Gly
            100                 105                 110

Gln Pro Arg Glu Pro Gln Val Tyr Thr Leu Pro Pro Ser Gln Glu Glu
        115                 120                 125

Met Thr Lys Asn Gln Val Ser Leu Thr Cys Leu Val Lys Gly Phe Tyr
    130                 135                 140

Pro Ser Asp Ile Ala Val Glu Trp Glu Ser Asn Gly Gln Pro Glu Asn
145                 150                 155                 160

Asn Tyr Lys Thr Thr Pro Pro Val Leu Asp Ser Asp Gly Ser Phe Phe
                165                 170                 175

Leu Tyr Ser Arg Leu Thr Val Asp Lys Ser Arg Trp Gln Glu Gly Asn
            180                 185                 190

Val Phe Ser Cys Ser Val Met His Glu Ala Leu His Asn His Tyr Thr
        195                 200                 205

Gln Lys Ser Leu Ser Leu Ser Leu Gly Lys
    210                 215
```

<210> SEQ ID NO 6
<211> LENGTH: 218
<212> TYPE: PRT
<213> ORGANISM: Artificial Sequence
<220> FEATURE:
<223> OTHER INFORMATION: IgG4 Fc

<400> SEQUENCE: 6

```
Pro Ala Pro Glu Leu Leu Gly Gly Pro Ser Val Phe Leu Phe Pro Pro
1               5                   10                  15

Lys Pro Lys Asp Thr Leu Met Ile Ser Arg Thr Pro Glu Val Thr Cys
            20                  25                  30

Val Val Val Asp Val Ser Gln Glu Asp Pro Glu Val Gln Phe Asn Trp
        35                  40                  45

Tyr Val Asp Gly Val Glu Val His Asn Ala Lys Thr Lys Pro Arg Glu
    50                  55                  60

Glu Gln Phe Asn Ser Thr Tyr Arg Val Val Ser Val Leu Thr Val Leu
65                  70                  75                  80

His Gln Asp Trp Leu Asn Gly Lys Glu Tyr Lys Cys Lys Val Ser Asn
                85                  90                  95

Lys Gly Leu Pro Ser Ser Ile Glu Lys Thr Ile Ser Lys Ala Lys Gly
            100                 105                 110

Gln Pro Arg Glu Pro Gln Val Tyr Thr Leu Pro Pro Ser Gln Glu Glu
        115                 120                 125

Met Thr Lys Asn Gln Val Ser Leu Thr Cys Leu Val Lys Gly Phe Tyr
    130                 135                 140

Pro Ser Asp Ile Ala Val Glu Trp Glu Ser Asn Gly Gln Pro Glu Asn
145                 150                 155                 160

Asn Tyr Lys Thr Thr Pro Pro Val Leu Asp Ser Asp Gly Ser Phe Phe
                165                 170                 175

Leu Tyr Ser Arg Leu Thr Val Asp Lys Ser Arg Trp Gln Glu Gly Asn
            180                 185                 190

Val Phe Ser Cys Ser Val Met His Glu Ala Leu His Asn His Tyr Thr
        195                 200                 205

Gln Lys Ser Leu Ser Leu Ser Leu Gly Lys
    210                 215
```

<210> SEQ ID NO 7
<211> LENGTH: 14
<212> TYPE: PRT
<213> ORGANISM: Artificial Sequence
<220> FEATURE:
<223> OTHER INFORMATION: Hinge

<400> SEQUENCE: 7

```
Glu Pro Lys Ser Ser Asp Lys Thr His Thr Cys Pro Pro Cys
1               5                   10
```

<210> SEQ ID NO 8
<211> LENGTH: 9
<212> TYPE: PRT
<213> ORGANISM: Artificial Sequence
<220> FEATURE:
<223> OTHER INFORMATION: Hinge

<400> SEQUENCE: 8

```
Asp Lys Thr His Thr Cys Pro Pro Cys
1               5
```

-continued

```
<210> SEQ ID NO 9
<211> LENGTH: 11
<212> TYPE: PRT
<213> ORGANISM: Artificial Sequence
<220> FEATURE:
<223> OTHER INFORMATION: Hinge

<400> SEQUENCE: 9

Glu Ser Lys Tyr Gly Pro Pro Cys Pro Pro Cys
1               5                   10

<210> SEQ ID NO 10
<211> LENGTH: 6
<212> TYPE: PRT
<213> ORGANISM: Artificial Sequence
<220> FEATURE:
<223> OTHER INFORMATION: Synthetic - Linker(GGS)2

<400> SEQUENCE: 10

Gly Gly Ser Gly Gly Ser
1               5

<210> SEQ ID NO 11
<211> LENGTH: 9
<212> TYPE: PRT
<213> ORGANISM: Artificial Sequence
<220> FEATURE:
<223> OTHER INFORMATION: Synthetic - Linker (GGS)3

<400> SEQUENCE: 11

Gly Gly Ser Gly Gly Ser Gly Gly Ser
1               5

<210> SEQ ID NO 12
<211> LENGTH: 12
<212> TYPE: PRT
<213> ORGANISM: Artificial Sequence
<220> FEATURE:
<223> OTHER INFORMATION: Synthetic - Linker (GGS)4

<400> SEQUENCE: 12

Gly Gly Ser Gly Gly Ser Gly Gly Ser Gly Gly Ser
1               5                   10

<210> SEQ ID NO 13
<211> LENGTH: 15
<212> TYPE: PRT
<213> ORGANISM: Artificial Sequence
<220> FEATURE:
<223> OTHER INFORMATION: Synthetic - Linker (GGS)5

<400> SEQUENCE: 13

Gly Gly Ser Gly Gly Ser Gly Gly Ser Gly Gly Ser Gly Gly Ser
1               5                   10                  15

<210> SEQ ID NO 14
<211> LENGTH: 125
<212> TYPE: PRT
<213> ORGANISM: Artificial Sequence
<220> FEATURE:
<223> OTHER INFORMATION: Synthetic - anti-CD3 Hv

<400> SEQUENCE: 14

Glu Val Gln Leu Val Glu Ser Gly Gly Gly Leu Val Gln Pro Lys Gly
1               5                   10                  15

Ser Leu Lys Leu Ser Cys Ala Ala Ser Gly Phe Thr Phe Asn Thr Tyr
            20                  25                  30
```

```
Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Gln Ser Ile
65                  70                  75                  80

Leu Tyr Leu Gln Met Asn Asn Leu Lys Thr Glu Asp Thr Ala Met Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ala
        115                 120                 125

<210> SEQ ID NO 15
<211> LENGTH: 109
<212> TYPE: PRT
<213> ORGANISM: Artificial Sequence
<220> FEATURE:
<223> OTHER INFORMATION: Synthetic - anti-CD3 Lv

<400> SEQUENCE: 15

Gln Ala Val Val Thr Gln Glu Ser Ala Leu Thr Thr Ser Pro Gly Glu
1               5                   10                  15

Thr Val Thr Leu Thr Cys Arg Ser Ser Thr Gly Ala Val Thr Thr Ser
            20                  25                  30

Asn Tyr Ala Asn Trp Val Gln Glu Lys Pro Asp His Leu Phe Thr Gly
        35                  40                  45

Leu Ile Gly Gly Thr Asn Lys Arg Ala Pro Gly Val Pro Ala Arg Phe
    50                  55                  60

Ser Gly Ser Leu Ile Gly Asp Lys Ala Ala Leu Thr Ile Thr Gly Ala
65                  70                  75                  80

Gln Thr Glu Asp Glu Ala Ile Tyr Phe Cys Ala Leu Trp Tyr Ser Asn
                85                  90                  95

Leu Trp Val Phe Gly Gly Gly Thr Lys Leu Thr Val Leu
            100                 105

<210> SEQ ID NO 16
<211> LENGTH: 5
<212> TYPE: PRT
<213> ORGANISM: Artificial Sequence
<220> FEATURE:
<223> OTHER INFORMATION: anti-CD3 VH CDR1

<400> SEQUENCE: 16

Thr Tyr Ala Met Asn
1               5

<210> SEQ ID NO 17
<211> LENGTH: 19
<212> TYPE: PRT
<213> ORGANISM: Artificial Sequence
<220> FEATURE:
<223> OTHER INFORMATION: anti-CD3 VH CDR2

<400> SEQUENCE: 17

Arg Ile Arg Ser Lys Tyr Asn Asn Tyr Ala Thr Tyr Tyr Ala Asp Ser
1               5                   10                  15

Val Lys Asp
```

```
<210> SEQ ID NO 18
<211> LENGTH: 14
<212> TYPE: PRT
<213> ORGANISM: Artificial Sequence
<220> FEATURE:
<223> OTHER INFORMATION: anti-CD3 VH CDR3

<400> SEQUENCE: 18

His Gly Asn Phe Gly Asn Ser Tyr Val Ser Trp Phe Ala Tyr
1               5                   10

<210> SEQ ID NO 19
<211> LENGTH: 14
<212> TYPE: PRT
<213> ORGANISM: Artificial Sequence
<220> FEATURE:
<223> OTHER INFORMATION: anti-CD3 VL CDR1

<400> SEQUENCE: 19

Arg Ser Ser Thr Gly Ala Val Thr Thr Ser Asn Tyr Ala Asn
1               5                   10

<210> SEQ ID NO 20
<211> LENGTH: 7
<212> TYPE: PRT
<213> ORGANISM: Artificial Sequence
<220> FEATURE:
<223> OTHER INFORMATION: anti-CD3 VL CDR2

<400> SEQUENCE: 20

Gly Thr Asn Lys Arg Ala Pro
1               5

<210> SEQ ID NO 21
<211> LENGTH: 9
<212> TYPE: PRT
<213> ORGANISM: Artificial Sequence
<220> FEATURE:
<223> OTHER INFORMATION: anti-CD3 VL CDR3

<400> SEQUENCE: 21

Ala Leu Trp Tyr Ser Asn Leu Trp Val
1               5

<210> SEQ ID NO 22
<211> LENGTH: 4
<212> TYPE: PRT
<213> ORGANISM: Artificial Sequence
<220> FEATURE:
<223> OTHER INFORMATION: Granzyme B substrate

<400> SEQUENCE: 22

Leu Glu Ala Asp
1

<210> SEQ ID NO 23
<211> LENGTH: 4
<212> TYPE: PRT
<213> ORGANISM: Artificial Sequence
<220> FEATURE:
<223> OTHER INFORMATION: Granzyme B substrate

<400> SEQUENCE: 23

Arg Gln Ala Arg
1

<210> SEQ ID NO 24
```

```
<211> LENGTH: 4
<212> TYPE: PRT
<213> ORGANISM: Artificial Sequence
<220> FEATURE:
<223> OTHER INFORMATION: MMP substrate

<400> SEQUENCE: 24

Pro Ala Gly Leu
1

<210> SEQ ID NO 25
<211> LENGTH: 19
<212> TYPE: PRT
<213> ORGANISM: Artificial Sequence
<220> FEATURE:
<223> OTHER INFORMATION: Linker

<400> SEQUENCE: 25

Thr Gly Leu Glu Ala Asp Gly Ser Pro Ala Gly Leu Gly Arg Gln Ala
1               5                   10                  15

Arg Val Gly

<210> SEQ ID NO 26
<211> LENGTH: 19
<212> TYPE: PRT
<213> ORGANISM: Artificial Sequence
<220> FEATURE:
<223> OTHER INFORMATION: Linker

<400> SEQUENCE: 26

Thr Gly Leu Glu Ala Asp Gly Ser Arg Gln Ala Arg Val Gly Pro Ala
1               5                   10                  15

Gly Leu Gly

<210> SEQ ID NO 27
<211> LENGTH: 19
<212> TYPE: PRT
<213> ORGANISM: Artificial Sequence
<220> FEATURE:
<223> OTHER INFORMATION: Linker

<400> SEQUENCE: 27

Thr Gly Ser Pro Ala Gly Leu Glu Ala Asp Gly Ser Arg Gln Ala Arg
1               5                   10                  15

Val Gly Ser

<210> SEQ ID NO 28
<211> LENGTH: 19
<212> TYPE: PRT
<213> ORGANISM: Artificial Sequence
<220> FEATURE:
<223> OTHER INFORMATION: Linker

<400> SEQUENCE: 28

Thr Gly Pro Ala Gly Leu Gly Leu Glu Ala Asp Gly Ser Arg Gln Ala
1               5                   10                  15

Arg Val Gly

<210> SEQ ID NO 29
<211> LENGTH: 19
<212> TYPE: PRT
<213> ORGANISM: Artificial Sequence
<220> FEATURE:
<223> OTHER INFORMATION: Linker
```

```
<400> SEQUENCE: 29

Thr Gly Arg Gln Ala Arg Val Gly Leu Glu Ala Asp Gly Ser Pro Ala
1               5                   10                  15

Gly Leu Gly

<210> SEQ ID NO 30
<211> LENGTH: 18
<212> TYPE: PRT
<213> ORGANISM: Artificial Sequence
<220> FEATURE:
<223> OTHER INFORMATION: Linker

<400> SEQUENCE: 30

Thr Gly Ser Arg Gln Ala Arg Val Gly Pro Ala Gly Leu Glu Ala Asp
1               5                   10                  15

Gly Ser

<210> SEQ ID NO 31
<211> LENGTH: 20
<212> TYPE: PRT
<213> ORGANISM: Artificial Sequence
<220> FEATURE:
<223> OTHER INFORMATION: Linker

<400> SEQUENCE: 31

Thr Gly Pro Ala Gly Leu Gly Ser Arg Gln Ala Arg Val Gly Leu Glu
1               5                   10                  15

Ala Asp Gly Ser
            20

<210> SEQ ID NO 32
<211> LENGTH: 125
<212> TYPE: PRT
<213> ORGANISM: Artificial Sequence
<220> FEATURE:
<223> OTHER INFORMATION: anti-CD3 VH1

<400> SEQUENCE: 32

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Gly Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125

<210> SEQ ID NO 33
<211> LENGTH: 125
<212> TYPE: PRT
<213> ORGANISM: Artificial Sequence
<220> FEATURE:
<223> OTHER INFORMATION: anti-CD3 VH2
```

<400> SEQUENCE: 33

```
Glu Val Lys Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Ser Ser
65                  70                  75                  80

Leu Tyr Leu Gln Met Asn Asn Leu Lys Thr Glu Asp Thr Ala Met Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125
```

<210> SEQ ID NO 34
<211> LENGTH: 125
<212> TYPE: PRT
<213> ORGANISM: Artificial Sequence
<220> FEATURE:
<223> OTHER INFORMATION: anti-CD3 VH3

<400> SEQUENCE: 34

```
Glu Val Lys Leu Val Glu Ser Gly Gly Gly Leu Val Lys Pro Gly Arg
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Ser Ile
65                  70                  75                  80

Leu Tyr Leu Gln Met Asn Asn Leu Lys Thr Glu Asp Thr Ala Met Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125
```

<210> SEQ ID NO 35
<211> LENGTH: 125
<212> TYPE: PRT
<213> ORGANISM: Artificial Sequence
<220> FEATURE:
<223> OTHER INFORMATION: anti-CD3 VH4

<400> SEQUENCE: 35

```
Glu Val Lys Leu Val Glu Ser Gly Gly Gly Leu Val Pro Gly Arg
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45
```

Ala Arg Ile Arg Ser Lys Tyr Asn Asn Tyr Ala Thr Tyr Tyr Ala Asp
            50                  55                  60

Ser Val Lys Asp Arg Phe Thr Ile Ser Arg Asp Asp Ser Lys Ser Ile
65                  70                  75                  80

Leu Tyr Leu Gln Met Asn Ser Leu Lys Thr Glu Asp Thr Ala Met Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
            115                 120                 125

<210> SEQ ID NO 36
<211> LENGTH: 125
<212> TYPE: PRT
<213> ORGANISM: Artificial Sequence
<220> FEATURE:
<223> OTHER INFORMATION: anti-CD3 VH5

<400> SEQUENCE: 36

Glu Val Lys Leu Val Glu Ser Gly Gly Gly Leu Val Lys Pro Gly Arg
1               5                   10                  15

Ser Leu Arg Leu Ser Cys Ala Ala Ser Gly Phe Thr Phe Asn Thr Tyr
                20                  25                  30

Ala Met Asn Trp Val Arg Gln Ala Pro Gly Lys Gly Leu Glu Trp Val
            35                  40                  45

Ala Arg Ile Arg Ser Lys Tyr Asn Asn Tyr Ala Thr Tyr Tyr Ala Asp
            50                  55                  60

Ser Val Lys Asp Arg Phe Thr Ile Ser Arg Asp Asp Ser Lys Ser Ile
65                  70                  75                  80

Leu Tyr Leu Gln Met Asn Ser Leu Lys Thr Glu Asp Thr Ala Met Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
            115                 120                 125

<210> SEQ ID NO 37
<211> LENGTH: 125
<212> TYPE: PRT
<213> ORGANISM: Artificial Sequence
<220> FEATURE:
<223> OTHER INFORMATION: anti-CD3 VH6

<400> SEQUENCE: 37

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
                20                  25                  30

Ala Met Asn Trp Val Arg Gln Ala Pro Gly Lys Gly Leu Glu Trp Val
            35                  40                  45

Ser Arg Ile Arg Ser Lys Tyr Asn Asn Tyr Ala Thr Tyr Tyr Ala Asp
            50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Asn Ser Tyr Val Ser Trp Phe

```
              100                 105                 110
Ala Tyr Trp Gly Gln Gly Thr Leu Val Thr Val Ser Ser
        115                 120                 125

<210> SEQ ID NO 38
<211> LENGTH: 125
<212> TYPE: PRT
<213> ORGANISM: Artificial Sequence
<220> FEATURE:
<223> OTHER INFORMATION: anti-CD3 VH7

<400> SEQUENCE: 38

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Ser Trp Val Arg Gln Ala Pro Gly Lys Gly Leu Glu Trp Val
        35                  40                  45

Gly Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Asp Ser Tyr Val Ser Trp Phe
            100                 105                 110

Ala Tyr Trp Gly Gln Gly Thr Leu Val Thr Val Ser Ser
        115                 120                 125

<210> SEQ ID NO 39
<211> LENGTH: 124
<212> TYPE: PRT
<213> ORGANISM: Artificial Sequence
<220> FEATURE:
<223> OTHER INFORMATION: anti-CD3 VH8

<400> SEQUENCE: 39

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Asn Lys Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Asn Thr
65                  70                  75                  80

Ala Tyr Leu Gln Met Asn Asn Leu Lys Thr Glu Asp Thr Ala Val Tyr
                85                  90                  95

Tyr Cys Val Arg His Gly Asn Phe Gly Asn Ser Tyr Ile Ser Tyr Trp
            100                 105                 110

Ala Tyr Trp Gly Gln Gly Thr Leu Val Thr Val Ser
        115                 120

<210> SEQ ID NO 40
<211> LENGTH: 125
<212> TYPE: PRT
<213> ORGANISM: Artificial Sequence
<220> FEATURE:
```

<223> OTHER INFORMATION: anti-CD3 VH9

<400> SEQUENCE: 40

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Thr Val Thr Val Ser Ser
        115                 120                 125

<210> SEQ ID NO 41
<211> LENGTH: 125
<212> TYPE: PRT
<213> ORGANISM: Artificial Sequence
<220> FEATURE:
<223> OTHER INFORMATION: anti-CD3 VH10

<400> SEQUENCE: 41

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Asn Ser Tyr Val Ser Tyr Phe
            100                 105                 110

Ala Tyr Trp Gly Gln Gly Thr Thr Val Thr Val Ser Ser
        115                 120                 125

<210> SEQ ID NO 42
<211> LENGTH: 125
<212> TYPE: PRT
<213> ORGANISM: Artificial Sequence
<220> FEATURE:
<223> OTHER INFORMATION: anti-CD3 VH11

<400> SEQUENCE: 42

Glu Val Gln Leu Val Glu Ser Gly Gly Gly Leu Val Gln Pro Lys Gly
1               5                   10                  15

Ser Leu Lys Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val

```
            35                  40                  45
Ala Arg Ile Arg Ser Lys Tyr Asn Asn Tyr Ala Thr Tyr Tyr Ala Asp
        50                  55                  60

Ser Val Lys Asp Arg Phe Thr Ile Ser Arg Asp Asp Ser Gln Ser Ile
 65                 70                  75                  80

Leu Tyr Leu Gln Met Asn Asn Leu Lys Thr Glu Asp Thr Ala Met Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125

<210> SEQ ID NO 43
<211> LENGTH: 125
<212> TYPE: PRT
<213> ORGANISM: Artificial Sequence
<220> FEATURE:
<223> OTHER INFORMATION: anti-CD3 VH12

<400> SEQUENCE: 43

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
        50                  55                  60

Ser Val Lys Gly Arg Phe Thr Ile Ser Arg Asp Asp Ala Lys Asn Thr
 65                 70                  75                  80

Leu Tyr Leu Gln Met Ser Ser Leu Arg Ala Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Lys Pro
        115                 120                 125

<210> SEQ ID NO 44
<211> LENGTH: 125
<212> TYPE: PRT
<213> ORGANISM: Artificial Sequence
<220> FEATURE:
<223> OTHER INFORMATION: anti-CD3 VH13

<400> SEQUENCE: 44

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Cys Leu Glu Trp Val
        35                  40                  45

Ala Arg Ile Arg Ser Lys Tyr Asn Asn Tyr Ala Thr Tyr Tyr Ala Asp
        50                  55                  60

Ser Val Lys Gly Arg Phe Thr Ile Ser Arg Asp Asp Ala Lys Asn Thr
 65                 70                  75                  80

Leu Tyr Leu Gln Met Ser Ser Leu Arg Ala Glu Asp Thr Ala Val Tyr
                85                  90                  95
```

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Lys Pro
        115                 120                 125

<210> SEQ ID NO 45
<211> LENGTH: 125
<212> TYPE: PRT
<213> ORGANISM: Artificial Sequence
<220> FEATURE:
<223> OTHER INFORMATION: anti-CD3 VH14

<400> SEQUENCE: 45

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ala Lys Asn Thr
65                  70                  75                  80

Leu Tyr Leu Gln Met Ser Ser Leu Arg Ala Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Cys Gly Thr Leu Val Thr Val Lys Pro
        115                 120                 125

<210> SEQ ID NO 46
<211> LENGTH: 125
<212> TYPE: PRT
<213> ORGANISM: Artificial Sequence
<220> FEATURE:
<223> OTHER INFORMATION: anti-CD3 VH15

<400> SEQUENCE: 46

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ala Lys Asn Thr
65                  70                  75                  80

Leu Tyr Leu Gln Met Ser Ser Leu Arg Ala Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125

<210> SEQ ID NO 47
<211> LENGTH: 125
<212> TYPE: PRT
<213> ORGANISM: Artificial Sequence

```
<220> FEATURE:
<223> OTHER INFORMATION: anti-CD3 VH16

<400> SEQUENCE: 47

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ser Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ala Lys Asn Thr
65                  70                  75                  80

Leu Tyr Leu Gln Met Ser Ser Leu Arg Ala Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125

<210> SEQ ID NO 48
<211> LENGTH: 125
<212> TYPE: PRT
<213> ORGANISM: Artificial Sequence
<220> FEATURE:
<223> OTHER INFORMATION: anti-CD3 VH17

<400> SEQUENCE: 48

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Ser Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ala Lys Asn Thr
65                  70                  75                  80

Leu Tyr Leu Gln Met Ser Ser Leu Arg Ala Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125

<210> SEQ ID NO 49
<211> LENGTH: 125
<212> TYPE: PRT
<213> ORGANISM: Artificial Sequence
<220> FEATURE:
<223> OTHER INFORMATION: anti-CD3 VH18

<400> SEQUENCE: 49

Glu Val Gln Leu Val Glu Ser Gly Gly Gly Leu Val Gln Pro Gly Gly
1               5                   10                  15

Ser Leu Arg Leu Ser Cys Ala Ser Gly Phe Thr Phe Ser Thr Tyr
            20                  25                  30
```

```
Ala Met Asn Trp Val Arg Gln Ala Pro Gly Lys Cys Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ala Lys Asn Thr
65                  70                  75                  80

Leu Tyr Leu Gln Met Ser Ser Leu Arg Ala Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
            115                 120                 125

<210> SEQ ID NO 50
<211> LENGTH: 125
<212> TYPE: PRT
<213> ORGANISM: Artificial Sequence
<220> FEATURE:
<223> OTHER INFORMATION: anti-CD3 VH19

<400> SEQUENCE: 50

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Cys Leu Glu Trp Val
        35                  40                  45

Ser Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ala Lys Asn Thr
65                  70                  75                  80

Leu Tyr Leu Gln Met Ser Ser Leu Arg Ala Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
            115                 120                 125

<210> SEQ ID NO 51
<211> LENGTH: 125
<212> TYPE: PRT
<213> ORGANISM: Artificial Sequence
<220> FEATURE:
<223> OTHER INFORMATION: anti-CD3 VH20

<400> SEQUENCE: 51

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Cys Leu Glu Trp Val
        35                  40                  45

Ser Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ala Lys Asn Thr
65                  70                  75                  80

Leu Tyr Leu Gln Met Ser Ser Leu Arg Ala Glu Asp Thr Ala Val Tyr
                85                  90                  95
```

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125

<210> SEQ ID NO 52
<211> LENGTH: 125
<212> TYPE: PRT
<213> ORGANISM: Artificial Sequence
<220> FEATURE:
<223> OTHER INFORMATION: anti-CD3 VH21

<400> SEQUENCE: 52

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Cys Leu Glu Trp Val
        35                  40                  45

Gly Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125

<210> SEQ ID NO 53
<211> LENGTH: 125
<212> TYPE: PRT
<213> ORGANISM: Artificial Sequence
<220> FEATURE:
<223> OTHER INFORMATION: anti-CD3 VH22

<400> SEQUENCE: 53

Glu Val Lys Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Cys Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Ser Ser
65                  70                  75                  80

Leu Tyr Leu Gln Met Asn Asn Leu Lys Thr Glu Asp Thr Ala Met Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125

<210> SEQ ID NO 54
<211> LENGTH: 125
<212> TYPE: PRT

```
<213> ORGANISM: Artificial Sequence
<220> FEATURE:
<223> OTHER INFORMATION: anti-CD3 VH23

<400> SEQUENCE: 54

Glu Val Lys Leu Val Glu Ser Gly Gly Gly Leu Val Lys Pro Gly Arg
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Cys Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Ser Ile
65                  70                  75                  80

Leu Tyr Leu Gln Met Asn Asn Leu Lys Thr Glu Asp Thr Ala Met Tyr
            85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125

<210> SEQ ID NO 55
<211> LENGTH: 125
<212> TYPE: PRT
<213> ORGANISM: Artificial Sequence
<220> FEATURE:
<223> OTHER INFORMATION: anti-CD3 VH24

<400> SEQUENCE: 55

Glu Val Lys Leu Val Glu Ser Gly Gly Gly Leu Val Lys Pro Gly Arg
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Cys Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Ser Ile
65                  70                  75                  80

Leu Tyr Leu Gln Met Asn Ser Leu Lys Thr Glu Asp Thr Ala Met Tyr
            85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125

<210> SEQ ID NO 56
<211> LENGTH: 125
<212> TYPE: PRT
<213> ORGANISM: Artificial Sequence
<220> FEATURE:
<223> OTHER INFORMATION: anti-CD3 VH25

<400> SEQUENCE: 56

Glu Val Lys Leu Val Glu Ser Gly Gly Gly Leu Val Lys Pro Gly Arg
1               5                   10                  15

Ser Leu Arg Leu Ser Cys Ala Ala Ser Gly Phe Thr Phe Asn Thr Tyr
            20                  25                  30
```

```
Ala Met Asn Trp Val Arg Gln Ala Pro Gly Lys Cys Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Ser Ile
65                  70                  75                  80

Leu Tyr Leu Gln Met Asn Ser Leu Lys Thr Glu Asp Thr Ala Met Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125

<210> SEQ ID NO 57
<211> LENGTH: 125
<212> TYPE: PRT
<213> ORGANISM: Artificial Sequence
<220> FEATURE:
<223> OTHER INFORMATION: anti-CD3 VH26

<400> SEQUENCE: 57

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Cys Leu Glu Trp Val
        35                  40                  45

Ser Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125

<210> SEQ ID NO 58
<211> LENGTH: 125
<212> TYPE: PRT
<213> ORGANISM: Artificial Sequence
<220> FEATURE:
<223> OTHER INFORMATION: anti-CD3 VH27

<400> SEQUENCE: 58

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Ser Trp Val Arg Gln Ala Pro Gly Lys Cys Leu Glu Trp Val
        35                  40                  45

Gly Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
```

```
                85                  90                  95
Tyr Cys Val Arg His Gly Asn Phe Gly Asp Ser Tyr Val Ser Trp Phe
                100                 105                 110
Ala Tyr Trp Gly Gln Gly Thr Leu Val Thr Val Ser Ser
        115                 120                 125

<210> SEQ ID NO 59
<211> LENGTH: 124
<212> TYPE: PRT
<213> ORGANISM: Artificial Sequence
<220> FEATURE:
<223> OTHER INFORMATION: anti-CD3 VH28

<400> SEQUENCE: 59

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Asn Lys Tyr
            20                  25                  30

Ala Met Asn Trp Val Arg Gln Ala Pro Gly Lys Cys Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Asn Thr
65                  70                  75                  80

Ala Tyr Leu Gln Met Asn Asn Leu Lys Thr Glu Asp Thr Ala Val Tyr
                85                  90                  95

Tyr Cys Val Arg His Gly Asn Phe Gly Asn Ser Tyr Ile Ser Tyr Trp
                100                 105                 110

Ala Tyr Trp Gly Gln Gly Thr Leu Val Thr Val Ser
        115                 120

<210> SEQ ID NO 60
<211> LENGTH: 125
<212> TYPE: PRT
<213> ORGANISM: Artificial Sequence
<220> FEATURE:
<223> OTHER INFORMATION: anti-CD3 VH29

<400> SEQUENCE: 60

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Cys Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Asn Ser Tyr Val Ser Trp Phe
                100                 105                 110

Ala Tyr Trp Gly Gln Gly Thr Thr Val Thr Val Ser Ser
        115                 120                 125

<210> SEQ ID NO 61
<211> LENGTH: 125
```

```
<212> TYPE: PRT
<213> ORGANISM: Artificial Sequence
<220> FEATURE:
<223> OTHER INFORMATION: anti-CD3 VH30

<400> SEQUENCE: 61

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Cys Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Asn Ser Tyr Val Ser Tyr Phe
            100                 105                 110

Ala Tyr Trp Gly Gln Gly Thr Thr Val Thr Val Ser Ser
        115                 120                 125

<210> SEQ ID NO 62
<211> LENGTH: 125
<212> TYPE: PRT
<213> ORGANISM: Artificial Sequence
<220> FEATURE:
<223> OTHER INFORMATION: anti-CD3 VH31

<400> SEQUENCE: 62

Glu Val Gln Leu Val Glu Ser Gly Gly Gly Leu Val Gln Pro Lys Gly
1               5                   10                  15

Ser Leu Lys Leu Ser Cys Ala Ala Ser Gly Phe Thr Phe Asn Thr Tyr
            20                  25                  30

Ala Met Asn Trp Val Arg Gln Ala Pro Gly Lys Cys Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Gln Ser Ile
65                  70                  75                  80

Leu Tyr Leu Gln Met Asn Asn Leu Lys Thr Glu Asp Thr Ala Met Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125

<210> SEQ ID NO 63
<211> LENGTH: 109
<212> TYPE: PRT
<213> ORGANISM: Artificial Sequence
<220> FEATURE:
<223> OTHER INFORMATION: anti-CD3 VL1

<400> SEQUENCE: 63

Gln Ala Val Val Thr Gln Glu Ser Ala Leu Thr Thr Ser Pro Gly Glu
1               5                   10                  15

Thr Val Thr Leu Thr Cys Arg Ser Ser Thr Gly Ala Val Thr Thr Ser
```

```
                20                  25                  30

Asn Tyr Ala Asn Trp Val Gln Glu Lys Pro Asp His Leu Phe Thr Gly
            35                  40                  45

Leu Ile Gly Gly Thr Asn Lys Arg Ala Pro Gly Val Pro Ala Arg Phe
        50                  55                  60

Ser Gly Ser Leu Ile Gly Asp Lys Ala Ala Leu Thr Ile Thr Gly Ala
65                  70                  75                  80

Gln Thr Glu Asp Glu Ala Ile Tyr Phe Cys Ala Leu Trp Tyr Ser Asn
                85                  90                  95

Leu Trp Val Phe Gly Gly Gly Thr Lys Leu Thr Val Leu
            100                 105

<210> SEQ ID NO 64
<211> LENGTH: 109
<212> TYPE: PRT
<213> ORGANISM: Artificial Sequence
<220> FEATURE:
<223> OTHER INFORMATION: anti-CD3 VL2

<400> SEQUENCE: 64

Gln Ala Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Thr Ser
            20                  25                  30

Asn Tyr Ala Asn Trp Val Gln Gln Lys Pro Gly Lys Ser Pro Arg Gly
            35                  40                  45

Leu Ile Gly Gly Thr Asn Lys Arg Ala Pro Gly Val Pro Ala Arg Phe
        50                  55                  60

Ser Gly Ser Leu Leu Gly Gly Lys Ala Ala Leu Thr Ile Ser Gly Ala
65                  70                  75                  80

Gln Pro Glu Asp Glu Ala Asp Tyr Tyr Cys Ala Leu Trp Tyr Ser Asn
                85                  90                  95

His Trp Val Phe Gly Cys Gly Thr Lys Leu Glu Ile Lys
            100                 105

<210> SEQ ID NO 65
<211> LENGTH: 109
<212> TYPE: PRT
<213> ORGANISM: Artificial Sequence
<220> FEATURE:
<223> OTHER INFORMATION: anti-CD3 VL3

<400> SEQUENCE: 65

Gln Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Gly Gln Ala Pro Arg Gly
            35                  40                  45

Leu Ile Gly Gly Thr Asn Lys Arg Ala Pro Trp Thr Pro Ala Arg Phe
        50                  55                  60

Ser Gly Ser Leu Leu Gly Gly Lys Ala Ala Leu Thr Ile Thr Gly Ala
65                  70                  75                  80

Gln Ala Glu Asp Glu Ala Asp Tyr Tyr Cys Ala Leu Trp Tyr Ser Asn
                85                  90                  95

Leu Trp Val Phe Gly Gly Gly Thr Lys Leu Thr Val Leu
            100                 105
```

<210> SEQ ID NO 66
<211> LENGTH: 109
<212> TYPE: PRT
<213> ORGANISM: Artificial Sequence
<220> FEATURE:
<223> OTHER INFORMATION: anti-CD3 VL4

<400> SEQUENCE: 66

Gln Ala Val Val Thr Gln Glu Pro Ser Phe Ser Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Thr Pro Gly Gln Ala Phe Arg Gly
        35                  40                  45

Leu Ile Gly Gly Thr Asn Lys Arg Ala Pro Gly Val Pro Ala Arg Phe
    50                  55                  60

Ser Gly Ser Leu Ile Gly Asp Lys Ala Ala Leu Thr Ile Thr Gly Ala
65                  70                  75                  80

Gln Ala Asp Asp Glu Ser Ile Tyr Phe Cys Ala Leu Trp Tyr Ser Asn
                85                  90                  95

Leu Trp Val Phe Gly Gly Gly Thr Lys Leu Thr Val Leu
            100                 105

<210> SEQ ID NO 67
<211> LENGTH: 109
<212> TYPE: PRT
<213> ORGANISM: Artificial Sequence
<220> FEATURE:
<223> OTHER INFORMATION: anti-CD3 VL5

<400> SEQUENCE: 67

Gln Ala Val Val Thr Gln Glu Pro Ser Phe Ser Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Thr Pro Gly Gln Ala Phe Arg Gly
        35                  40                  45

Leu Ile Gly Gly Thr Asn Lys Arg Ala Pro Gly Val Pro Ala Arg Phe
    50                  55                  60

Ser Gly Ser Ile Leu Gly Asn Lys Ala Ala Leu Thr Ile Thr Gly Ala
65                  70                  75                  80

Gln Ala Asp Asp Glu Ser Ile Tyr Phe Cys Ala Leu Trp Tyr Ser Asn
                85                  90                  95

Leu Trp Val Phe Gly Gly Gly Thr Lys Leu Thr Val Leu
            100                 105

<210> SEQ ID NO 68
<211> LENGTH: 109
<212> TYPE: PRT
<213> ORGANISM: Artificial Sequence
<220> FEATURE:
<223> OTHER INFORMATION: anti-CD3 VL6

<400> SEQUENCE: 68

Gln Ala Val Val Thr Gln Glu Pro Ser Phe Ser Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Thr Pro Gly Gln Ala Phe Arg Gly

```
                     35                  40                  45

Leu Ile Gly Gly Thr Asn Lys Arg Ala Pro Gly Val Pro Ala Arg Phe
                 50                  55                  60

Ser Gly Ser Ile Leu Gly Asn Lys Ala Ala Leu Thr Ile Thr Gly Ala
 65                  70                  75                  80

Gln Ala Asp Asp Glu Ser Asp Tyr Tyr Cys Ala Leu Trp Tyr Ser Asn
                 85                  90                  95

Leu Trp Val Phe Gly Gly Gly Thr Lys Leu Thr Val Leu
            100                 105

<210> SEQ ID NO 69
<211> LENGTH: 109
<212> TYPE: PRT
<213> ORGANISM: Artificial Sequence
<220> FEATURE:
<223> OTHER INFORMATION: anti-CD3 VL7

<400> SEQUENCE: 69

Gln Ala Val Val Thr Gln Glu Pro Ser Leu Thr Val Ser Pro Gly Gly
 1               5                  10                  15

Thr Val Thr Leu Thr Cys Gly Ser Ser Thr Gly Ala Val Thr Thr Ser
                 20                  25                  30

Asn Tyr Ala Asn Trp Val Gln Glu Lys Pro Gly Gln Ala Phe Arg Gly
             35                  40                  45

Leu Ile Gly Gly Thr Asn Lys Arg Ala Pro Gly Thr Pro Ala Arg Phe
         50                  55                  60

Ser Gly Ser Leu Leu Gly Gly Lys Ala Ala Leu Thr Leu Ser Gly Ala
 65                  70                  75                  80

Gln Pro Glu Asp Glu Ala Glu Tyr Tyr Cys Ala Leu Trp Tyr Ser Asn
                 85                  90                  95

Leu Trp Val Phe Gly Gly Gly Thr Lys Leu Thr Val Leu
            100                 105

<210> SEQ ID NO 70
<211> LENGTH: 109
<212> TYPE: PRT
<213> ORGANISM: Artificial Sequence
<220> FEATURE:
<223> OTHER INFORMATION: anti-CD3 VL8

<400> SEQUENCE: 70

Gln Thr Val Val Thr Gln Glu Pro Ser Leu Thr Val Ser Pro Gly Gly
 1               5                  10                  15

Thr Val Thr Leu Thr Cys Gly Ser Ser Thr Gly Ala Val Thr Ser Gly
                 20                  25                  30

Asn Tyr Pro Asn Trp Val Gln Gln Lys Pro Gly Gln Ala Pro Arg Gly
             35                  40                  45

Leu Ile Gly Gly Thr Lys Phe Leu Ala Pro Gly Thr Pro Ala Arg Phe
         50                  55                  60

Ser Gly Ser Leu Leu Gly Gly Lys Ala Ala Leu Thr Leu Ser Gly Val
 65                  70                  75                  80

Gln Pro Glu Asp Glu Ala Glu Tyr Tyr Cys Val Leu Trp Tyr Ser Asn
                 85                  90                  95

Arg Trp Val Phe Gly Gly Gly Thr Lys Leu Thr Val Leu
            100                 105

<210> SEQ ID NO 71
<211> LENGTH: 109
```

```
<212> TYPE: PRT
<213> ORGANISM: Artificial Sequence
<220> FEATURE:
<223> OTHER INFORMATION: anti-CD3 VL9

<400> SEQUENCE: 71

Gln Ala Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Thr Ser
            20                  25                  30

Asn Tyr Ala Asn Trp Val Gln Gln Lys Pro Gly Gln Ala Phe Arg Gly
        35                  40                  45

Leu Ile Gly Gly Thr Asn Lys Arg Ala Pro Gly Val Pro Ala Arg Phe
    50                  55                  60

Ser Gly Ser Leu Leu Gly Gly Lys Ala Ala Leu Thr Ile Ser Gly Ala
65                  70                  75                  80

Gln Pro Glu Asp Glu Ala Asp Tyr Tyr Cys Ala Leu Trp Tyr Ser Asn
                85                  90                  95

His Trp Val Phe Gly Gly Gly Thr Lys Leu Glu Ile Lys
            100                 105

<210> SEQ ID NO 72
<211> LENGTH: 109
<212> TYPE: PRT
<213> ORGANISM: Artificial Sequence
<220> FEATURE:
<223> OTHER INFORMATION: anti-CD3 VL10

<400> SEQUENCE: 72

Gln Ala Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Thr Ser
            20                  25                  30

Asn Tyr Ala Asn Trp Val Gln Gln Lys Pro Gly Gln Ala Phe Arg Gly
        35                  40                  45

Leu Ile Gly Gly Thr Asn Lys Arg Ala Pro Gly Val Pro Ala Arg Phe
    50                  55                  60

Ser Gly Ser Leu Leu Gly Gly Lys Ala Ala Leu Thr Ile Ser Gly Ala
65                  70                  75                  80

Gln Pro Glu Asp Glu Ala Asp Tyr Tyr Cys Ala Leu Trp Tyr Ser Asn
                85                  90                  95

His Trp Val Phe Gly Cys Gly Thr Lys Leu Glu Ile Lys
            100                 105

<210> SEQ ID NO 73
<211> LENGTH: 109
<212> TYPE: PRT
<213> ORGANISM: Artificial Sequence
<220> FEATURE:
<223> OTHER INFORMATION: anti-CD3 VL11

<400> SEQUENCE: 73

Gln Ala Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Thr Ser
            20                  25                  30

Asn Tyr Ala Asn Trp Val Gln Gln Lys Pro Gly Gln Cys Phe Arg Gly
        35                  40                  45

Leu Ile Gly Gly Thr Asn Lys Arg Ala Pro Gly Val Pro Ala Arg Phe
```

```
                    50                  55                  60
Ser Gly Ser Leu Leu Gly Gly Lys Ala Ala Leu Thr Ile Ser Gly Ala
 65                  70                  75                  80

Gln Pro Glu Asp Glu Ala Asp Tyr Tyr Cys Ala Leu Trp Tyr Ser Asn
                 85                  90                  95

His Trp Val Phe Gly Gly Gly Thr Lys Leu Glu Ile Lys
            100                 105

<210> SEQ ID NO 74
<211> LENGTH: 109
<212> TYPE: PRT
<213> ORGANISM: Artificial Sequence
<220> FEATURE:
<223> OTHER INFORMATION: anti-CD3 VL12

<400> SEQUENCE: 74

Gln Ala Val Val Thr Gln Glu Ser Ala Leu Thr Thr Ser Pro Gly Glu
 1               5                  10                  15

Thr Val Thr Leu Thr Cys Arg Ser Ser Thr Gly Ala Val Thr Thr Ser
                20                  25                  30

Asn Tyr Ala Asn Trp Val Gln Glu Lys Pro Asp His Leu Phe Thr Gly
             35                  40                  45

Leu Ile Gly Gly Thr Asn Lys Arg Ala Pro Gly Val Pro Ala Arg Phe
         50                  55                  60

Ser Gly Ser Leu Ile Gly Asp Lys Ala Ala Leu Thr Ile Thr Gly Ala
 65                  70                  75                  80

Gln Thr Glu Asp Glu Ala Ile Tyr Phe Cys Ala Leu Trp Tyr Ser Asn
                 85                  90                  95

Leu Trp Val Phe Gly Cys Gly Thr Lys Leu Thr Val Leu
            100                 105

<210> SEQ ID NO 75
<211> LENGTH: 109
<212> TYPE: PRT
<213> ORGANISM: Artificial Sequence
<220> FEATURE:
<223> OTHER INFORMATION: anti-CD3 VL13

<400> SEQUENCE: 75

Gln Ala Val Val Thr Gln Glu Pro Ser Leu Thr Val Ser Pro Gly Gly
 1               5                  10                  15

Thr Val Thr Leu Thr Cys Gly Ser Ser Thr Gly Ala Val Thr Thr Ser
                20                  25                  30

Asn Tyr Ala Asn Trp Val Gln Gln Lys Pro Gly Lys Ser Pro Arg Gly
             35                  40                  45

Leu Ile Gly Gly Thr Asn Lys Arg Ala Pro Gly Val Pro Ala Arg Phe
         50                  55                  60

Ser Gly Ser Leu Leu Gly Gly Lys Ala Ala Leu Thr Ile Ser Gly Ala
 65                  70                  75                  80

Gln Pro Glu Asp Glu Ala Asp Tyr Tyr Cys Ala Leu Trp Tyr Ser Asn
                 85                  90                  95

His Trp Val Phe Gly Gly Gly Thr Lys Leu Glu Ile Lys
            100                 105

<210> SEQ ID NO 76
<211> LENGTH: 109
<212> TYPE: PRT
<213> ORGANISM: Artificial Sequence
<220> FEATURE:
```

<223> OTHER INFORMATION: anti-CD3 VL14

<400> SEQUENCE: 76

Gln Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Gly Gln Ala Pro Arg Gly
        35                  40                  45

Leu Ile Gly Gly Thr Asn Lys Arg Ala Pro Trp Thr Pro Ala Arg Phe
    50                  55                  60

Ser Gly Ser Leu Leu Gly Gly Lys Ala Ala Leu Thr Ile Thr Gly Ala
65                  70                  75                  80

Gln Ala Glu Asp Glu Ala Asp Tyr Tyr Cys Ala Leu Trp Tyr Ser Asn
                85                  90                  95

Leu Trp Val Phe Gly Cys Gly Thr Lys Leu Thr Val Leu
            100                 105

<210> SEQ ID NO 77
<211> LENGTH: 109
<212> TYPE: PRT
<213> ORGANISM: Artificial Sequence
<220> FEATURE:
<223> OTHER INFORMATION: anti-CD3 VL15

<400> SEQUENCE: 77

Gln Ala Val Val Thr Gln Glu Pro Ser Phe Ser Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Thr Pro Gly Gln Ala Phe Arg Gly
        35                  40                  45

Leu Ile Gly Gly Thr Asn Lys Arg Ala Pro Gly Val Pro Ala Arg Phe
    50                  55                  60

Ser Gly Ser Leu Ile Gly Asp Lys Ala Ala Leu Thr Ile Thr Gly Ala
65                  70                  75                  80

Gln Ala Asp Asp Glu Ser Ile Tyr Phe Cys Ala Leu Trp Tyr Ser Asn
                85                  90                  95

Leu Trp Val Phe Gly Gly Gly Thr Lys Leu Thr Val Leu
            100                 105

<210> SEQ ID NO 78
<211> LENGTH: 109
<212> TYPE: PRT
<213> ORGANISM: Artificial Sequence
<220> FEATURE:
<223> OTHER INFORMATION: anti-CD3 VL16

<400> SEQUENCE: 78

Gln Ala Val Val Thr Gln Glu Pro Ser Phe Ser Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Thr Pro Gly Gln Ala Phe Arg Gly
        35                  40                  45

Leu Ile Gly Gly Thr Asn Lys Arg Ala Pro Gly Val Pro Ala Arg Phe
    50                  55                  60

Ser Gly Ser Ile Leu Gly Asn Lys Ala Ala Leu Thr Ile Thr Gly Ala

| | | | 65 | | | | 70 | | | | 75 | | | | 80 |

Gln Ala Asp Asp Glu Ser Ile Tyr Phe Cys Ala Leu Trp Tyr Ser Asn
                    85                      90                      95

Leu Trp Val Phe Gly Cys Gly Thr Lys Leu Thr Val Leu
                100                     105

<210> SEQ ID NO 79
<211> LENGTH: 109
<212> TYPE: PRT
<213> ORGANISM: Artificial Sequence
<220> FEATURE:
<223> OTHER INFORMATION: anti-CD3 VL17

<400> SEQUENCE: 79

Gln Ala Val Val Thr Gln Glu Pro Ser Phe Ser Val Ser Pro Gly Gly
1               5                   10                  15

Thr Val Thr Leu Thr Cys Arg Ser Ser Thr Gly Ala Val Thr Thr Ser
                20                  25                  30

Asn Tyr Ala Asn Trp Val Gln Gln Thr Pro Gly Gln Ala Phe Arg Gly
            35                  40                  45

Leu Ile Gly Gly Thr Asn Lys Arg Ala Pro Gly Val Pro Ala Arg Phe
        50                  55                  60

Ser Gly Ser Ile Leu Gly Asn Lys Ala Ala Leu Thr Ile Thr Gly Ala
65                  70                  75                  80

Gln Ala Asp Asp Glu Ser Asp Tyr Tyr Cys Ala Leu Trp Tyr Ser Asn
                85                  90                  95

Leu Trp Val Phe Gly Cys Gly Thr Lys Leu Thr Val Leu
                100                 105

<210> SEQ ID NO 80
<211> LENGTH: 109
<212> TYPE: PRT
<213> ORGANISM: Artificial Sequence
<220> FEATURE:
<223> OTHER INFORMATION: anti-CD3 VL18

<400> SEQUENCE: 80

Gln Ala Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Thr Ser
                20                  25                  30

Asn Tyr Ala Asn Trp Val Gln Glu Lys Pro Gly Gln Ala Phe Arg Gly
            35                  40                  45

Leu Ile Gly Gly Thr Asn Lys Arg Ala Pro Gly Thr Pro Ala Arg Phe
        50                  55                  60

Ser Gly Ser Leu Leu Gly Gly Lys Ala Ala Leu Thr Leu Ser Gly Ala
65                  70                  75                  80

Gln Pro Glu Asp Glu Ala Glu Tyr Tyr Cys Ala Leu Trp Tyr Ser Asn
                85                  90                  95

Leu Trp Val Phe Gly Cys Gly Thr Lys Leu Thr Val Leu
                100                 105

<210> SEQ ID NO 81
<211> LENGTH: 109
<212> TYPE: PRT
<213> ORGANISM: Artificial Sequence
<220> FEATURE:
<223> OTHER INFORMATION: anti-CD3 VL19

<400> SEQUENCE: 81

```
Gln Thr Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Ser Gly
            20                  25                  30

Asn Tyr Pro Asn Trp Val Gln Gln Lys Pro Gly Gln Ala Pro Arg Gly
        35                  40                  45

Leu Ile Gly Gly Thr Lys Phe Leu Ala Pro Gly Thr Pro Ala Arg Phe
50                  55                  60

Ser Gly Ser Leu Leu Gly Gly Lys Ala Ala Leu Thr Leu Ser Gly Val
65                  70                  75                  80

Gln Pro Glu Asp Glu Ala Glu Tyr Tyr Cys Val Leu Trp Tyr Ser Asn
                85                  90                  95

Arg Trp Val Phe Gly Cys Gly Thr Lys Leu Thr Val Leu
                100                 105
```

<210> SEQ ID NO 82
<211> LENGTH: 226
<212> TYPE: PRT
<213> ORGANISM: Artificial Sequence
<220> FEATURE:
<223> OTHER INFORMATION: Knob Fc

<400> SEQUENCE: 82

```
Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
                100                 105                 110

Glu Lys Thr Ile Ser Lys Ala Lys Gly Gln Pro Arg Glu Pro Gln Val
                115                 120                 125

Tyr Thr Leu Pro Pro Cys Arg Asp Glu Leu Thr Lys Asn Gln Val Ser
                130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
                180                 185                 190

Asp Lys Ser Arg Trp Gln Gln Gly Asn Val Phe Ser Cys Ser Val Met
                195                 200                 205

His Glu Ala Leu His Asn His Tyr Thr Gln Lys Ser Leu Ser Leu Ser
            210                 215                 220

Pro Thr
225
```

<210> SEQ ID NO 83

<211> LENGTH: 226
<212> TYPE: PRT
<213> ORGANISM: Artificial Sequence
<220> FEATURE:
<223> OTHER INFORMATION: Hole Fc

<400> SEQUENCE: 83

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Arg Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Cys Thr Leu Pro Pro Ser Arg Asp Glu Leu Thr Lys Asn Gln Val Ser
130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Thr
225

<210> SEQ ID NO 84
<211> LENGTH: 223
<212> TYPE: PRT
<213> ORGANISM: Artificial Sequence
<220> FEATURE:
<223> OTHER INFORMATION: Knob Fc

<400> SEQUENCE: 84

Asp Lys Thr His Thr Cys Pro Pro Cys Pro Ala Pro Gly Gly Pro Ser
1               5                   10                  15

Val Phe Leu Phe Pro Pro Lys Pro Lys Asp Thr Leu Met Ile Ser Arg
            20                  25                  30

Thr Pro Glu Val Thr Cys Val Val Val Asp Val Ser His Glu Asp Pro
        35                  40                  45

Glu Val Lys Phe Asn Trp Tyr Val Asp Gly Val Glu Val His Asn Ala
    50                  55                  60

Lys Thr Lys Pro Arg Glu Glu Gln Tyr Asn Ser Thr Tyr Arg Val Val
65                  70                  75                  80

Ser Val Leu Thr Val Leu His Gln Asp Trp Leu Asn Gly Lys Glu Tyr

```
                85                  90                  95
Lys Cys Lys Val Ser Asn Lys Ala Leu Pro Ala Pro Ile Glu Lys Thr
            100                 105                 110

Ile Ser Lys Ala Lys Gly Gln Pro Arg Glu Pro Gln Val Tyr Thr Leu
            115                 120                 125

Pro Pro Cys Arg Asp Glu Leu Thr Lys Asn Gln Val Ser Leu Trp Cys
            130                 135                 140

Leu Val Lys Gly Phe Tyr Pro Ser Asp Ile Ala Val Glu Trp Glu Ser
145                 150                 155                 160

Asn Gly Gln Pro Glu Asn Asn Tyr Lys Thr Thr Pro Pro Val Leu Asp
                165                 170                 175

Ser Asp Gly Ser Phe Phe Leu Tyr Ser Lys Leu Thr Val Asp Lys Ser
                180                 185                 190

Arg Trp Gln Gln Gly Asn Val Phe Ser Cys Ser Val Met His Glu Ala
                195                 200                 205

Leu His Asn His Tyr Thr Gln Lys Ser Leu Ser Leu Ser Pro Thr
                210                 215                 220
```

<210> SEQ ID NO 85
<211> LENGTH: 223
<212> TYPE: PRT
<213> ORGANISM: Artificial Sequence
<220> FEATURE:
<223> OTHER INFORMATION: Hole Fc

<400> SEQUENCE: 85

```
Asp Lys Thr His Thr Cys Pro Pro Cys Pro Ala Pro Gly Gly Pro Ser
1               5                   10                  15

Val Phe Leu Phe Pro Pro Lys Pro Lys Asp Thr Leu Met Arg Ser Arg
                20                  25                  30

Thr Pro Glu Val Thr Cys Val Val Val Asp Val Ser His Glu Asp Pro
            35                  40                  45

Glu Val Lys Phe Asn Trp Tyr Val Asp Gly Val Glu Val His Asn Ala
        50                  55                  60

Lys Thr Lys Pro Arg Glu Glu Gln Tyr Asn Ser Thr Tyr Arg Val Val
65                  70                  75                  80

Ser Val Leu Thr Val Leu His Gln Asp Trp Leu Asn Gly Lys Glu Tyr
                85                  90                  95

Lys Cys Lys Val Ser Asn Lys Ala Leu Pro Ala Pro Ile Glu Lys Thr
            100                 105                 110

Ile Ser Lys Ala Lys Gly Gln Pro Arg Glu Pro Gln Val Cys Thr Leu
            115                 120                 125

Pro Pro Ser Arg Asp Glu Leu Thr Lys Asn Gln Val Ser Leu Ser Cys
            130                 135                 140

Ala Val Lys Gly Phe Tyr Pro Ser Asp Ile Ala Val Glu Trp Glu Ser
145                 150                 155                 160

Asn Gly Gln Pro Glu Asn Asn Tyr Lys Thr Thr Pro Pro Val Leu Asp
                165                 170                 175

Ser Asp Gly Ser Phe Phe Leu Val Ser Lys Leu Thr Val Asp Lys Ser
                180                 185                 190

Arg Trp Gln Gln Gly Asn Val Phe Ser Cys Ser Val Met His Glu Ala
                195                 200                 205

Leu His Asn His Tyr Thr Gln Lys Ser Leu Ser Leu Ser Pro Thr
                210                 215                 220
```

-continued

```
<210> SEQ ID NO 86
<211> LENGTH: 226
<212> TYPE: PRT
<213> ORGANISM: Artificial Sequence
<220> FEATURE:
<223> OTHER INFORMATION: Knob Fc

<400> SEQUENCE: 86

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Cys Arg Asp Glu Leu Thr Lys Asn Gln Val Ser
    130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly
225

<210> SEQ ID NO 87
<211> LENGTH: 226
<212> TYPE: PRT
<213> ORGANISM: Artificial Sequence
<220> FEATURE:
<223> OTHER INFORMATION: Hole Fc

<400> SEQUENCE: 87

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Arg Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80
```

Arg Val Val Ser Val Leu Thr Val Leu His Gln Asp Trp Leu Asn Gly
                85                  90                  95
Lys Glu Tyr Lys Cys Lys Val Ser Asn Lys Ala Leu Pro Ala Pro Ile
            100                 105                 110
Glu Lys Thr Ile Ser Lys Ala Lys Gly Gln Pro Arg Glu Pro Gln Val
        115                 120                 125
Cys Thr Leu Pro Pro Ser Arg Asp Glu Leu Thr Lys Asn Gln Val Ser
    130                 135                 140
Leu Ser Cys Ala Val Lys Gly Phe Tyr Pro Ser Asp Ile Ala Val Glu
145                 150                 155                 160
Trp Glu Ser Asn Gly Gln Pro Glu Asn Asn Tyr Lys Thr Thr Pro Pro
                165                 170                 175
Val Leu Asp Ser Asp Gly Ser Phe Phe Leu Val Ser Lys Leu Thr Val
            180                 185                 190
Asp Lys Ser Arg Trp Gln Gln Gly Asn Val Phe Ser Cys Ser Val Met
        195                 200                 205
His Glu Ala Leu His Asn His Tyr Thr Gln Lys Ser Leu Ser Leu Ser
    210                 215                 220
Pro Gly
225

<210> SEQ ID NO 88
<211> LENGTH: 223
<212> TYPE: PRT
<213> ORGANISM: Artificial Sequence
<220> FEATURE:
<223> OTHER INFORMATION: Knob Fc

<400> SEQUENCE: 88

Asp Lys Thr His Thr Cys Pro Pro Cys Pro Ala Pro Gly Gly Pro Ser
1               5                   10                  15
Val Phe Leu Phe Pro Pro Lys Pro Lys Asp Thr Leu Met Ile Ser Arg
            20                  25                  30
Thr Pro Glu Val Thr Cys Val Val Asp Val Ser His Glu Asp Pro
        35                  40                  45
Glu Val Lys Phe Asn Trp Tyr Val Asp Gly Val Glu Val His Asn Ala
    50                  55                  60
Lys Thr Lys Pro Arg Glu Glu Gln Tyr Asn Ser Thr Tyr Arg Val Val
65                  70                  75                  80
Ser Val Leu Thr Val Leu His Gln Asp Trp Leu Asn Gly Lys Glu Tyr
                85                  90                  95
Lys Cys Lys Val Ser Asn Lys Ala Leu Pro Ala Pro Ile Glu Lys Thr
            100                 105                 110
Ile Ser Lys Ala Lys Gly Gln Pro Arg Glu Pro Gln Val Tyr Thr Leu
        115                 120                 125
Pro Pro Cys Arg Asp Glu Leu Thr Lys Asn Gln Val Ser Leu Trp Cys
    130                 135                 140
Leu Val Lys Gly Phe Tyr Pro Ser Asp Ile Ala Val Glu Trp Glu Ser
145                 150                 155                 160
Asn Gly Gln Pro Glu Asn Asn Tyr Lys Thr Thr Pro Pro Val Leu Asp
                165                 170                 175
Ser Asp Gly Ser Phe Phe Leu Tyr Ser Lys Leu Thr Val Asp Lys Ser
            180                 185                 190
Arg Trp Gln Gln Gly Asn Val Phe Ser Cys Ser Val Met His Glu Ala
        195                 200                 205

Leu His Asn His Tyr Thr Gln Lys Ser Leu Ser Leu Ser Pro Gly
    210                 215                 220

<210> SEQ ID NO 89
<211> LENGTH: 223
<212> TYPE: PRT
<213> ORGANISM: Artificial Sequence
<220> FEATURE:
<223> OTHER INFORMATION: Hole Fc

<400> SEQUENCE: 89

Asp Lys Thr His Thr Cys Pro Pro Cys Pro Ala Pro Gly Gly Pro Ser
1               5                   10                  15

Val Phe Leu Phe Pro Pro Lys Pro Lys Asp Thr Leu Met Arg Ser Arg
            20                  25                  30

Thr Pro Glu Val Thr Cys Val Val Val Asp Val Ser His Glu Asp Pro
        35                  40                  45

Glu Val Lys Phe Asn Trp Tyr Val Asp Gly Val Glu Val His Asn Ala
    50                  55                  60

Lys Thr Lys Pro Arg Glu Glu Gln Tyr Asn Ser Thr Tyr Arg Val Val
65                  70                  75                  80

Ser Val Leu Thr Val Leu His Gln Asp Trp Leu Asn Gly Lys Glu Tyr
                85                  90                  95

Lys Cys Lys Val Ser Asn Lys Ala Leu Pro Ala Pro Ile Glu Lys Thr
            100                 105                 110

Ile Ser Lys Ala Lys Gly Gln Pro Arg Glu Pro Gln Val Cys Thr Leu
        115                 120                 125

Pro Pro Ser Arg Asp Glu Leu Thr Lys Asn Gln Val Ser Leu Ser Cys
    130                 135                 140

Ala Val Lys Gly Phe Tyr Pro Ser Asp Ile Ala Val Glu Trp Glu Ser
145                 150                 155                 160

Asn Gly Gln Pro Glu Asn Asn Tyr Lys Thr Thr Pro Pro Val Leu Asp
                165                 170                 175

Ser Asp Gly Ser Phe Phe Leu Val Ser Lys Leu Thr Val Asp Lys Ser
            180                 185                 190

Arg Trp Gln Gln Gly Asn Val Phe Ser Cys Ser Val Met His Glu Ala
        195                 200                 205

Leu His Asn His Tyr Thr Gln Lys Ser Leu Ser Leu Ser Pro Gly
    210                 215                 220

<210> SEQ ID NO 90
<211> LENGTH: 226
<212> TYPE: PRT
<213> ORGANISM: Artificial Sequence
<220> FEATURE:
<223> OTHER INFORMATION: Hole Fc

<400> SEQUENCE: 90

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Cys Thr Leu Pro Pro Ser Arg Asp Glu Leu Thr Lys Asn Gln Val Ser
130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn Arg Tyr Thr Gln Lys Ser Leu Ser Leu Ser
    210                 215                 220

Pro Thr
225

<210> SEQ ID NO 91
<211> LENGTH: 223
<212> TYPE: PRT
<213> ORGANISM: Artificial Sequence
<220> FEATURE:
<223> OTHER INFORMATION: Hole Fc

<400> SEQUENCE: 91

Asp Lys Thr His Thr Cys Pro Pro Cys Pro Ala Pro Gly Gly Pro Ser
1               5                   10                  15

Val Phe Leu Phe Pro Pro Lys Pro Lys Asp Thr Leu Met Ile Ser Arg
            20                  25                  30

Thr Pro Glu Val Thr Cys Val Val Val Asp Val Ser His Glu Asp Pro
        35                  40                  45

Glu Val Lys Phe Asn Trp Tyr Val Asp Gly Val Glu Val His Asn Ala
    50                  55                  60

Lys Thr Lys Pro Arg Glu Glu Gln Tyr Asn Ser Thr Tyr Arg Val Val
65                  70                  75                  80

Ser Val Leu Thr Val Leu His Gln Asp Trp Leu Asn Gly Lys Glu Tyr
                85                  90                  95

Lys Cys Lys Val Ser Asn Lys Ala Leu Pro Ala Pro Ile Glu Lys Thr
            100                 105                 110

Ile Ser Lys Ala Lys Gly Gln Pro Arg Glu Pro Gln Val Cys Thr Leu
        115                 120                 125

Pro Pro Ser Arg Asp Glu Leu Thr Lys Asn Gln Val Ser Leu Ser Cys
130                 135                 140

Ala Val Lys Gly Phe Tyr Pro Ser Asp Ile Ala Val Glu Trp Glu Ser
145                 150                 155                 160

Asn Gly Gln Pro Glu Asn Asn Tyr Lys Thr Thr Pro Pro Val Leu Asp
                165                 170                 175

Ser Asp Gly Ser Phe Phe Leu Val Ser Lys Leu Thr Val Asp Lys Ser
            180                 185                 190

Arg Trp Gln Gln Gly Asn Val Phe Ser Cys Ser Val Met His Glu Ala
        195                 200                 205

Leu His Asn Arg Tyr Thr Gln Lys Ser Leu Ser Leu Ser Pro Thr
            210                 215                 220

<210> SEQ ID NO 92
<211> LENGTH: 226
<212> TYPE: PRT
<213> ORGANISM: Artificial Sequence
<220> FEATURE:
<223> OTHER INFORMATION: Hole Fc

<400> SEQUENCE: 92

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Cys Thr Leu Pro Pro Ser Arg Asp Glu Leu Thr Lys Asn Gln Val Ser
130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn Arg Tyr Thr Gln Lys Ser Leu Ser Leu Ser
    210                 215                 220

Pro Gly
225

<210> SEQ ID NO 93
<211> LENGTH: 223
<212> TYPE: PRT
<213> ORGANISM: Artificial Sequence
<220> FEATURE:
<223> OTHER INFORMATION: Hole Fc

<400> SEQUENCE: 93

Asp Lys Thr His Thr Cys Pro Pro Cys Pro Ala Pro Gly Gly Pro Ser
1               5                   10                  15

Val Phe Leu Phe Pro Pro Lys Pro Lys Asp Thr Leu Met Ile Ser Arg
            20                  25                  30

Thr Pro Glu Val Thr Cys Val Val Val Asp Val Ser His Glu Asp Pro
        35                  40                  45

Glu Val Lys Phe Asn Trp Tyr Val Asp Gly Val Glu Val His Asn Ala

Lys Thr Lys Pro Arg Glu Glu Gln Tyr Asn Ser Thr Tyr Arg Val Val
65                  70                  75                  80

Ser Val Leu Thr Val Leu His Gln Asp Trp Leu Asn Gly Lys Glu Tyr
            85                  90                  95

Lys Cys Lys Val Ser Asn Lys Ala Leu Pro Ala Pro Ile Glu Lys Thr
            100                 105                 110

Ile Ser Lys Ala Lys Gly Gln Pro Arg Glu Pro Gln Val Cys Thr Leu
            115                 120                 125

Pro Pro Ser Arg Asp Glu Leu Thr Lys Asn Gln Val Ser Leu Ser Cys
            130                 135                 140

Ala Val Lys Gly Phe Tyr Pro Ser Asp Ile Ala Val Glu Trp Glu Ser
145                 150                 155                 160

Asn Gly Gln Pro Glu Asn Asn Tyr Lys Thr Thr Pro Pro Val Leu Asp
                165                 170                 175

Ser Asp Gly Ser Phe Phe Leu Val Ser Lys Leu Thr Val Asp Lys Ser
            180                 185                 190

Arg Trp Gln Gln Gly Asn Val Phe Ser Cys Ser Val Met His Glu Ala
            195                 200                 205

Leu His Asn Arg Tyr Thr Gln Lys Ser Leu Ser Leu Ser Pro Gly
            210                 215                 220

<210> SEQ ID NO 94
<211> LENGTH: 226
<212> TYPE: PRT
<213> ORGANISM: Artificial Sequence
<220> FEATURE:
<223> OTHER INFORMATION: Knob Fc

<400> SEQUENCE: 94

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Tyr
            20                  25                  30

Ile Ser Arg Thr Pro Glu Val Thr Cys Val Val Val Asp Val Ser His
            35                  40                  45

Glu Asp Pro Glu Val Lys Phe Asn Trp Tyr Val Asp Gly Val Glu Val
50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
            85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
            115                 120                 125

Tyr Thr Leu Pro Pro Cys Arg Asp Glu Leu Thr Lys Asn Gln Val Ser
            130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Val

```
              195                 200                 205
His Glu Ala Leu His Asn His Tyr Thr Gln Lys Ser Leu Ser Leu Ser
    210                 215                 220

Pro Thr
225

<210> SEQ ID NO 95
<211> LENGTH: 223
<212> TYPE: PRT
<213> ORGANISM: Artificial Sequence
<220> FEATURE:
<223> OTHER INFORMATION: Knob Fc

<400> SEQUENCE: 95

Asp Lys Thr His Thr Cys Pro Pro Cys Pro Ala Pro Gly Gly Pro Ser
1               5                   10                  15

Val Phe Leu Phe Pro Pro Lys Pro Lys Asp Thr Leu Tyr Ile Ser Arg
            20                  25                  30

Thr Pro Glu Val Thr Cys Val Val Val Asp Val Ser His Glu Asp Pro
        35                  40                  45

Glu Val Lys Phe Asn Trp Tyr Val Asp Gly Val Glu Val His Asn Ala
    50                  55                  60

Lys Thr Lys Pro Arg Glu Glu Gln Tyr Asn Ser Thr Tyr Arg Val Val
65                  70                  75                  80

Ser Val Leu Thr Val Leu His Gln Asp Trp Leu Asn Gly Lys Glu Tyr
                85                  90                  95

Lys Cys Lys Val Ser Asn Lys Ala Leu Pro Ala Pro Ile Glu Lys Thr
            100                 105                 110

Ile Ser Lys Ala Lys Gly Gln Pro Arg Glu Pro Gln Val Tyr Thr Leu
        115                 120                 125

Pro Pro Cys Arg Asp Glu Leu Thr Lys Asn Gln Val Ser Leu Trp Cys
    130                 135                 140

Leu Val Lys Gly Phe Tyr Pro Ser Asp Ile Ala Val Glu Trp Glu Ser
145                 150                 155                 160

Asn Gly Gln Pro Glu Asn Asn Tyr Lys Thr Thr Pro Pro Val Leu Asp
                165                 170                 175

Ser Asp Gly Ser Phe Phe Leu Tyr Ser Lys Leu Thr Val Asp Lys Ser
            180                 185                 190

Arg Trp Gln Gln Gly Asn Val Phe Ser Cys Ser Val Val His Glu Ala
        195                 200                 205

Leu His Asn His Tyr Thr Gln Lys Ser Leu Ser Leu Ser Pro Thr
    210                 215                 220

<210> SEQ ID NO 96
<211> LENGTH: 226
<212> TYPE: PRT
<213> ORGANISM: Artificial Sequence
<220> FEATURE:
<223> OTHER INFORMATION: Knob Fc

<400> SEQUENCE: 96

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Tyr
            20                  25                  30

Ile Ser Arg Thr Pro Glu Val Thr Cys Val Val Val Asp Val Ser His
        35                  40                  45
```

```
Glu Asp Pro Glu Val Lys Phe Asn Trp Tyr Val Asp Gly Val Glu Val
 50                  55                  60

His Asn Ala Lys Thr Lys Pro Arg Glu Gln Tyr Asn Ser Thr Tyr
 65                  70                  75                  80

Arg Val Val Ser Val Leu Thr Val Leu His Gln Asp Trp Leu Asn Gly
                 85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Cys Arg Asp Glu Leu Thr Lys Asn Gln Val Ser
130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Val
        195                 200                 205

His Glu Ala Leu His Asn His Tyr Thr Gln Lys Ser Leu Ser Leu Ser
    210                 215                 220

Pro Gly
225

<210> SEQ ID NO 97
<211> LENGTH: 223
<212> TYPE: PRT
<213> ORGANISM: Artificial Sequence
<220> FEATURE:
<223> OTHER INFORMATION: Knob Fc

<400> SEQUENCE: 97

Asp Lys Thr His Thr Cys Pro Pro Cys Pro Ala Pro Gly Gly Pro Ser
1               5                   10                  15

Val Phe Leu Phe Pro Pro Lys Pro Lys Asp Thr Leu Tyr Ile Ser Arg
            20                  25                  30

Thr Pro Glu Val Thr Cys Val Val Val Asp Val Ser His Glu Asp Pro
        35                  40                  45

Glu Val Lys Phe Asn Trp Tyr Val Asp Gly Val Glu Val His Asn Ala
 50                  55                  60

Lys Thr Lys Pro Arg Glu Glu Gln Tyr Asn Ser Thr Tyr Arg Val Val
 65                  70                  75                  80

Ser Val Leu Thr Val Leu His Gln Asp Trp Leu Asn Gly Lys Glu Tyr
                 85                  90                  95

Lys Cys Lys Val Ser Asn Lys Ala Leu Pro Ala Pro Ile Glu Lys Thr
            100                 105                 110

Ile Ser Lys Ala Lys Gly Gln Pro Arg Glu Pro Gln Val Tyr Thr Leu
        115                 120                 125

Pro Pro Cys Arg Asp Glu Leu Thr Lys Asn Gln Val Ser Leu Trp Cys
130                 135                 140

Leu Val Lys Gly Phe Tyr Pro Ser Asp Ile Ala Val Glu Trp Glu Ser
145                 150                 155                 160

Asn Gly Gln Pro Glu Asn Asn Tyr Lys Thr Thr Pro Pro Val Leu Asp
                165                 170                 175
```

```
Ser Asp Gly Ser Phe Phe Leu Tyr Ser Lys Leu Thr Val Asp Lys Ser
            180                 185                 190

Arg Trp Gln Gln Gly Asn Val Phe Ser Cys Ser Val Val His Glu Ala
        195                 200                 205

Leu His Asn His Tyr Thr Gln Lys Ser Leu Ser Leu Ser Pro Gly
    210                 215                 220
```

<210> SEQ ID NO 98
<211> LENGTH: 226
<212> TYPE: PRT
<213> ORGANISM: Artificial Sequence
<220> FEATURE:
<223> OTHER INFORMATION: Hole Fc

<400> SEQUENCE: 98

```
Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Tyr
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Cys Thr Leu Pro Pro Ser Arg Asp Glu Leu Thr Lys Asn Gln Val Ser
130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
            180                 185                 190

Asp Lys Ser Arg Trp Gln Gln Gly Asn Val Phe Ser Cys Ser Val Val
        195                 200                 205

His Glu Ala Leu His Asn Arg Tyr Thr Gln Lys Ser Leu Ser Leu Ser
    210                 215                 220

Pro Thr
225
```

<210> SEQ ID NO 99
<211> LENGTH: 223
<212> TYPE: PRT
<213> ORGANISM: Artificial Sequence
<220> FEATURE:
<223> OTHER INFORMATION: Hole Fc

<400> SEQUENCE: 99

```
Asp Lys Thr His Thr Cys Pro Pro Cys Pro Ala Pro Gly Gly Pro Ser
1               5                   10                  15

Val Phe Leu Phe Pro Pro Lys Pro Lys Asp Thr Leu Tyr Ile Ser Arg
            20                  25                  30
```

Thr Pro Glu Val Thr Cys Val Val Asp Val Ser His Glu Asp Pro
            35                  40                  45

Glu Val Lys Phe Asn Trp Tyr Val Asp Gly Val Glu Val His Asn Ala
 50                  55                  60

Lys Thr Lys Pro Arg Glu Glu Gln Tyr Asn Ser Thr Tyr Arg Val Val
 65                  70                  75                  80

Ser Val Leu Thr Val Leu His Gln Asp Trp Leu Asn Gly Lys Glu Tyr
                 85                  90                  95

Lys Cys Lys Val Ser Asn Lys Ala Leu Pro Ala Pro Ile Glu Lys Thr
            100                 105                 110

Ile Ser Lys Ala Lys Gly Gln Pro Arg Glu Pro Gln Val Cys Thr Leu
            115                 120                 125

Pro Pro Ser Arg Asp Glu Leu Thr Lys Asn Gln Val Ser Leu Ser Cys
130                 135                 140

Ala Val Lys Gly Phe Tyr Pro Ser Asp Ile Ala Val Glu Trp Glu Ser
145                 150                 155                 160

Asn Gly Gln Pro Glu Asn Asn Tyr Lys Thr Thr Pro Pro Val Leu Asp
                165                 170                 175

Ser Asp Gly Ser Phe Phe Leu Val Ser Lys Leu Thr Val Asp Lys Ser
            180                 185                 190

Arg Trp Gln Gln Gly Asn Val Phe Ser Cys Ser Val Val His Glu Ala
            195                 200                 205

Leu His Asn Arg Tyr Thr Gln Lys Ser Leu Ser Leu Ser Pro Thr
            210                 215                 220

<210> SEQ ID NO 100
<211> LENGTH: 226
<212> TYPE: PRT
<213> ORGANISM: Artificial Sequence
<220> FEATURE:
<223> OTHER INFORMATION: Hole Fc

<400> SEQUENCE: 100

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Tyr
            20                  25                  30

Ile Ser Arg Thr Pro Glu Val Thr Cys Val Val Val Asp Val Ser His
            35                  40                  45

Glu Asp Pro Glu Val Lys Phe Asn Trp Tyr Val Asp Gly Val Glu Val
 50                  55                  60

His Asn Ala Lys Thr Lys Pro Arg Glu Glu Gln Tyr Asn Ser Thr Tyr
 65                  70                  75                  80

Arg Val Val Ser Val Leu Thr Val Leu His Gln Asp Trp Leu Asn Gly
                 85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
            115                 120                 125

Cys Thr Leu Pro Pro Ser Arg Asp Glu Leu Thr Lys Asn Gln Val Ser
130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

```
Val Leu Asp Ser Asp Gly Ser Phe Phe Leu Val Ser Lys Leu Thr Val
            180                 185                 190

Asp Lys Ser Arg Trp Gln Gln Gly Asn Val Phe Ser Cys Ser Val Val
            195                 200                 205

His Glu Ala Leu His Asn Arg Tyr Thr Gln Lys Ser Leu Ser Leu Ser
210                 215                 220

Pro Gly
225

<210> SEQ ID NO 101
<211> LENGTH: 223
<212> TYPE: PRT
<213> ORGANISM: Artificial Sequence
<220> FEATURE:
<223> OTHER INFORMATION: Hole Fc

<400> SEQUENCE: 101

Asp Lys Thr His Thr Cys Pro Pro Cys Pro Ala Pro Gly Gly Pro Ser
1               5                   10                  15

Val Phe Leu Phe Pro Pro Lys Pro Lys Asp Thr Leu Tyr Ile Ser Arg
            20                  25                  30

Thr Pro Glu Val Thr Cys Val Val Asp Val Ser His Glu Asp Pro
        35                  40                  45

Glu Val Lys Phe Asn Trp Tyr Val Asp Gly Val Glu Val His Asn Ala
    50                  55                  60

Lys Thr Lys Pro Arg Glu Glu Gln Tyr Asn Ser Thr Tyr Arg Val Val
65                  70                  75                  80

Ser Val Leu Thr Val Leu His Gln Asp Trp Leu Asn Gly Lys Glu Tyr
                85                  90                  95

Lys Cys Lys Val Ser Asn Lys Ala Leu Pro Ala Pro Ile Glu Lys Thr
            100                 105                 110

Ile Ser Lys Ala Lys Gly Gln Pro Arg Glu Pro Gln Val Cys Thr Leu
        115                 120                 125

Pro Pro Ser Arg Asp Glu Leu Thr Lys Asn Gln Val Ser Leu Ser Cys
130                 135                 140

Ala Val Lys Gly Phe Tyr Pro Ser Asp Ile Ala Val Glu Trp Glu Ser
145                 150                 155                 160

Asn Gly Gln Pro Glu Asn Asn Tyr Lys Thr Thr Pro Pro Val Leu Asp
                165                 170                 175

Ser Asp Gly Ser Phe Phe Leu Val Ser Lys Leu Thr Val Asp Lys Ser
            180                 185                 190

Arg Trp Gln Gln Gly Asn Val Phe Ser Cys Ser Val Val His Glu Ala
        195                 200                 205

Leu His Asn Arg Tyr Thr Gln Lys Ser Leu Ser Leu Ser Pro Gly
    210                 215                 220

<210> SEQ ID NO 102
<211> LENGTH: 5
<212> TYPE: PRT
<213> ORGANISM: Artificial Sequence
<220> FEATURE:
<223> OTHER INFORMATION: Peptide Linker

<400> SEQUENCE: 102

Pro Gly Gly Gly Gly
1               5
```

```
<210> SEQ ID NO 103
<211> LENGTH: 4
<212> TYPE: PRT
<213> ORGANISM: Artificial Sequence
<220> FEATURE:
<223> OTHER INFORMATION: Peptide Linker

<400> SEQUENCE: 103

Gly Gly Gly Gly
1

<210> SEQ ID NO 104
<211> LENGTH: 18
<212> TYPE: PRT
<213> ORGANISM: Artificial Sequence
<220> FEATURE:
<223> OTHER INFORMATION: Linker

<400> SEQUENCE: 104

Gly Pro Ala Gly Leu Gly Leu Glu Pro Asp Gly Ser Arg Gln Ala Arg
1               5                   10                  15

Val Gly

<210> SEQ ID NO 105
<211> LENGTH: 18
<212> TYPE: PRT
<213> ORGANISM: Artificial Sequence
<220> FEATURE:
<223> OTHER INFORMATION: Linker

<400> SEQUENCE: 105

Gly Gly Ser Gly Gly Gly Gly Ile Glu Pro Asp Ile Gly Gly Ser Gly
1               5                   10                  15

Gly Ser

<210> SEQ ID NO 106
<211> LENGTH: 18
<212> TYPE: PRT
<213> ORGANISM: Artificial Sequence
<220> FEATURE:
<223> OTHER INFORMATION: Linker

<400> SEQUENCE: 106

Gly Gly Ser Gly Gly Gly Gly Leu Glu Ala Asp Thr Gly Gly Ser Gly
1               5                   10                  15

Gly Ser

<210> SEQ ID NO 107
<211> LENGTH: 9
<212> TYPE: PRT
<213> ORGANISM: Artificial Sequence
<220> FEATURE:
<223> OTHER INFORMATION: Linker

<400> SEQUENCE: 107

Gly Ser Ile Glu Pro Asp Ile Gly Ser
1               5

<210> SEQ ID NO 108
<211> LENGTH: 9
<212> TYPE: PRT
<213> ORGANISM: Artificial Sequence
<220> FEATURE:
<223> OTHER INFORMATION: Linker

<400> SEQUENCE: 108
```

```
Gly Ser Leu Glu Ala Asp Thr Gly Ser
1               5

<210> SEQ ID NO 109
<211> LENGTH: 18
<212> TYPE: PRT
<213> ORGANISM: Artificial Sequence
<220> FEATURE:
<223> OTHER INFORMATION: Linker

<400> SEQUENCE: 109

Gly Gly Ser Gly Gly Gly Gly Ile Glu Pro Asp Gly Gly Ser Gly
1               5                   10                  15

Gly Ser

<210> SEQ ID NO 110
<211> LENGTH: 18
<212> TYPE: PRT
<213> ORGANISM: Artificial Sequence
<220> FEATURE:
<223> OTHER INFORMATION: Linker

<400> SEQUENCE: 110

Gly Gly Ser Gly Gly Gly Gly Ile Glu Pro Asp Val Gly Gly Ser Gly
1               5                   10                  15

Gly Ser

<210> SEQ ID NO 111
<211> LENGTH: 18
<212> TYPE: PRT
<213> ORGANISM: Artificial Sequence
<220> FEATURE:
<223> OTHER INFORMATION: Linker

<400> SEQUENCE: 111

Gly Gly Ser Gly Gly Gly Gly Ile Glu Pro Asp Ser Gly Gly Ser Gly
1               5                   10                  15

Gly Ser

<210> SEQ ID NO 112
<211> LENGTH: 18
<212> TYPE: PRT
<213> ORGANISM: Artificial Sequence
<220> FEATURE:
<223> OTHER INFORMATION: Linker

<400> SEQUENCE: 112

Gly Gly Ser Gly Gly Gly Gly Ile Glu Pro Asp Thr Gly Gly Ser Gly
1               5                   10                  15

Gly Ser

<210> SEQ ID NO 113
<211> LENGTH: 12
<212> TYPE: PRT
<213> ORGANISM: Artificial Sequence
<220> FEATURE:
<223> OTHER INFORMATION: Linker

<400> SEQUENCE: 113

Gly Gly Gly Ser Leu Glu Pro Asp Gly Ser Gly Ser
1               5                   10

<210> SEQ ID NO 114
```

```
<211> LENGTH: 18
<212> TYPE: PRT
<213> ORGANISM: Artificial Sequence
<220> FEATURE:
<223> OTHER INFORMATION: Linker

<400> SEQUENCE: 114

Gly Pro Ala Gly Leu Gly Leu Glu Ala Asp Gly Ser Arg Gln Ala Arg
1               5                   10                  15

Val Gly

<210> SEQ ID NO 115
<211> LENGTH: 15
<212> TYPE: PRT
<213> ORGANISM: Artificial Sequence
<220> FEATURE:
<223> OTHER INFORMATION: Linker

<400> SEQUENCE: 115

Gly Gly Glu Gly Gly Gly Gly Ser Gly Gly Ser Gly Gly Gly Ser
1               5                   10                  15

<210> SEQ ID NO 116
<211> LENGTH: 18
<212> TYPE: PRT
<213> ORGANISM: Artificial Sequence
<220> FEATURE:
<223> OTHER INFORMATION: Linker

<400> SEQUENCE: 116

Gly Ser Ser Ala Gly Ser Glu Ala Gly Gly Ser Gly Gln Ala Gly Val
1               5                   10                  15

Gly Ser

<210> SEQ ID NO 117
<211> LENGTH: 18
<212> TYPE: PRT
<213> ORGANISM: Artificial Sequence
<220> FEATURE:
<223> OTHER INFORMATION: Linker

<400> SEQUENCE: 117

Gly Gly Ser Gly Gly Gly Gly Leu Glu Ala Glu Gly Ser Gly Gly Gly
1               5                   10                  15

Gly Ser

<210> SEQ ID NO 118
<211> LENGTH: 18
<212> TYPE: PRT
<213> ORGANISM: Artificial Sequence
<220> FEATURE:
<223> OTHER INFORMATION: Linker

<400> SEQUENCE: 118

Gly Gly Ser Gly Gly Gly Gly Ile Glu Pro Asp Pro Gly Gly Ser Gly
1               5                   10                  15

Gly Ser

<210> SEQ ID NO 119
<211> LENGTH: 18
<212> TYPE: PRT
<213> ORGANISM: Artificial Sequence
<220> FEATURE:
<223> OTHER INFORMATION: Linker
```

<400> SEQUENCE: 119

Gly Gly Gly Gly Gly Ser Gly Gly Gly Gly Ser Gly Gly Gly Gly
1               5                   10                  15
Gly Ser

<210> SEQ ID NO 120
<211> LENGTH: 129
<212> TYPE: PRT
<213> ORGANISM: Artificial Sequence
<220> FEATURE:
<223> OTHER INFORMATION: FR alpha sdAb

<400> SEQUENCE: 120

Gln Leu Gln Leu Gln Glu Ser Gly Gly Gly Leu Val Gln Pro Gly Gly
1               5                   10                  15

Ser Leu Arg Leu Ser Cys Ala Ala Ser Gly Phe Thr Leu Asp Asn Tyr
            20                  25                  30

Ala Ile Gly Trp Phe Arg Gln Ala Pro Gly Lys Glu Arg Glu Gly Val
        35                  40                  45

Ser Cys Ile Ser Ser Ser Asp Gly Ser Thr Tyr Tyr Ala Asp Ser Val
    50                  55                  60

Lys Gly Arg Phe Thr Ile Ser Arg Asn Asn Ala Lys Gly Thr Val Tyr
65                  70                  75                  80

Leu Leu Met Asn Ser Leu Lys Pro Glu Asp Thr Ala Val Tyr Tyr Cys
                85                  90                  95

Ala Thr Glu Leu Val Pro Ala Cys Thr Tyr Ser Asn Gly Arg Gly Pro
            100                 105                 110

Leu Asp Gly Met Asp Tyr Trp Gly Lys Gly Thr Gln Val Thr Val Lys
        115                 120                 125

Pro

<210> SEQ ID NO 121
<211> LENGTH: 119
<212> TYPE: PRT
<213> ORGANISM: Artificial Sequence
<220> FEATURE:
<223> OTHER INFORMATION: FR alpha sdAb

<400> SEQUENCE: 121

Glu Val Gln Leu Leu Glu Ser Gly Gly Gly Glu Val Gln Pro Gly Gly
1               5                   10                  15

Ser Leu Arg Leu Ser Cys Ala Ala Ser Gly Ser Ile Phe Ser Ile Asp
            20                  25                  30

Ala Thr Ala Trp Tyr Arg Gln Ala Pro Gly Lys Gln Arg Glu Leu Val
        35                  40                  45

Ala Ile Ile Thr Ser Ser Gly Ser Thr Asn Tyr Pro Glu Ser Val Lys
    50                  55                  60

Gly Arg Phe Thr Ile Ser Arg Asp Asn Ala Lys Asn Thr Val Tyr Leu
65                  70                  75                  80

Gln Met Ser Ser Leu Arg Ala Glu Asp Thr Ala Val Tyr Tyr Cys Asn
                85                  90                  95

Ala Ile Thr Arg Tyr Gly Gly Ser Thr Tyr Asp Phe Trp Gly Gln Gly
            100                 105                 110

Thr Leu Val Thr Val Lys Pro
        115

<210> SEQ ID NO 122

<211> LENGTH: 101
<212> TYPE: PRT
<213> ORGANISM: Artificial Sequence
<220> FEATURE:
<223> OTHER INFORMATION: FR alpha sdAb

<400> SEQUENCE: 122

Glu Val Gln Pro Gly Gly Ser Leu Arg Leu Ser Cys Ala Ala Ser Glu
1               5                   10                  15

Thr Phe Gly Val Val Phe Thr Leu Gly Trp Tyr Arg Gln Ala Pro Gly
            20                  25                  30

Lys Gly Arg Glu Phe Val Ala Arg Val Thr Gly Thr Asp Thr Val Asp
        35                  40                  45

Tyr Ala Glu Ser Val Lys Gly Arg Phe Thr Ile Ser Ser Asp Phe Ala
    50                  55                  60

Arg Asn Thr Val Tyr Leu Gln Met Asn Ser Leu Arg Ala Glu Asp Thr
65                  70                  75                  80

Ala Val Tyr Tyr Cys Asn Thr Gly Ala Tyr Trp Gly Gln Gly Thr Leu
                85                  90                  95

Val Thr Val Lys Pro
            100

<210> SEQ ID NO 123
<211> LENGTH: 125
<212> TYPE: PRT
<213> ORGANISM: Artificial Sequence
<220> FEATURE:
<223> OTHER INFORMATION: cMET sdAb

<400> SEQUENCE: 123

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ile Leu Asp Tyr Tyr
            20                  25                  30

Ala Ile Gly Trp Phe Arg Gln Ala Pro Gly Lys Glu Arg Glu Gly Val
        35                  40                  45

Leu Cys Ile Asp Ala Ser Asp Asp Ile Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Gly Val Tyr Tyr Cys
                85                  90                  95

Ala Thr Pro Ile Gly Leu Ser Ser Cys Leu Leu Glu Tyr Asp Tyr
            100                 105                 110

Asp Tyr Trp Gly Gln Gly Thr Leu Val Thr Val Lys Pro
        115                 120                 125

<210> SEQ ID NO 124
<211> LENGTH: 245
<212> TYPE: PRT
<213> ORGANISM: Artificial Sequence
<220> FEATURE:
<223> OTHER INFORMATION: B7H3 scFv

<400> SEQUENCE: 124

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Gly Met His Trp Val Arg Gln Ala Pro Gly Lys Gly Leu Glu Trp Val
         35                  40                  45

Ala Tyr Ile Ser Ser Asp Ser Ala Ile Tyr Tyr Ala Asp Thr Val
 50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Asp Glu Asp Thr Ala Val Tyr Tyr Cys
                 85                  90                  95

Gly Arg Gly Arg Glu Asn Ile Tyr Tyr Gly Ser Arg Leu Asp Tyr Trp
                100                 105                 110

Gly Gln Gly Thr Thr Val Thr Val Ser Ser Ser Gly Gly Gly Gly Ser
                115                 120                 125

Gly Gly Gly Gly Ser Gly Gly Gly Ser Asp Ile Gln Leu Thr Gln
                130                 135                 140

Ser Pro Ser Phe Leu Ser Ala Ser Val Gly Asp Arg Val Thr Ile Thr
145                 150                 155                 160

Cys Lys Ala Ser Gln Asn Val Asp Thr Asn Val Ala Trp Tyr Gln Gln
                165                 170                 175

Lys Pro Gly Lys Ala Pro Lys Ala Leu Ile Tyr Ser Ala Ser Tyr Arg
                180                 185                 190

Tyr Ser Gly Val Pro Ser Arg Phe Ser Gly Ser Gly Ser Gly Thr Asp
                195                 200                 205

Phe Thr Leu Thr Ile Ser Ser Leu Gln Pro Glu Asp Phe Ala Thr Tyr
                210                 215                 220

Tyr Cys Gln Gln Tyr Asn Asn Tyr Pro Phe Thr Phe Gly Gln Gly Thr
225                 230                 235                 240

Lys Leu Glu Ile Lys
                245

<210> SEQ ID NO 125
<211> LENGTH: 247
<212> TYPE: PRT
<213> ORGANISM: Artificial Sequence
<220> FEATURE:
<223> OTHER INFORMATION: CD20 scFv

<400> SEQUENCE: 125

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Ser Tyr Ser
                20                  25                  30

Trp Ile Asn Trp Val Arg Gln Ala Pro Gly Gln Gly Leu Glu Trp Met
                35                  40                  45

Gly Arg Ile Phe Pro Gly Asp Gly Asp Thr Asp Tyr Asn Gly Lys Phe
 50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                 85                  90                  95

Ala Arg Asn Val Phe Asp Gly Tyr Trp Leu Val Tyr Trp Gly Gln Gly
                100                 105                 110

Thr Leu Val Thr Val Ser Gly Ser Gly Gly Gly Ser Gly Gly Gly
                115                 120                 125

Gly Thr Gly Gly Gly Gly Ser Asp Ile Val Met Thr Gln Thr Pro Leu
                130                 135                 140

Ser Leu Pro Val Thr Pro Gly Glu Pro Ala Ser Ile Ser Cys Arg Ser
145                 150                 155                 160

Ser Lys Ser Leu Leu His Ser Asn Gly Ile Thr Tyr Leu Tyr Trp Tyr
            165                 170                 175

Leu Gln Lys Pro Gly Gln Ser Pro Gln Leu Leu Ile Tyr Gln Met Ser
            180                 185                 190

Asn Leu Val Ser Gly Val Pro Asp Arg Phe Ser Gly Ser Gly Ser Gly
            195                 200                 205

Thr Asp Phe Thr Leu Lys Ile Ser Arg Val Glu Ala Glu Asp Val Gly
            210                 215                 220

Val Tyr Tyr Cys Ala Gln Asn Leu Glu Leu Pro Tyr Thr Phe Gly Gly
225                 230                 235                 240

Gly Thr Lys Val Glu Ile Lys
                245

<210> SEQ ID NO 126
<211> LENGTH: 241
<212> TYPE: PRT
<213> ORGANISM: Artificial Sequence
<220> FEATURE:
<223> OTHER INFORMATION: DLL3 scFv

<400> SEQUENCE: 126

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Pro Gly Lys Gly Leu Glu Trp Ile
            35                  40                  45

Gly Tyr Val Tyr Tyr Ser Gly Thr Thr Asn Tyr Asn Pro Ser Leu Lys
        50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Ser Ile Ala Val Thr Gly Phe Tyr Phe Asp Tyr Trp Gly Gln Gly Thr
            100                 105                 110

Leu Val Thr Val Ser Ser Gly Gly Gly Gly Ser Gly Gly Gly Gly Ser
            115                 120                 125

Gly Gly Gly Gly Ser Glu Ile Val Leu Thr Gln Ser Pro Gly Thr Leu
        130                 135                 140

Ser Leu Ser Pro Gly Glu Arg Val Thr Leu Ser Cys Arg Ala Ser Gln
145                 150                 155                 160

Arg Val Asn Asn Asn Tyr Leu Ala Trp Tyr Gln Gln Arg Pro Gly Gln
                165                 170                 175

Ala Pro Arg Leu Leu Ile Tyr Gly Ala Ser Ser Arg Ala Thr Gly Ile
            180                 185                 190

Pro Asp Arg Phe Ser Gly Ser Gly Ser Gly Thr Asp Phe Thr Leu Thr
            195                 200                 205

Ile Ser Arg Leu Glu Pro Glu Asp Phe Ala Val Tyr Tyr Cys Gln Gln
            210                 215                 220

Tyr Asp Arg Ser Pro Leu Thr Phe Gly Gly Gly Thr Lys Leu Glu Ile
225                 230                 235                 240

Lys

```
<210> SEQ ID NO 127
<211> LENGTH: 225
<212> TYPE: PRT
<213> ORGANISM: Artificial Sequence
<220> FEATURE:
<223> OTHER INFORMATION: B7H3 Fd

<400> SEQUENCE: 127

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Gly Met His Trp Val Arg Gln Ala Pro Gly Lys Gly Leu Glu Trp Val
        35                  40                  45

Ala Tyr Ile Ser Ser Asp Ser Ser Ala Ile Tyr Tyr Ala Asp Thr Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Asp Glu Asp Thr Ala Val Tyr Tyr Cys
                85                  90                  95

Gly Arg Gly Arg Glu Asn Ile Tyr Tyr Gly Ser Arg Leu Asp Tyr Trp
            100                 105                 110

Gly Gln Gly Thr Thr Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Cys
225

<210> SEQ ID NO 128
<211> LENGTH: 214
<212> TYPE: PRT
<213> ORGANISM: Artificial Sequence
<220> FEATURE:
<223> OTHER INFORMATION: B7H3 LC

<400> SEQUENCE: 128

Asp Ile Gln Leu Thr Gln Ser Pro Ser Phe Leu Ser Ala Ser Val Gly
1               5                   10                  15

Asp Arg Val Thr Ile Thr Cys Lys Ala Ser Gln Asn Val Asp Thr Asn
            20                  25                  30

Val Ala Trp Tyr Gln Gln Lys Pro Gly Lys Ala Pro Lys Ala Leu Ile
        35                  40                  45

Tyr Ser Ala Ser Tyr Arg Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80
```

```
Glu Asp Phe Ala Thr Tyr Tyr Cys Gln Gln Tyr Asn Asn Tyr Pro Phe
                85                  90                  95
Thr Phe Gly Gln Gly Thr Lys Leu Glu Ile Lys Arg Thr Val Ala Ala
            100                 105                 110
Pro Ser Val Phe Ile Phe Pro Pro Ser Asp Glu Gln Leu Lys Ser Gly
        115                 120                 125
Thr Ala Ser Val Val Cys Leu Leu Asn Asn Phe Tyr Pro Arg Glu Ala
    130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
            180                 185                 190
Ala Cys Glu Val Thr His Gln Gly Leu Ser Ser Pro Val Thr Lys Ser
        195                 200                 205
Phe Asn Arg Gly Glu Cys
    210

<210> SEQ ID NO 129
<211> LENGTH: 225
<212> TYPE: PRT
<213> ORGANISM: Artificial Sequence
<220> FEATURE:
<223> OTHER INFORMATION: 5T4 Fd

<400> SEQUENCE: 129

Glu Val Gln Leu Val Glu Ser Gly Gly Gly Leu Val Gln Pro Lys Gly
1               5                   10                  15
Ser Leu Lys Leu Ser Cys Ala Ala Ser Gly Phe Thr Phe Asn Thr Tyr
            20                  25                  30
Ala Met Asn Trp Val Arg Gln Ala Pro Gly Lys Gly Leu Glu Trp Val
        35                  40                  45
Ala Arg Ile Arg Ser Lys Ser Asn Asn Tyr Ala Thr Tyr Tyr Ala Asp
    50                  55                  60
Ser Val Lys Asp Arg Phe Thr Ile Ser Arg Asp Asp Ser Gln Ser Met
65                  70                  75                  80
Leu Tyr Leu Gln Met Asn Asn Leu Lys Thr Glu Asp Thr Ala Met Tyr
                85                  90                  95
Tyr Cys Val Arg Gln Trp Asp Tyr Asp Val Arg Ala Met Asn Tyr Trp
            100                 105                 110
Gly Gln Gly Thr Ser Val Thr Val Ser Ser Ala Ser Thr Lys Gly Pro
        115                 120                 125
Ser Val Phe Pro Leu Ala Pro Ser Ser Lys Ser Thr Ser Gly Gly Thr
    130                 135                 140
Ala Ala Leu Gly Cys Leu Val Lys Asp Tyr Phe Pro Glu Pro Val Thr
145                 150                 155                 160
Val Ser Trp Asn Ser Gly Ala Leu Thr Ser Gly Val His Thr Phe Pro
                165                 170                 175
Ala Val Leu Gln Ser Ser Gly Leu Tyr Ser Leu Ser Ser Val Val Thr
            180                 185                 190
Val Pro Ser Ser Ser Leu Gly Thr Gln Thr Tyr Ile Cys Asn Val Asn
        195                 200                 205
His Lys Pro Ser Asn Thr Lys Val Asp Lys Lys Val Glu Pro Lys Ser
    210                 215                 220
```

Cys
225

<210> SEQ ID NO 130
<211> LENGTH: 214
<212> TYPE: PRT
<213> ORGANISM: Artificial Sequence
<220> FEATURE:
<223> OTHER INFORMATION: 5T4 LC

<400> SEQUENCE: 130

Asp Ile Val Met Thr Gln Ser His Ile Phe Met Ser Thr Ser Val Gly
1               5                   10                  15

Asp Arg Val Ser Ile Thr Cys Lys Ala Ser Gln Asp Val Asp Thr Ala
            20                  25                  30

Val Ala Trp Tyr Gln Gln Lys Pro Gly Gln Ser Pro Lys Leu Leu Ile
        35                  40                  45

Tyr Trp Ala Ser Thr Arg Leu Thr Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Asp Tyr Phe Cys Gln Gln Tyr Ser Ser Tyr Pro Tyr
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 131
<211> LENGTH: 222
<212> TYPE: PRT
<213> ORGANISM: Artificial Sequence
<220> FEATURE:
<223> OTHER INFORMATION: gpNMB Fd

<400> SEQUENCE: 131

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Phe
            20                  25                  30

Asn Tyr Tyr Trp Ser Trp Ile Arg His Pro Gly Lys Gly Leu Glu
        35                  40                  45

Trp Ile Gly Tyr Ile Tyr Tyr Ser Gly Ser Thr Tyr Ser Asn Pro Ser
    50                  55                  60

Leu Lys Ser Arg Val Thr Ile Ser Val Asp Thr Ser Lys Asn Gln Phe
65                  70                  75                  80

```
Ser Leu Thr Leu Ser Ser Val Thr Ala Ala Asp Ala Val Tyr Tyr
                85                  90                  95

Cys Ala Arg Gly Tyr Asn Trp Asn Tyr Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys
210                 215                 220
```

<210> SEQ ID NO 132
<211> LENGTH: 215
<212> TYPE: PRT
<213> ORGANISM: Artificial Sequence
<220> FEATURE:
<223> OTHER INFORMATION: gpNMB LC

<400> SEQUENCE: 132

```
Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Asp Asn Asn
            20                  25                  30

Leu Val Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Pro
                85                  90                  95

Trp Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215
```

-continued

```
<210> SEQ ID NO 133
<211> LENGTH: 223
<212> TYPE: PRT
<213> ORGANISM: Artificial Sequence
<220> FEATURE:
<223> OTHER INFORMATION: DLL3 Fd

<400> SEQUENCE: 133
```

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asn Tyr
            20                  25                  30

Gly Met Asn Trp Val Lys Gln Ala Pro Gly Lys Gly Leu Lys Trp Met
        35                  40                  45

Ala Trp Ile Asn Thr Tyr Thr Gly Glu Pro Thr Tyr Ala Asp Asp Phe
    50                  55                  60

Lys Gly Arg Phe Ala Phe Ser Leu Glu Thr Ser Ala Ser Thr Ala Ser
65                  70                  75                  80

Leu Gln Ile Ile Asn Leu Lys Asn Glu Asp Thr Ala Thr Tyr Phe Cys
                85                  90                  95

Ala Arg Ile Gly Asp Ser Ser Pro Ser Asp Tyr Trp Gly Gln Gly Thr
            100                 105                 110

Thr Leu Thr Val Ser Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys
    210                 215                 220

```
<210> SEQ ID NO 134
<211> LENGTH: 214
<212> TYPE: PRT
<213> ORGANISM: Artificial Sequence
<220> FEATURE:
<223> OTHER INFORMATION: DLL3 LC

<400> SEQUENCE: 134
```

Ser Ile Val Met Thr Gln Thr Pro Lys Phe Leu Leu Val Ser Ala Gly
1               5                   10                  15

Asp Arg Val Thr Ile Thr Cys Lys Ala Ser Gln Ser Val Ser Asn Asp
            20                  25                  30

Val Val Trp Tyr Gln Gln Lys Pro Gly Gln Ser Pro Lys Leu Leu Ile
        35                  40                  45

Tyr Tyr Ala Ser Asn Arg Tyr Thr Gly Val Pro Asp Arg Phe Ala Gly
    50                  55                  60

Ser Gly Tyr Gly Thr Asp Phe Ser Phe Thr Ile Ser Thr Val Gln Ala
65                  70                  75                  80

Glu Asp Leu Ala Val Tyr Phe Cys Gln Gln Asp Tyr Thr Ser Pro Trp

```
                85                  90                  95
Thr Phe Gly Gly Gly Thr Lys Leu Glu Ile Arg Arg Thr Val Ala Ala
                100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 135
<211> LENGTH: 6
<212> TYPE: PRT
<213> ORGANISM: Artificial Sequence
<220> FEATURE:
<223> OTHER INFORMATION: Linker

<400> SEQUENCE: 135

Gly Gly Gly Gly Gly Ser
1               5

<210> SEQ ID NO 136
<211> LENGTH: 5
<212> TYPE: PRT
<213> ORGANISM: Artificial Sequence
<220> FEATURE:
<223> OTHER INFORMATION: Linker

<400> SEQUENCE: 136

Ile Glu Pro Asp Ile
1               5

<210> SEQ ID NO 137
<211> LENGTH: 5
<212> TYPE: PRT
<213> ORGANISM: Artificial Sequence
<220> FEATURE:
<223> OTHER INFORMATION: Linker

<400> SEQUENCE: 137

Leu Glu Ala Asp Thr
1               5

<210> SEQ ID NO 138
<211> LENGTH: 5
<212> TYPE: PRT
<213> ORGANISM: Artificial Sequence
<220> FEATURE:
<223> OTHER INFORMATION: Linker

<400> SEQUENCE: 138

Ile Glu Pro Asp Gly
1               5
```

```
<210> SEQ ID NO 139
<211> LENGTH: 5
<212> TYPE: PRT
<213> ORGANISM: Artificial Sequence
<220> FEATURE:
<223> OTHER INFORMATION: Linker

<400> SEQUENCE: 139

Ile Glu Pro Asp Val
1               5

<210> SEQ ID NO 140
<211> LENGTH: 5
<212> TYPE: PRT
<213> ORGANISM: Artificial Sequence
<220> FEATURE:
<223> OTHER INFORMATION: Linker

<400> SEQUENCE: 140

Ile Glu Pro Asp Ser
1               5

<210> SEQ ID NO 141
<211> LENGTH: 5
<212> TYPE: PRT
<213> ORGANISM: Artificial Sequence
<220> FEATURE:
<223> OTHER INFORMATION: Linker

<400> SEQUENCE: 141

Ile Glu Pro Asp Thr
1               5

<210> SEQ ID NO 142
<211> LENGTH: 4
<212> TYPE: PRT
<213> ORGANISM: Artificial Sequence
<220> FEATURE:
<223> OTHER INFORMATION: Linker

<400> SEQUENCE: 142

Leu Glu Pro Asp
1

<210> SEQ ID NO 143
<211> LENGTH: 4
<212> TYPE: PRT
<213> ORGANISM: Artificial Sequence
<220> FEATURE:
<223> OTHER INFORMATION: Linker

<400> SEQUENCE: 143

Leu Glu Ala Glu
1

<210> SEQ ID NO 144
<211> LENGTH: 5
<212> TYPE: PRT
<213> ORGANISM: Artificial Sequence
<220> FEATURE:
<223> OTHER INFORMATION: Linker

<400> SEQUENCE: 144

Ile Glu Pro Asp Pro
1               5

<210> SEQ ID NO 145
```

```
<211> LENGTH: 274
<212> TYPE: PRT
<213> ORGANISM: Artificial Sequence
<220> FEATURE:
<223> OTHER INFORMATION: Second Polypeptide Chain of B7-H3 x CD3
      Bispecific DART-A Diabody

<400> SEQUENCE: 145

Gln Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Gly Gln Ala Pro Arg Gly
        35                  40                  45

Leu Ile Gly Gly Thr Asn Lys Arg Ala Pro Trp Thr Pro Ala Arg Phe
    50                  55                  60

Ser Gly Ser Leu Leu Gly Gly Lys Ala Ala Leu Thr Ile Thr Gly Ala
65                  70                  75                  80

Gln Ala Glu Asp Glu Ala Asp Tyr Tyr Cys Ala Leu Trp Tyr Ser Asn
                85                  90                  95

Leu Trp Val Phe Gly Gly Gly Thr Lys Leu Thr Val Leu Gly Gly Gly
            100                 105                 110

Gly Ser Gly Gly Gly Gly Glu Val Gln Leu Val Glu Ser Gly Gly Gly
        115                 120                 125

Leu Val Gln Pro Gly Gly Ser Leu Arg Leu Ser Cys Ala Ala Ser Gly
    130                 135                 140

Phe Thr Phe Ser Ser Phe Gly Met His Trp Val Arg Gln Ala Pro Gly
145                 150                 155                 160

Lys Gly Leu Glu Trp Val Ala Tyr Ile Ser Ser Asp Ser Ser Ala Ile
                165                 170                 175

Tyr Tyr Ala Asp Thr Val Lys Gly Arg Phe Thr Ile Ser Arg Asp Asn
            180                 185                 190

Ala Lys Asn Ser Leu Tyr Leu Gln Met Asn Ser Leu Arg Asp Glu Asp
        195                 200                 205

Thr Ala Val Tyr Tyr Cys Gly Arg Gly Arg Glu Asn Ile Tyr Tyr Gly
    210                 215                 220

Ser Arg Leu Asp Tyr Trp Gly Gln Gly Thr Thr Val Thr Val Ser Ser
225                 230                 235                 240

Gly Gly Cys Gly Gly Gly Lys Val Ala Ala Leu Lys Glu Lys Val Ala
                245                 250                 255

Ala Leu Lys Glu Lys Val Ala Ala Leu Lys Glu Lys Val Ala Ala Leu
            260                 265                 270

Lys Glu

<210> SEQ ID NO 146
<211> LENGTH: 227
<212> TYPE: PRT
<213> ORGANISM: Artificial Sequence
<220> FEATURE:
<223> OTHER INFORMATION: Third Polypeptide Chain of B7-H3 x CD3
      Bispecific DART-A Diabody

<400> SEQUENCE: 146

Asp Lys Thr His Thr Cys Pro Pro Cys Pro Ala Pro Glu Ala Ala Gly
1               5                   10                  15

Gly Pro Ser Val Phe Leu Phe Pro Pro Lys Pro Lys Asp Thr Leu Met
            20                  25                  30
```

-continued

```
Ile Ser Arg Thr Pro Glu Val Thr Cys Val Val Val Asp Val Ser His
         35                  40                  45
Glu Asp Pro Glu Val Lys Phe Asn Trp Tyr Val Asp Gly Val Glu Val
 50                  55                  60
His Asn Ala Lys Thr Lys Pro Arg Glu Glu Gln Tyr Asn Ser Thr Tyr
 65                  70                  75                  80
Arg Val Val Ser Val Leu Thr Val Leu His Gln Asp Trp Leu Asn Gly
                 85                  90                  95
Lys Glu Tyr Lys Cys Lys Val Ser Asn Lys Ala Leu Pro Ala Pro Ile
            100                 105                 110
Glu Lys Thr Ile Ser Lys Ala Lys Gly Gln Pro Arg Glu Pro Gln Val
        115                 120                 125
Tyr Thr Leu Pro Pro Ser Arg Glu Glu Met Thr Lys Asn Gln Val Ser
130                 135                 140
Leu Ser Cys Ala Val Lys Gly Phe Tyr Pro Ser Asp Ile Ala Val Glu
145                 150                 155                 160
Trp Glu Ser Asn Gly Gln Pro Glu Asn Asn Tyr Lys Thr Thr Pro Pro
                165                 170                 175
Val Leu Asp Ser Asp Gly Ser Phe Phe Leu Val Ser Lys Leu Thr Val
            180                 185                 190
Asp Lys Ser Arg Trp Gln Gln Gly Asn Val Phe Ser Cys Ser Val Met
        195                 200                 205
His Glu Ala Leu His Asn Arg Tyr Thr Gln Lys Ser Leu Ser Leu Ser
    210                 215                 220
Pro Gly Lys
225

<210> SEQ ID NO 147
<211> LENGTH: 18
<212> TYPE: PRT
<213> ORGANISM: Artificial Sequence
<220> FEATURE:
<223> OTHER INFORMATION: Linker

<400> SEQUENCE: 147

Gly Gly Ser Gly Gly Gly Gly Ser Gly Gly Gly Gly Ser Gly Gly Gly
 1               5                  10                  15
Gly Ser

<210> SEQ ID NO 148
<211> LENGTH: 19
<212> TYPE: PRT
<213> ORGANISM: Artificial Sequence
<220> FEATURE:
<223> OTHER INFORMATION: Linker

<400> SEQUENCE: 148

Thr Gly Gly Ser Gly Gly Gly Gly Ile Glu Pro Asp Ile Gly Gly Ser
 1               5                  10                  15
Gly Gly Ser

<210> SEQ ID NO 149
<211> LENGTH: 5
<212> TYPE: PRT
<213> ORGANISM: Artificial Sequence
<220> FEATURE:
<223> OTHER INFORMATION: Linker

<400> SEQUENCE: 149
```

```
Gly Gly Gly Gly Ser
1               5

<210> SEQ ID NO 150
<211> LENGTH: 5
<212> TYPE: PRT
<213> ORGANISM: Artificial Sequence
<220> FEATURE:
<223> OTHER INFORMATION: Linker consensus
<220> FEATURE:
<221> NAME/KEY: VARIANT
<222> LOCATION: (1)..(1)
<223> OTHER INFORMATION: X1= I, L, Y, M, F, V, or A
<220> FEATURE:
<221> NAME/KEY: VARIANT
<222> LOCATION: (2)..(2)
<223> OTHER INFORMATION: X2 = A, G, S, V, E, D, Q, N, or Y
<220> FEATURE:
<221> NAME/KEY: VARIANT
<222> LOCATION: (3)..(3)
<223> OTHER INFORMATION: X3 = H, P, A, V, G, S, or T
<220> FEATURE:
<221> NAME/KEY: VARIANT
<222> LOCATION: (4)..(4)
<223> OTHER INFORMATION: X4 = D or E
<220> FEATURE:
<221> NAME/KEY: VARIANT
<222> LOCATION: (5)..(5)
<223> OTHER INFORMATION: X5 = I, L, Y, M, F, V, T, S, G or A

<400> SEQUENCE: 150

Xaa Xaa Xaa Xaa Xaa
1               5

<210> SEQ ID NO 151
<211> LENGTH: 5
<212> TYPE: PRT
<213> ORGANISM: Artificial Sequence
<220> FEATURE:
<223> OTHER INFORMATION: Linker consensus
<220> FEATURE:
<221> NAME/KEY: VARIANT
<222> LOCATION: (1)..(1)
<223> OTHER INFORMATION: X1 = I or L
<220> FEATURE:
<221> NAME/KEY: VARIANT
<222> LOCATION: (3)..(3)
<223> OTHER INFORMATION: X3 = P or A
<220> FEATURE:
<221> NAME/KEY: VARIANT
<222> LOCATION: (5)..(5)
<223> OTHER INFORMATION: X5 = I, V, T, S, or G

<400> SEQUENCE: 151

Xaa Glu Xaa Asp Xaa
1               5

<210> SEQ ID NO 152
<211> LENGTH: 5
<212> TYPE: PRT
<213> ORGANISM: Artificial Sequence
<220> FEATURE:
<223> OTHER INFORMATION: Linker

<400> SEQUENCE: 152

Leu Glu Pro Asp Gly
1               5

<210> SEQ ID NO 153
<211> LENGTH: 5
<212> TYPE: PRT
<213> ORGANISM: Artificial Sequence
```

```
<220> FEATURE:
<223> OTHER INFORMATION: Linker

<400> SEQUENCE: 153

Leu Glu Ala Asp Gly
1               5

<210> SEQ ID NO 154
<211> LENGTH: 5
<212> TYPE: PRT
<213> ORGANISM: Artificial Sequence
<220> FEATURE:
<223> OTHER INFORMATION: Linker consensus
<220> FEATURE:
<221> NAME/KEY: VARIANT
<222> LOCATION: (1)..(1)
<223> OTHER INFORMATION: X1 = any amino acid
<220> FEATURE:
<221> NAME/KEY: VARIANT
<222> LOCATION: (5)..(5)
<223> OTHER INFORMATION: X5 = A or V

<400> SEQUENCE: 154

Xaa Gln Ala Arg Xaa
1               5

<210> SEQ ID NO 155
<211> LENGTH: 5
<212> TYPE: PRT
<213> ORGANISM: Artificial Sequence
<220> FEATURE:
<223> OTHER INFORMATION: Linker consensus
<220> FEATURE:
<221> NAME/KEY: VARIANT
<222> LOCATION: (5)..(5)
<223> OTHER INFORMATION: X5 = A or V

<400> SEQUENCE: 155

Arg Gln Ala Arg Xaa
1               5

<210> SEQ ID NO 156
<211> LENGTH: 5
<212> TYPE: PRT
<213> ORGANISM: Artificial Sequence
<220> FEATURE:
<223> OTHER INFORMATION: Linker

<400> SEQUENCE: 156

Arg Gln Ala Arg Val
1               5

<210> SEQ ID NO 157
<211> LENGTH: 4
<212> TYPE: PRT
<213> ORGANISM: Artificial Sequence
<220> FEATURE:
<223> OTHER INFORMATION: Linker consensus
<220> FEATURE:
<221> NAME/KEY: VARIANT
<222> LOCATION: (1)..(1)
<223> OTHER INFORMATION: X1 = P, V or A
<220> FEATURE:
<221> NAME/KEY: VARIANT
<222> LOCATION: (2)..(2)
<223> OTHER INFORMATION: X2 = Q or D
<220> FEATURE:
<221> NAME/KEY: VARIANT
<222> LOCATION: (3)..(3)
<223> OTHER INFORMATION: X3 = A or N
<220> FEATURE:
```

```
<221> NAME/KEY: VARIANT
<222> LOCATION: (4)..(4)
<223> OTHER INFORMATION: X4 = L, I or M

<400> SEQUENCE: 157

Xaa Xaa Xaa Xaa
1

<210> SEQ ID NO 158
<211> LENGTH: 4
<212> TYPE: PRT
<213> ORGANISM: Artificial Sequence
<220> FEATURE:
<223> OTHER INFORMATION: Linker consensus
<220> FEATURE:
<221> NAME/KEY: VARIANT
<222> LOCATION: (2)..(2)
<223> OTHER INFORMATION: X2 = Q or D
<220> FEATURE:
<221> NAME/KEY: VARIANT
<222> LOCATION: (3)..(3)
<223> OTHER INFORMATION: X3 = A or N
<220> FEATURE:
<221> NAME/KEY: VARIANT
<222> LOCATION: (4)..(4)
<223> OTHER INFORMATION: X4 = L or I

<400> SEQUENCE: 158

Pro Xaa Xaa Xaa
1

<210> SEQ ID NO 159
<211> LENGTH: 22
<212> TYPE: PRT
<213> ORGANISM: Artificial Sequence
<220> FEATURE:
<223> OTHER INFORMATION: P2A

<400> SEQUENCE: 159

Gly Ser Gly Ala Thr Asn Phe Ser Leu Leu Lys Gln Ala Gly Asp Val
1               5                   10                  15

Glu Glu Asn Pro Gly Pro
            20

<210> SEQ ID NO 160
<211> LENGTH: 19
<212> TYPE: PRT
<213> ORGANISM: Artificial Sequence
<220> FEATURE:
<223> OTHER INFORMATION: P2A

<400> SEQUENCE: 160

Ala Thr Asn Phe Ser Leu Leu Lys Gln Ala Gly Asp Val Glu Glu Asn
1               5                   10                  15

Pro Gly Pro

<210> SEQ ID NO 161
<211> LENGTH: 20
<212> TYPE: PRT
<213> ORGANISM: Artificial Sequence
<220> FEATURE:
<223> OTHER INFORMATION: E2A

<400> SEQUENCE: 161

Gln Cys Thr Asn Tyr Ala Leu Leu Lys Leu Ala Gly Asp Val Glu Ser
1               5                   10                  15

Asn Pro Gly Pro
```

```
<210> SEQ ID NO 162
<211> LENGTH: 22
<212> TYPE: PRT
<213> ORGANISM: Artificial Sequence
<220> FEATURE:
<223> OTHER INFORMATION: F2A

<400> SEQUENCE: 162

Val Lys Gln Thr Leu Asn Phe Asp Leu Leu Lys Leu Ala Gly Asp Val
1               5                   10                  15

Glu Ser Asn Pro Gly Pro
            20

<210> SEQ ID NO 163
<211> LENGTH: 18
<212> TYPE: PRT
<213> ORGANISM: Artificial Sequence
<220> FEATURE:
<223> OTHER INFORMATION: T2A

<400> SEQUENCE: 163

Glu Gly Arg Gly Ser Leu Leu Thr Cys Gly Asp Val Glu Glu Asn Pro
1               5                   10                  15

Gly Pro

<210> SEQ ID NO 164
<211> LENGTH: 24
<212> TYPE: PRT
<213> ORGANISM: Artificial Sequence
<220> FEATURE:
<223> OTHER INFORMATION: T2A

<400> SEQUENCE: 164

Leu Glu Gly Gly Gly Glu Gly Arg Gly Ser Leu Leu Thr Cys Gly Asp
1               5                   10                  15

Val Glu Glu Asn Pro Gly Pro Arg
            20

<210> SEQ ID NO 165
<211> LENGTH: 66
<212> TYPE: DNA
<213> ORGANISM: Artificial Sequence
<220> FEATURE:
<223> OTHER INFORMATION: P2A

<400> SEQUENCE: 165
ggatctggag caacaaactt ctcactactc aaacaagcag gtgacgtgga ggagaatccc      60
ggaccc                                                                66

<210> SEQ ID NO 166
<211> LENGTH: 18
<212> TYPE: PRT
<213> ORGANISM: Artificial Sequence
<220> FEATURE:
<223> OTHER INFORMATION: Linker

<400> SEQUENCE: 166

Gly Ser Pro Ala Gly Leu Glu Ala Asp Gly Ser Arg Gln Ala Arg Val
1               5                   10                  15

Gly Ser
```

```
<210> SEQ ID NO 167
<211> LENGTH: 122
<212> TYPE: PRT
<213> ORGANISM: Mus musculus
<220> FEATURE:
<221> NAME/KEY: MISC_FEATURE
<223> OTHER INFORMATION: anti-5T4 VH
<220> FEATURE:
<221> NAME/KEY: misc_feature
<222> LOCATION: (97)..(97)
<223> OTHER INFORMATION: Xaa can be any naturally occurring amino acid

<400> SEQUENCE: 167

Glu Val Gln Leu Val Glu Ser Gly Gly Gly Leu Val Gln Pro Lys Gly
1               5                   10                  15

Ser Leu Lys Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Ser Asn Asn Tyr Ala Thr Tyr Tyr Ala Asp
    50                  55                  60

Ser Val Lys Asp Arg Phe Thr Ile Ser Arg Asp Asp Ser Gln Ser Met
65                  70                  75                  80

Leu Tyr Leu Gln Met Asn Asn Leu Lys Thr Glu Asp Thr Ala Met Tyr
                85                  90                  95

Xaa Cys Val Arg Gln Trp Asp Tyr Asp Val Arg Ala Met Asn Tyr Trp
            100                 105                 110

Gly Gln Gly Thr Ser Val Thr Val Ser Ser
        115                 120

<210> SEQ ID NO 168
<211> LENGTH: 107
<212> TYPE: PRT
<213> ORGANISM: Mus musculus
<220> FEATURE:
<221> NAME/KEY: MISC_FEATURE
<223> OTHER INFORMATION: anti-5T4  VL

<400> SEQUENCE: 168

Asp Ile Val Met Thr Gln Ser His Ile Phe Met Ser Thr Ser Val Gly
1               5                   10                  15

Asp Arg Val Ser Ile Thr Cys Lys Ala Ser Gln Asp Val Asp Thr Ala
            20                  25                  30

Val Ala Trp Tyr Gln Gln Lys Pro Gly Gln Ser Pro Lys Leu Leu Ile
        35                  40                  45

Tyr Trp Ala Ser Thr Arg Leu Thr Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Asp Tyr Phe Cys Gln Gln Tyr Ser Ser Tyr Pro Tyr
                85                  90                  95

Thr Phe Gly Gly Gly Thr Lys Leu Glu Ile Lys
            100                 105

<210> SEQ ID NO 169
<211> LENGTH: 504
<212> TYPE: PRT
<213> ORGANISM: Artificial Sequence
<220> FEATURE:
<223> OTHER INFORMATION: First Polypeptide Chain of B7-H3 x CD3
      Bispecific DART-A Diabody
```

```
<400> SEQUENCE: 169

Asp Ile Gln Leu Thr Gln Ser Pro Ser Phe Leu Ser Ala Ser Val Gly
1               5                   10                  15

Asp Arg Val Thr Ile Thr Cys Lys Ala Ser Gln Asn Val Asp Thr Asn
            20                  25                  30

Val Ala Trp Tyr Gln Gln Lys Pro Gly Lys Ala Pro Lys Ala Leu Ile
        35                  40                  45

Tyr Ser Ala Ser Tyr Arg Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Asn Tyr Pro Phe
                85                  90                  95

Thr Phe Gly Gln Gly Thr Lys Leu Glu Ile Lys Gly Gly Gly Ser Gly
            100                 105                 110

Gly Gly Gly Glu Val Gln Leu Val Glu Ser Gly Gly Gly Leu Val Gln
        115                 120                 125

Pro Gly Gly Ser Leu Arg Leu Ser Cys Ala Ala Ser Gly Phe Thr Phe
130                 135                 140

Ser Thr Tyr Ala Met Asn Trp Val Arg Gln Ala Pro Gly Lys Gly Leu
145                 150                 155                 160

Glu Trp Val Gly Arg Ile Arg Ser Lys Tyr Asn Asn Tyr Ala Thr Tyr
                165                 170                 175

Tyr Ala Asp Ser Val Lys Asp Arg Phe Thr Ile Ser Arg Asp Asp Ser
            180                 185                 190

Lys Asn Ser Leu Tyr Leu Gln Met Asn Ser Leu Lys Thr Glu Asp Thr
        195                 200                 205

Ala Val Tyr Tyr Cys Val Arg His Gly Asn Phe Gly Asn Ser Tyr Val
    210                 215                 220

Ser Trp Phe Ala Tyr Trp Gly Gln Gly Thr Leu Val Thr Val Ser Ser
225                 230                 235                 240

Gly Gly Cys Gly Gly Gly Glu Val Ala Ala Leu Glu Lys Glu Val Ala
                245                 250                 255

Ala Leu Glu Lys Glu Val Ala Ala Leu Glu Lys Glu Val Ala Ala Leu
            260                 265                 270

Glu Lys Gly Gly Gly Asp Lys Thr His Thr Cys Pro Pro Cys Pro Ala
        275                 280                 285

Pro Glu Ala Ala Gly Gly Pro Ser Val Phe Leu Phe Pro Pro Lys Pro
290                 295                 300

Lys Asp Thr Leu Met Ile Ser Arg Thr Pro Glu Val Thr Cys Val Val
305                 310                 315                 320

Val Asp Val Ser His Glu Asp Pro Glu Val Lys Phe Asn Trp Tyr Val
                325                 330                 335

Asp Gly Val Glu Val His Asn Ala Lys Thr Lys Pro Arg Glu Glu Gln
            340                 345                 350

Tyr Asn Ser Thr Tyr Arg Val Val Ser Val Leu Thr Val Leu His Gln
        355                 360                 365

Asp Trp Leu Asn Gly Lys Glu Tyr Lys Cys Lys Val Ser Asn Lys Ala
370                 375                 380

Leu Pro Ala Pro Ile Glu Lys Thr Ile Ser Lys Ala Lys Gly Gln Pro
385                 390                 395                 400

Arg Glu Pro Gln Val Tyr Thr Leu Pro Pro Ser Arg Glu Glu Met Thr
                405                 410                 415
```

Lys Asn Gln Val Ser Leu Trp Cys Leu Val Lys Gly Phe Tyr Pro Ser
            420                 425                 430

Asp Ile Ala Val Glu Trp Glu Ser Asn Gly Gln Pro Glu Asn Asn Tyr
        435                 440                 445

Lys Thr Thr Pro Pro Val Leu Asp Ser Asp Gly Ser Phe Phe Leu Tyr
450                 455                 460

Ser Lys Leu Thr Val Asp Lys Ser Arg Trp Gln Gln Gly Asn Val Phe
465                 470                 475                 480

Ser Cys Ser Val Met His Glu Ala Leu His Asn His Tyr Thr Gln Lys
                485                 490                 495

Ser Leu Ser Leu Ser Pro Gly Lys
            500

<210> SEQ ID NO 170
<211> LENGTH: 15
<212> TYPE: PRT
<213> ORGANISM: Artificial Sequence
<220> FEATURE:
<223> OTHER INFORMATION: Linker

<400> SEQUENCE: 170

Gly Gly Gly Gly Ser Gly Gly Gly Gly Ser Gly Gly Gly Gly Ser
1               5                   10                  15

<210> SEQ ID NO 171
<211> LENGTH: 6
<212> TYPE: PRT
<213> ORGANISM: Artificial Sequence
<220> FEATURE:
<223> OTHER INFORMATION: Linker
<220> FEATURE:
<221> NAME/KEY: REPEAT
<222> LOCATION: (4)..(6)
<223> OTHER INFORMATION: repeated 0 to 10 times

<400> SEQUENCE: 171

Gly Gly Ser Gly Gly Ser
1               5

<210> SEQ ID NO 172
<211> LENGTH: 6
<212> TYPE: PRT
<213> ORGANISM: Artificial Sequence
<220> FEATURE:
<223> OTHER INFORMATION: Linker
<220> FEATURE:
<221> NAME/KEY: REPEAT
<222> LOCATION: (1)..(6)
<223> OTHER INFORMATION: repeated 1 to 4 times

<400> SEQUENCE: 172

Gly Gly Gly Gly Gly Ser
1               5

<210> SEQ ID NO 173
<211> LENGTH: 5
<212> TYPE: PRT
<213> ORGANISM: Artificial Sequence
<220> FEATURE:
<223> OTHER INFORMATION: Linker
<220> FEATURE:
<221> NAME/KEY: REPEAT
<222> LOCATION: (1)..(5)
<223> OTHER INFORMATION: Repeated 1 to 5 times

<400> SEQUENCE: 173

Gly Gly Gly Gly Ser
1               5

<210> SEQ ID NO 174
<211> LENGTH: 5
<212> TYPE: PRT
<213> ORGANISM: Artificial Sequence
<220> FEATURE:
<223> OTHER INFORMATION: Linker
<220> FEATURE:
<221> NAME/KEY: REPEAT
<222> LOCATION: (1)..(1)
<223> OTHER INFORMATION: Repeated 1 to 5 times
<220> FEATURE:
<221> NAME/KEY: VARIANT
<222> LOCATION: (2)..(2)
<223> OTHER INFORMATION: X2= A, V, L, I, M,F, W, P, G, S, T, C, Y, N,Q,
      K, R, H, D, or E
<220> FEATURE:
<221> NAME/KEY: REPEAT
<222> LOCATION: (3)..(3)
<223> OTHER INFORMATION: Repeated 1 to 5 times
<220> FEATURE:
<221> NAME/KEY: VARIANT
<222> LOCATION: (4)..(4)
<223> OTHER INFORMATION: X4 = A, V, L, I, M,F, W, P, G, S, T, C, Y, N,Q,
      K, R, H, D, or E
<220> FEATURE:
<221> NAME/KEY: REPEAT
<222> LOCATION: (5)..(5)
<223> OTHER INFORMATION: Repeated 1 to 5 times

<400> SEQUENCE: 174

Gly Xaa Gly Xaa Gly
1               5

<210> SEQ ID NO 175
<211> LENGTH: 11
<212> TYPE: PRT
<213> ORGANISM: Artificial Sequence
<220> FEATURE:
<223> OTHER INFORMATION: Linker
<220> FEATURE:
<221> NAME/KEY: VARIANT
<222> LOCATION: (4)..(4)
<223> OTHER INFORMATION: X4 = A, V, L, I, M,F, W, P, G, S, T, C, Y, N,Q,
      K, R, H, D, or E
<220> FEATURE:
<221> NAME/KEY: VARIANT
<222> LOCATION: (8)..(8)
<223> OTHER INFORMATION: X8 = A, V, L, I, M,F, W, P, G, S, T, C, Y, N,Q,
      K, R, H, D, or E

<400> SEQUENCE: 175

Gly Gly Gly Xaa Gly Gly Gly Xaa Gly Gly Gly
1               5                   10

<210> SEQ ID NO 176
<211> LENGTH: 11
<212> TYPE: PRT
<213> ORGANISM: Artificial Sequence
<220> FEATURE:
<223> OTHER INFORMATION: Linker

<400> SEQUENCE: 176

Ala Thr Thr Thr Gly Ser Ser Pro Gly Pro Thr
1               5                   10

<210> SEQ ID NO 177
<211> LENGTH: 11
<212> TYPE: PRT

```
<213> ORGANISM: Artificial Sequence
<220> FEATURE:
<223> OTHER INFORMATION: Linker

<400> SEQUENCE: 177

Gly Gly Gly Gly Gly Cys Gly Gly Gly Gly
1               5                   10

<210> SEQ ID NO 178
<211> LENGTH: 5
<212> TYPE: PRT
<213> ORGANISM: Artificial Sequence
<220> FEATURE:
<223> OTHER INFORMATION: Linker
<220> FEATURE:
<221> NAME/KEY: REPEAT
<222> LOCATION: (1)..(5)
<223> OTHER INFORMATION: Repeated 2 to 20 times

<400> SEQUENCE: 178

Glu Ala Ala Ala Lys
1               5

<210> SEQ ID NO 179
<211> LENGTH: 6
<212> TYPE: PRT
<213> ORGANISM: Artificial Sequence
<220> FEATURE:
<223> OTHER INFORMATION: Linker
<220> FEATURE:
<221> NAME/KEY: REPEAT
<222> LOCATION: (3)..(4)
<223> OTHER INFORMATION: Repeated 2 to 20 times

<400> SEQUENCE: 179

Ala Ser Ala Pro Gly Thr
1               5

<210> SEQ ID NO 180
<211> LENGTH: 9
<212> TYPE: PRT
<213> ORGANISM: Artificial Sequence
<220> FEATURE:
<223> OTHER INFORMATION: Linker
<220> FEATURE:
<221> NAME/KEY: REPEAT
<222> LOCATION: (3)..(7)
<223> OTHER INFORMATION: Repeated 2 to 20 times

<400> SEQUENCE: 180

Ala Ser Glu Ala Ala Ala Lys Gly Thr
1               5

<210> SEQ ID NO 181
<211> LENGTH: 5
<212> TYPE: PRT
<213> ORGANISM: Artificial Sequence
<220> FEATURE:
<223> OTHER INFORMATION: Linker
<220> FEATURE:
<221> NAME/KEY: REPEAT
<222> LOCATION: (1)..(5)
<223> OTHER INFORMATION: Repeated 2 to 20 times

<400> SEQUENCE: 181

Gly Gly Gly Gly Ala
1               5

<210> SEQ ID NO 182
```

```
<211> LENGTH: 5
<212> TYPE: PRT
<213> ORGANISM: Artificial Sequence
<220> FEATURE:
<223> OTHER INFORMATION: Linker
<220> FEATURE:
<221> NAME/KEY: REPEAT
<222> LOCATION: (1)..(5)
<223> OTHER INFORMATION: Repeated 2 to 20 times

<400> SEQUENCE: 182

Pro Gly Gly Gly Ser
1               5

<210> SEQ ID NO 183
<211> LENGTH: 5
<212> TYPE: PRT
<213> ORGANISM: Artificial Sequence
<220> FEATURE:
<223> OTHER INFORMATION: Linker
<220> FEATURE:
<221> NAME/KEY: REPEAT
<222> LOCATION: (1)..(5)
<223> OTHER INFORMATION: Repeated 2 to 20 times

<400> SEQUENCE: 183

Ala Gly Gly Gly Ser
1               5

<210> SEQ ID NO 184
<211> LENGTH: 20
<212> TYPE: PRT
<213> ORGANISM: Artificial Sequence
<220> FEATURE:
<223> OTHER INFORMATION: Linker
<220> FEATURE:
<221> NAME/KEY: REPEAT
<222> LOCATION: (4)..(17)
<223> OTHER INFORMATION: Repeated 2 to 20 times

<400> SEQUENCE: 184

Gly Gly Ser Glu Gly Lys Ser Ser Gly Ser Gly Ser Glu Ser Lys Ser
1               5                   10                  15
Thr Gly Gly Ser
            20

<210> SEQ ID NO 185
<211> LENGTH: 5
<212> TYPE: PRT
<213> ORGANISM: Artificial Sequence
<220> FEATURE:
<223> OTHER INFORMATION: Linker
<220> FEATURE:
<221> NAME/KEY: REPEAT
<222> LOCATION: (1)..(5)
<223> OTHER INFORMATION: Repeated 1 to 9 times

<400> SEQUENCE: 185

Ser Ser Ser Ser Gly
1               5

<210> SEQ ID NO 186
<211> LENGTH: 9
<212> TYPE: PRT
<213> ORGANISM: Artificial Sequence
<220> FEATURE:
<223> OTHER INFORMATION: Linker

<400> SEQUENCE: 186
```

```
Ser Ser Ser Ala Ser Ala Ser Ser Ala
1               5
```

<210> SEQ ID NO 187
<211> LENGTH: 7
<212> TYPE: PRT
<213> ORGANISM: Artificial Sequence
<220> FEATURE:
<223> OTHER INFORMATION: Linker

<400> SEQUENCE: 187

```
Gly Ser Pro Gly Ser Pro Gly
1               5
```

<210> SEQ ID NO 188
<211> LENGTH: 241
<212> TYPE: PRT
<213> ORGANISM: Artificial Sequence
<220> FEATURE:
<223> OTHER INFORMATION: DLL3 scFv

<400> SEQUENCE: 188

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Pro Gly Lys Gly Leu Glu Trp Ile
        35                  40                  45

Gly Tyr Val Tyr Tyr Ser Gly Thr Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Ser Ile Ala Val Thr Gly Phe Tyr Phe Asp Tyr Trp Gly Gln Gly Thr
            100                 105                 110

Leu Val Thr Val Ser Ser Gly Gly Gly Gly Ser Gly Gly Gly Gly Ser
        115                 120                 125

Gly Gly Gly Gly Ser Glu Ile Val Leu Thr Gln Ser Pro Gly Thr Leu
    130                 135                 140

Ser Leu Ser Pro Gly Glu Arg Val Thr Leu Ser Cys Arg Ala Ser Gln
145                 150                 155                 160

Arg Val Asn Asn Asn Tyr Leu Ala Trp Tyr Gln Gln Arg Pro Gly Gln
                165                 170                 175

Ala Pro Arg Leu Leu Ile Tyr Gly Ala Ser Ser Arg Ala Thr Gly Ile
            180                 185                 190

Pro Asp Arg Phe Ser Gly Ser Gly Ser Gly Thr Asp Phe Thr Leu Thr
        195                 200                 205

Ile Ser Arg Leu Glu Pro Glu Asp Phe Ala Val Tyr Tyr Cys Gln Gln
    210                 215                 220

Tyr Asp Arg Ser Pro Leu Thr Phe Gly Gly Gly Thr Lys Leu Glu Ile
225                 230                 235                 240

Lys
```

<210> SEQ ID NO 189
<211> LENGTH: 119
<212> TYPE: PRT
<213> ORGANISM: Artificial Sequence
<220> FEATURE:

<223> OTHER INFORMATION: CD20 VH

<400> SEQUENCE: 189

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Ser Tyr Ser
            20                  25                  30

Trp Ile Asn Trp Val Arg Gln Ala Pro Gly Gln Gly Leu Glu Trp Met
        35                  40                  45

Gly Arg Ile Phe Pro Gly Asp Gly Asp Thr Asp Tyr Asn Gly Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Val Phe Asp Gly Tyr Trp Leu Val Tyr Trp Gly Gln Gly
            100                 105                 110

Thr Leu Val Thr Val Ser Ser
            115

<210> SEQ ID NO 190
<211> LENGTH: 115
<212> TYPE: PRT
<213> ORGANISM: Artificial Sequence
<220> FEATURE:
<223> OTHER INFORMATION: CD20 VL

<400> SEQUENCE: 190

Asp Ile Val Met Thr Gln Thr Pro Leu Ser Leu Pro Val Thr Pro Gly
1               5                   10                  15

Glu Pro Ala Ser Ile Ser Cys Arg Ser Ser Lys Ser Leu Leu His Ser
            20                  25                  30

Asn Gly Ile Thr Tyr Leu Tyr Trp Tyr Leu Gln Lys Pro Gly Gln Ser
        35                  40                  45

Pro Gln Leu Leu Ile Tyr Gln Met Ser Asn Leu Val Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Asn
                85                  90                  95

Leu Glu Leu Pro Tyr Thr Phe Gly Gly Gly Thr Lys Val Glu Ile Lys
            100                 105                 110

Arg Thr Val
        115